US008741898B2

(12) United States Patent
Goff et al.

(10) Patent No.: US 8,741,898 B2
(45) Date of Patent: *Jun. 3, 2014

(54) POLYCYCLIC HETEROARYL SUBSTITUTED TRIAZOLES USEFUL AS AXL INHIBITORS

(75) Inventors: Dane Goff, Redwood City, CA (US); Jing Zhang, Foster City, CA (US); Rajinder Singh, Belmont, CA (US); Sacha Holland, San Francisco, CA (US); Jiaxin Yu, San Carlos, CA (US); Thilo J. Heckrodt, San Francisco, CA (US); Pingyu Ding, Foster City, CA (US); Joane Litvak, Oakland, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/423,924

(22) Filed: Mar. 19, 2012

(65) Prior Publication Data

US 2012/0264740 A1 Oct. 18, 2012

Related U.S. Application Data

(60) Continuation of application No. 12/986,951, filed on Jan. 7, 2011, now Pat. No. 8,168,636, which is a continuation of application No. 12/720,448, filed on Mar. 9, 2010, which is a division of application No. 11/967,172, filed on Dec. 29, 2007, now Pat. No. 7,709,482.

(60) Provisional application No. 60/970,931, filed on Sep. 7, 2007, provisional application No. 60/895,400, filed on Mar. 16, 2007, provisional application No. 60/882,850, filed on Dec. 29, 2006.

(51) Int. Cl.
*A61K 31/502* (2006.01)

(52) U.S. Cl.
USPC .......................................................... 514/248

(58) Field of Classification Search
USPC .......................................................... 514/248
See application file for complete search history.

(56) References Cited

U.S. PATENT DOCUMENTS

| | | | |
|---|---|---|---|
| 3,813,400 A | 5/1974 | Boyle et al. | |
| 7,709,482 B2 * | 5/2010 | Goff et al. | ...................... 514/248 |
| 7,872,000 B2 | 1/2011 | Goff et al. | |
| 7,879,856 B2 | 2/2011 | Goff et al. | |
| 7,884,119 B2 | 2/2011 | Singh et al. | |
| 7,935,693 B2 | 5/2011 | Singh et al. | |
| 8,012,965 B2 | 9/2011 | Goff et al. | |
| 8,097,630 B2 | 1/2012 | Singh et al. | |
| 2004/0077699 A1 | 4/2004 | Lin et al. | |
| 2004/0214817 A1 | 10/2004 | Pierce et al. | |
| 2005/0118604 A1 | 6/2005 | Lorens et al. | |
| 2006/0293256 A1 | 12/2006 | Yamada et al. | |
| 2008/0182862 A1 | 7/2008 | Ding et al. | |
| 2008/0188474 A1 | 8/2008 | Goff et al. | |
| 2009/0258864 A1 | 10/2009 | Bhamidipati et al. | |
| 2010/0196511 A1 | 8/2010 | Hitoshi et al. | |
| 2011/0071133 A1 | 3/2011 | Goff et al. | |
| 2011/0082131 A1 | 4/2011 | Singh et al. | |
| 2011/0092502 A1 | 4/2011 | Goff et al. | |
| 2011/0105511 A1 | 5/2011 | Singh | |
| 2011/0105512 A1 | 5/2011 | Singh | |
| 2011/0183986 A1 | 7/2011 | Singh et al. | |
| 2011/0281846 A1 | 11/2011 | Goff et al. | |
| 2012/0088768 A1 | 4/2012 | Singh et al. | |
| 2013/0018041 A1 | 1/2013 | Bhamidipati et al. | |
| 2013/0018051 A1 | 1/2013 | Singh et al. | |
| 2013/0090330 A1 | 4/2013 | Ding et al. | |
| 2013/0109695 A1 | 5/2013 | Singh et al. | |

FOREIGN PATENT DOCUMENTS

| | | |
|---|---|---|
| EP | 0 710 654 A1 | 5/1996 |
| FR | 2 908 131 A1 | 5/2008 |
| WO | WO 01/09106 A1 | 2/2001 |
| WO | WO 02/057240 A1 | 7/2002 |
| WO | WO 03/027275 A1 | 4/2003 |
| WO | WO 03/093344 A1 | 11/2003 |
| WO | WO 2004/017997 A1 | 3/2004 |
| WO | WO 2004/039955 A2 | 5/2004 |
| WO | WO 2004/046120 A2 | 6/2004 |
| WO | WO 2005/013982 A1 | 2/2005 |
| WO | WO 2005/077922 A2 | 8/2005 |
| WO | WO 2006/020767 A2 | 2/2006 |
| WO | WO 2006/034116 A1 | 3/2006 |
| WO | WO 2007/030680 A2 | 3/2007 |
| WO | WO 2008/059141 A1 | 5/2008 |
| WO | WO 2008/083367 A2 | 7/2008 |
| WO | WO 2008/157131 A1 | 12/2008 |
| WO | WO 2010/005876 A2 | 1/2010 |
| WO | WO 2010/005879 A1 | 1/2010 |

OTHER PUBLICATIONS

Yoshii et al., "Conformational Analysis and Selection of Odor-Active Conformers: Synthesis of Molecules Designed for the Lily-of-the-Valley(Muguet)-Type Odor," *Helvetica Chimica Acta 84*: 2051-2063, 2001.
Agrafiotis et al., "SAR Maps: A New SAR Visualization Technique for Medicinal Chemists," *J. Med. Chem. 50*(24): 5926-5937, 2007.
Alexander et al., "Human Parathyroid Hormone 1-34 Reverses Bone Loss in Ovariectomized Mice," *Journal of Bone and Mineral Research 16*(9): 1665-1673, 2001.
Angelillo-Scherrer et al., "Role of Gas6 receptors in platelet signaling during thrombus stabilization and implications for antithrombotic therapy," *Journal of Clinical Investigation 115*(2): 237-246, Feb. 2005.
Bora et al., "Immunotherapy for choroidal neovascularization in a laser-induced mouse model simulating exudative (wet) macular degeneration," *Proc. Natl. Acad. Sci U.S.A. 100*(5): 2679-2684, Mar. 4, 2003.
Brewster et al., "Ro 32/3555, an orally active collagenase selective inhibitor, prevents structural damage in the STR/ORT mouse model of osteoarthritis," *Arthritis & Rheumatism 41*(9): 1639-1644, Sep. 1998.

(Continued)

*Primary Examiner* — Samantha Shterengarts
(74) *Attorney, Agent, or Firm* — Seed IP Law Group PLLC; Travis Young

(57) ABSTRACT

Polycyclic heteroaryl substituted triazoles and pharmaceutical compositions containing the compounds are disclosed as being useful in inhibiting the activity of the receptor protein tyrosine kinase Axl. Methods of using the compounds in treating diseases or conditions associated with Axl activity are also disclosed.

15 Claims, No Drawings

(56) References Cited

OTHER PUBLICATIONS

Fristad et al., "Silanes in Organic Synthesis. 9. Enesilylation as a Method for 1,2-Carbonyl Migration within Ketones and for Conversion to 1,2-Transposed Allylic Alcohols," *J. Org. Chem. 45*: 3028-3037, 1980.

Fujioka et al., "Equol, a Metabolite of Daidzein, Inhibits Bone Loss in Ovariectomized Mice," *Journal of Nutrition 134*: 2623-2627, 2004.

Golub et al., "Molecular Classification of Cancer: Class Discovery and Class Prediction by Gene Expression Monitoring," *Science 286*: 531-537, Oct. 15, 1999.

Holland et al., "Multiple Roles for the Receptor Tyrosine Kinase Axl in Tumor Formation," *Cancer Res. 65*(20): 9294-9303, Oct. 15, 2005.

Holland et al., "Requirement for the Receptor Tyrosine Kinase Axl in Angiogenesis and Tumor Growth", 7th Annual Symposium on Anti-Angiogenic Agents, Feb. 10-13, 2005, San Diego, California, 1 page.

Kadoya et al., "Role of calpain in hydrogen peroxide induced cataract," *Current Eye Research 12*(4): 341-346, 1993.

Katritzky et al., "Syntheses of 5-(2-arylazenyl)-1,2,4-triazoles and 2-amino-5-aryl-1,3,4-oxadiazoles," *ARKIVOC 6*: 82-90, 2002.

Kim et al., "Novel Oral Formulation of Paclitaxel Inhibits Neointimal Hyperplasia in a Rat Carotid Artery Injury Model," *Circulation 109*: 1558-1563, Mar. 8, 2004.

Kurzer and Douraghi-Zadeh, "Heterocyclic Compounds from Urea Derivatives. Part VI. Synthesis and Cyclisation of 1-Amino-3-($NN'$-diarylamidino)guanidines and Some Analogues," *J. Chem. Soc.* 932-937, 1965.

Lala et al., "Role of nitric oxide in tumor progression: Lessons from experimental tumors," *Cancer and Metastasis Reviews 17*(1): 91-106, 1988.

Lebovic et al., "Peroxisome proliferator-activated receptor-gamma induces regression of endometrial explants in a rat model of endometriosis," *Fertility and Sterility 82*(Suppl 3): 1008-1013, Oct. 2004.

Mataka et al., "[3.3]Orthocyclophanes with Facing Benzene and Naphthalene Rings," *J. Org. Chem. 52*(13): 2653-2656, 1987.

Nakashima et al., "ApoE-Deficient Mice Develop Lesions of All Phases of Atherosclerosis Throughout the Arterial Tree," *Arterioscler. Thromb. Vasc. Biol. 14*(1): 133-140, Jan. 1994.

Nickoloff et al., "Severe Combined Immunodeficiency Mouse and Human Psoriatic Skin Chimeras. Validation of a New Animal Model," *American Journal of Pathology 146*(3): 580-588, Mar. 1995.

Peesapati and Venkata, "Synthesis and antimicrobial activity of new triazolo / tetrazolo-pyridazine [6,7] benzocycloheptenes," *Indian Journal of Chemistry 41B*: 839-844, Apr. 2002.

Phadke et al., "Evaluation of the Effects of Various Anti-Arthritic Drugs on Type II Collagen-Induced Mouse Arthritis Model," *Immunopharmacology 10*: 51-60, 1985.

Reiter and Pongó, "On Triazoles. VI [1]. The Acylation of 5-Amino-1,2,4-triazoles," *J. Heterocyclic Chem. 24*: 127-142, Jan.-Feb. 1987.

Sarayba et al , "Inhibition of corneal neovascularization by a peroxisome proliferator-activated receptor-γ ligand," *Experimental Eye Research 80*: 435-442, 2005.

Sheets et al., "Cataract- and Lens-Specific Upregulation of ARK Receptor Tyrosine Kinase in Emory Mouse Cataract," *Investigative Ophthalmology & Visual Science 43*(6): 1870-1875, Jun. 2002.

Smith et al., "Oxygen-Induced Retinopathy in the Mouse," *Investigative Ophthalmology & Visual Science 35*(1): 101-111, Jan. 1994.

Somigliana et al., "Endometrial ability to implant in ectopic sites can be prevented by interleukin-12 in a murine model of endometriosis," *Human Reproduction 14*(12): 2944-2950, 1999.

Von Der Thüsen et al., "Adenoviral Transfer of Endothelial Nitric Oxide Synthase Attenuates Lesion Formation in a Novel Murine Model of Postangioplasty Restenosis," *Arterioscler. Thromb. Vasc. Biol. 24*: 357-362, Feb. 2004.

Wronski et al., "Endocrine and Pharmacological Suppressors of Bone Turnover Protect against Osteopenia in Ovariectomized Rats," *Endocrinology 125*(2): 810-816, 1989.

Xu et al., "Requirement for the tyrosine kinase Axl in angiogenesis and tumor growth," *Proc. Amer. Assoc. Cancer Res. 46*, 2005. Tumor Biology 14: Signaling and Angiogenesis; Abstract #2019 of observations disclosed at American Association Cancer Research General Meeting, Apr. 16-20, 2005, Anaheim, California, 1 page.

Yin et al., "Expression of growth arrest-specific gene 6 and its receptors in a rat model of chronic renal transplant rejection," *Transplantation 73*(4): 657-660, Feb. 27, 2002.

Auclair et al., "Clues from the MMRC Genomics Initiative about the multiple myeloma druggable genome," Abstract #4130 disclosed at American Association Cancer Research Meeting, Apr. 12-16, 2008, San Diego, California, 2 pages.

Berclaz et al., "Estrogen dependent expression of the receptor tyrosine kinase axl in normal and malignant human breast," *Annals of Oncology 12*: 819-824, 2001.

Chung et al., "Expression of the proto-oncogene Axl in renal cell carcinoma," *DNA Cell Biol. 22*(8): 533-540, Aug. 2003 (abstract only).

Fernebro et al., "Gene expression profiles relate to SS18/SSX fusion type in synovial sarcoma," *Int. J. Cancer 118*: 1165-1172, 2006.

Green et al., "Overexpression of the Axl tyrosine kinase receptor in cutaneous SCC-derived cell lines and tumours," *British Journal of Cancer 94*(10): 1446-1451, 2006.

Holland et al., "R428, a Selective Small Molecule Inhibitor of Axl Kinase, Blocks Tumor Spread and Prolongs Survival in Models of Metastatic Breast Cancer," *Cancer Res 70*(4): 1544-1554, Feb. 15, 2010.

Hutterer et al., "Axl and Growth Arrest-Specific Gene 6 Are Frequently Overexpressed in Human Gliomas and Predict Poor Prognosis in Patients with Glioblastoma Multiforme," *Clin. Cancer Res 14*(1): 130-138, Jan. 1, 2008.

Ito et al., "Expression of Receptor-Type Tyrosine Kinase, Axl, and its Ligand, Gas6, in Pediatric Thyroid Carcinomas Around Chernobyl," *Thyroid 12*(11): 971-975, 2002.

Rochlitz et al., "Axl expression is associated with adverse prognosis and with expression of Bcl-2 and CD34 in *de novo* acute myeloid leukemia (AML): results from a multicenter trial of the Swiss Group for Clinical Cancer Research (SAKK)," *Leukemia 13*: 1352-1358, 1999.

Shieh et al., "Expression of Axl in Lung Adenocarcinoma and Correlation with Tumor Progression," *Neoplasia 7*(12): 1058-1064, Dec. 2005.

Sun et al., "Clinical implications of coexpression of growth arrest-specific gene 6 and receptor tyrosine kinases Axl and Sky in human uterine leiomyoma," *Molecular Human Reproduction 9*(11): 701-707, 2003.

Sun et al., "Coexpression of growth arrest-specific gene 6 and receptor tyrosine kinases Axl and Sky in human uterine endometrial cancers," *Annals of Oncology 14*: 898-906, 2003.

Sun et al., "Coexpression of Gas6/Axl in Human Ovarian Cancers," *Oncology 66*: 450-457, 2004.

Zhang et al., "AXL Is a Potential Target for Therapeuetic Intervention in Breast Cancer Progression," *Cancer Research 68*(6): 1905-1915, Mar. 13, 2008.

\* cited by examiner

POLYCYCLIC HETEROARYL SUBSTITUTED TRIAZOLES USEFUL AS AXL INHIBITORS

CROSS-REFERENCE TO RELATED APPLICATIONS

This application is a continuation application of U.S. patent application Ser. No. 12/986,951, filed Jan. 7, 2011 (now allowed); which is a continuation of U.S. patent application Ser. No. 12/720,448, filed Mar. 9, 2010 ; which application is a divisional application of U.S. patent application Ser. No. 11/967,172, filed Dec. 29, 2007 (now U.S. Pat. No. 7,709,482, issued on May 4, 2010); which applications claim the benefit under 35 U.S.C. §119(e) of U.S. Provisional Patent Application No. 60/970,931, filed Sep. 7, 2007, U.S. Provisional Patent Application No. 60/895,400, filed Mar. 16, 2007, and U.S. Provisional Patent Application No. 60/882, 850, filed Dec. 29, 2006. These applications are incorporated herein by reference in their entireties.

FIELD OF THE INVENTION

This invention is directed to polycyclic heteroaryl substituted triazoles and pharmaceutical compositions thereof which are useful as inhibitors of the receptor protein tyrosine kinase known as Axl. This invention is also directed to methods of using the compounds and compositions in treating diseases and conditions associated with Axl activity, particularly in treating diseases and conditions associated with angiogenesis and/or cell proliferation.

BACKGROUND OF THE INVENTION

All of the protein kinases that have been identified to date in the human genome share a highly conserved catalytic domain of around 300 aa. This domain folds into a bi-lobed structure in which reside ATP-binding and catalytic sites. The complexity of protein kinase regulation allows many potential mechanisms of inhibition including competition with activating ligands, modulation of positive and negative regulators, interference with protein dimerization, and allosteric or competitive inhibition at the substrate or ATP binding sites.

Axl (also known as UFO, ARK, and Tyro7; nucleotide accession numbers NM_021913 and NM_001699; protein accession numbers NP_068713 and NP_001690) is a receptor protein tyrosine kinase (RTK) that comprises a C-terminal extracellular ligand-binding domain and N-terminal cytoplasmic region containing the catalytic domain. The extracellular domain of Axl has a unique structure that juxtaposes immunoglobulin and fibronectin Type III repeats and is reminiscent of the structure of neural cell adhesion molecules. Axl and its two close relatives, Mer/Nyk and Sky (Tyro3/Rse/Dtk), collectively known as the Tyro3 family of RTK's, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

Axl is predominantly expressed in the vasculature in both endothelial cells (EC's) and vascular smooth muscle cells (VSMC's) and in cells of the myeloid lineage and is also detected in breast epithelial cells, chondrocytes, Sertoli cells and neurons. Several functions including protection from apoptosis induced by serum starvation, TNF-α or the viral protein E1A, as well as migration and cell differentiation have been ascribed to Axl signaling in cell culture. However, Axl-/- mice exhibit no overt developmental phenotype and the physiological function of Axl in vivo is not clearly established in the literature.

Angiogenesis (the formation of new blood vessels) is limited to functions such as wound healing and the female reproductive cycle in healthy adults. This physiological process has been co-opted by tumors, thus securing an adequate blood supply that feeds tumor growth and facilitates metastasis. Deregulated angiogenesis also a feature of many other diseases (for example, psoriasis, rheumatoid arthritis, endometriosis and blindness due to age-related macular degeneration (AMD), retinopathy of prematurity and diabetes) and often contributes to the progression or pathology of the condition.

The overexpression of Axl and/or its ligand has also been reported in a wide variety of solid tumor types including, but not limited to, breast, renal, endometrial, ovarian, thyroid, non-small cell lung carcinoma, and uveal melanoma as well as in myeloid leukemia's. Furthermore, it possesses transforming activity in NIH3T3 and 32D cells. It has been demonstrated that loss of Axl expression in tumor cells blocks the growth of solid human neoplasms in an in vivo MDA-MB-231 breast carcinoma xenograft model. Taken together, these data suggest Axl signaling can independently regulate EC angiogenesis and tumor growth and thus represents a novel target class for tumor therapeutic development.

The expression of Axl and Gas6 proteins is upregulated in a variety of other disease states including endometriosis, vascular injury and kidney disease and Axl signaling is functionally implicated in the latter two indications. Axl-Gas6 signaling amplifies platelet responses and is implicated in thrombus formation. Axl may thus potentially represent a therapeutic target for a number of diverse pathological conditions including solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoporosis, osteoarthritis and cataracts.

SUMMARY OF THE INVENTION

This invention is directed to certain polycyclic heteroaryl substituted triazoles which are useful as Axl inhibitors, methods of using such compounds in treating diseases and conditions associated with Axl activity and pharmaceutical compositions comprising such compounds.

Accordingly, in one aspect this invention is directed to a compound of formula (I):

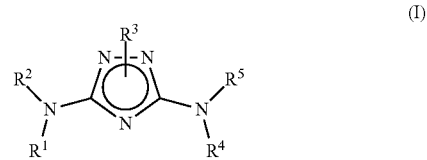

wherein:

$R^1$, $R^4$ and $R^5$ are each independently selected from the group consisting of hydrogen, alkyl, aryl, aralkyl, —C(O)$R^8$, —C(O)N($R^6$)$R^7$, and —C(=N$R^6$)N($R^6$)$R^7$;

$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—O$R^8$, —$R^9$—O—$R^{10}$—O$R^8$, —$R^9$—O—$R^{10}$—O—$R^{10}$—O$R^8$, —$R^9$—O—$R^{10}$—CN, —$R^9$—O—$R^{10}$—C(O)O$R^8$, —$R^9$—O—$R^{10}$—C(O)N($R^6$)$R^7$, —$R^9$—O—$R^{10}$—S(O)$_p R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N($R^6$)C(O)O$R^8$, —$R^9$—N($R^6$)C(O)$R^8$, —$R^9$—N($R^6$)S(O)$_t R^8$ (where t is 1 or 2), —$R^9$—S(O)$_t R^8$ (where t is 1 or 2), —$R^9$—S(O)$_p R^8$ (where p is 0, 1 or 2), and —$R^9$—S(O)$_t$N($R^6$)$R^7$ (where t is 1 or 2);

or $R^2$ is a polycyclic heteroaryl containing more than 14 ring atoms as described above and $R^3$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$), —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t R^{12}$ (where t is 1 or 2), —$R^{13}$—S(O)$_t$O$R^{12}$ (where t is 1 or 2), —$R^{13}$—S(O)$_p R^{12}$ (where p is 0, 1 or 2), and —$R^{13}$—S(O)$_t$N($R^{12}$)$_2$ (where t is 1 or 2);

or $R^3$ is a polycyclic heteroaryl containing more than 14 ring atoms as described above, and $R^2$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)O$R^{12}$, $R^{13}$—C(O)O$R^{12}$, —$R^{13}$—C(O)N($R^{12}$)$_2$, —$R^{13}$—CO)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t R^{12}$ (where t is 1 or 2), —$R^{13}$—S(O)$_t$O$R^{12}$ (where t is 1 or 2), —$R^{13}$—S(O)$_p R^{12}$ (where p is 0, 1 or 2), and —$R^{13}$—S(O)$_t$N($R^{12}$)$_2$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—O$R^8$, —$R^{10}$—CN, —$R^{10}$—NO$_2$, —$R^{10}$—N($R^8$)$_2$, —$R^{10}$—C(O)O$R^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and —O$R^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12's}$, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain;

as an isolated stereoisomer or mixture thereof or as a tautomer or mixture thereof, or a pharmaceutically acceptable salt or N-oxide thereof.

In another aspect, this invention is directed to pharmaceutical compositions comprising a pharmaceutically acceptable excipient and a compound of formula (I), as described above, as an isolated stereoisomer or mixture thereof or as a tautomer or mixture thereof, or a pharmaceutically acceptable salt or N-oxide thereof.

In another aspect, this invention is directed to methods of treating a disease or condition associated with Axl activity in a mammal, wherein the methods comprise administering to the mammal a therapeutically effective amount of a compound of formula (I), as described above, as an isolated stereoisomer or mixture thereof or as a tautomer or mixture thereof, or a pharmaceutically acceptable salt or N-oxide thereof, or a therapeutically effective amount of a pharmaceutical composition comprising a pharmaceutically acceptable excipient and a compound of formula (I), as described above, as an isolated stereoisomer or mixture thereof or as a tautomer or mixture thereof, or a pharmaceutically acceptable salt or N-oxide thereof.

In another aspect, this invention provides assays to determine a compound of the invention effectiveness in inhibiting Axl activity in a cell-based assay.

In another aspect, this invention is directed to processes for preparing an aryl-fused cycloheptanone or a heteroaryl-fused cycloheptanone of formula (I):

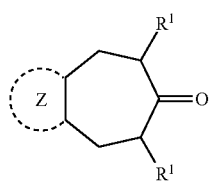

(i)

wherein Z is an aryl or a heteroaryl and each $R^1$ is independently selected from the group consisting of hydrogen, optionally substituted alkyl, optionally substituted aralkyl, and optionally substituted heteroarylalkyl;

wherein the process comprises:

a) combining a reactant of formula (II):

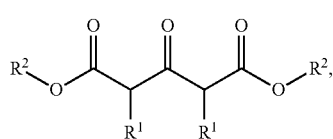

(ii)

wherein each $R^2$ is independently selected from the group consisting of optionally substituted alkyl, optionally substituted aralkyl, and optionally substituted heteroarylalkyl, with a reactant of formula (iii):

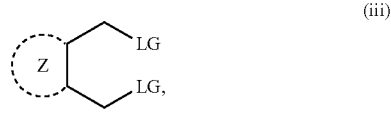

(iii)

wherein Z is the aryl or the heteroaryl, as defined above, and each LG is independently a suitable leaving group, in the presence of a protic solvent, an aprotic solvent, and a base to form a product; and b) subjecting the product of step a) to a basic hydrolytic media followed by acid to form the aryl-fused cycloheptanone or a heteroaryl-fused cycloheptanone of formula (I).

DETAILED DESCRIPTION OF THE INVENTION

Definitions

As used in the specification and appended claims, unless specified to the contrary, the following terms have the meaning indicated:

"Amino" refers to the —$NH_2$ radical.
"Carboxy" refers to the —C(O)OH radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms ("lower alkyl"), and which is attached to the rest of the molecule by a single bond, for example, methyl, ethyl, n-propyl, 1-methylethyl(iso-propyl), n-butyl, n-pentyl, 1,1-dimethylethyl (t-butyl), 3-methylhexyl, 2-methylhexyl, and the like. Unless stated otherwise specifically in the specification, an alkyl radical may be optionally substituted by one or more of the following substituents: halo, cyano, nitro, oxo, thioxo, trimethylsilanyl, —$OR^{20}$, —OC(O)—$R^{20}$, —$N(R^{20})_2$, —C(O)$R^{20}$, —C(O)$R^{20}$, —C(O)N($R^{20})_2$, —N($R^{20}$)C(O)O$R^{20}$, —N($R^{20}$)C(O)$R^{20}$, —N($R^{20}$)S(O)$_t R^{20}$ (where t is 1 or 2), —S(O)$_t$O$R^{20}$ (where t is 1 or 2), —S(O)$_p R^{20}$ (where p is 0, 1 or 2), and —S(O)$_t$N($R^{20})_2$ (where t is 1 or 2) where each $R^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkenyl" refers to a straight or branched hydrocarbon chain radical consisting solely of carbon and hydrogen atoms, containing at least one double bond, having from two to twelve carbon atoms, preferably one to eight carbon atoms and which is attached to the rest of the molecule by a single bond, for example, ethenyl, prop-1-enyl, but-1-enyl, pent-1-enyl, penta-1,4-dienyl, and the like. Unless stated otherwise specifically in the specification, an alkenyl radical may be optionally substituted by one or more of the following substituents: halo, cyano, nitro, oxo, thioxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —N($R^{20}$)C(O)O$R^{20}$, —N($R^{20}$)C(O)$R^{20}$, —N($R^{20}$)S(O)$_t R^{20}$ (where t is 1 or 2), —S(O)$_t$O$R^{20}$ (where t is 1 or 2), —S(O)$_p$ $R^{20}$ (Where p is 0, 1 or 2), and —S(O)$_t$N($R^{20})_2$ (where t is 1 or 2) where each $R^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkynyl" refers to a straight or branched hydrocarbon chain radical consisting solely of carbon and hydrogen atoms, containing at least one triple bond, optionally containing at least one double bond, having from two to twelve carbon atoms, preferably one to eight carbon atoms and which is attached to the rest of the molecule by a single bond, for example, ethynyl, propynyl, butynyl, pentynyl, hexynyl, and the like. Unless stated otherwise specifically in the specification, an alkynyl radical may be optionally substituted by one or more of the following substituents: halo, cyano, nitro, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_t$R$^{20}$ (where t is 1 or 2), —S(O)$_t$OR$^{20}$ (where t is 1 or 2), —S(O)$_p$R$^{20}$ (where p is 0, 1 or 2), and —S(O)$_t$N(R$^{20}$)$_2$ (where t is 1 or 2) where each R$^{20}$ is independently hydrogen, alkyl, haloalkyl, cycloalkyl, cycloalkylalkyl, aralkyl, heterocyclyl, heterocylylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain may be optionally substituted by one or more of the following substituents: halo, cyano, nitro, aryl, cycloalkyl, heterocyclyl, heteroaryl, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_t$R$^{20}$ (where t is 1 or 2), —S(O)$_t$OR$^{20}$ (where t is 1 or 2), —S(O)$_p$R$^{20}$ (where p is 0, 1 or 2), and —S(O)$_t$N(R$^{20}$)$_2$ (where t is 1 or 2) where each R$^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one or more of the following substituents: halo, cyano, nitro, aryl, cycloalkyl, heterocyclyl, heteroaryl, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_t$R$^{20}$ (where t is 1 or 2), —S(O)$_t$OR$^{20}$ (where t is 1 or 2), —S(O)$_p$R$^{20}$ (where p is 0, 1 or 2), and —S(O)$_t$N(R$^{20}$)$_2$ (where t is 1 or 2) where each R$^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one or more of the following substituents: alkyl, alkenyl, halo, haloalkenyl, cyano, nitro, aryl, cycloalkyl, heterocyclyl, heteroaryl, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_t$R$^{20}$ (where t is 1 or 2), —S(O)$_t$OR$^{20}$ (where t is 1 or 2), —S(O)$_p$R$^{20}$ (where p is 0, 1 or 2), and —S(O)$_t$N(R$^{20}$)$_2$ (where t is 1 or 2) where each R$^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkoxy" refers to a radical of the formula —OR$_a$ where R$_a$ is an alkyl radical as defined above containing one to twelve carbon atoms. The alkyl part of the alkoxy radical may be optionally substituted as defined above for an alkyl radical.

"Alkoxyalkyl" refers to a radical of the formula —R$_b$—O—R$_a$ where R$_a$ is an alkyl radical as defined above and R$_b$ is an alkylene chain as defined above. The oxygen atom may be bonded to any carbon in the alkyl radical or the alkylene chain. The alkyl part of the alkoxyalkyl radical may be optionally substituted as defined above for an alkyl radical and the alkylene chain part of the alkoxyalkyl radical may be optionally substituted as defined above for an alkylene chain.

"Aryl" refers to a hydrocarbon ring system radical comprising hydrogen, 6 to 14 carbon atoms and at least one aromatic ring. For purposes of this invention, the aryl radical may be a monocyclic, bicyclic, or tricyclic system and which may include spiro ring systems. An aryl radical is commonly, but not necessarily, attached to the parent molecule via an aromatic ring of the aryl radical. For purposes of this invention, an "aryl" radical as defined herein can not contain rings having more than 7 members and cannot contain rings wherein two non-adjacent ring atoms thereof are connected through an atom or a group of atoms (i.e., a bridged ring system). Aryl radicals include, but are not limited to, aryl radicals derived from acenaphthylene, anthracene, azulene, benzene, 6,7,8,9-tetrahydro-5H-benzo[7]annulene, fluorene, as-indacene, s-indacene, indane, indene, naphthalene, phenalene, and phenanthrene. Unless stated otherwise specifically in the specification, the term "optionally substituted aryl" is meant to include aryl radicals optionally substituted by one or more substituents independently selected from the group consisting of alkyl, alkenyl, alkynyl, halo, haloalkyl, haloalkenyl, haloalkynyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—O—R$^{22}$—C(O)N(R$^{20}$)$_2$, —R$^{21}$—N(R$^{20}$)C(O)OR$^{20}$, —R$^{21}$—N(R$^{20}$)C(O)R$^{20}$, —R$^{21}$—N(R$^{20}$)S(O)$_t$R$^{20}$ (where t is 1 or 2), —R$^{21}$—S(O)$_t$OR$^{20}$ (where t is 1 or 2), —R$^{21}$—S(O)$_p$R$^{20}$ (where p is 0, 1 or 2), and —R$^{21}$—S(O)$_t$N (R$^{20}$)$_2$ (where t is 1 or 2), where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20'}$$^s$, together with the common nitrogen to which they are both attached, may optionally form an optionally substituted N-heterocyclyl or an optionally substituted N-heteroaryl, each R$^{21}$ is independently a direct bond or a straight or branched alkylene or alkenylene chain, and R$^{22}$ is a straight or branched alkylene or alkenylene chain.

"Aralkyl" refers to a radical of the formula —R$_b$-R$_c$ where R$_b$ is an alkylene chain as defined above and R$_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl.

"Aralkenyl" refers to a radical of the formula —R$_d$—R$_c$ where R$_d$ is an alkenylene chain as defined above and R$_c$ is one or more aryl radicals as defined above. The aryl part of the aralkenyl radical may be optionally substituted as described above for an aryl. The alkenylene chain part of the aralkenyl radical may be optionally substituted as defined above for an alkenylene group.

"Aralkynyl" refers to a radical of the formula —R$_e$R$_c$ where R$_e$ is an alkynylene chain as defined above and R$_c$ is one or more aryl radicals as defined above. The aryl part of the aralkynyl radical may be optionally substituted as described above for an aryl. The alkynylene chain part of the aralkynyl radical may be optionally substituted as defined above for an alkynylene chain.

"Aryloxy" refers to a radical of the formula —OR$_c$ where R$_c$ is an aryl as defined above. The aryl part of the aryloxy radical may be optionally substituted as defined above.

"Aralkyloxy" refers to a radical of the formula —OR$_f$ where R$_f$ is an aralkyl radical as defined above. The aralkyl part of the aralkyloxy radical may be optionally substituted as defined above.

"Cycloalkyl" refers to a stable non-aromatic monocyclic or polycyclic hydrocarbon radical consisting solely of carbon and hydrogen atoms, which may include spiro or bridged ring systems, having from three to fifteen carbon atoms, preferably having from three to ten carbon atoms, more preferably from five to seven carbons and which is saturated or unsaturated and attached to the rest of the molecule by a single bond. For purposes of this invention, a bridged ring system is a system wherein two non-adjacent ring atoms thereof are connected through an atom or a group of atoms. Monocyclic cycloalkyl radicals include non-bridged cycloalkyl radicals, for example, cyclopropyl, cyclobutyl, cyclopentyl, cyclohexyl, cycloheptyl, and cyclooctyl. Polycyclic radicals include fused, spiro or bridged cycloalkyl radicals, for example, O$_{10}$ radicals such as adamantanyl (bridged) and decalinyl (fused), and O$_7$ radicals such as bicyclo[3.2.0]heptanyl (fused), norbornanyl and norbornenyl (bridged), as well as substituted polycyclic radicals, for example, substituted C$_7$ radicals such as 7,7-dimethylbicyclo[2.2.1]heptanyl (bridged), and the like. Unless otherwise stated specifically in the specification, the term "optionally substituted cycloalkyl" is meant to include cycloalkyl radicals which are optionally substituted by one or more substituents independently selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{20}$, —R$^{21}$—N(R$^{20}$)C(O)R$^{20}$, —R$^{21}$—N(R$^{20}$)S(O)$_t$R$^{20}$ (where t is 1 or 2), —R$^{21}$—S(O)$_t$OR$^{20}$ (where t is 1 or 2), —R$^{21}$—S(O)$_p$R$^{20}$ (where p is 0, 1 or 2), and —R$^{21}$—S(O)$_t$N(R$^{20}$)$_2$ (where t is 1 or 2), where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20}$'s, together with the common nitrogen to which they are both attached, may optionally form an optionally substituted N-heterocyclyl or an optionally substituted N-heteroaryl, and each R$^{21}$ is independently a direct bond or a straight or branched alkylene or alkenylene chain.

"Cycloalkylalkyl" refers to a radical of the formula —R$_b$R$_g$ where R$_b$ is an alkylene chain as defined above and R$_g$ is a cycloalkyl radical as defined above. The alkylene chain and the cycloalkyl radical may be optionally substituted as defined above.

"Cycloalkylalkenyl" refers to a radical of the formula —R$_e$R$_g$ where R$_e$ is an alkenylene chain as defined above and R$_g$ is a cycloalkyl radical as defined above. The alkenylene chain and the cycloalkyl radical may be optionally substituted as defined above.

"Cycloalkylalkynyl" refers to a radical of the formula —R$_e$R$_g$ where R$_e$ is an alkynylene radical as defined above and R$_g$ is a cycloalkyl radical as defined above. The alkynylene chain and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl radical.

"Haloalkoxy" refers to an alkoxy radical, as defined above, that is substituted by one or more halo radicals, as defined above, for example, trifluoromethoxy, difluoromethoxy, trichloromethoxy, 2,2,2-trifluoroethoxy, and the like. The alkoxy part of the haloalkoxy radical may be optionally substituted as defined above for an alkoxy radical.

"Haloalkenyl" refers to an alkenyl radical, as defined above, that is substituted by one or more halo radicals, as defined above. The alkenyl part of the haloalkyl radical may be optionally substituted as defined above for an alkenyl radical.

"Haloalkynyl" refers to an alkynyl radical, as defined above, that is substituted by one or more halo radicals, as defined above. The alkynyl part of the haloalkyl radical may be optionally substituted as defined above for an alkynyl radical.

"Heterocyclyl" refers to a stable 3- to 18-membered non-aromatic ring radical which comprises one to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, 1,4-diazepanyl, decahydroisoquinolyl, imidazolinyl, imidazolidinyl, isothiazolidinyl, isoxazolidinyl, morpholinyl, octahydroindolyl, octahydroisoindolyl, octahydro-1H-pyrrolo[3,2-c]pyridinyl, octahydro-1H-pyrrolo[2,3-c]pyridinyl, octahydro-1H-pyrrolo[2,3-b]pyridinyl, octahydro-1H-pyrrolo[3,4-b]pyridinyl, octahydropyrrolo[3,4-c]pyrrolyl, octahydro-1H-pyrido[1,2-a]pyrazinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuranyl, thienyl[1,3] dithianyl, trithianyl, tetrahydropyranyl, thiomorpholinyl, thiamorpholinyl, 1-oxo-thiomorpholinyl, 1,1-dioxo-thiomorpholinyl, azetidinyl, octahydropyrrolo[3,4-c]pyrrolyl, octahydropyrrolo[3,4-b]pyrrolyl, decahydroprazino[1,2-a]azepinyl, azepanyl, azabicyclo[3.2.1]octyl, and 2,7-diazaspiro[4.4]nonanyl. Unless stated otherwise specifically in the specification, the term "optionally substituted heterocyclyl" is meant to include heterocyclyl radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{21}$—$OR^{20}$, $-R^{21}$—$OC(O)$—$R^{20}$, $-R^{21}$—$N(R^{20})_2$, $-R^{21}$—$C(O)R^{20}$, $-R^{21}$—$C(O)OR^{20}$, $-R^{21}$—$C(O)N(R^{20})_2$, $-R^{21}$—$N(R^{20})C(O)OR^{20}$, $R^{21}$—$N(R^{20})C(O)R^{20}$, $-R^{21}$—$N(R^{20})S(O)_tR^{20}$ (where t is 1 or 2), $-R^{21}$—$S(O)_tOR^{20}$ (where t is 1 or 2), $-R^{21}$—$S(O)_pR^{20}$ (where p is 0, 1 or 2), and $-R^{21}$—$S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, and each $R^{21}$ is independently a direct bond or a straight or branched alkylene or alkenylene chain.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula —$R_dR_h$ where $R_d$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkyene chain. The heterocyclyl part of the heterocyclylalkyl radical may be optionally substituted as defined above for a heterocyclyl radical.

"Heterocyclylalkenyl" refers to a radical of the formula —$R_dR_h$ where $R_d$ is an alkenylene chain as defined above and $R_h$ is a heterocyclyl radical as defined above, and if the heterocyclyl is a nitrogen-containing heterocyclyl, the heterocyclyl may be attached to the alkenylene chain at the nitrogen atom. The alkenylene chain of the heterocyclylalkenyl radical may be optionally substituted as defined above for an alkenylene chain. The heterocyclyl part of the heterocyclylalkenyl radical may be optionally substituted as defined above for a heterocyclyl radical.

"Heterocyclylalkynyl" refers to a radical of the formula —$R_eR_h$ where $R_e$ is an alkynylene chain as defined above and $R_h$ is a heterocyclyl radical as defined above, and if the heterocyclyl is a nitrogen-containing heterocyclyl, the heterocyclyl may be attached to the alkynyl radical at the nitrogen atom. The alkynylene chain part of the heterocyclylalkynyl radical may be optionally substituted as defined above for an alkynylene chain. The heterocyclyl part of the heterocyclylalkynyl radical may be optionally substituted as defined above for a heterocyclyl radical.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. A heteroaryl radical is commonly, but not necessarily, attached to the parent molecule via an aromatic ring of the heteroaryl radical. For purposes of this invention, the heteroaryl radical may be a monocyclic, bicyclic or tricyclic ring system, which may include spiro ring systems; and the nitrogen, carbon or sulfur atoms in the heteroaryl radical may be optionally oxidized; the nitrogen atom may be optionally quaternized. For purposes of this invention, the aromatic ring of the heteroaryl radical need not contain a heteroatom, as long as one ring of the heteroaryl radical contains a heteroatom. For example, 1,2,3,4-tetrahydroisoquinolin-7-yl is considered a "heteroaryl" for the purposes of this invention. Except for the polycyclic heteroaryls containing more than 14 ring atoms, as described above in the Summary of the Invention, a "heteroaryl" radical as defined herein can not contain rings having more than 7 members and cannot contain rings wherein two non-adjacent members thereof are connected through an atom or a group of atoms (i.e., a bridged ring system). Examples of heteroaryl radicals include, but are not limited to, azepinyl, acridinyl, benzimidazolyl, benzindolyl, 1,3-benzodioxolyl, benzofuranyl, benzooxazolyl, benzothiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 1,2,3,4,5,6-hexahydrobenzo[d]azocin-8-yl, isothiazolyl, imidazolyl, indazolyl, indolyl, indazolyl, isoindolyl, indolinyl, isoindolinyl, isoquinolyl, indolizinyl, isoxazolyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, 5,6,7,8-tetrahydroquinazolinyl, 2,3,4,5-tetrahydrobenzo[b]oxepin-7-yl, 3,4-dihydro-2H-benzo[b][1,4]dioxepin-7-yl, 6,7,8,9-tetrahydro-5H-cyclohepta[b]pyridinyl, 6,7,8,9-tetrahydro-5H-pyrido[3,2-c]azepinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, 1,2,3,4-tetrahydroisoquinolin-7-yl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "optionally substituted heteroaryl" is meant to include heteroaryl radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{20}$, —R$^{21}$—N(R$^{20}$)C(O)R$^{20}$, R$^{21}$—N(R$^{20}$)S(O)$_t$R$^{20}$ (where t is 1 or 2), —R$^{21}$—S(O)$_t$OR$^{20}$ (where t is 1 or 2), —R$^{21}$—S(O)$_p$R$^{20}$ (where p is 0, 1 or 2), and —R$^{21}$—S(O)$_t$N(R$^{20}$)$_2$ (where t is 1 or 2), where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20}$'s, together with the common nitrogen to which they are both attached, may optionally form an optionally substituted N-heterocyclyl or an optionally substituted N-heteroaryl, and each R$^{21}$ is independently a direct bond or a straight or branched alkylene or alkenylene chain. "Polycyclic heteroaryl containing more than 14 ring atoms" refers to a 15- to 20-membered ring system radical comprising hydrogen atoms, one to fourteen carbon atoms, one to eight heteroatoms selected from the group consisting of nitrogen, oxygen and sulfur, and at least one aromatic ring. A "polycyclic heteroaryl containing more than 14 ring atoms" radical is commonly, but not necessarily, attached to the parent molecule via an aromatic ring of the "polycyclic heteroaryl containing more than 14 ring atoms" radical. For purposes of this invention, the "polycyclic heteroaryl containing more than 14 ring atoms" radical may be a bicyclic, tricyclic or tetracyclic ring system, which may include fused or spiro ring systems; and the nitrogen, carbon or sulfur atoms in the "polycyclic heteroaryl containing more than 14 ring atoms" radical may be optionally oxidized and the nitrogen atom may also be optionally quaternized. For purposes of this invention, the aromatic ring of the "polycyclic heteroaryl containing more than 14 ring atoms" radical need not contain a heteroatom, as long as one ring of the "polycyclic heteroaryl containing more than 14 ring atoms" radical contains a heteroatom. Examples of "polycyclic heteroaryl containing more than 14 ring atoms" radicals include, but are not limited to, 6,7-dihydro-5H-benzo[6,7]cyclohepta[1,2-c]pyridazin-3-yl, 6,7,8,9-tetrahydro-5H-cyclohepta[4,5]thieno[2,3-c]pyrimidin-4-yl, 6,7-dihydro-5H-benzo[6,7]cyclohepta[1,2-c]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]-dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl. Unless stated otherwise specifically in the specification, the term "optionally substituted polycyclic heteroaryl containing more than 14 ring atoms" is meant to include "polycyclic heteroaryl containing more than 14 ring atoms" radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, C(O)OR$^{20}$, R$^{21}$—C(O)N(R$^{20}$)$_2$, —R$^{21}$—N(R$^{20}$)C(O)OR$^{20}$, —R$^{21}$—N(R$^{20}$)C(O)R$^{20}$, —R$^{21}$—N(R$^{20}$)S(O)$_t$R$^{20}$ (where t is 1 or 2), —R$^{21}$—S(O)$_t$OR$^{20}$ (where t is 1 or 2), —R$^{21}$—S(O)$_p$R$^{20}$ (where p is 0, 1 or 2), and —R$^{21}$—S(O)$_t$N(R$^{20}$)$_2$ (where t is 1 or 2), where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20}$'s, together with the common nitrogen to which they are both attached, may optionally form an optionally substituted N-heterocyclyl or an optionally substituted N-heteroaryl, and each R$^{21}$ is independently a direct bond or a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Polycyclic heteroaryls containing more than 14 ring atoms" refers to a 15- to 20-membered ring system radical comprising hydrogen atoms, one to fourteen carbon atoms, one to eight heteroatoms selected from the group consisting of nitrogen, oxygen and sulfur, and at least one aromatic ring. A "polycyclic heteroaryls containing more than 14 ring atoms" radical is commonly, but not necessarily, attached to the parent molecule via an aromatic ring of the "polycyclic heteroaryls containing more than 14 ring atoms" radical. For purposes of this invention, the "polycyclic heteroaryls containing more than 14 ring atoms" radical may be a monocyclic, bicyclic, tricyclic or tetracyclic ring system, which may include fused ring systems; and the nitrogen, carbon or sulfur atoms in the "polycyclic heteroaryls containing more than 14 ring atoms" radical may be optionally oxidized; the nitrogen atom may be optionally quaternized. For purposes of this invention, the aromatic ring of the "polycyclic heteroaryls containing more than 14 ring atoms" radical need not contain a heteroatom, as long as one ring of the "polycyclic heteroaryls containing more than 14 ring atoms" radical contains a heteroatom. Examples of "polycyclic heteroaryls containing more than 14 ring atoms" radicals include, but are not limited to, 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl. Unless stated otherwise specifically in the specification, the term "optionally substituted polycyclic heteroaryls containing more than 14 ring atoms" is meant to include "polycyclic heteroaryls containing more than 14 ring atoms" radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{21}-OR^{20}$, $-R^{21}-OC(O)-R^{20}$, $R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{20}$, $-R^{21}-N(R^{20})C(O)R^{20}$, $-R^{21}-N(R^{20})S(O)_tR^{20}$ (where t is 1 or 2), $-R^{21}-S(O)_tOR^{20}$ (where t is 1 or 2), $-R^{21}-S(O)_pR^{20}$ (where p is 0, 1 or 2), and $-R^{21}-S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, and each $R^{21}$ is independently a direct bond or a straight or branched alkylene or alkenylene chain.

"Heteroarylalkyl" refers to a radical of the formula $-R_bR_i$ where $R_b$ is an alkylene chain as defined above and $R_i$ is a heteroaryl radical as defined above. The heteroaryl part of the heteroarylalkyl radical may be optionally substituted as defined above for a heteroaryl. The alkylene chain part of the heteroarylalkyl radical may be optionally substituted as defined above for an alkylene chain.

"Heteroarylalkenyl" refers to a radical of the formula $-R_dR_i$ where $R_d$ is an alkenylene chain as defined above and $R_i$ is a heteroaryl radical as defined above. The heteroaryl part of the heteroarylalkenyl radical may be optionally substituted as defined above for a heteroaryl. The alkenylene chain part of the heteroarylalkenyl radical may be optionally substituted as defined above for an alkenylene chain.

"Heteroarylalkynyl" refers to a radical of the formula $-R_eR_i$ where $R_e$ is an alkynylene chain as defined above and $R_i$ is a heteroaryl radical as defined above. The heteroaryl part of the heteroarylalkynyl radical may be optionally substituted as defined above for a heteroaryl. The alkynylene chain part of the heteroarylalkynyl radical may be optionally substituted as defined above for an alkynylene chain.

"Hydroxyalkyl" refers to an alkyl radical as defined above which is substituted by one or more hydroxy radicals (—OH).

"Hydroxyalkenyl" refers to an alkenyl radical as defined above which is substituted by one or more hydroxy radicals (—OH).

"Hydroxyalkenyl" refers to an alkynyl radical as defined above which is substituted by one or more hydroxy radicals (—OH).

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substitutents on the functional group are also "optionally substituted" and so on, for the purposes of this invention, such iterations are limited to five.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

"Atropisomers" are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers, for example in cases of limited rotation around the single bonds emanating from the core triazole structure, atropisomers are also possible and are also specifically included in the compounds of the invention.

The chemical naming protocol and structure diagrams used herein are a modified form of the I.U.P.A.C. nomenclature system wherein the compounds of the invention are named herein as derivatives of the central core structure, i.e., the triazole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

For purposes of this invention, the depiction of the bond attaching the R³ substituent to the parent triazole moiety in formula (I), as shown below:

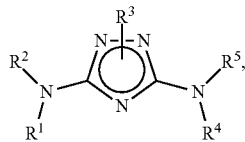

is intended to include only the two regioisomers shown below, i.e., compounds of formula (Ia) and (Ib):

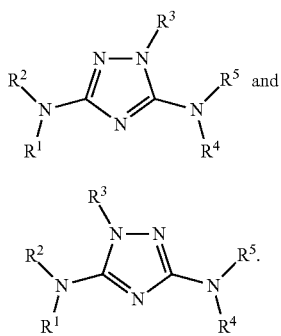

The numbering system of the ring atoms in compounds of formula (Ia) is shown below:

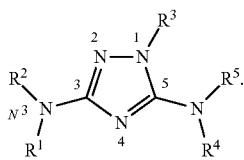

For example, a compound of formula (Ia) wherein R¹, R⁴ and R⁵ are each hydrogen, R² is 4-(2-(pyrrolidin-1-yl)ethoxy) phenyl and R³ is 6,7-dihydro-5H-benzo[6,7]cyclohepta[1,2-c]pyridazin-3-yl; i.e., a compound of the following formula:

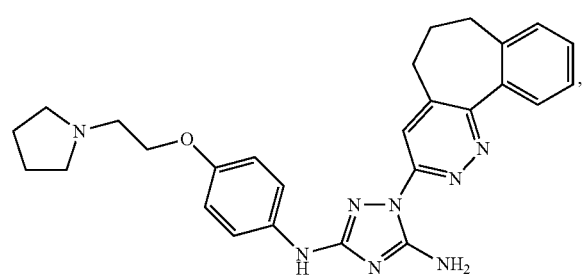 [SMILES: Nc1nc(Nc2ccc(OCCN3CCCC3)cc2)nn1-c1cc2c(nn1)-c1ccccc1CCC2]

is named herein as 1-(6,7-dihydro-5H-benzo[6,7]cyclohepta [1,2-c]pyridazin-3-yl)-N³-(4-(2-(pyrrolidin-1-yl)ethoxy) phenyl)-1H-1,2,4-triazole-3,5-diamine.

The numbering system of the ring atoms in compounds of formula (Ib) is shown below:

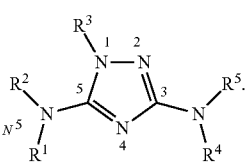

Compounds of formula (Ib) are similarly named herein.

Embodiments of the Invention

Of the various aspects of the compounds of formula (I), as set forth above in the Summary of the Invention, certain embodiments are preferred.

Accordingly, one embodiment of the compounds of formula (I), as set forth above in the Summary of the Invention, is wherein the compound of formula (I) is a compound of formula (Ia):

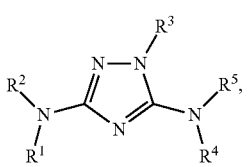

wherein:

R¹, R⁴ and R⁵ are each independently selected from the group consisting of hydrogen, alkyl, aryl, aralkyl, —C(O)R⁸, —C(O)N(R⁶)R⁷, and —C(=NR⁶)N(R⁶)R⁷;

R² and R³ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R⁹—OR⁸, —R⁹—O—R¹⁰—OR⁸, —R⁹—O—R¹⁰—OR⁸, —R⁹—O—R¹⁰—CN, —R⁹—O—R¹⁰—C(O)OR⁸, —R⁹—O—R¹⁰—C(O)N(R⁶)R⁷, —R⁹—O—R¹⁰—S(O)$_p$R⁸ (where p is 0, 1 or 2), —R⁹—O—R¹⁰—N(R⁶)R⁷, R⁹—O—R¹⁰—C(NR¹¹)N (R¹¹)H, —R⁹—OC(O)—R⁸, —R⁹—N(R⁶)R⁷, —R⁹—C (O)R⁸, —R⁹—C(O)OR⁸, —R⁹—C(O)N(R⁶)R⁷, —R⁹—N (R⁶)C(O)OR¹², —R⁹—N(R⁶)C(O)R⁸, —R⁹—N(R⁶)S (O)$_t$R⁸ (where t is 1 or 2), —R⁹—S(O)$_t$OR⁸ (where t is 1 or 2), —R⁹—S(O)$_p$R⁸ (where p is 0, 1 or 2), and —R⁹—S(O)$_t$ N(R⁶)R⁷ (where t is 1 or 2);

or R² is a polycyclic heteroaryl containing more than 14 ring atoms as described above and R³ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)OR$^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—$OR^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t R^{12}$ (where t is 1 or 2), —$R^{13}$—S(O)$_t$ $OR^{12}$ (where t is 1 or 2), —$R^{13}$—S(O)$_p R^{12}$ (where p is 0, 1 or 2), and —$R^{13}$—S(O)$_t$N($R^{12}$)$_2$ (where t is 1 or 2);

or $R^3$ is a polycyclic heteroaryl containing more than 14 ring atoms as described above, and $R^2$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)OR$^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—O(O)N($R^{12}$)—$R^{14}$—$OR^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t R^{12}$ (where t is 1 or 2), —$R^{13}$—S(O)$_t$ $OR^{12}$ (where t is 1 or 2), —$R^{13}$—S(O)$_p R^{12}$ (where p is 0, 1 or 2), and —$R^{13}$—S(O)$_t$N($R^{12}$)$_2$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—$OR^8$, —$R^{10}$—CN, —$R^{10}$—NO$_2$, —$R^{10}$—N($R^8$)$_2$, —$R^{10}$—C(O)O$R^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and —$OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12's}$, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain.

Another embodiment is a compound of formula (Ia), as described above, wherein:

$R^1$, $R^4$ and $R^5$ are each independently selected from the group consisting of hydrogen, alkyl, aryl, aralkyl, —C(O)$R^8$, —C(O)N($R^6$)$R^7$, and —C(=N$R^6$)N($R^6$)$R^7$;

$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—CN, —$R^9$—O—$R^{10}$—C(O)O$R^8$, —$R^9$—O—$R^{10}$—C(O)N($R^6$)$R^7$, —$R^6$—O—$R^{10}$—S(O)$_p R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N($R^6$)C(O)O$R^{12}$, —$R^9$—N($R^6$)C(O)$R^8$, —$R^9$—N($R^6$)S(O)$_t R^6$ (where t is 1 or 2), —$R^9$—S(O)$_t$O$R^8$ (where t is 1 or 2), —W—S(O)$_p R^6$ (where p is 0, 1 or 2), and —$R^9$—S(O)$_t$N($R^6$)$R^7$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—C(O)$N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain; and each $R^{11}$ is independently selected from the group consisting of hydrogen, alkyl, cyano, nitro and —$OR^8$.

Another embodiment is a compound of formula (Ia), as described above, wherein:

$R^1$, $R^4$ and $R^5$ are each hydrogen;

$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—CN, —$R^9$—O—$R^{10}$—$C(O)OR^8$, —$R^9$—O—$R^{10}$—$C(O)N(R^6)R^7$, —$R^9$—O—$R^{10}$—$S(O)_pR^8$ (where p is 0, 1 or 2), —$R^9$—O—$R^{10}$—$N(R^6)R^7$, —$R^9$—O—$R^{10}$—$C(NR^{11})N(R^{11})H$, —$R^9$—$OC(O)$—$R^8$, —$R^9$—$N(R)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—$C(O)OR^6$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain; and each $R^{11}$ is independently selected from the group consisting of hydrogen, alkyl, cyano, nitro and —$OR^8$.

Another embodiment is a compound of formula (Ia), as described above, wherein:

$R^1$, $R^4$ and $R^5$ are each hydrogen;

$R^2$ and $R^3$ are each independently a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—$OC(O)$—$R^9$, —$R^9$—$N(R^6)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^9$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2)

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain; and each $R^{11}$ is independently selected from the group consisting of hydrogen, alkyl, cyano, nitro and —$OR^8$.

Another embodiment is a compound of formula (Ia), as described above, which is 1-(6,7-dihydro-5H-benzo[6,7]cyclohepta[1,2-c]pyridazin-3-yl)-$N^3$-(5',5'-dimethyl-6,8,9,10-tetrahydro-5H-spiro[cycloocta[b]pyridine-7,2'-[1,3]dioxane]-3-yl)-1H-1,2,4-triazole-3,5-diamine.

Another embodiment is a compound of formula (Ia), as described above, wherein:

$R^1$, $R^4$ and $R^5$ are each independently selected from the group consisting of hydrogen, alkyl, aryl, aralkyl, —C(O)$R^8$, —C(O)N($R^6$)$R^7$, and —C(N$R^6$)N($R^6$)$R^7$;

$R^2$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—CN, —$R^9$—O—$R^{10}$—C(O)$OR^8$, —$R^9$—O—$R^{10}$—C(O)N($R^6$)$R^7$, —$R^9$—O—$R^{10}$—S(O)$_p$$R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)$OR^8$, —$R^9$—C(O)N($R^6$)$R^7$, —$R^9$—N($R^6$)C(O)$OR^{12}$, —$R^9$—N($R^6$)C(O)$R^8$, —$R^9$—N($R^6$)S(O)$_t$$R^8$ (where t is 1 or 2), —$R^9$—S(O)$_t$$OR^8$ (where t is 1 or 2), —$R^9$—S(O)$_p$$R^8$ (where p is 0, 1 or 2), and —$R^9$—S(O)$_t$N($R^6$)$R^7$ (where t is 1 or 2);

$R^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—$OR^{12}$, —$R^{13}$—N($R^{12}$)C(O)OR$^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—S(O)$_t$$OR^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—$OR^8$, —$R^{10}$—CN, —$R^{10}$—$NO_2$, —$R^{10}$—N($R^8$)$_2$, —$R^{10}$—C(O)$OR^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and —$OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain.

Another embodiment is a compound of formula (Ia), as described above, wherein:

$R^1$, $R^4$ and $R^5$ are each hydrogen;

$R^2$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—CN, —$R^9$—O—$R^{10}$—C(O)$OR^8$, —$R^9$—O—$R^{10}$—C(O)N($R^6$)$R^7$, —$R^9$—O—$R^{10}$—S(O)$_p$$R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—O(O)$R^8$, —$R^9$—C(O)$OR^8$, —$R^9$—C(O)N($R^6$)$R^7$, —$R^9$—N($R^6$)C(O)$OR^{12}$, —$R^9$—N($R^6$)C(O)$R^8$, —$R^9$—N($R^6$)S(O)$_t$$R^8$ (where t is 1 or 2), —$R^9$—S(O)$_t$$OR^5$ (where t is 1 or 2), —$R^9$—S(O)$_p$$R^8$ (where p is 0, 1 or 2), and —$R^9$—S(O)$_t$N($R^6$)$R^7$ (where t is 1 or 2);

$R^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)$OR^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—$OR^{12}$, —$R^{13}$—N($R^{12}$)C(O)$OR^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—S(O)$_t$$OR^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, $R^{10}$—CN, —$R^{10}$—$NO_2$, —$R^{10}$—N($R^8$)$_2$, —$R^{10}$—C(O)$OR^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{11}$ is independently selected from the group consisting of hydrogen, alkyl, cyano, nitro and —$OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, wherein:

$R^1$, $R^4$ and $R^5$ are each hydrogen;

$R^2$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—N($R^6$)$R^7$, —$R^9$—C(O)$R^8$, —$R^9$—C(O)$OR^8$, —$R^9$—C(O)N($R^6$)$R^7$, —$R^9$—N($R^6$)C(O)$OR^{12}$, —$R^9$—N($R^6$)C(O)$R^8$, —$R^9$—N($R^6$)S(O)$_t$$R^8$ (where t is 1 or 2), —$R^9$—S(O)$_t$$OR^8$ (where t is 1 or 2), —$R^9$—S(O)$_p$$R^8$ (where p is 0, 1 or 2), and —$R^9$—S(O)$_t$N($R^6$)$R^7$ (where t is 1 or 2);

$R^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{13}-OR^{12}$, $-R^{13}-OC(O)-R^{12}$, $-R^{13}-O-R^{14}-N(R^{12})_2$, $-R^{13}-N(R^{12})-R^{14}-N(R^{12})_2$, $-R^{13}-N(R^{12})_2$, $-R^{13}-C(O)R^{12}$, $-R^{13}-C(O)OR^{12}$, $-R^{13}-C(O)N(R^{12})_2$, $-R^{13}-C(O)N(R^{12})-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^{13}-S(O)_tN(R^{12})_2$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, wherein:

$R^1$, $R^4$ and $R^6$ are each hydrogen;

$R^2$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^6)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2);

$R^3$ is heteroaryl selected from the group consisting of pyridinyl, pyrimidinyl, 4,5-dihydro-1H-benzo[b]azepin-2(3H)-on-8-yl, benzo[d]imidazolyl, 6,7,8,9-tetrahydro-5H-pyrido[3,2-c]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, and 6,7,8,9-tetrahydro-5H-cyclohepta[b]pyridin-3-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally $R^{13}-O-R^{14}-N(R^{12})_2$, substituted heteroarylalkenyl, $-R^{13}-OR^{12}$, $-R^{13}-OC(O)-R^{12}$, $-R^{13}-O-R^{14}-N(R^{12})_2$, $-R^{13}-N(R^{12})_2$, $-R^{13}-C(O)R^{12}$, $-R^{13}-C(O)OR^{12}$, $-R^{13}-C(O)N(R^{12})_2$, $-R^{13}-C(O)N(R^{12})-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^{13}-S(O)_tN(R^{12})_2$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^{10}-OR^8$, $R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bondand an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, which is selected from the group consisting of:

1-(6,7-dimethoxy-quinazolin-4-yl)-$N^3$-(5,7,8,9-tetrahydrospiro[cyclohepta[b]pyridine-6,2'-[1,3]dioxolane]-3-yl)-1H-1,2,4-triazole-3,5-diamine;

1-(2-chloro-7-methylthieno[3,2-d]pyrimidin-4-yl)-$N^3$-(5,7,8,9-tetrahydrospiro[cyclohepta[b]pyridine-6,2'-[1,3]dioxolane]-3-yl)-1H-1,2,4-triazole-3,5-diamine;

1-(2-chloro-7-methylthieno[3,2-d]pyrimidin-4-yl)-$N^3$-(5,6,8,9-tetrahydrospiro[cyclohepta[b]pyridine-7,2'-[1,3]dioxolane]-3-yl)-1H-1,2,4-triazole-3,5-diamine; and 1-(2-chloro-7-methylthieno[3,2-d]pyrimidin-4-yl)-$N^3$-(5',5'-dimethyl-6,8,9,10-9tetrahydro-5H-spiro[cycloocta[b]pyridine-7,2'-[1,3]dioxane]-3-yl)-1H-1,2,4-triazole-3,5-diamine.

Another embodiment is a compound of formula (Ia), as described above, wherein:

$R^1$, $R^4$ and $R^5$ are each independently selected from the group consisting of hydrogen, alkyl, aryl, aralkyl, —C(O)$R^8$, —C(O)N($R^6$)$R^7$, and —C(N$R^{11}$)N($R^6$)$R^7$;

$R^2$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$R^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

$R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—O$R^8$, —$R^9$—O—$R^{10}$—O$R^8$, —$R^9$—O—$R^{10}$—O—$R^{10}$—O$R^8$, —$R^9$—O—$R^{10}$—CN, —$R^9$—O—$R^{10}$—C(O)O$R^8$, —$R^9$—O—$R^{10}$—C(O)N($R^6$)$R^7$, —$R^9$—O—$R^{10}$—S(O)$_p$$R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N($R^6$)C(O)O$R^{12}$, —$R^9$—N($R^6$)C(O)$R^8$, —$R^9$—N($R^6$)S(O)$R^8$ (where t is 1 or 2), —$R^9$—S(O)$_t$O$R^8$ (where t is 1 or 2), —$R^9$—S(O)$_p$$R^8$ (where p is 0, 1 or 2), and —$R^9$—S(O)$_t$N($R^6$)$R^7$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—O$R^8$, —$R^{10}$—CN, —$R^{10}$—NO$_2$, —$R^{10}$—N($R^8$)$_2$, —$R^{10}$—C(O)O$R^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and —$OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain.

Another embodiment is a compound of formula (Ia), as described above, wherein:

$R^1$, $R^4$ and $R^5$ are each independently hydrogen;

$R^2$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—$OC(O)$—$R^{12}$, —$R^{13}$—$O$—$R^{14}$—$N(R^{12})_2$, —$R^{13}$—$N(R^{12})$—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2);

$R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—$O$—$R^{10}$—$OR^8$, —$R^9$—$O$—$R^{10}$—$O$—$R^{10}$—$OR^8$, —$R^9$—$O$—$R^{10}$—$CN$, —$R^9$—$O$—$R^{10}$—$C(O)OR^8$, —$R^9$—$O$—$R^{10}$—$C(O)N(R^6)R^7$, —$R^9$—$O$—$R^{10}$—$S(O)_pR^8$ (where p is 0, 1 or 2), —$R^9$—$O$—$R^{10}$—$N(R^6)R^7$, —$R^9$—$O$—$R^{10}$—$C(NR^{11})N(R^{11})H$, —$R^9$—$OC(O)$—$R^8$, —$R^9$—$N(R^6)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—$CN$, —$R^{10}$—$NO_2$, —$R^{10}$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{11}$ is independently selected from the group consisting of hydrogen, alkyl, cyano, nitro and —$OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, wherein:

$R^1$, $R^4$ and $R^5$ are each independently hydrogen;

$R^2$ is aryl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—$OC(O)$—$R^{12}$, —$R^{13}$—$O$—$R^{14}$—$N(R^{12})_2$, —$R^{13}$—$N(R^{12})$—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)$ OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)$_t$OR$^{12}$ (where t is 1 or 2), —R$^{13}$—S(O)$_p$R$^{12}$ (where p is 0, 1 or 2), and —R$^{13}$—S(O)$_t$N(R$^{12}$)$_2$ (where t is 1 or 2);

R$^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—O—R$^{10}$—OR$^8$, —R$^9$—O—R$^{10}$—O—R$^{10}$—OR$^8$, —R$^9$—O—R$^{10}$—CN, —R$^9$—O—R$^{10}$—C(O)OR$^8$, —R$^9$—O—R$^{10}$—C(O)N(R$^6$)R$^7$, —R$^9$—O—R$^{10}$—S(O)$_p$R$^8$ (where p is 0, 1 or 2), —R$^9$—O—R$^{10}$—N(R$^6$)R$^7$, —R$^9$—O—R$^{10}$—C(NR$^{11}$)N(R$^{11}$)H, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^{12}$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2);

each R$^6$ and R$^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^9$)$_2$, —R$^{10}$—C(O)OR$^8$ and —R$^{10}$—C(O)N(R$^8$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each R$^9$ is independently selected from the group consisting of a direct bond and an optionally substituted straight or branched alkylene chain;

each R$^{10}$ is an optionally substituted straight or branched alkylene chain;

each R$^{11}$ is independently selected from the group consisting of hydrogen, alkyl, cyano, nitro and —OR$^8$;

each R$^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{12}$'s, together with the common nitrogen to which they are both attached, form an optionally substituted N-heterocyclyl or an optionally substituted N-heteroaryl;

each R$^{13}$ is independently selected from the group consisting of a direct bond and an optionally substituted straight or branched alkylene chain; and each R$^{14}$ is an optionally substituted straight or branched alkylene chain.

Another embodiment is a compound of formula (Ia), as described above, wherein:

R$^1$, R$^4$ and R$^5$ are each independently hydrogen;

R$^2$ is aryl selected from the group consisting of phenyl and 6,7,8,9-tetrahydro-5H-benzo[7]annulene-2-yl, each optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)—R$^{14}$—N(R$^{12}$)$_2$, —R$^{13}$—N(R$^{12}$)$_2$, —R$^{13}$—C(O)R$^{12}$, R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)$_t$OR$^{12}$ (where t is 1 or 2), —R$^{13}$—S(O)$_p$R$^{12}$ (where p is 0, 1 or 2), and —R$^{13}$—S(O)$_t$N(R$^{12}$)$_2$ (where t is 1 or 2);

R$^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7, 2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^{12}$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2);

each R$^6$ and R$^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N (R$^8$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each R$^9$ is independently selected from the group consisting of a direct bond and an optionally substituted straight or branched alkylene chain;

each R$^{10}$ is an optionally substituted straight or branched alkylene chain;

each R$^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{12's}$, together with the common nitrogen to which they are both attached, form an optionally substituted N-heterocyclyl or an optionally substituted N-heteroaryl;

each R$^{13}$ is independently selected from the group consisting of a direct bond and an optionally substituted straight or branched alkylene chain; and each R$^{14}$ is an optionally substituted straight or branched alkylene chain.

Another embodiment is a compound of formula (Ia), as described above, wherein:

R$^1$, R$^4$ and R$^5$ are each independently hydrogen;

R$^2$ is phenyl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)—R$^{14}$—N(R$^{12}$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{14}$—OR$^{12}$, —R$^{13}$—N(R$^{12}$)C(O) OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)$_t$OR$^{12}$ (where t is 1 or 2), —R$^{13}$—S(O)$_p$R$^{12}$ (where p is 0, 1 or 2), and —R$^{13}$—S(O)$_t$ N(R$^{12}$)$_2$ (where t is 1 or 2);

R$^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-c] pyrimidin-4-yl, 6,7-dihydro-5H-benzo[2,3]azepino[4,5-c] pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7, 2'-[1,3]dioxolane]-3-yl, 5,6,8,9-tetrahydrospiro[benzo[7] annulene-7,2'-[1,3]dioxolane]-3-yl, 5,7,8,9-tetrahydrospiro[cyclohepta[b]pyridine-6,2'-[1,3] dioxolane]-3-yl, 6,7-dihydro-5H-benzo[2,3]thiepino[4,5-c]pyridazin-3-yl, 6,7-dihydro-5H-benzo[6,7]cyclohepta [1,2-d]pyrimidin-2-yl, 5,6,8,9-tetrahydrospiro[cyclohepta [b]pyridine-7,2'-[1,3]dioxolane]-3-yl, 6,8,9,10-tetrahydro-5H-spiro[cycloocta[b]pyridine-7,2'-[1,3] dioxane]-3-yl and 6,7-dihydro-5H-benzo[6,7]cyclohepta [1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^{12}$, —R$^9$—N (R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2);

each R$^6$ and R$^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N (R$^8$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each R$^9$ is independently selected from the group consisting of a direct bond and an optionally substituted straight or branched alkylene chain;

each R$^{10}$ is an optionally substituted straight or branched alkylene chain;

each R$^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{12's}$, together with the common nitrogen to which they are both attached, form an optionally substituted N-heterocyclyl or an optionally substituted N-heteroaryl;

each R$^{13}$ is independently selected from the group consisting of a direct bond and an optionally substituted straight or branched alkylene chain; and each R$^{14}$ is an optionally substituted straight or branched alkylene chain.

Another embodiment is a compound of formula (Ia), as described above, wherein:

R$^1$, R$^4$ and R$^5$ are each independently hydrogen;

R$^2$ is phenyl optionally substituted by one or more substitutents selected from the group consisting of alkyl, halo, haloalkyl, cyano, and optionally substituted heterocyclyl where the optionally substituted heterocyclyl is selected from the group consisting of piperidinyl, piperazinyl, pyrrolidinyl, azepanyl, decahydropyrazino[1,2-a]azepinyl, octahydropyrrolo[3,4-c]pyrrolyl, azabicyclo[3.2.1]octyl, octahydropyrrolo[3,4-b]pyrrolyl, octahydropyrrolo[3,2-c]pyridinyl, 2,7-diazaspiro[4.4]nonanyl and azetidinyl; each independently optionally substituted by one or two substituents selected from the group consisting of —$R^9$—$OR^8$, —$R^9$—$N(R^6)R^7$, —$R^9$—$C(O)OR^6$, —$R^9$—$C(O)N(R^6)R^7$, —$R^9$—$N(R^6)C(O)R^7$, —$R^9$—$N(R^6)C(O)OR^7$, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

$R^3$ is selected from the group consisting of 6,7-dihydro-5H-benzo[6,7]cyclohepta[1,2-c]pyridazin-3-yl, 6,7-dihydro-5H-benzo[2,3]thiepino[4,5-c]pyridazin-3-yl, 6,7-dihydro-5H-benzo[6,7]cyclohepta[1,2-b]pyridin-2-yl, spiro[chromeno[4,3-c]pyridazine-5,1'-cyclopentane]-3-yl and 6,7-dihydro-5H-benzo[6,7]cyclohepta[4,5-c]pyridazin-3-yl, each optionally substituted by one or more substituents selected from the group consisting of alkyl, aryl, halo and —$R^9$—$OR^8$.

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—$C(O)N(R^6)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and each $R^9$ is independently selected from the group consisting of a direct bond and an optionally substituted straight or branched alkylene chain.

Another embodiment is a compound of formula (Ia), as described above, selected from the group consisting of:

$N^3$-(4-(4-cyclohexanylpiperazin-1-yl)phenyl)-1-(6,7-dihydro-5H-benzo[6,7]cyclohepta[1,2-c]pyridazin-3-yl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-(pyrrolidin-1-yl)piperidin-1-yl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-methyl-3-phenylpiperazin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-(4-(4-piperidin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-(indolin-2-on-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-(morpholin-4-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(4-(4-cyclopentyl-2-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(4-(3,5-dimethylpiperazin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(4-(4-(pyrrolidin-1-yl)piperidin-1-yl)-3-cyanophenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(3-(diethylamino)pyrrolidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(4-(4-(bicyclo[2.2.1]heptan-2-yl)piperazin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(4-(4-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-(diethylamino)piperidin-1-yl)phenyl)-1H-1,2,4-triazole-3,5-diamine;

1-(6,7-dihydro-5H-9-methoxybenzo[6,7]cyclohepta[1,2-c]pyridazin-3-yl)-$N^3$-(3-fluoro-4-(4-(pyrrolidin-1-yl)piperidin-1-yl)phenyl)-1H-1,2,4-triazole-3,5-diamine;

1-(6,7-dihydro-5H-10-fluorobenzo[6,7]cyclohepta[1,2-c]pyridazin-3-yl)-$N^3$-(3-fluoro-4-(4-(pyrrolidin-1-yl)piperidin-1-yl)phenyl)-1H-1,2,4-triazole-3,5-diamine;

1-(6,7-dihydro-5H-10-fluorobenzo[6,7]cyclohepta[1,2-c]pyridazin-3-yl)-$N^3$-(3-fluoro-4-(4-(cyclohexyl)piperazin-1-yl)phenyl)-1H-1,2,4-triazole-3,5-diamine;

1-(6,7-dihydro-5H-9-methoxybenzo[6,7]cyclohepta[1,2-c]pyridazin-3-yl)-$N^3$-(3-fluoro-4-(4-(cyclohexyl)piperazin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-(4-methylpiperazin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-(4-methylpiperidin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-dimethylaminopiperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-chloro-4-(4-pyrrolidin-1-yl-piperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-trifluoromethyl-4-(4-pyrrolidin-1-yl-piperidin-1-yl)phenyl)-1H-1,2,4-triazole-3,5-diamine;

1-(6,7-dihydro-5H-9,10-dimethoxybenzo[6,7]cyclohepta[1,2-c]pyridazin-3-yl)-$N^3$-(3-fluoro-4-(4-pyrrolidin-1-yl-piperidin-1-yl)phenyl)-1H-1,2,4-triazole-3,5-diamine;

1-(6,7-dihydro-5H-9,10,11-trimethoxybenzo[6,7]cyclohepta[1,2-c]pyridazin-3-yl)-$N^3$-(3-fluoro-4-(4-pyrrolidin-1-yl-piperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(5-methyloctahydropyrrolo[3,4-c]pyrrolyl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(3-pyrrolidin-1-yl-piperidin-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(3-pyrrolidin-1-yl-azepan-1-yl)phenyl)-1H-1,2,4-triazole-3,5-diamine;

1-(6,7-dihydro-5H-benzo[6,7]cyclohepta[1,2-c]pyridazin-3-yl)-$N^3$-(3-fluoro-4-(4-N-methylpiperidin-4-yl-piperidin-1-yl)phenyl)-1H-1,2,4-triazole-3,5-diamine;
1-(6,7-dihydro-5H-benzo[6,7]cyclohepta[4,5-c]pyridazin-2-yl)-$N^3$-(3-fluoro-4-(4-(pyrrolidinyl)piperidinyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(5-propyloctahydropyrrolo[3,4-c]pyrrolyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(decahydropyrazino[1,2-a]azepin-2-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(5-cyclopentyloctahydropyrrolo[3,4-c]pyrrolyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(3-(pyrrolidin-1-yl)-8-azabicyclo[3.2.1]oct-8-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-pyrrolidin-1-yl-azepan-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(4-methylpiperazin-1-yl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(4-isopropylpiperazin-1-yl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(1-methyloctahydropyrrolo[3,4-b]pyrrol-5-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(N-methylcyclopentylamino)piperidinyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(dipropylamino)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(1-propyloctahydro-1H-pyrrolo[3,2-c]pyridine-5-yl)phenyl)-1H-1,2,4-triazole-3,5-diamine;
1-(6,7-dihydro-5H-benzo[6,7]cyclohepta[4,5-c]pyridazin-2-yl)-$N^3$-(3-fluoro-4-(4-(N-methylpiperazin-1-yl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(tert-butyloxycarbonylamino)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-aminopiperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(5-cyclohexyloctahydropyrrolo[3,4-c]pyrrolyl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(4-(methylpiperidin-4-yl)phenyl)-1H-1,2,4-triazole-3,5-diamine;
1-(6,7-dihydro-5H-benzo[6,7]cyclohepta[1,2-c]pyridazin-3-yl)-$N^3$-(4-(4-pyrrolidin-1-ylpiperidinyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-pyrrolidin-1-ylpiperidinyl)phenyl)-1H-1,2,4-triazole-3,5-diamine;
1-(6,7-dihydro-5H-benzo[6,7]cyclohepta[1,2-c]pyridazin-3-yl)-$N^3$-(3-methyl-4-(4-pyrrolidin-1-ylpiperidinyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-cyclopentylpiperazinyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-N-methylpiperidin-4-ylpiperazinyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(7-methyl-2,7-diazaspiro[4.4]nonan-2-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(N-isopropylpiperazin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(3-pyrrolidin-1-ylazetidinyl)phenyl)-1H-1,2,4-triazole-3,5-diamine;
1-(6,7-dihydro-5H-benzo[6,7]cyclohepta[1,2-c]pyridazin-3-yl)-$N^3$-(3-methyl-4-(4-(N-methylpiperazin-4-yl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-((S)-3-(pyrrolidin-1-ylmethyl)pyrrolidinyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(pyrrolidinylmethyl)piperidinyl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-((4aR,8aS)-decahydroisoquinolin-2-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(octahydro-1H-pyrido[1,2-a]pyrazin-2-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-(4-(3-pyrrolidin-1-yl)pyrrolidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(5-methyloctahydropyrrolo[3,4-c]pyrrolyl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(octahydropyrrolo[3,4-c]pyrrolyl)phenyl)-1H-1,2,4-triazole-3,5-diamine;
1-(6,7-dihydro-9-chloro-5H-benzo[6,7]cyclohepta[1,2-c]pyridazin-3-yl)-$N^3$-(3-fluoro-4-(4-pyrrolidin-1-ylpiperidin-1-yl)phenyl)-1H-1,2,4-triazole-3,5-diamine;
1-(6,7-dihydro-9-chloro-5H-benzo[6,7]cyclohepta[1,2-c]pyridazin-3-yl)-$N^3$-(3-fluoro-4-(4-(N-methylpiperazin-1-yl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(4-iodophenyl)-1H-1,2,4-triazole-3,5-diamine;
1-(spiro[chromeno[4,3-c]pyridazine-5,1'-cyclopentane]-3-yl)-$N^3$-(3-fluoro-4-(4-(4-methylpiperazin-1-yl)piperidin-1-yl)phenyl)-1H-1,2,4-triazole-3,5-diamine;
1-(spiro[chromeno[4,3-c]pyridazine-5,1'-cyclopentane]-3-yl)-$N^3$-(3-fluoro-4-(4-(pyrrolidin-1-yl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-pyrrolidin-1-ylpiperidin-1-yl)phenyl)-1H-1,2,4-triazole-3,5-diamine;
1-(6,7-dihydro-5H-benzo[6,7]cyclohepta[4,5-c]pyridazin-2-yl)-$N^3$-(3-fluoro-4-(4-pyrrolidin-1-ylpiperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(4-(4-methylpiperazin-1-yl)piperidin-1-yl)phenyl)-1H-1,2,4-triazole-3,5-diamine;
1-(6,7-dihydro-5H-benzo[6,7]cyclohepta[1,2-c]pyridazin-3-yl)-$N^3$-(3-fluoro-4-(3-(3R)-dimethylaminopyrrolidin-1-yl)phenyl)-1H-1,2,4-triazole-3,5-diamine;
1-(6,7-dihydro-5H-benzo[6,7]cyclohepta[4,5-c]pyridazin-2-yl)-$N^3$-(3-methyl-4-(4-pyrrolidin-1-ylpiperidin-1-yl)phenyl)-1H-1,2,4-triazole-3,5-diamine;

1-(6,7-dihydro-5H-benzo[6,7]cyclohepta[4,5-c]pyridazin-2-yl)-N³-(3-fluoro-4-(4-pyrrolidin-1-ylpiperidin-1-yl)phenyl)-1H-1,2,4-triazole-3,5-diamine;

1-(4-phenyl-6,7-dihydro-5H-benzo[6,7]cyclohepta[1,2-b]pyridin-2-yl)-N³-(3-fluoro-4-(4-cyclohexylpiperazin-1-yl)phenyl)-1H-1,2,4-triazole-3,5-diamine;

1-(4-phenyl-6,7-dihydro-5H-benzo[6,7]cyclohepta[1,2-b]pyridin-2-yl)-N³-(4-(4-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-N³-(4-(1-bicyclo[2.2.1]heptan-2-yl)-piperidin-4-yl)phenyl)-1H-1,2,4-triazole-3,5-diamine;

1-(6,7-dihydro-5H-benzo[6,7]cyclohepta[1,2-c]pyridazin-3-yl)-N³-(4-(1-cyclopropylmethylpiperidin-4-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-cyclopropylmethylpiperazin-1-yl)phenyl)-1H-1,2,4-triazole-3,5-diamine;

1-(6,7-dihydro-5H-benzo[2,3]thiepino[4,5-c]pyridazin-3-yl)-N³-(4-(1-bicyclo[2.2.1]heptan-2-yl)-piperidin-4-yl)phenyl)-1H-1,2,4-triazole-3,5-diamine; and 1-(4-phenyl-6,7-dihydro-5H-benzo[6,7]cyclohepta[1,2-b]pyridin-2-yl)-N³-(3-fluoro-4-(4-pyrrolidin-1-ylpiperidin-1-yl)phenyl)-1H-1,2,4-triazole-3,5-diamine.

Another embodiment is a compound of formula (Ia), as described above, wherein:

$R^1$, $R^4$ and $R^5$ are each independently hydrogen;

$R^2$ is phenyl optionally substituted by one or more substitutents selected from the group consisting of halo, alkyl, heterocyclylalkenyl, $—R^{13}—OR^{12}$, $—R^{13}—O—R^{14}—N(R^{12})_2$, $—R^{13}—N(R^{12})—R^{14}—N(R^{12})_2$, $—R^{13}—N(R^{12})_2$, $—R^{13}—C(O)R^{12}$, $—R^{13}—C(O)N(R^{12})_2$, and $—R^{13}—N(R^{12})C(O)R^{12}$;

$R^3$ is selected from the group consisting of 6,7-dihydro-5H-benzo[6,7]cyclohepta[1,2-c]pyridazin-3-yl and 6,7-dihydro-5H-benzo[6,7]cyclohepta[4,5-c]pyridazin-3-yl, each optionally substituted by one or more substituents selected from the group consisting of alkyl, aryl, halo and $—R^9—OR^8$.

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $—R^{10}—OR^8$, $—R^{10}—CN$, $—R^{10}—NO_2$, $—R^{10}—N(R^6)_2$, $—R^{10}—C(O)OR^8$ and $—R^{10}—C(O)N(R^6)_2$, or any $R^6$ and $R^7$, together with the common nitrogen to which they are both attached, form an optionally substituted N-heteroaryl or an optionally substituted N-heterocyclyl;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, selected from the group consisting of:

1-(6,7-Dihydro-5H-benzo[6,7]cyclohepta[1,2-c]pyridazin-3-yl)-N³-(4-(2-(pyrrolidin-1-yl)ethoxy)phenyl)-1H-1,2,4-triazole-3,5-diamine;

1-(6,7-dihydro-5H-benzo[6,7]cyclohepta[1,2-c]pyridazin-3-yl)-N³-(4-(4-(cyclopentyl)piperazin-1-ylcarbonyl)phenyl)-1H-1,2,4-triazole-3,5-diamine;

1-(6,7-dihydro-5H-benzo[6,7]cyclohepta[1,2-c]pyridazin-3-yl)-N³-(4-((2-pyrrolidin-1-ylethyl)aminocarbonyl)phenyl)-1H-1,2,4-triazole-3,5-diamine;

1-(6,7-dihydro-5H-benzo[6,7]cyclohepta[1,2-c]pyridazin-3-yl)-N³-(4-(2,2,6,6-tetramethylpiperidin-1-yl)ethoxyphenyl)-1H-1,2,4-triazole-3,5-diamine;

1-(6,7-dihydro-5H-benzo[6,7]cyclohepta[1,2-c]pyridazin-3-yl)-N³-(4-((2-(dimethylamino)ethyl)aminocarbonyl)phenyl)-1H-1,2,4-triazole-3,5-diamine;

1-(6,7-dihydro-5H-benzo[6,7]cyclohepta[1,2-c]pyridazin-3-yl)-N³-(4-((2-(methoxy)ethyl)aminocarbonyl)phenyl)-1H-1,2,4-triazole-3,5-diamine;

1-(6,7-dihydro-5H-benzo[6,7]cyclohepta[1,2-c]pyridazin-3-yl)-N³-(4-((2-(pyrrolidin-1-yl)ethyl)aminocarbonyl)phenyl)-1H-1,2,4-triazole-3,5-diamine;

1-(6,7-dihydro-5H-benzo[6,7]cyclohepta[1,2-c]pyridazin-3-yl)-N³-(4-((4-(pyrrolidin-1-yl)piperidin-1-yl)carbonyl)phenyl)-1H-1,2,4-triazole-3,5-diamine;

1-(6,7-dihydro-5H-benzo[6,7]cyclohepta[1,2-c]pyridazin-3-yl)-N³-(3-chloro-4-(2-(pyrrolidin-1-yl)ethoxy)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(2-(pyrrolidin-1-yl)ethoxy)phenyl)-1H-1,2,4-triazole-3,5-diamine;

1-(6,7-dihydro-5H-10-fluorobenzo[6,7]cyclohepta[1,2-c]pyridazin-3-yl)-N³-(3-fluoro-4-(2-(pyrrolidin-1-yl)ethoxy)phenyl)-1H-1,2,4-triazole-3,5-diamine;

1-(6,7-dihydro-5H-9-methoxybenzo[6,7]cyclohepta[1,2-c]pyridazin-3-yl)-N³-(3-fluoro-4-(2-(pyrrolidin-1-yl)ethoxy)phenyl)-1H-1,2,4-triazole-3,5-diamine;

1-(6,7-dihydro-5H-benzo[6,7]cyclohepta[1,2-c]pyridazin-3-yl)-N³-(4-(2-(N-methylcyclopentylamino)ethoxy)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(N-methylpiperidin-4-yl-N-methylamino)phenyl)-1H-1,2,4-triazole-3,5-diamine;

1-(6,7-dihydro-5H-benzo[6,7]cyclohepta[1,2-c]pyridazin-3-yl)-N³-(4-((N-butyl-N-acetoamino)methyl)phenyl)-1H-1,2,4-triazole-3,5-diamine;

1-(6,7-dihydro-5H-benzo[6,7]cyclohepta[1,2-c]pyridazin-3-yl)-N³-(4-(4-(4-methylpiperazin-1-yl)piperidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(4-(piperidin-1-yl)piperidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(piperidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(pyrrolidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(3-dimethylaminopyrrolidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N$^3$-(4-(3-diethylaminopyrrolidin-1-ylprop-1-enyl)phenyl)-1H-1,2,4-triazole-3,5-diamine;
1-(6,7-dihydro-5H-benzo[6,7]cyclohepta[1,2-c]pyridazin-3-yl)-N$^3$-(4-(4-pyrrolidin-1-ylpiperidin-1-ylprop-1-enyl)phenyl)-1H-1,2,4-triazole-3,5-diamine;
1-(6,7-dihydro-5H-benzo[6,7]cyclohepta[1,2-c]pyridazin-3-yl)-N$^3$-(4-(4-methylpiperazin-1-ylprop-1-enyl)phenyl)-1H-1,2,4-triazole-3,5-diamine;
1-(6,7-dihydro-5H-benzo[6,7]cyclohepta[1,2-c]pyridazin-3-yl)-N$^3$-(4-(4-isopropylpiperazin-1-ylprop-1-enyl)phenyl)-1H-1,2,4-triazole-3,5-diamine;
1-(6,7-dihydro-5H-benzo[6,7]cyclohepta[1,2-c]pyridazin-3-yl)-N$^3$-(4-(4-cyclopentylpiperazin-1-ylprop-1-enyl)phenyl)-1H-1,2,4-triazole-3,5-diamine;
1-(6,7-dihydro-5H-benzo[6,7]cyclohepta[1,2-c]pyridazin-3-yl)-N$^3$-(4-(morpholin-4-ylprop-1-enyl)phenyl)-1H-1,2,4-triazole-3,5-diamine; and
1-(6,7-dihydro-5H-benzo[6,7]cyclohepta[1,2-c]pyridazin-3-yl)-N$^3$-(4-(1-methylpiperidin-3-yl-oxy)phenyl)-1H-1,2,4-triazole-3,5-diamine.

Another embodiment is a compound of formula (Ia), as described above, wherein:
$R^1$, $R^4$ and $R^5$ are each independently hydrogen;
$R^2$ is phenyl optionally substituted by one or more substituents selected from the group consisting of alkyl, halo, haloalkyl, cyano, and optionally substituted heterocyclyl where the optionally substituted heterocyclyl is selected from the group consisting of piperidinyl, piperazinyl, pyrrolidinyl, azepanyl, decahydropyrazino[1,2-a]azepinyl, octahydropyrrolo[3,4-c]pyrrolyl, azabicyclo[3.2.1]octyl, octahydropyrrolo[3,4-b]pyrrolyl, octahydropyrrolo[3,2-c]pyridinyl, 2,7-diazaspiro[4.4]nonanyl and azetidinyl; each independently optionally substituted by one or two substituents selected from the group consisting of —R$^9$—OR$^8$, —R$^9$—N(R$^6$)R$^7$, —R$^9$—C(O)OR$^6$, —R$^9$—C(O)N(R$^6$)R$^7$, —R$^9$—N(R$^6$)C(O)R$^7$, —R$^9$—N(R$^6$)C(O)OR$^7$, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;
$R^3$ is selected from the group consisting of 6,7-dihydro-5H-benzo[6,7]cyclohepta[1,2-c]pyrimidin-4-yl and 6,7-dihydro-5H-benzo[6,7]cyclohepta[1,2-d]pyrimidin-2-yl, each optionally substituted by one or more substituents selected from the group consisting of alkyl, aryl, halo and —R$^9$—OR$^8$.
each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N(R$^8$)$_2$, or any R$^6$ and R$^7$, together with the common nitrogen to which they are both attached, form an optionally substituted N-heteroaryl or an optionally substituted N-heterocyclyl;
each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and
each $R^9$ is independently selected from the group consisting of a direct bond and an optionally substituted straight or branched alkylene chain.

Another embodiment is a compound of formula (Ia), as described above, selected from the group consisting of:
1-(6,7-dihydro-5H-benzo[6,7]cyclohepta[1,2-d]pyrimidin-4-yl)-N$^3$-(4-(4-(bicyclo[2.2.1]heptan-2-yl)piperazin-1-yl)phenyl)-1H-1,2,4-triazole-3,5-diamine;
1-(6,7-dihydro-5H-benzo[6,7]cyclohepta[1,2-d]pyrimidin-4-yl)-N$^3$-(3-fluoro-4-(4-(diethylamino)piperidin-1-yl)phenyl)-1H-1,2,4-triazole-3,5-diamine;
1-(6,7-dihydro-5H-benzo[6,7]cyclohepta[1,2-d]pyrimidin-2-yl)-N$^3$-(4-(N-methylpiperazin-1-yl)phenyl)-1H-1,2,4-triazole-3,5-diamine;
1-(6,7-dihydro-5H-benzo[6,7]cyclohepta[1,2-d]pyrimidin-2-yl)-N$^3$-(3-fluoro-4-(4-cyclohexylpiperazinyl)phenyl)-1H-1,2,4-triazole-3,5-diamine; and
1-(6,7-dihydro-5H-benzo[6,7]cyclohepta[1,2-d]pyrimidin-2-yl)-N$^3$-(4-(4-(2S)-bicyclo[2.2.1]heptan-2-yl)-piperazinylphenyl)-1H-1,2,4-triazole-3,5-diamine.

Another embodiment is a compound of formula (Ia), as described above, wherein:
$R^1$, $R^4$ and $R^5$ are each independently hydrogen;
$R^2$ is phenyl optionally substituted by one or more substituents selected from the group consisting of halo, alkyl, heterocyclylalkenyl, —R$^{13}$—OR$^{12}$, —R$^{13}$—O—R$^{14}$—N(R$^{12}$)$_2$, —R$^{13}$—N(R$^{12}$)—R$^{14}$—N(R$^{12}$)$_2$, R$^{13}$—N(R$^{12}$)$_2$, —R$^{13}$—C(O)R$^{12}$, —R$^{13}$—C(O)N(R$^{12}$)$_2$, and —R$^{13}$—N(R$^{12}$)C(O)R$^{12}$;
$R^3$ is selected from the group consisting of 6,7-dihydro-5H-benzo[6,7]cyclohepta[1,2-d]pyrimidin-4-yl and 6,7-dihydro-5H-benzo[6,7]cyclohepta[1,2-d]pyrimidin-2-yl, each optionally substituted by one or more substituents selected from the group consisting of alkyl, aryl, halo and —R$^9$—OR$^8$.
each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N(R$^8$)$_2$, or any R$^6$ and R$^7$, together with the common nitrogen to which they are both attached, form an optionally substituted N-heteroaryl or an optionally substituted N-heterocyclyl;
each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{12}$'s, together with the common nitrogen to which they are both attached, form an optionally substituted N-heterocyclyl or an optionally substituted N-heteroaryl;
each $R^{13}$ is independently selected from the group consisting of a direct bond and an optionally substituted straight or branched alkylene chain; and
each $R^{14}$ is an optionally substituted straight or branched alkylene chain.

Another embodiment is a compound of formula (Ia), as described above, selected from the group consisting of:

1-(6,7-dihydro-5H-benzo[6,7]cyclohepta[1,2-d]pyrimidin-2-yl)-$N^3$-(3-fluoro-4-(2-(pyrrolidin-1-yl)ethoxy)phenyl)-1H-1,2,4-triazole-3,5-diamine; and 1-(6,7-dihydro-5H-benzo[6,7]cyclohepta[1,2-d]pyrimidin-4-yl)-$N^3$-(4-(2-(pyrrolidin-1-yl)ethoxy)phenyl)-1H-1,2,4-triazole-3,5-diamine.

Another embodiment is a compound of formula (Ia), as described above, wherein:

$R^1$, $R^4$ and $R^5$ are each independently hydrogen;

$R^2$ is phenyl optionally substituted by one or more substitutents selected from the group consisting of alkyl, halo, haloalkyl, cyano, and optionally substituted heterocyclyl where the optionally substituted heterocyclyl is selected from the group consisting of piperidinyl, piperazinyl, pyrrolidinyl, azepanyl, decahydropyrazino[1,2-a]azepinyl, octahydropyrrolo[3,4-c]pyrrolyl, azabicyclo[3.2.1]octyl, octahydropyrrolo[3,4-b]pyrrolyl, octahydropyrrolo[3,2-c]pyridinyl, 2,7-diazaspiro[4.4]nonanyl and azetidinyl; each independently optionally substituted by one or two substituents selected from the group consisting of —$R^9$—$OR^8$, —$R^9$—$N(R^6)R^7$, —$R^9$—$C(O)OR^6$, —$R^9$—$C(O)N(R^6)R^7$, —$R^9$—$N(R^6)C(O)R^7$, —$R^9$—$N(R^6)C(O)OR^7$, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

$R^3$ is selected from the group consisting of 6,7-dihydro-5H-benzo[2,3]azepino[4,5-c]pyridazin-3-yl, (Z)-dibenzo[b,f][1,4]thiazepin-11-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, each optionally substituted by one or more substituents selected from the group consisting of alkyl, aryl, halo and —$R^9$—$OR^8$.

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^w$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and each $R^9$ is independently selected from the group consisting of a direct bond and an optionally substituted straight or branched alkylene chain.

Another embodiment is a compound of formula (Ia), as described above, selected from the group consisting of:

1-(7-methyl-6,7-dihydro-5H-benzo[2,3]azepino[4,5-c]pyridazin-3-yl)-$N^3$-(4-(N-methylpiperazin-1-yl)phenyl)-1H-1,2,4-triazole-3,5-diamine;

1-(7-methyl-6,7-dihydro-5H-benzo[2,3]azepino[4,5-c]pyridazin-3-yl)-$N^3$-(3-fluoro-4-(4-cyclohexylpiperazinyl)phenyl)-1H-1,2,4-triazole-3,5-diamine;

1-((Z)-dibenzo[b,f][1,4]thiazepin-11-yl)-$N^3$-(4-(4-N-methylpiperazinyl)phenyl)-1H-1,2,4-triazole-3,5-diamine;

1-((Z)-dibenzo[b,f][1,4]thiazepin-11-yl)-$N^3$-(3-fluoro-4-(4-diethylaminopiperidin-1-yl)phenyl)-1H-1,2,4-triazole-3,5-diamine;

1-(6,7-dihydro-5H-benzo[2,3]oxepino[4,5-c]pyridazin-3-yl)-$N^3$-(4-(4-pyrrolidin-1-ylpiperidinyl)phenyl)-1H-1,2,4-triazole-3,5-diamine;

1-(6,7-dihydro-5H-benzo[2,3]oxepino[4,5-c]pyridazin-3-yl)-$N^3$-(3-fluoro-4-(4-pyrrolidin-1-ylpiperidinyl)phenyl)-1H-1,2,4-triazole-3,5-diamine;

1-(6,7-dihydro-5H-benzo[2,3]thiepino[4,5-c]pyridazin-3-yl)-$N^3$-(3-fluoro-4-(4-pyrrolidin-1-ylpiperidinyl)phenyl)-1H-1,2,4-triazole-3,5-diamine;

1-(6,7-dihydro-5H-benzo[2,3]thiepino[4,5-c]pyridazin-3-yl)-$N^3$-(4-(4-pyrrolidin-1-ylpiperidinyl)phenyl)-1H-1,2,4-triazole-3,5-diamine;

1-(6,7-dihydro-5H-benzo[2,3]thiepino[4,5-c]pyridazin-3-yl)-$N^3$-(3-fluoro-4-(4-(pyrrolidinylmethyl)piperidinyl)phenyl)-1H-1,2,4-triazole-3,5-diamine;

1-(6,7-dihydro-5H-benzo[2,3]thiepino[4,5-c]pyridazin-3-yl)-$N^3$-(3-fluoro-4-((4aR,8aS)-decahydroisoquinolin-2-yl)phenyl)-1H-1,2,4-triazole-3,5-diamine; and 1-(6,7-dihydro-5H-benzo[2,3]thiepino[4,5-c]pyridazin-3-yl)-$N^3$-(3-fluoro-4-(octahydro-1H-pyrido[1,2-a]pyrazin-2-yl)phenyl)-1H-1,2,4-triazole-3,5-diamine.

Another embodiment is a compound of formula (Ia), as described above, wherein:

$R^1$, $R^4$ and $R^5$ are each independently hydrogen;

$R^2$ is phenyl optionally substituted by one or more substitutents selected from the group consisting of halo, alkyl, heterocyclylalkenyl, —$R^{13}$—$OR^{12}$, —$R^{13}$—O—$R^{14}$—$N(R^{12})_2$, —$R^{13}$—$N(R^{12})$—$R^{14}$—$N(R^{12})_2$, —$R^{13}$—$N(R^{12})_2$, —$R^{13}$—$C(O)R^{12}$, —$R^{13}$—$C(O)N(R^{12})_2$, and —$R^{13}$—$N(R^{12})C(O)R^{12}$;

$R^3$ is selected from the group consisting of 6,7-dihydro-5H-benzo[2,3]azepino[4,5-c]pyridazin-3-yl, (Z)-dibenzo[b,f][1,4]thiazepin-11-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—$OC(O)$—$R^8$, —$R^9$—$N(R^6)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^8)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2);

each $R^8$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—$C(O)N(R^8)_2$, or any $R^8$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, selected from the group consisting of:

1-(7-methyl-6,7-dihydro-5H-benzo[2,3]azepino[4,5-c]pyridazin-3-yl)-$N^3$-(3-fluoro-4-(2-(pyrrolidin-1-yl)ethoxy)phenyl)-1H-1,2,4-triazole-3,5-diamine; and 1-((Z)-dibenzo[b,f][1,4]thiazepin-11-yl)-$N^3$-(4-(2-(pyrrolidin-1-yl)ethoxy)phenyl)-1H-1,2,4-triazole-3,5-diamine.

Another embodiment is a compound of formula (Ia), as described above, wherein:

$R^1$, $R^4$ and $R^5$ are each independently hydrogen;

$R^2$ is phenyl optionally substituted by a substitutent selected from the group consisting of optionally substituted heterocyclylalkyl, optionally substituted heteroaryl and optionally substituted heteroarylalkyl;

$R^3$ is selected from the group consisting of 6,7-dihydro-5H-benzo[6,7]cyclohepta[1,2-c]pyridazin-3-yl and 6,7-dihydro-5H-benzo[2,3]thiepino[4,5-c]pyridazin-3-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—$OC(O)$—$R^8$, —$R^9$—$N(R^6)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2)

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—$CN$, —$R^{10}$—$NO_2$, —$R^{10}$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain; and $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl.

Another embodiment is a compound of formula (Ia), as described above, selected from the group consisting of:

1-(6,7-dihydro-5H-benzo[6,7]cyclohepta[1,2-c]pyridazin-3-yl)-$N^3$-(4-((4-methylpiperazin-1-yl)methyl)phenyl)-1H-1,2,4-triazole-3,5-diamine;

1-(6,7-dihydro-5H-benzo[6,7]cyclohepta[1,2-c]pyridazin-3-yl)-$N^3$-(4-((5-fluoroindolin-2-on-3-yl)methyl)phenyl)-1H-1,2,4-triazole-3,5-diamine;

1-(6,7-dihydro-5H-benzo[6,7]cyclohepta[1,2-c]pyridazin-3-yl)-$N^3$-(4-((4-pyrrolidin-1-ylpiperidinyl)methyl)phenyl)-1H-1,2,4-triazole-3,5-diamine;

1-(6,7-dihydro-5H-benzo[6,7]cyclohepta[1,2-c]pyridazin-3-yl)-$N^3$-(4-((4-cyclopentylpiperazinyl)methyl)phenyl)-1H-1,2,4-triazole-3,5-diamine;

1-(6,7-dihydro-5H-benzo[6,7]cyclohepta[1,2-c]pyridazin-3-yl)-$N^3$-(4-((4-isopropylpiperazinyl)methyl)phenyl)-1H-1,2,4-triazole-3,5-diamine; and 1-(6,7-dihydro-5H-benzo[2,3]thiepino[4,5-c]pyridazin-3-yl)-$N^3$-(3-fluoro-4-(isoindolin-2-yl)phenyl)-1H-1,2,4-triazole-3,5-diamine.

Another embodiment is a compound of formula (Ia), as described above, wherein:

$R^1$, $R^4$ and $R^5$ are each independently hydrogen;

$R^2$ is 6,7,8,9-tetrahydro-5H-benzo[7]annulene-2-yl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —$R^{13}$—$OR^{12}$, —$R^{13}$—$OC(O)$—$R^{12}$, —$R^{13}$—$O$—$R^{14}$—$N(R^{12})_2$, —$R^{13}$—$N(R^{12})$—$R^{14}$—$N(R^{12})_2$, —$R^{13}$—$N(R^{12})_2$, —$R^{13}C(O)R^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)R^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2);

$R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]

pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—OC(O)—R$^8$, —R$^9$—N(R$^6$)R$^7$, —R$^9$—C(O)R$^8$, —R$^9$—C(O)OR$^6$, —R$^9$—C(O)N(R$^6$)R$^7$, —R$^9$—N(R$^6$)C(O)OR$^{12}$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2);

each R$^6$ and R$^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—NO$_2$, —R$^{10}$—N(R$^8$)$_2$, —R$^{10}$—C(O)OR$^8$ and —R$^{10}$—C(O)N(R$^8$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each R$^9$ is independently selected from the group consisting of a direct bond and an optionally substituted straight or branched alkylene chain;

each R$^{10}$ is an optionally substituted straight or branched alkylene chain;

each R$^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{12}$'s, together with the common nitrogen to which they are both attached, form an optionally substituted N-heterocyclyl or an optionally substituted N-heteroaryl;

each R$^{13}$ is independently selected from the group consisting of a direct bond and an optionally substituted straight or branched alkylene chain; and each R$^{14}$ is an optionally substituted straight or branched alkylene chain.

Another embodiment is a compound of formula (Ia), as described above, selected from the group consisting of:

1-(6,7-dihydro-5H-benzo[6,7]cyclohepta[1,2-c]pyridazin-3-yl)-N$^3$-(7-(pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-((bicyclo[2.2.1]heptan-2-yl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-((bicyclo[2.2.1]heptan-2-yl)(methyl)amino)6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7-piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7-azetidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7-(R)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-diethylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-cyclopentylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7-pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7-(2-(S)-methyloxycarbonyl)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7-(2-(S)-carboxy)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(8-diethylaminoethyl-9hydroxy-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-(3-(S)-fluoropyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-(2-(S)-methylpyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7-c]cyclohepta[1,2-c]pyridazin-3-yl)-N$^3$-(7-(3-(R)-hydroxypyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-(2-(R)-methylpyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-(3-(S)-hydroxypyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-(3-(R)-fluoropyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-oxo-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-cyclohexylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-cyclopropylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-hydroxy-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-methylpiperazin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(tetrahydrofuran-2-ylmethyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-cyclobutylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(cyclopropylmethyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(2-(diethylamino)ethyl)methylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-pyrrolidin-1-ylpiperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-(piperidin-1-ylmethyl)piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(2-(dimethylamino)ethyl)amino-6,7,8,9-tetrahydro-5H-benzo[7]annulene-2-yl)-1H-1,2,4-triazole-3,5-diamine; and 1-(6,7-dihydro-5H-benzo[6,7]cyclohepta[1,2-c]pyridazin-3-yl)-$N^3$-(7-(carboxymethyl)amino-6,7,8,9-tetrahydro-5H-benzo[7]annulene-2-yl)-1H-1,2,4-triazole-3,5-diamine.

Another embodiment is a compound of formula (Ia), as described above, wherein:

$R^1$, $R^4$ and $R^5$ are each independently hydrogen;

$R^2$ is heteroaryl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{13}-OR^{12}$, $-R^{13}-OC(O)-R^{12}$, $-R^{13}-O-R^{14}-N(R^{12})_2$, $-R^{13}-N(R^{12})-R^{14}-N(R^{12})_2$, $-R^{13}-C(O)N(R^{12})_2$, $-R^{13}-C(O)N(R^{12})-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^{13}-S(O)_tN(R^{12})_2$ (where t is 1 or 2);

$R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-O-R^{10}-OR^8$, $-R^9-O-R^{10}-O-R^{10}-OR^8$, $-R^9-O-R^{10}-CN$, $-R^9-O-R^{10}-C(O)OR^8$, $-R^9-O-R^{10}-C(O)N(R^6)^7$, $-R^9-O-R^{10}-S(O)_pR^8$ (where p is 0, 1 or 2), $-R^9-O-R^{10}-N(R^6)R^7$, $-R^9-O-R^{10}-C(NR^{11})N(R^{11})H$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^6)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{11}$ is independently selected from the group consisting of hydrogen, alkyl, cyano, nitro and $-OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, wherein:

$R^1$, $R^4$ and $R^5$ are each independently hydrogen;

$R^2$ is heteroaryl selected from the group consisting of pyridinyl, pyrimidinyl, 4,5-dihydro-1H-benzo[b]azepin-2(3H)-on-8-yl, benzo[d]imidazolyl, 6,7,8,9-tetrahydro-5H-pyrido[3,2-d]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, and 6,7,8,9-tetrahydro-5H-cyclohepta[b]pyridin-3-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —$R^{13}$—$OR^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)OR$^{12}$, $R^{13}$—C(O)$R^{12}$, —$R^{13}$—C(O)OR$^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—OR$^{12}$, —$R^{13}$—N($R^{12}$)C(O)OR$^{12}$, —$R^{13}$—N($R^{12}$)C(O)$R^{12}$, —$R^{13}$—N($R^{12}$)S(O)$_t R^{12}$ (where t is 1 or 2), —$R^{13}$—S(O)$_t$OR$^{12}$ (where t is 1 or 2), —$R^{13}$—S(O)$_p R^{12}$ (where p is 0, 1 or 2), and —$R^{13}$—S(O)$_t$N($R^{12}$)$_2$ (where t is 1 or 2);

$R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—OR$^8$, —$R^9$—OC(O)—$R^8$, —$R^9$—N($R^6$)$R^7$, —$R^9$—C(O)$R^8$, —$R^9$—C(O)OR$^8$, —$R^9$—C(O)N($R^6$)$R^7$, —$R^9$—N($R^6$)C(O)OR$^{12}$, —$R^9$—N($R^6$)C(O)$R^8$, —$R^9$—N($R^6$)S(O)$_t R^8$ (where t is 1 or 2), —$R^9$—S(O)$_t$OR$^6$ (where t is 1 or 2), —$R^9$—S(O)$_p R^8$ (where p is 0, 1 or 2), and —$R^9$—S(O)$_t$N($R^6$)$R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—OR$^8$, —$R^{10}$—CN, —$R^{10}$—NO$_2$, —$R^{10}$—N($R^8$)$_2$, —$R^{10}$—C(O)OR$^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, wherein:

$R^1$, $R^4$ and $R^5$ are each independently hydrogen;

$R^2$ is selected from the group consisting of pyridinyl and pyrimidinyl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —$R^{13}$—OR$^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)OR$^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—OR$^{12}$, —$R^{13}$—N($R^{12}$)C(O)OR$^{12}$, —$R^{13}$—N($R^{12}$)C(O)$R^{12}$, —$R^{13}$—N($R^{12}$)S(O)$_t R^{12}$ (where t is 1 or 2), —$R^{13}$—S(O)$_t$OR$^{12}$ (where t is 1 or 2), —$R^{13}$—S(O)$_p R^{12}$ (where p is 0, 1 or 2), and —$R^{13}$—S(O)$_t$N($R^{12}$)$_2$ (where t is 1 or 2);

$R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9- tetrahydro-5H-cyclohepta[4,5]thieno[2,3-c]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—$OC(O)$—$R^8$, —$R^9$—$N(R^6)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^6$ (where t is 1 or 2), —$R^9$—$S(O)_tOR^8$ (where t is 1 or 2), —$R^9$—$S(O)_pR^8$ (where p is 0, 1 or 2), and —$R^3$—$S(O)_tN(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—$CN$, —$R^{10}$—$NO_2$, —$R^{10}$—$N(R^8)_2$, $R^{10}$—$C(O)OR^9$ and $R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12's}$, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, selected from the group consisting of:

1-(6,7-dihydro-5H-benzo[6,7]cyclohepta[1,2-c]pyridazin-3-yl)-$N^3$-(6-(4-(bicyclo[2.2.1]heptan-2-yl)piperazin-1-yl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(4-cyclopentyl-1,4-diazepan-1-yl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(4-methylpiperazin-1-yl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(4-(4-methylpiperazin-1-yl)piperidin-1-yl)pyridine-3-yl)-1H-1,2,4-triazole-3,5-diamine;

1-(6,7-dihydro-5H-benzo[6,7]cyclohepta[1,2-c]pyridazin-3-yl)-$N^3$-(pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(6-aminopyridin-3-yl)pyridine-3-yl)-1H-1,2,4-triazole-3,5-diamine;

1-(6,7-dihydro-5H-benzo[6,7]cyclohepta[1,2-c]pyridazin-3-yl)-$N^3$-(6-(3-aminophenyl)pyridine-3-yl)-1H-1,2,4-triazole-3,5-diamine;

1-(6,7-dihydro-5H-benzo[6,7]cyclohepta[1,2-c]pyridazin-3-yl)-$N^3$-(6-(3-cyanophenyl)pyridine-3-yl)-1H-1,2,4-triazole-3,5-diamine;

1-(6,7-dihydro-5H-benzo[6,7]cyclohepta[1,2-c]pyridazin-3-yl)-$N^3$-(64 benzo[d][1,3]dioxole-6-yl)pyridine-3-yl)-1H-1,2,4-triazole-3,5-diamine;

1-(6,7-dihydro-5H-benzo[6,7]cyclohepta[1,2-c]pyridazin-3-yl)-$N^3$-(6-(3-methylsulfonamidylphenyl)pyridine-3-yl)-1H-1,2,4-triazole-3,5-diamine;

1-(6,7-dihydro-5H-benzo[6,7]cyclohepta[1,2-c]pyridazin-3-yl)-$N^3$-(6-(2-diethylaminomethyl)pyrrolidin-1-ylpyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(3-diethylaminopyrrolidin-1-yl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(3-(4-(N-methylpiperazin-4-yl)piperidin-1-yl)-(E)-propenyl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(4-(pyrrolidin-1-yl)piperidin-1-yl)-5-methylpyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(3-piperidin-1-yl-(E)-propenyl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(4-(bicyclo[2.2.1]heptan-2-yl)-1,4-diazepan-1-yl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(3-(4-(pyrrolidin-1-yl)piperidin-1-yl)-(E)-propenyl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(3-piperidin-1-yl)-propanylpyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(3-(4-(piperidin-1-yl)piperidin-1-yl)-(E)-propenyl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(6-(3-(4-dimethylaminopiperidin-1-yl)-(E)-propenyl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(2-(4-pyrrolidin-1-ylpiperidin-1-yl)pyrimidin-5-yl)-1H-1,2,4-triazole-3,5-diamine;

1-(6,7-dihydro-5H-benzo[6,7]cyclohepta[1,2-c]pyridazin-3-yl)-$N^3$-(2-(4-(piperidin-1-ylmethyl)piperidin-1-yl)pyrimidin-5-yl)-1H-1,2,4-triazole-3,5-diamine;

1-(6,7-dihydro-5H-benzo[6,7]cyclohepta[1,2-c]pyridazin-3-yl)-$N^3$-(6-((4-piperidin-1-ylpiperidin-1-yl)carbonyl)pyridin-3-yl)-1H-1,2,4-triazole-3,5-diamine;

1-(6,7-dihydro-5H-benzo[6,7]cyclohepta[1,2-c]pyridazin-3-yl)-$N^3$-(2-(4-cyclopropylmethylpiperazin-1-yl)pyridine-5-yl)-1H-1,2,4-triazole-3,5-diamine; and 1-(6,7-dihydro-5H-benzo[6,7]cyclohepta[1,2-c]pyridazin-3-yl)-$N^3$-(2-(3-(S)-methyl-4-cyclopropylmethylpiperazin-1-yl)pyridine-5-yl)-1H-1,2,4-triazole-3,5-diamine.

Another embodiment is a compound of formula (Ia), as described above, wherein:

$R^1$, $R^4$ and $R^5$ are each independently hydrogen;

$R^2$ is selected from the group consisting of 4,5-dihydro-1H-benzo[b]azepin-2(31-1)-on-8-yl, benzo[d]imidazolyl, 6,7,8,9-tetrahydro-5H-pyrido[3,2-d]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, and 6,7,8,9-tetrahydro-5H-cyclohepta[b]pyridin-3-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —$R^{13}$—$OR^{12}$, —$R^{13}$—$OC(O)$—$R^{12}$, —$R^{13}$—$O$—$R^{14}$—$N(R^{12})_2$, —$R^{13}$—$N(R^{12})$—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2);

$R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-c]pyrimidin-4-yl, 6,7-dihydro-5H-benzo[6,7]cyclohepta[1,2-c]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—$OC(O)$—$R^8$, —$R^9$—$N(R^6)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^8$—$N(R^6)S(O)_tR^8$ (where t is 1 or 2), —$R^8$—$S(O)_tOR^8$ (where t is 1 or 2), —$R^8$—$S(O)_pR^8$ (where p is 0, 1 or 2), and —$R^8$—$S(O)_tN(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—$CN$, —$R^{10}$—$NO_2$, —$R^{10}$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ia), as described above, selected from the group consisting of:

1-(6,7-dihydro-5H-benzo[6,7]cyclohepta[1,2-c]pyridazin-3-yl)-$N^3$-(4,5-dihydro-1H-benzo[b]azepin-2(3H)-on-8-yl)-1H-1,2,4-triazole-3,5-diamine;

1-(6,7-dihydro-5H-benzo[6,7]cyclohepta[1,2-c]pyridazin-3-yl)-$N^3$-(2-(dimethylaminomethyl)-1H-benzo[d]imidazol-5-yl)-1H-1,2,4-triazole-3,5-diamine;

1-(6,7-dihydro-5H-benzo[6,7]cyclohepta[1,2-c]pyridazin-3-yl)-$N^3$-(7-cyclopentyl-6,7,8,9-tetrahydro-5H-pyrido[3,2-d]azepin-3-yl)-1H-1,2,4-triazole-3,5-diamine;

1-(6,7-dihydro-5H-benzo[6,7]cyclohepta[1,2-c]pyridazin-3-yl)-N³-(6-methyl-5,6,7,8-tetrahydro-1,6-naphthyridin-3-yl)-1H-1,2,4-triazole-3,5-diamine;

1-(6,7-dihydro-5H-benzo[6,7]cyclohepta[1,2-c]pyridazin-3-yl)-N³-(6-(4-(4-methylpiperazin-1-yl)piperidin-1-yl)pyridine-3-yl)-1H-1,2,4-triazole-3,5-diamine;

1-(6,7-dihydro-5H-benzo[6,7]cyclohepta[1,2-c]pyridazin-3-yl)-N³-(6-(4-methylpiperazin-1-yl)carbonyl-5,6,7,8-tetrahydroquinolin-3-yl)-1H-1,2,4-triazole-3,5-diamine, compound #31, 1H-1,2,4-triazole-3,5-diamine;

1-(6,7-dihydro-5H-benzo[6,7]cyclohepta[1,2-c]pyridazin-3-yl)-N³-(2,3,4,5-tetrahydrobenzo[b]oxepin-7-yl)-1H-1,2,4-triazole-3,5-diamine;

1-(6,7-dihydro-5H-benzo[6,7]cyclohepta[1,2-c]pyridazin-3-yl)-N³-(3,4-dihydro-2H-benzo[b][1,4]dioxepin-7-yl)-1H-1,2,4-triazole-3,5-diamine;

1-(6,7-dihydro-5H-benzo[2,3]oxepino[4,5-c]pyridazin-3-yl)-N³-(2-(pyrrolidin-1-ylmethyl)benzo[d]oxazol-5-yl)-1H-1,2,4-triazole-3,5-diamine;

1-(6,7-dihydro-5H-benzo[6,7]cyclohepta[1,2-c]pyridazin-3-yl)-N³-(4-(2-dimethylaminoethyl)-(3,4-dihydro-2H-benzo[b][1,4]oxazin-7-yl))-1H-1,2,4-triazole-3,5-diamine;

1-(6,7-dihydro-5H-benzo[2,3]oxepino[4,5-c]pyridazin-3-yl)-N³-(4-(2-dimethylaminoethyl)-(3,4-dihydro-2H-benzo[b][1,4]oxazin-7-yl))-1H-1,2,4-triazole-3,5-diamine;

1-(6,7-dihydro-5H-benzo[2,3]thiepino[4,5-c]pyridazin-3-yl)-N³-(2-(1-(4-(2-(dimethylamino)ethyl)piperazin-1-yl)oxomethyl)benzo[b]thiophen-5-yl)-1H-1,2,4-triazole-3,5-diamine;

1-(6,7-dihydro-5H-benzo[6,7]cyclohepta[1,2-c]pyridazin-3-yl)-N³-(6-cyclopentyl-6,7,8,9-tetrahydro-5H-pyrido[3,2-c]azepin-3-yl)-1H-1,2,4-triazole-3,5-diamine;

1-(6,7-dihydro-5H-benzo[6,7]cyclohepta[1,2-c]pyridazin-3-yl)-N³-((7-pyrrolidin-1-yl)-6,7,8,9-tetrahydro-5H-cyclohepta[b]pyridine-3-yl)-1H-1,2,4-triazole-3,5-diamine;

1-(6,7-dihydro-5H-benzo[6,7]cyclohepta[1,2-c]pyridazin-3-yl)-N³ (2-cyclopentyl-1,2,3,4-tetrahydroisoquinolin-7-yl)-1H-1,2,4-triazole-3,5-diamine;

1-(6,7-dihydro-5H-benzo[6,7]cyclohepta[1,2-c]pyridazin-3-yl)-N³-(6-(pyrrolidin-1-yl)-5,6,7,8-tetrahydroquinolin-3-yl)-1H-1,2,4-triazole-3,5-diamine;

1-(6,7-dihydro-5H-benzo[6,7]cyclohepta[1,2-c]pyridazin-3-yl)-N³-(6-cyclopentyl-5,6,7,8-tetrahydro-1,6-naphthyridine-3-yl)-1H-1,2,4-triazole-3,5-diamine;

1-(6,7-dihydro-5H-benzo[6,7]cyclohepta[1,2-c]pyridazin-3-yl)-N³—((S)-7-(pyrrolidin-1-yl)-6,7,8,9-tetrahydro-5H-cyclohepta[b]pyridine-3-yl)-1H-1,2,4-triazole-3,5-diamine;

1-(6,7-dihydro-5H-benzo[6,7]cyclohepta[1,2-c]pyridazin-3-yl)-N³-(1,2,3,4-tetrahydroisoquinolin-7-yl)-1H-1,2,4-triazole-3,5-diamine;

1-(6,7-dihydro-5H-benzo[6,7]cyclohepta[1,2-c]pyridazin-3-yl)-N³-(2-(1-methylpiperidin-4-yl)-1,2,3,4-tetrahydroisoquinolin-7-yl)-1H-1,2,4-triazole-3,5-diamine; and 1-(6,7-dihydro-5H-benzo[6,7]cyclohepta[1,2-c]pyridazin-3-yl)-N³-(2-(cyclopropylmethyl)-1,2,3,4-tetrahydroisoquinolin-7-yl)-1H-1,2,4-triazole-3,5-diamine.

Another embodiment of the compounds of formula (I) is wherein the compound of formula (I) is a compound of formula (Ib):

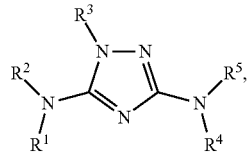

(Ib)

wherein:
R¹, R⁴ and R⁵ are each independently selected from the group consisting of hydrogen, alkyl, aryl, aralkyl, —C(O)R⁸, —C(O)N(R⁸)R⁷, and —C(=NR⁶)N(R⁶)R⁷;

R² and R³ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R⁹—OR⁸, —R⁹—O—R¹⁰—OR⁸, —R⁹—O—R¹⁰—O—R¹⁰—OR⁸, —R⁹—O—R¹⁰—CN, —R⁹—O—R¹⁰—C(O)OR⁸, —R⁹—O—R¹⁰—C(O)N(R⁸)R⁷; —R⁹—O—R¹⁰—S(O)$_p$R⁸ (where p is 0, 1 or 2), —R⁹—O—R¹⁰—N(R⁶)R⁷, —R⁹—O—R¹⁰—C(NR¹¹)N(R¹¹)H, —R⁹—OC(O)—R⁸, —R⁹—N(R⁶)R⁷, —R⁹—C(O)R⁸, —R⁹—C(O)OR⁸, —R⁹—C(O)N(R⁶)R⁷, —R⁹—N(R⁶)C(O)OR¹², —R⁹—N(R⁶)C(O)R⁸, —R⁹—N(R⁸)S(O)$_t$R⁸ (where t is 1 or 2), —R⁹—S(O)$_t$OR⁸ (where t is 1 or 2), —R⁹—S(O)$_p$R⁸ (where p is 0, 1 or 2), and —R⁹—S(O)$_t$N(R⁶)R⁷ (where t is 1 or 2);

or R² is a polycyclic heteroaryl containing more than 14 ring atoms as described above and R³ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R¹³—OR¹², —R¹³—OC(O)—R¹², —R¹³—O—R¹⁴—N(R¹²)₂, —R¹³—N(R¹²)—R¹⁴—N(R¹²)₂, —R¹³—N(R¹²)₂, —R¹³—C(O)R¹², —R¹³—C(O)OR¹², —R¹³—C(O)N(R¹²)₂, —R¹³—C(O)N(R¹²)—R¹⁴—N(R¹²)R¹³, —R¹³—C(O)N(R¹²)—R¹⁴—OR¹², —R¹³—N(R¹²)C(O)OR¹², —R¹³—N(R¹²)C(O)R¹², —R¹³—N(R¹²)S(O)$_t$R¹² (where t is 1 or 2), —R¹³—S(O)$_t$OR¹² (where t is 1 or 2), —R¹³—S(O)$_p$R¹² (where p is 0, 1 or 2), and —R¹³—S(O)$_t$N(R¹²)₂ (where t is 1 or 2);

or R³ is a polycyclic heteroaryl containing more than 14 ring atoms as described above, and R² is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{13}-OR^{12}$, $-R^{13}-OC(O)-R^{12}$, $-R^{13}-O-R^{14}-N(R^{12})_2$, $-R^{13}-N(R^{12})-R^{14}-N(R^{12})_2$, $-R^{13}-N(R^{12})_2$, $-R^{13}-C(O)R^{12}$, $-R^{13}-C(O)OR^{12}$, $-R^{13}-C(O)N(R^{12})_2$, $-R^{13}-C(O)N(R^{12})-R^{14}-N(R^{12})R^{13}$, $-R-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^{13}-S(O)_tN(R^{12})_2$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and $-OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain.

Another embodiment is a compound of formula (Ib), as described above, wherein:

$R^1$, $R^4$ and $R^5$ are each independently selected from the group consisting of hydrogen, alkyl, aryl, aralkyl, $-C(O)R^8$, $-C(O)N(R^6)R^7$, and $-C(=NR^6)N(R^6)R^7$;

$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-O-R^{10}-OR^8$, $-R^9-O-R^{10}-O-R^{10}-OR^8$, $-R^9-O-R^{10}-CN$, $-R^9-O-R^{10}-C(O)OR^8$, $-R^9-O-R^{10}-C(O)N(R^6)R^7$, $-R^9-O-R^{10}-S(O)_pR^8$ (where p is 0, 1 or 2), $-R^9-O-R^{10}-N(R^6)R^7$, $-R^9-O-R^{10}-C(NR^{11})N(R^{11})H$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^6)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain; and each $R^{11}$ is independently selected from the group consisting of hydrogen, alkyl, cyano, nitro and —$OR^8$.

Another embodiment is a compound of formula (Ib), as described above, wherein:

$R^1$, $R^4$ and $R^5$ are each hydrogen;

$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—CN, —$R^9$—O—$R^{10}$—C(O)$OR^8$, —$R^9$—O—$R^{10}$—C(O)N($R^6$)$R^7$, —$R^9$—O—$R^{10}$—S(O)$_p R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)$OR^8$, —$R^9$—C(O)N(R)$R^7$, —$R^9$—N($R^6$)C(O)$OR^{12}$, —$R^9$—N($R^6$)C(O)$R^8$, —$R^9$—N($R^6$)S(O)$_t R^8$ (where t is 1 or 2), —$R^9$—S(O)$_t OR^8$ (where t is 1 or 2), —$R^9$—S(O)$_p R^8$ (where p is 0, 1 or 2), and —$R^9$—S(O)$_t N(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—N($R^8$)$_2$, —$R^{10}$—C(O)$OR^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain; and each $R^{10}$ is an optionally substituted straight or branched alkylene chain; and each $R^{11}$ is independently selected from the group consisting of hydrogen, alkyl, cyano, nitro and —$OR^8$.

Another embodiment is a compound of formula (Ib), as described above, wherein:

$R^1$, $R^4$ and $R^5$ are each hydrogen;

$R^2$ and $R^3$ are each independently a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—N($R^6$)$R^7$, —$R^9$—C(O)$R^8$, —$R^9$—C(O)$OR^8$, —$R^9$—C(O)N($R^6$)$R^7$, —$R^9$—N($R^6$)C(O)$OR^{12}$, —$R^9$—N($R^6$)C(O)$R^8$, —$R^9$—N($R^6$)S(O)$_t R^6$ (where t is 1 or 2), —$R^9$—S(O)$_t OR^8$ (where t is 1 or 2), —$R^9$—S(O)$_p R^8$ (where p is 0, 1 or 2), and —$R^9$—S(O)$_t N(R^6)R^7$ (where t is 1 or 2)

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—N($R^8$)$_2$, —$R^{10}$—C(O)$OR^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain; and each $R^{10}$ is an optionally substituted straight or branched alkylene chain.

Another embodiment is a compound of formula (Ib), as described above, which is 1-(6,7-dihydro-5H-benzo[6,7]cyclohepta[1,2-c]pyridazin-3-yl)-$N^8$-(5,7,8,9-tetrahydrospiro[cyclohepta[b]pyridine-6,2"[1,3]dioxolane]-3-yl)-1H-1,2,4-triazole-3,5-diamine.

Another embodiment is a compound of formula (Ib), as described above, wherein:

$R^1$, $R^4$ and $R^5$ are each independently selected from the group consisting of hydrogen, alkyl, aryl, aralkyl, —C(O)$R^8$, —C(O)N($R^6$)$R^7$, and —C(=N$R^6$)N($R^6$)$R^7$;

$R^2$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—O$R^8$, —$R^9$—O—$R^{10}$—O$R^8$, —$R^9$—O—$R^{10}$—O—$R^{10}$—O$R^8$, —$R^9$—O—$R^{10}$—CN, —$R^9$—O—$R^{10}$—C(O)O$R^8$, —$R^9$—O—$R^{10}$—C(O)N($R^8$)$R^7$, —$R^9$—O—$R^{10}$—S(O)$_p R^8$ (where p is 0, 1 or 2), —$R^9$—O—$R^{10}$—N($R^8$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N(R)C(O)O$R^{12}$, —$R^9$—N(R)C(O)$R^8$, —$R^9$—N($R^8$)S(O)$_t R^8$ (where t is 1 or 2), —$R^9$—S(O)$_t$O$R^8$ (where t is 1 or 2), —$R^9$—S(O)$_p R^8$ (where p is 0, 1 or 2), and —$R^9$—S(O)$_t$N($R^8$)$R^7$ (where t is 1 or 2);

$R^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t R^{12}$ (where t is 1 or 2), —$R^{13}$—S(O)$_t$O$R^{12}$ (where t is 1 or 2), —$R^{13}$—S(O)$_p R^{12}$ (where p is 0, 1 or 2), and —$R^{13}$—S(O)$_t$N($R^{12}$)$_2$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—O$R^8$, —$R^{10}$—CN, —$R^{10}$—NO$_2$, —$R^{10}$—N($R^6$)$_2$, —$R^{10}$—C(O)O$R^8$ and —$R^{10}$—C(O)N($R^6$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and —O$R^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12's}$, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain.

Another embodiments a compound of formula (Ib), as described above, wherein:

$R^1$, $R^4$ and $R^5$ are each hydrogen;

$R^2$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—O$R^8$, —$R^9$—O—$R^{13}$—O$R^8$, —$R^9$—O—$R^{10}$—CN, —$R^9$—O—$R^{10}$—C(O)O$R^8$, —$R^9$—O—$R^{10}$—C(O)N($R^6$)$R^7$, —$R^9$—O—$R^{10}$—S(O)$_p R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N($R^8$)C(O)O$R^{12}$, —$R^9$—N($R^6$)C(O)$R^8$, —$R^9$—N($R^8$)S(O)$_t R^8$ (where t is 1 or 2), —$R^9$—S(O)$_t$O$R^8$ (where t is 1 or 2), —$R^9$—S(O)$_p R^8$ (where p is 0, 1 or 2), and —$R^9$—S(O)$_1$N($R^6$)$R^7$ (where t is 1 or 2);

$R^3$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—$OC(O)$—$R^{12}$, —$R^{13}$—$O$—$R^{14}$—$N(R^{12})_2$, —$R^{13}$—$N(R^{12})$—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{11}$ is independently selected from the group consisting of hydrogen, alkyl, cyano, nitro and —$OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ib), as described above, wherein:

$R^1$, $R^4$ and $R^5$ are each hydrogen;

$R^2$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-c]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—$OC(O)$—$R^8$, —$R^9$—$N(R^6)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2);

$R^3$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—$OC(O)$—$R^{12}$, —$R^{13}$—$O$—$R^{14}$—$N(R^{12})_2$, —$R^{13}$—$N(R^{12})$—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ib), as described above, wherein:

$R^1$, $R^4$ and $R^5$ are each independently selected from the group consisting of hydrogen, alkyl, aryl, aralkyl, —$C(O)R^8$, —$C(O)N(R^6)R^7$, and —$C(=NR^6)N(R^6)R^7$;

$R^2$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterdcyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—$OC(O)$—$R^{12}$, —$R^{13}$—O—$R^{14}$—$N(R^{12})_2$, —$R^{13}$—$N(R^{12})$—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2);

$R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^5$, —$R^9$—O—$R^{10}$—O—$R^{10}$—$OR^9$, —$R^9$—O—$R^{10}$—CN, —$R^9$—O—$R^{10}$—$C(O)OR^9$, —$R^9$—O—$R^{10}$—$C(O)N(R^6)R^7$, —$R^9$—O—$R^{10}$—$S(O)_pR^8$ (where p is 0, 1 or 2), —$R^9$—O—$R^{10}$—$N(R^6)R^7$, —$R^9$—O—$R^{10}$—$C(NR^{11})N(R^{11})H$, —$R^9$—$OC(O)$—$R^5$, —$R^9$—$N(R^6)R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^6$, —$R^9$—$N(R^6)S(O)_tR^6$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and —$OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain.

Another embodiment is a compound of formula (Ib), as described above, wherein:

$R^1$, $R^4$ and $R^5$ are each independently hydrogen;

$R^2$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{13}-OR^{12}$, $-R^{13}-OC(O)-R^{12}$, $-R^{13}-O-R^{14}-N(R^{12})_2$, $-R^{13}-N(R^{12})-R^{14}-N(R^{12})_2$, $R^{13}-N(R^{12})_2$, $-R^{13}-C(O)R^{12}$, $-R^{13}-C(O)OR^{12}$, $-R^{13}-C(O)N(R^{12})_2$, $-R^{13}-C(O)N(R^{12})-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^{13}-S(O)_tN(R^{12})_2$ (where t is 1 or 2);

$R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-O-R^{10}-OR^8$, $-R^9-O-R^{10}-O-R^{10}-OR^8$, $-R^9-O-R^{10}-CN$, $-R^9-O-R^{10}-C(O)OR^8$, $-R^9-O-R^{10}-C(O)N(R^6)R^7$, $-R^9-O-R^{10}-S(O)_pR^8$ (where p is 0, 1 or 2), $-R^9-O-R^{10}-N(R^6)R^7$, $-R^9-O-R^{10}-C(NR^{11})N(R^{11})H$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^8)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{11}$ is independently selected from the group consisting of hydrogen, alkyl, cyano, nitro and $-OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12's}$, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ib), as described above, wherein:

$R^1$, $R^4$ and $R^5$ are each independently hydrogen;

$R^2$ is aryl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{13}-OR^{12}$, $-R^{13}-OC(O)-R^{12}$, $-R^{13}-O-R^{14}-N(R^{12})_2$, $-R^{13}-N(R^{12})-R^{14}-N(R^{12})_2$, $-R^{13}-N(R^{12})_2$, $-R^{13}-C(O)R^{12}$, $-R^{13}-O(O)OR^{12}$, $-R^{13}-O(O)N(R^{12})_2$, $-R^{13}-C(O)N(R^{12})-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^{13}-S(O)_tN(R^{12})_2$ (where t is 1 or 2);

$R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^6-O-R^{10}-OR^8$, $-R^6-O-R^{10}-O-R^{10}-OR^8$, $-R^6-O-R^{10}-ON$, $-R^6-O-R^{16}-O$ (O)OR$^8$, —W—O—R$^{16}$—O(O)N(R$^6$)R$^7$, —R$^6$—O—R$^{10}$—S(O)$_p$R$^8$ (where p is 0, 1 or 2), —W—O—R$^{10}$—N(R$^6$)R$^7$, —R$^6$—O—R$^{10}$—O(NR$^{11}$)N(R$^{11}$)H, —R$^9$—N(R$^6$)R$^7$, —R$^9$—C(O)R$^8$, —R$^9$—C(O)OR$^8$, —W-0(O)N(R$^6$)R$^7$, —R$^9$—N(R$^6$)C(O)OR$^{12}$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2);

each R$^6$ and R$^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N(R$^8$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each R$^9$ is independently selected from the group consisting of a direct bond and an optionally substituted straight or branched alkylene chain;

each R$^{10}$ is an optionally substituted straight or branched alkylene chain;

each R$^{11}$ is independently selected from the group consisting of hydrogen, alkyl, cyano, nitro and —OR$^8$;

each R$^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{12}$'s, together with the common nitrogen to which they are both attached, form an optionally substituted N-heterocyclyl or an optionally substituted N-heteroaryl;

each R$^{13}$ is independently selected from the group consisting of a direct bond and an optionally substituted straight or branched alkylene chain; and each R$^{14}$ is an optionally substituted straight or branched alkylene chain.

Another embodiment is a compound of formula (Ib), as described above, wherein:

R$^1$, R$^4$ and R$^5$ are each independently hydrogen;

R$^2$ is aryl selected from the group consisting of phenyl and 6,7,8,9-tetrahydro-5H-benzo[7]annulene-2-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)—R$^{14}$—N(R$^{12}$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)$_t$OR$^{12}$ (where t is 1 or 2), —R$^{13}$—S(O)$_p$R$^{12}$ (where p is 0, 1 or 2), and —R$^{13}$—S(O)$_t$N(R$^{12}$)$_2$ (where t is 1 or 2);

R$^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-c]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyfidazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^{12}$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^6$—S(O)$_t$N(R$^6$)R$^7$ (where t is 1 or 2);

each R$^6$ and R$^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N(R$^8$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each R$^9$ is independently selected from the group consisting of a direct bond and an optionally substituted straight or branched alkylene chain;

each R$^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ib), as described above, wherein:

$R^1$, $R^4$ and $R^5$ are each independently hydrogen;

$R^2$ is phenyl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —$R^{13}$—$OR^{12}$, —$R^{13}$—OC(O)—$R^{12}$, $R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

$R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-c]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N($R^6$)C(O)O$R^{12}$, —$R^9$—N($R^6$)C(O)$R^8$, —$R^9$—N($R^6$)S(O)$_t$$R^8$ (where t is 1 or 2), —$R^9$—S(O)$_t$O$R^8$ (where t is 1 or 2), —$R^9$—S(O)$_p$$R^8$ (where p is 0, 1 or 2), and —$R^9$—S(O)$_t$N($R^6$)$R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—NO$_2$, —$R^{10}$—N($R^8$)$_2$, —$R^{10}$—C(O)O$R^8$ and —$R^{10}$—C(O)N($R^6$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ib), as described above, selected from the group consisting of:

1-(6,7-dihydro-5H-benzo[6,7]cyclohepta[1,2-c]pyridazin-3-yl)-$N^5$-(3-fluoro-4-(4-(indolin-2-on-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(3-fluoro-4-(4-(morpholin-4-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(4-(3,5-dimethylpiperazin-1-yl)phenyl)-1H-1,2,4-triazole-3,5-diamine;

1-(7-methyl-6,7-dihydro-5H-benzo[2,3]azepino[4,5-c]pyridazin-3-yl)-$N^5$-(4-(N-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(4-((5-fluoroindolin-2-on-3-yl)methyl)phenyl)-1H-1,2,4-triazole-3,5-diamine;

1-(6,7-dihydro-5H-benzo[6,7]cyclohepta[1,2-c]pyridazin-3-yl)-$N^5$-(4-(4-pyrrolidin-1-ylpiperidinyl)phenyl)-1H-1,2,4-triazole-3,5-diamine;

1-(6,7-dihydro-5H-benzo[6,7]cyclohepta[1,2-c]pyridazin-3-yl)-$N^5$-(4-((4-pyrrolidin-1-ylpiperidinyl)methyl)phenyl)-1H-1,2,4-triazole-3,5-diamine;

1-(6,7-dihydro-5H-benzo[6,7]cyclohepta[1,2-c]pyridazin-3-yl)-N⁵-(4-((4-cyclopentylpiperazinyl)methyl)phenyl)-1H-1,2,4-triazole-3,5-diamine;
1-(6,7-dihydro-5H-benzo[6,7]cyclohepta[1,2-c]pyridazin-3-yl)-N⁵-(4-((4-isopropylpiperazinyl)methyl)phenyl)-1H-1,2,4-triazole-3,5-diamine;
1-(6,7-dihydro-5H-benzo[6,7]cyclohepta[1,2-c]pyridazin-3-yl)-N⁵-(3-fluoro-4-(4-N-methylpiperid-4-ylpiperazinyl)phenyl)-1H-1,2,4-triazole-3,5-diamine;
1-(6,7-dihydro-5H-benzo[6,7]cyclohepta[1,2-c]pyridazin-3-yl)-N⁵-(3-fluoro-4-(7-methyl-2,7-diazaspiro[4.4]nonan-2-yl)phenyl)-1H-1,2,4-triazole-3,5-diamine;
1-(6,7-dihydro-5H-benzo[6,7]cyclohepta[1,2-c]pyridazin-3-yl)-N⁵-(3-fluoro-4-(3-pyrrolidin-1-ylazetidinyl)phenyl)-1H-1,2,4-triazole-3,5-diamine;
1-(6,7-dihydro-5H-benzo[6,7]cyclohepta[1,2-c]pyridazin-3-yl)-N⁵-(3-methyl-4-(4-(N-methylpiperazin-4-yl)piperidin-1-yl)phenyl)-1H-1,2,4-triazole-3,5-diamine;
1-(6,7-dihydro-5H-benzo[2,3]thiepino[4,5-c]pyridazin-3-yl)-N⁵-(4-(4-pyrrolidin-1-ylpiperidinyl)phenyl)-1H-1,2,4-triazole-3,5-diamine;
1-(6,7-dihydro-5H-benzo[6,7]cyclohepta[1,2-c]pyridazin-3-yl)-N⁵-(3-fluoro-(4-(3-pyrrolidin-1-yl)pyrrolidin-1-yl)phenyl)-1H-1,2,4-triazole-3,5-diamine;
1-(6,7-dihydro-5H-benzo[6,7]cyclohepta[1,2-c]pyridazin-3-yl)-N⁵-(3-fluoro-4-(4-methylpiperazin-1-yl)phenyl)-1H-1,2,4-triazole-3,5-diamine; and
1-(6,7-dihydro-5H-benzo[6,7]cyclohepta[1,2-c]pyridazin-3-yl)-N⁵-(3-fluoro-4-(4-cyclopropylmethylpiperazin-1-yl)phenyl)-1H-1,2,4-triazole-3,5-diamine.

Another embodiment is a compound of formula (Ib), as described above, wherein:

$R^1$, $R^4$ and $R^5$ are each independently hydrogen;

$R^2$ is 6,7,8,9-tetrahydro-5H-benzo[7]annulene-2-yl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —R¹³—OR¹², —R¹³—OC(O)—R¹², —R¹³—O—R¹⁴—N(R¹²)₂, —R¹³—N(R¹²)—R¹⁴—N(R¹²)₂, —R¹³—N(R¹²)₂, —R¹³—C(O)R¹², —R¹³—C(O)OR¹², —R¹³—C(O)N(R¹²)₂, —R¹³—C(O)N(R¹²)—R¹⁴—N(R¹²)R¹³, —R¹³—C(O)N(R¹²)—R¹⁴—OR¹², —R¹³—N(R¹²)C(O)OR¹², —R¹³—N(R¹²)C(O)R¹², —R¹³—N(R¹²)S(O)ₜR¹² (where t is 1 or 2), —R¹³—S(O)ₜOR¹² (where t is 1 or 2), —R¹³—S(O)ₚR¹² (where p is 0, 1 or 2), and —R¹³—S(O)ₜN(R¹²)₂ (where t is 1 or 2);

$R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R⁹—OR⁸, —R⁹—OC(O)—R⁸, —R⁹—N(R⁶)R⁷, —R⁹—C(O)R⁸, —R⁹—C(O)OR⁸, —R⁹—C(O)N(R⁶)R⁷, —R⁹—N(R⁶)C(O)OR¹², —R⁹—N(R⁶)C(O)R⁸, —R⁹—N(R⁶)S(O)ₜR⁸ (where t is 1 or 2), —R⁹—S(O)ₜOR⁸ (where t is 1 or 2), —R⁹—S(O)ₚR⁸ (where p is 0, 1 or 2), and —R⁹—S(O)ₜN(R⁶)R⁷ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R¹⁰—OR⁸, —R¹⁰—CN, —R¹⁰—NO₂, —R¹⁰—N(R⁸)₂, —R¹⁰—C(O)OR⁸ and —R¹⁰—C(O)N(R⁸)₂, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ib), as described above, selected from the group consisting of:

1-(6,7-dihydro-5H-benzo[6,7]cyclohepta[1,2-c]pyridazin-3-yl)-N⁵-(7-((bicyclo[2.2.1]heptan-2-yl)(methyl)amino)-6,7,8,9-tetrahydro-5H-benzo[7]annulene-2-yl)-1H-1,2,4-triazole-3,5-diamine; and 1-(6,7-dihydro-5H-benzo[6,7]cyclohepta[1,2-c]pyridazin-3-yl)-$N^5$-(7-(S)-pyrrolidin-1-yl-6,7,8,9-tetrahydro-5H-benzo[7]annulene-2-yl)-1H-1,2,4-triazole-3,5-diamine.

Another embodiment is a compound of formula (Ib), as described above, wherein:

$R^1$, $R^4$ and $R^5$ are each independently hydrogen;

$R^2$ is heteroaryl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{13}-OR^{12}$, $-R^{13}-OC(O)-R^{12}$, $-R^{13}-O-R^{14}-N(R^{12})_2$, $-R^{13}-N(R^{12})-R^{14}-N(R^{12})_2$, $-R^{13}-N(R^{12})_2$, $-R^{13}-C(O)R^{12}$, $-R^{13}-C(O)OR^{12}$, $-R^{13}-C(O)N(R^{12})_2$, $-R^{13}-C(O)N(R^{12})-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^{13}-S(O)_tN(R^{12})_2$ (where t is 1 or 2);

$R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-O-R^{10}-OR^8$, $-R^9-O-R^{10}-O-R^{10}-OR^8$, $-R^9-O-R^{10}-CN$, $-R^9-O-R^{10}-C(O)OR^8$, $-R^9-O-R^{10}-C(O)N(R^6)R^7$, $-R^9-O-R^{10}-S(O)_pR^8$ (where p is 0, 1 or 2), $-R^9-O-R^{10}-N(R^6)R^7$, $-R^9-O-R^{10}-C(NR^{11})N(R^{11})H$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^6)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{11}$ is independently selected from the group consisting of hydrogen, alkyl, cyano, nitro and $-OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12's}$, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ib), as described above, wherein:

$R^1$, $R^4$ and $R^5$ are each independently hydrogen;

$R^2$ is heteroaryl selected from the group consisting of pyridinyl, pyrimidinyl, 4,5-dihydro-1H-benzo[b]azepin-2(3H)-on-8-yl, benzo[d]imidazolyl, 6,7,8,9-tetrahydro-5H-pyrido[3,2-c]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, and 6,7,8,9-tetrahydro-5H-cyclohepta[b]pyridin-3-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, $-R^{13}-OR^{12}$, $-R^{13}-OC(O)-R^{12}$, $-R^{13}-O-R^{14}-N(R^{12})_2$, $-R^{13}-N(R^{12})-R^{14}-N(R^{12})_2$, $-R^{13}-N(R^{12})_2$, $-R^{13}-C(O)R^{12}$, $-R^{13}-C(O)OR^{12}$, $-R^{13}-C(O)N(R^{12})_2$, $-R^{13}-C(O)N(R^{12})-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^{13}-S(O)_tN(R^{12})_2$ (where t is 1 or 2);

$R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]

annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—$OC(O)$—$R^8$, —$R^9$—$N(R^6)R^7$, —$R^9$—$C(O)R^9$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2);

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—$CN$, —$R^{10}$—$NO_2$, —$R^{10}$—$N(R^8)_2$, —$R^{10}$—$C(O)OR^8$ and —$R^{10}$—$C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a compound of formula (Ib), as described above, selected from the group consisting of:

1-(6,7-dihydro-5H-benzo[6,7]cyclohepta[1,2-c]pyridazin-3-yl)-$N^5$-(6-(4-(pyrrolidin-1-yl)piperidin-1-yl)-5-methylpyridin-3-yl)-1H-1,2,4-triazole-3,5-diamine;

1-(6,7-dihydro-5H-benzo[6,7]cyclohepta[1,2-c]pyridazin-3-yl)-$N^5$-(4-(3,5-dimethylpiperazin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(1,2,3,4-tetrahydroisoquinolin-7-yl)-1H-1,2,4-triazole-3,5-diamine; and 1-(6,7-dihydro-5H-benzo[6,7]cyclohepta[1,2-c]pyridazin-3-yl)-$N^5$-(2-(1-methylpiperidin-4-yl)-1,2,3,4-tetrahydroisoquinolin-7-yl)-1H-1,2,4-triazole-3,5-diamine.

Of the heteroaryls for $R^2$ and $R^3$, preferred embodiments are selected from the group consisting of pyridinyl, pyrimidinyl, 4,5-dihydro-1H-benzo[b]azepin-2(3H)-on-8-yl, benzo[d]imidazolyl, 6,7,8,9-tetrahydro-5H-pyrido[3,2-d]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, thieno[3,2-d]pyrimidinyl and 6,7,8,9-tetrahydro-5H-cyclohepta[b]pyridin-3-yl, each optionally substituted as described herein.

Of the polycyclic heteroaryls containing more than 14 ring atoms for $R^2$ and $R^3$, preferred embodiments are selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-c]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted as described herein for polycyclic heteroaryls containing more than 14 ring atoms.

In another embodiment of the invention, the compounds are according to formula (Ia1):

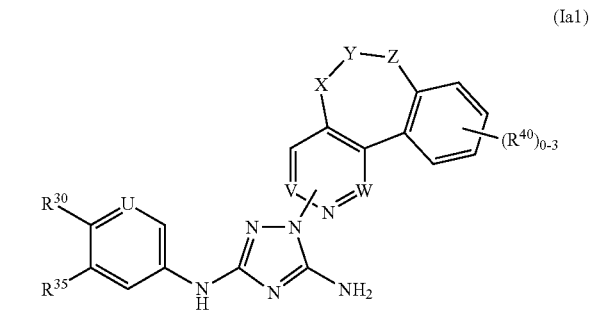

(Ia1)

where:

U is N or $CR^{25}$;

V and W are each independently selected from N and CH, where N1 of the triazole can connect to the C of V, W or the depicted CH in the ring containing V and W;

X, Y, and Z are each independently selected from $C(R^{26})_2$, NR, O and S; provided there are no contiguous heteroatoms in the X, Y, Z atom chain;

each of $R^{25}$, $R^{26}$, $R^{35}$, and $R^{40}$ is selected from the group consisting of hydrogen, cyano, nitro, halo, haloalkyl, optionally substituted alkyl, optionally substituted cycloalkyl, optionally substituted heterocyclyl, $-R^9-OR^8$, $-R^9-O-R^{10}-OR^8$, $-R^9-O-R^{10}-O-R^{10}-OR^8$, $-R^9-O-R^{10}-CN$, $-R^9-O-R^{10}-C(O)OR^8$, $-R^9-O-R^{10}-C(O)N(R^6)R^7$, $-R^9-O-R^{10}-S(O)_pR^8$ (where p is 0, 1 or 2), $-R^9-O-R^{10}-N(R^6)R^7$, $-R^9-O-R^{10}-C(NR^{11})N(R^{11})H$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^8)C(O)OR^8$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and $-OR^8$;

two of $R^{26}$ on the same carbon can form oxo or thioxo;

$R^{30}$ and $R^{35}$ can combine, together with the atoms to which they are attached, to form an optionally substituted $O_{3-5}$ alkylene wherein one or two of the alkylene carbons is optionally replaced by O, $S(O)_{0-2}$ or $N(R^{26})$.

Of the various aspects of the pharmaceutical compositions of the invention comprising a pharmaceutically acceptable excipient and a compound of formula (I), as set forth above in the Summary of the Invention, certain embodiments are preferred.

One embodiment of these pharmaceutical compositions is wherein the compound of formula (I) therein is selected from any one embodiment of the compound of formula (Ia), as set forth above, or from any combination of embodiments of the compound of formula (Ia), as set forth above, or the compound of formula (I) therein is selected from any one embodiment of the compound of formula (Ib), as set forth above, or from any combination of embodiments of the compound of formula (Ib), as set forth above.

Of the various aspects of methods of treating a disease or condition associated with Axl activity in a mammal, wherein the method comprises administering to a mammal in need thereof a therapeutically effective amount of a compound of formula (I), certain embodiments are preferred.

One embodiment of these methods is the method wherein the disease or condition is selected from the group consisting of rheumatoid arthritis, vascular disease, vascular injury, psoriasis, visual impairment due to macular degeneration, diabetic retinopathy, retinopathy of prematurity, kidney disease, osteoarthritis and cataracts.

One embodiment of these methods is the method wherein a manifestation of the disease or condition is solid tumor formation in said mammal.

One embodiment of these methods is the method wherein the disease or condition is selected from the group consisting of breast carcinoma, renal carcinoma, endometrial carcinoma, ovarian carcinoma, thyroid carcinoma, non-small cell lung carcinoma, and uveal melanoma.

One embodiment of these methods is the method wherein a manifestation of the disease or condition is liquid tumor formation in said mammal.

One embodiment of these methods is the method wherein the disease or condition is myeloid leukemia or lymphoma.

One embodiment of these methods is the method wherein the disease or condition is endometriosis.

One embodiment of these methods is the method wherein the compounds of formula (I) utilized therein is selected from any one embodiment of the compound of formula (Ia), as set forth above, or from any combination of embodiments of the compound of formula (Ia), as set forth above, or the compound of formula (I) therein is selected from any one embodiment of the compound of formula (Ib), as set forth above, or from any combination of embodiments of the compound of formula (Ib), as set forth above.

Another embodiment of the invention are those methods of treating a disease or condition associated with Axl activity by administering to the mammal a therapeutically effective amount of a pharmaceutical composition of the invention, as set forth above in the Summary of the Invention, wherein the disease or condition is selected from the group consisting of rheumatoid arthritis, vascular disease/injury (including but not limited to restenosis, atherosclerosis and thrombosis), psoriasis, visual impairment due to macular degeneration, diabetic retinopathy or retinopathy of prematurity, kidney disease (including but not limited to glomerulonephritis, diabetic nephropathy and renal transplant rejection), osteoarthritis and cataracts.

Another embodiment of the invention are those methods of treating a disease or condition associated with Axl activity by administering to the mammal a therapeutically effective amount of a pharmaceutical composition of the invention, as set forth above in the Summary of the Invention, wherein the disease or condition is selected from the group consisting of breast carcinoma, renal carcinoma, endometrial carcinoma, ovarian carcinoma, thyroid carcinoma, non-small cell lung carcinoma, uveal melanoma, myeloid leukemia and lymphoma.

Another embodiment of the invention are those methods of treating a disease or condition associated with Axl activity by administering to the mammal of therapeutically effective amount of a pharmaceutical composition of the invention, as set forth above in the Summary of the Invention, wherein the disease or condition is endometriosis.

Of the various aspects of the processes for preparing an aryl-fused cycloheptanone or a heteroaryl-fused cycloheptanone of formula (I), as set forth above in the Summary of the Invention, certain embodiments are preferred, as described in more detailed below in the Preparation of the Compounds of the Invention section. One embodiment is wherein the aryl-fused cycloheptanone or a heteroaryl-fused cycloheptanone of formula (I) so form by the processes are used as intermediates in the preparation of the compounds of the invention.

Specific embodiments of the invention are described in more detail in the following sections.

Utility and Testing of the Compounds of the Invention

The oncogenic RTK, Axl, was recently identified, using a retroviral-based functional genetic screening protocol, as a regulator of haptotactic migration, which is a key event in angiogenesis. Axl inhibition by RNAi-mediated silencing blocked endothelial cell migration, proliferation and in vitro tube formation. These observations, which were disclosed at the American Association Cancer Research General Meeting, Apr. 16-20, 2005, Anaheim, Calif., and The 7th Annual Symposium on Anti-Angiogenic Agents, Feb. 10-13, 2005, San Diego, Calif.; (*Requirement for The Receptor Tyrosine Kinase Axl in Angiogenesis and Tumor Growth*, Holland, S. J. Powell, M. J., Franci, C., Chan, E., Friera, A. M., Atchison, R., Xu, W., McLaughlin, J., Swift, S. E., Pali, E., Yam, G., Wong, S., Xu, X., Hu, Y., Lasaga, J., Shen, M., Yu, S., Daniel, R., Hitoshi, Y., Bogenberger, J., Nor, J. E., Payan, D. G and Lorens, J. B), were substantiated by an in vivo study which demonstrated that stable, shRNAi-mediated Axl knockdown impaired formation of functional human blood vessels in a mouse model of human angiogenesis. These observations were published in a peer reviewed journal (Holland S J, Powell M J, Franci C, Chan E W, Friera A M, Atchison R E, McLaughlin J, Swift S E, Pali E S, Yam G, Wong S, Lasaga J, Shen M R, Yu S, Xu W, Hitoshi Y, Bogenberger J, Nor J E, Payan D G, Lorens J B. "Multiple roles for the receptor tyrosine kinase axl in tumor formation." *Cancer Res*. (2005) Vol 65 pp 9294-303. These observations are also disclosed in U.S. Published Patent Application 2005/0118604 and European Patent Application 1 563 094, the disclosures of which are incorporated in full by reference. Axl signaling, therefore, impacts multiple functions required for neovascularization in vitro, and regulates angiogenesis in vivo. Regulation of these pro-angiogenic processes required the catalytic activity of Axl. Thus, Axl-mediated angiogenic stimulation would be amenable to modulation by a small molecule inhibitor of Axl catalytic activity.

Accordingly, the compounds of the invention are small molecule inhibitors of Axl catalytic activity, and are therefore useful in treating diseases and conditions which are associated with Axl catalytic activity including those diseases and conditions which are characterized by angiogenesis and/or cell proliferation. In particular, the compounds of the invention and pharmaceutical compositions of the invention are useful in treating diseases and conditions which are alleviated by the modulation of Axl activity. For purposes of this invention, diseases and conditions which are alleviated by the "modulation of Axl activity" includes diseases and conditions which are alleviated by a decrease in Axl activity and diseases and conditions which are alleviated by an increase in Axl activity. Preferably such diseases and conditions are alleviated by a decrease in Axl activity. Diseases and conditions which are alleviated by the modulation of Axl activity include, but are not limited to, solid tumors, including, but not limited to, breast, renal, endometrial, ovarian, thyroid, and non-small cell lung carcinoma, melanoma, prostate carcinoma, sarcoma, gastric cancer and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis, osteoporosis and cataracts.

In addition to the foregoing, the compounds of the invention are useful in treating diseases and conditions which are affected by the following biological processes: Invasion, migration, metastasis, or drug resistance as manifested in cancer; stem cell biology as manifested in cancer; invasion, migration, adhesion, or angiogenesis as manifested in endometriosis; vascular remodeling as manifested in cardiovascular disease, hypertension or vascular injury; bone homeostasis as manifested in osteoporosis or osteoarthritis; viral infection as manifested, for example, in ebola virus infection; or differentiation as manifested in obesity. The compounds of the invention may also be used to modulate inflammatory processes by treating sepsis, acting as vaccine adjuvants, and/or potentiating the immune response in immuno-compromised patients.

The following animal models provide guidance to one of ordinary skill in the art in testing the compounds of the invention for their use in treating the disease or condition indicated.

The compounds of the invention may be tested for their use in treating leukemias and lymphomas by testing the compounds in the xenograft in SCID mouse model using human Axl-expressing cancer cell lines including, but not limited to, HeLa, MDA-MB-231, SK-OV-3, OVCAR-8, DU145, H1299, ACHN, A498 and Caki-1.

The compounds of the invention may be tested for their use in treating leukemias in the xenograft in SCID or nu/nu mouse model using human Axl-expressing AML and CML leukemia cell lines.

The compounds of the invention may be tested for their use in treating endometriosis by using the syngeneic mouse model of endometriosis (see Somigliana, E. et al., "Endometrial ability to implant in ectopic sites can be prevented by interleukin-12 in a murine model of endometriosis", *Hum. Reprod*. (1999), Vol. 14, NO. 12, pp. 2944-50). The compounds may also be tested for their use in treating endometriosis by using the rat model of endometriosis (see Lebovic, D. I. et at., "Peroxisome proliferator-activated receptor-gamma induces regression of endometrial explants in a rat model of endometriosis", *Fertil. Steril*. (2004), 82 Suppl 3, pp. 1008-13).

The compounds of the invention may be tested for their use in treating restenosis by using the balloon-injured rate carotid artery model (see Kim, D. W. et al., "Novel oral formulation of paclitaxel inhibits neointimal hyperplasia in a rat carotid artery injury model", *Circulation* (2004), Vol. 109, No. 12, pp. 1558-63, Epub 2004 Mar. 8).

The compounds of the invention may also be tested for their use in treating restenosis by using the percutaneous transluminal coronary angioplasty in apoE deficient mouse model (see von der Thusen, J. H. et al., "Adenoviral transfer of endothelial nitric oxide synthase attenuates lesion formation in a novel murine model of postangioplasty restenosis", *Arterioscler. Thromb. Vasc. Biol.* (2004), Vol. 24, No. 2, pp. 357-62).

The compounds of the invention may be tested for their use in treating atherosclerosis/thrombosis in the ApoE deficient mouse model (see Nakashima, Y. et al., "ApoE-deficient mice develop lesions of all phases of atherosclerosis throughout the arterial tree", *Arterioscler. Thromb.* (1994), Vol. 14, No. 1, pp. 133-40).

The compounds of the invention may also be tested for their use in treating thrombosis using the collagen-epinephrine-induced pulmonary thromboembolism model and the stasis induced venous thrombosis model (see Angelillo-Scherrer A. et al., "Role of Gas6 receptors in platelet signaling during thrombus stabilization and implications for antithrombotic therapy", *J Clin Invest.* (2005) Vol 115 pp 237-46).

The compounds of the invention may be tested for their use in treating psoriasis by using the SCID mouse model or the human skin model of psoriasis (see Nickoloff, B. J. et al., "Severe combined immunodeficiency mouse and human psoriatic skin chimeras. Validation of a new animal model", *Am. J. Pathol.* (1995), Vol. 146, No. 3, pp. 580-8).

The compounds of the invention may be tested for their use in treating age-related macular degeneration or diabetic retinopathy by using the rat corneal angiogenesis model (see Sarayba M A, Li L, Tungsiripat T, Liu N H, Sweet P M, Patel A J, Osann K E, Chittiboyina A, Benson S C, Pershadsingh H A, Chuck R S. Inhibition of corneal neovascularization by a peroxisome proliferator-activated receptor-gamma ligand. *Exp Eye Res.* 2005 March; 80(3):435-42) or the laser-induced mouse choroidal neovasculation model (see Bora, P. S., et al., "Immunotherapy for choroidal neovascularization in a laser-induced mouse model simulating exudative (wet) macular degeneration", *Proc. Natl. Acad. Sci. U.S.A.* (2003), Vol. 100, No. 5, pp. 2679-84, Epub Feb. 14).

The compounds of the invention may be tested for their use in treating retinopathy of prematurity in the mouse retinopathy of prematurity model (see Smith, L. E. et al., "Oxygen-induced retinopathy in the mouse", *Invest. Ophthalmol. Vis. Sci.* (1994), Vol. 35, No. 1, pp. 101-11).

The compounds of the invention may be tested for their use in treating glomerulonephritis or diabetic nephropathy in the rat anti-Thy1,1-induced experimental mesangial proliferative glomerulonephritis model (see Smith, L. E. et al. cited above).

The compounds of the invention may be tested for their use in treating renal transplant rejection by using a rat model of chronic renal transplant rejection (see Yin, J. L. et al., "Expression of growth arrest-specific gene 6 and its receptors in a rat model of chronic renal transplant rejection", *Transplantation* (2002), Vol. 73, No. 4, pp. 657-60).

The compounds of the invention may be tested for their use in treating rheumatoid arthritis by using the CAIA mouse model (see Phadke, K. et al., "Evaluation of the effects of various anti-arthritic drugs on type II collagen-induced mouse arthritis model", *Immunopharmacology* (1985), Vol. 10, No. 1, pp. 51-60).

The compounds of the invention may be tested for their use in treating osteoarthritis by using the STR/ORT mouse model (see Brewster, M. et al., "Ro 32-3555, an orally active collagenase selective inhibitor, prevents structural damage in the STR/ORT mouse model of osteoarthritis", *Arthritis. Rheum.* (1998), Vol. 41, No. 9, pp. 1639-44).

The compounds of the invention may be tested for their use in treating osteoporosis by using the ovariectomized rat model (see Wronski, T. J. et al., "Endocrine and pharmacological suppressors of bone turnover protect against osteopenia in ovariectomized rats", *Endocrinology* (1989), Vol. 125, no. 2, pp 810-6) or the ovariectomized mouse model (see Alexander, J. M. et al., "Human parathyroid hormone 1-34 reverses bone loss in ovariectomized mice", *J Bone Miner Res.* (2001), Vol. 16, no. 9, pp 1665-73; Fujioka, M. et al., "Equol, a metabolite of daidzein, inhibits bone loss in ovariectomized mice", *J Nutr.* (2004), Vol. 134, no. 10, pp 2623-7).

The compounds of the invention may be tested for their use in treating cataracts by using the $H_2O_2$-induced model (see Kadoya, K. et al., "Role of calpain in hydrogen peroxide induced cataract", *Curr. Eye Res.* (1993), Vol. 12, No. 4, pp. 341-6) or the Emory mouse model (see Sheets, N. L. et al., "Cataract- and lens-specific upregulation of ARK receptor tyrosine kinase in Emory mouse cataract", *Invest. Ophthalmol. Vis. Sci.* (2002), Vol. 43, No. 6, pp. 1870-5).

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 75% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 gm); preferably a therapeutically effective dose is (for a 70 kg mammal) from about 0.01 mg/kg (i.e., 0.7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable salts thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation of the Compounds of the Invention

The following Reaction Scheme illustrates methods to make compounds of this invention, i.e., compounds of formula (I):

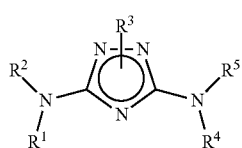

(I)

where $R^1$, $R^2$, $R^3$, $R^4$ and $R^5$ are described above in the Summary of the Invention for compounds of formula (I), as isolated stereoisomers or mixtures thereof, as tautomers or mixtures thereof, or as pharmaceutically acceptable salts or N-oxides. In particular, the following Reaction Scheme illustrates methods to make compounds of formula (Ia):

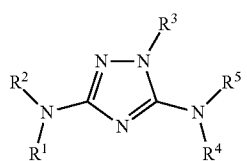

(Ia)

where $R^1$, $R^2$, $R^3$, $R^4$ and $R^5$ are as described above in the Summary of the Invention for compounds of formula (Ia), as isolated stereoisomers or mixtures thereof, as tautomers or mixtures thereof, or as pharmaceutically acceptable salts or N-oxides, and methods to make compounds of formula (Ib);

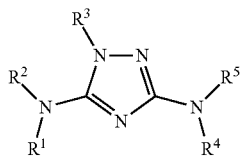

(Ib)

where $R^1$, $R^2$, $R^3$, $R^4$ and $R^5$ are as described above in the Summary of the Invention for compounds of formula (Ib), as isolated stereoisomers or mixtures thereof, as tautomers or mixtures thereof, or as pharmaceutically acceptable salts or N-oxides. It is understood that in the following Reaction Schemes and throughout this description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include benzyl, t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acids include alkyl, aryl or arylalkyl esters.

Protecting groups may be added or removed in accordance with standard techniques, which are known to one of ordinary skill in the art and as described herein.

The use of protecting groups is described in detail in Green, T. W. and P. G. M. Wuts, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs".

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention. $^1$H NMR spectra were recorded in CDCl$_3$, DMSO-d$_6$, CD$_3$OD, Acetone-d$_6$ with trimethylsilane (TMS) as internal reference using Gemini 300 MHz instrument. Reagents and solvents were purchased from commercial sources and used without further purification. Flash column chromatography was conducted using silica gel (230-400 mesh) under a positive pressure of nitrogen. LCMS spectra for purity and mass were recorded using Waters LCMS instruments. Deionized water was used to dilute the reactions and wash the products. Brine used was prepared by dissolving sodium chloride into deionized water to saturation point.

Compounds of formula (Ia), as set forth below in Reaction Scheme 1 below, where $R^1$, $R^2$ and $R^3$ are as defined above in the Summary of the Invention for compounds of formula (I) and $R^4$ and $R^5$ are hydrogen, are generally prepared as illustrated below in Reaction Scheme 1 where $R^1$, $R^2$ and $R^3$ are as defined above in the Summary of the Invention for compounds of formula (I):

REACTION SCHEME 1

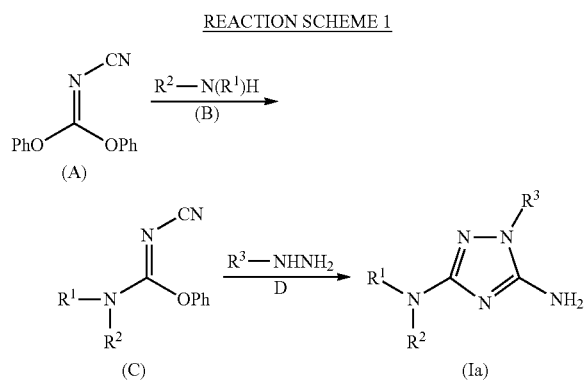

Compounds of formula (A), formula (B) and formula (D) are commercially available or can be prepared by methods known to one skilled in the art or by methods disclosed herein.

In general, compounds of formula (Ia) are prepared, as set forth by Reaction Scheme 1, by first treating a compound of formula (A) (where the phenyl groups therein may be replaced with other suitable groups or suitably substituted groups known to one skilled in the art) (1.1 equiv) with an equivalent amount of an aniline of formula (B) in an polar solvent, including, but not limited to, isopropyl alcohol, at ambient temperatures overnight. The diarylisourea product of formula (C) generally precipitates and isolation can be accomplished via filtration, washing with an appropriate solvent, and drying. Hydrazine hydrate of formula (D) (2 equivalents) is added to a slurry of the compound of formula (C) in an alcohol or other appropriate solvent. Generally, the ring formation reaction occurs at ambient temperature and the product triazole of formula (Ia) can be isolated by standard isolation techniques. Compounds of formula (Ia) can be subsequently treated with an appropriately substituted alkylating or acylating agent under standard conditions to form compounds of formula (Ia) where $R^4$ and $R^5$ are as described above in the Summary of the Invention for compounds of formula (I).

Compounds of formula (Ib) can be prepared using the synthetic route outlined in Reaction Scheme 1 in varying amounts depending on the steric and electronic nature of $R^1$, $R^2$ and $R^3$ as well as the particular reaction conditions employed. In some instances, compounds of formula (Ib) are isolated as minor isomers along with compounds of formula (Ia) as major isomers, e.g., during column chromatography as described herein.

Compounds of formula (C-1) are compounds of formula (C), as set forth above in Reaction Scheme 1, where $R^1$ is hydrogen and $R^2$ is 7-(pyrrolidin-1-yl)-6,7,8,9-tetrahydro-5H-benzo[7]annulene-2-yl, that is, where $R^2$ has the following structure:

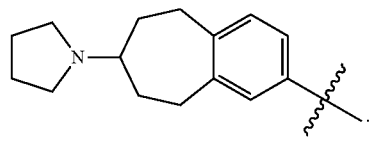 [SMILES: *c1ccc2c(c1)CCC(N1CCCC1)CC2]

Compounds of formula (C-1) can be prepared according to the method described below in relation to Reaction Scheme 2:

REACTION SCHEME 2

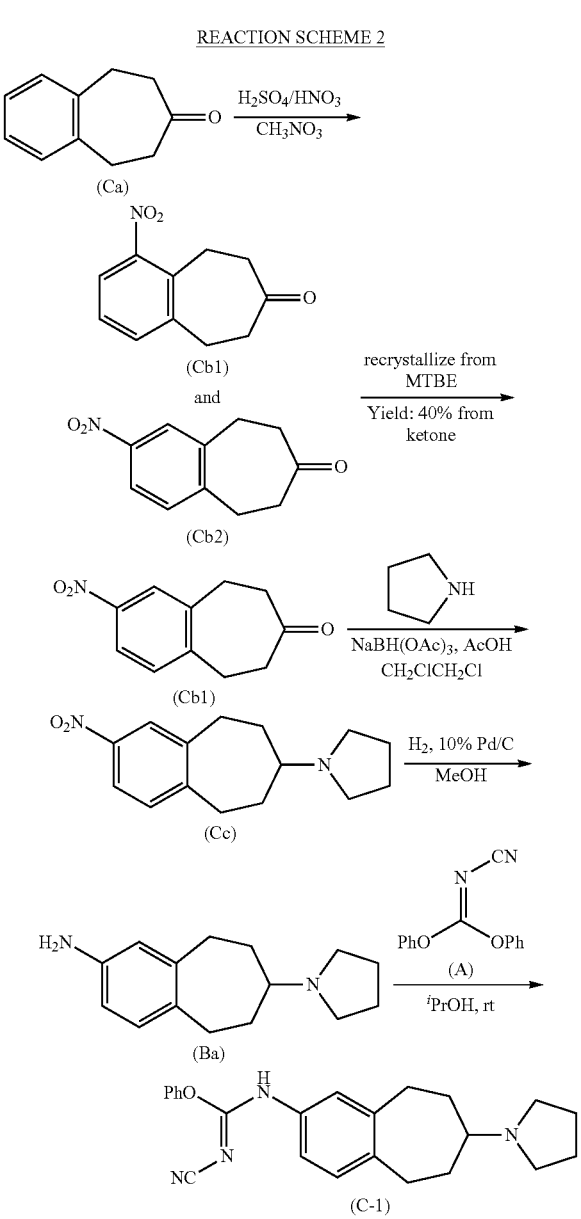

Compounds of formula (Ca) and formula (A) are commercially available or can be prepared according to methods described herein or known to one skilled in the art. Compounds of formula (Ba) are compounds of formula (B), as set forth above in Reaction Scheme 1.

In general, compounds of formula (C-1) are prepared, for example, as set forth above in Reaction Scheme 2, by nitration of the benzo[7]annulene of formula (Ca), followed by isolation of the ketone of formula (Cb1), for example, by crystallization. Reductive amination of the keto group in the ketone of formula (Cb1) yields the pyrrolidine-substituted compound of formula (Cc). Reduction of the nitro group of the pyrrolidine-substituted compound of formula (Cc), for example, by catalytic hydrogenation, gives the aniline of formula (Ba). Reaction of the aniline of formula (Ba) with, for example, diphenyl cyanocarbonimidate of formula (A), yields the compound of formula (C-1). Compounds of formula (C-1) are enantiomeric. The enantiomers of compound (C-1), and similar compounds, are separable by, e.g., chiral phase HPLC. The enantiomers of compounds (C-1) were separated in this manner. Each of the enantiomers of compounds (C-1) were used to synthesize compounds of formula (I) (see SYNTHETIC EXAMPLE 2 below). One aspect of the invention is a process for preparing an aryl-fused cycloheptanone or a heteroaryl-fused cycloheptanone of formula (I):

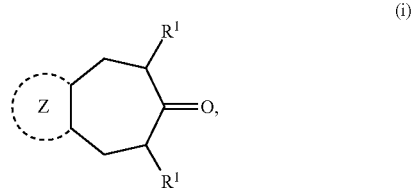

(i)

where Z is an aryl or a heteroaryl and each $R^1$ is independently selected from the group consisting of hydrogen, optionally substituted alkyl, optionally substituted aralkyl, and optionally substituted heteroarylalkyl. These compounds are useful as intermediates in the preparation of the compounds of the invention, and can be prepared as described below in REACTION SCHEME 2A wherein Z is an aryl or a heteroaryl, each $R^1$ is independently selected from the group consisting of hydrogen, optionally substituted alkyl, optionally substituted aralkyl, and optionally substituted heteroarylalkyl, each $R^2$ is independently selected from the group consisting of optionally substituted alkyl, optionally substituted arylalkyl, and optionally substituted heteroarylalkyl, and each LG is independently a suitable leaving group:

REACTION SCHEME 2A

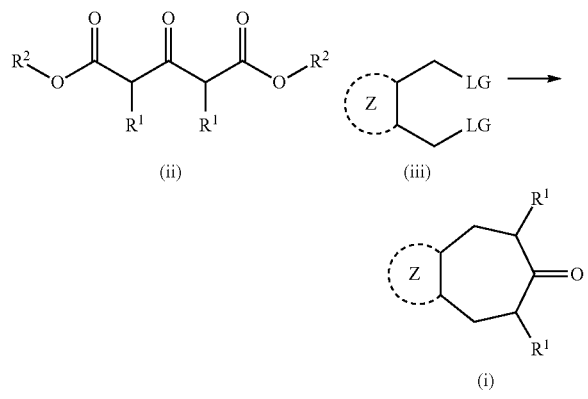

In this process, a reactant of formula (II) is first combined with a reactant of formula (iii) in the presence of a protic solvent, an aprotic solvent, and a base to give an intermediate, for example, 8,9-dihydro-5H-benzo[7]annulen-7(6H)-one substituted at the 6-, 8-, or 6- and 8-positions or mixtures thereof with carboxy ester groups. Suitable leaving groups for this process include, but are not limited to, quaternary ammonium salts, alkyl or aryl sulfonates (e.g., methane sulfonate, tosylate, triflate), alkyl or aryl sulfides, phosphonates, and halogens (e.g., F, Cl, Br, I). In a specific embodiment, the leaving group LG is halogen. In a more specific embodiment LG is bromo. The intermediate, for example, 8,9-dihydro-5H-benzo[7]annulen-7(6H)-one, is then exposed to basic hydrolytic media followed by an acid to form compounds of formula (I). In some embodiments, the intermediate, for example, 8,9-dihydro-5H-benzo[7]annulen-7(6H)-one, is subjected to an acid media prior to exposure to the basic hydrolytic media. In some embodiments the intermediate, for example, 8,9-dihydro-5H-benzo[7]annulen-7(6H)-one, is subjected to an acid media and isolated prior to exposure to the basic hydrolytic media.

In some embodiments, Z is phenyl, $R^2$ is lower alkyl and $R^1$ is hydrogen. Exemplary protic solvents include, but are limited to, alcohols, preferably alkanols, e.g., methanol, ethanol and the like. Exemplary aprotic solvents include, but are not limited to, ethers, e.g. THF, crown ethers and the like. In some embodiments, the aprotic and protic solvents are in about a 1:1 ratio by volume. Exemplary bases include, but are not limited to, metal alkoxides, e.g., lithium, sodium or potassium alkoxides. In one exemplary embodiment, the metal alkoxide is sodium methoxide. Exemplary acids and acidic media include inorganic and organic acids, typically diluted with water. Such inorganic and organic acids are described above in the Definitions section, under "pharmaceutically acceptable acid addition salt" and "pharmaceutically acceptable base addition salt". Exemplary basic hydrolytic media include, but are not limited to, alcoholic solutions of metal hydroxides or metal alkoxides. In some embodiments, the basic hydrolytic media includes an alcoholic solution of a metal hydroxide.

Preferably the combination of a reactant of formula (II) with a reactant of formula (iii) in the presence of a protic solvent, an aprotic solvent, and a base process described above is performed within a temperature range of between about −10° C. and about 100° C., more preferably within a temperature range of between about 0° C. and about 50° C., even more preferably, within a temperature range of between about 0° C. and about 30° C.

Preferably, exposure of the intermediate of the first step of the process to basic hydrolytic media followed by an acid to form compounds of formula (I) is performed within a temperature range of between about 40° C. and about 150° C., more preferably within a temperature range of between about 60° C. and about 100° C., even more preferably within a temperature range of between about 60° C. and about 100° C.

Accordingly, an exemplary process for making the compound of formula (Ca), i.e., 8,9-dihydro-5H-benzo[7]annulen-7(6H)-one, as described above in Reaction Scheme 2, is described below in relation to REACTION SCHEME 2B.

REACTION SCHEME 2B

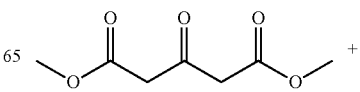

-continued

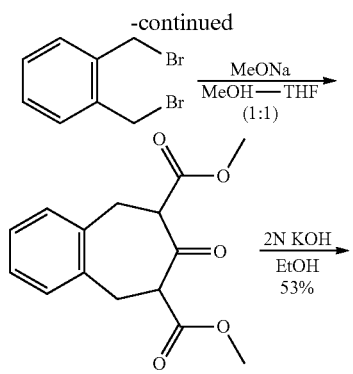

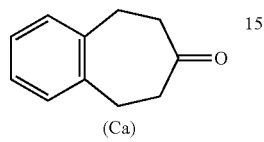

(Ca)

Dimethyl 3-oxopentanedioate and 1,2-bis(2-bromomethyl)benzene are commercially available, or can be prepared according to methods disclosed herein or methods known to one skilled in the art. The ester groups need not be methyl esters and the bromo groups need not be bromo groups in that any suitable leaving group will suffice. Also, as described above, the 3-oxopentanedioate may be substituted at the 2- and 4-positions as long as one proton on each of the 2- and 4-positions exists given that at least one proton is needed for the deprotonation and subsequent C-C bond formation with the carbon bearing the leaving group.

Accordingly, compounds of formula (Ca) are prepared, as set forth above in REACTION SCHEME 2B, by first combining a pentane-3-dioate, e.g. dimethyl 3-oxopentanedioate shown, with a 1,2-bismethyl aromatic having a suitable leaving group on each methyl group, e.g., 1,2-bis(bromomethyl)benzene, in a mixed protic/aprotic solvent medium, e.g., THF-MeOH, and a metal alkoxide, e.g., sodium methoxide. The metal alkoxide can be added as such or made in situ via careful addition (e.g., at low temperature) of the appropriate metal to at least the protic solvent, preferably prior to combination with the remaining reactants. The intermediate benzo[7]annulene product so formed can be optionally isolated and may contain one or two carboxy ester groups depending on the reaction conditions, e.g., methyl 7-oxo-6,7,8,9-tetrahydro-5H-benzo[7]annulene-6,8-dicarboxylate, as shown above. The intermediate, dimethyl 7-oxo-6,7,8,9-tetrahydro-5H-benzo[7]annulene-6,8-dicarboxylate, is subjected to basic hydrolysis (saponification) conditions followed by acidification to give compounds of formula (Ca).

Compounds of formula (Da) are compounds of formula (D), as shown above in Reaction Scheme 1, where $R^3$ is 6,7-dihydro-5H-benzo[6,7]cyclohepta[1,2-c]pyridazin-3-yl, that is, where $R^3$ has the following structure:

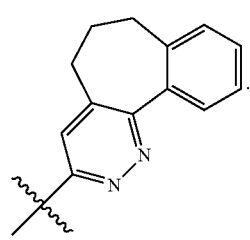 [SMILES: *c1cc2c(nn1)-c1ccccc1CCC2]

Compounds of formula (Da) can be prepared according to the method disclosed below in Reaction Scheme 3:

REACTION SCHEME 3

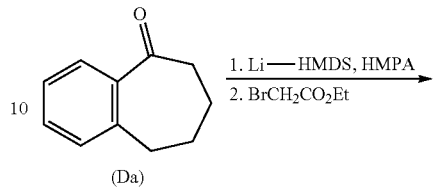

(Da)

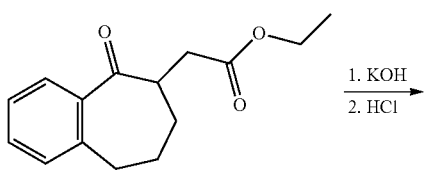

(Db)

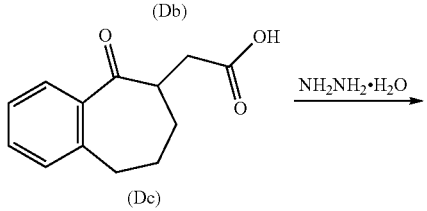

(Dc)

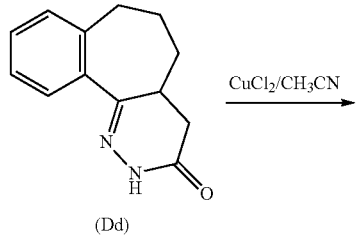

(Dd)

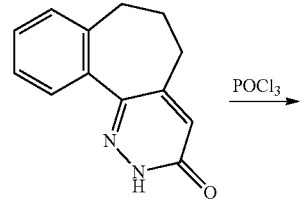

(De)

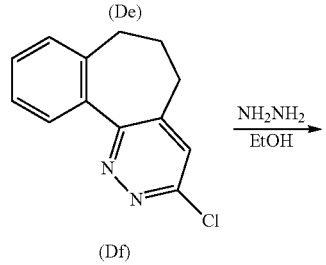

(Df)

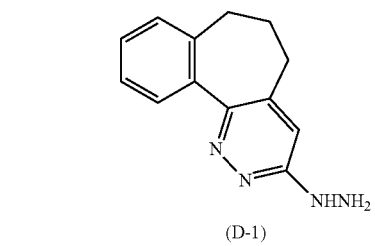

(D-1)

Compounds of formula (Da) are commercially available or can be prepared by methods known to one skilled in the art or by methods disclosed herein.

In general, compounds of formula (D-1) are prepared, as set forth above in Reaction Scheme 3, by first dissolving the compound of formula (Da) (1.0 equiv) in an anhydrous aprotic polar solvent or mixture of such solvents, for example, tetrahydrofuran with hexamethylphosphoramide (HMPA) (1.2 equiv). The resulting solution is stirred at ambient temperature for about 10 minutes and then cooled to a temperature of between about −10° C. and about 5° C., preferably at 0° C. A strong base, lithium bis(trimethylsilyl)amide (Li-HMDS) (1.1 equiv), is then added dropwise to the stirred mixture over a period of time of between about 20 minutes and 40 minutes, preferably over 30 minutes, while maintaining the temperature of the resulting mixture at between about −10° C. and about 5° C., preferably at 0° C. Ethyl bromoacetate (2.5 equiv) is then added to the resulting anion of (Da) and the resulting mixture is stirred for additional period of time of between about 5 minutes and 15 minutes, preferably for about 10 minutes, and then allowed to warm to ambient temperature and stirred at ambient temperature for a period of time of between about 30 minutes and 3 hours, preferably for about 2 hours. The compound of formula (Db) is then isolated from the reaction mixture by standard isolation techniques known to one skilled in the art, such as solvent evaporation and purification by flash column chromatography.

The compound of formula (Db) is then treated under basic hydrolysis conditions to form the compound of formula (Dc), which is isolated from the reaction mixture by standard isolation techniques known to one skilled in the art.

The compound of formula (Dc) (1.0 equiv) is then treated with hydrazine hydrate (1.25 equiv) in the presence of a polar protic solvent, such as ethanol, to yield the compound of formula (Dd), which is isolated from the reaction mixture by standard isolation techniques known to one skilled in the art.

A mixture of the compound of formula (Dd) (1.0 equiv) and anhydrous copper(II) chloride (2.0 equiv) is then refluxed in acetonitrile to yield the unsaturated compound of formula (De), which is isolated from the reaction mixture by standard isolation techniques known to one skilled in the art.

A mixture of the compound of formula (De) and phosphoryl chloride, is refluxed for a period of time of between about 1 hour and 3 hours, preferably for about 2 hours to aromatize and chlorinate the ring containing the N—N linkage. After cooling to ambient temperature, the compound of formula (Df) is isolated from the reaction mixture by standard isolation techniques known to one skilled in the art.

Skilled artisans would appreciate that the compound of formula (Df) can be used to make the corresponding 3-aniline which can be used as an aniline of formula (B), as outlined in Reaction Scheme 1 above, to make embodiments of the invention.

A mixture of the compound of formula (Df) (1.0 equiv) and anhydrous hydrazine (19.8 equiv) in a protic solvent, such as ethanol, is refluxed for a period time of between about 4 hours and 24 hours, preferably for about 16 hours. After cooling to ambient temperature, water is added to the mixture and the compound of formula (D-1) is then isolated from the reaction mixture by standard isolation techniques known to one skilled in the art.

Compounds of formula (C-2) are compounds of formula (C), as shown above in Reaction Scheme 1, where $R^1$ is hydrogen and $R^2$ is 5',5'-dimethyl-6,8,9,10-tetrahydro-5H-spiro[cycloocta[b]pyridine-7,2'-[1,3]dioxane]-3-yl, that is, where $R^2$ has the following structure:

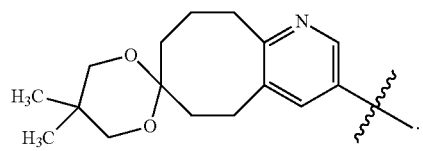

Compounds of formula (C-2) can be prepared according to the method described below in Reaction Scheme 4:

REACTION SCHEME 4

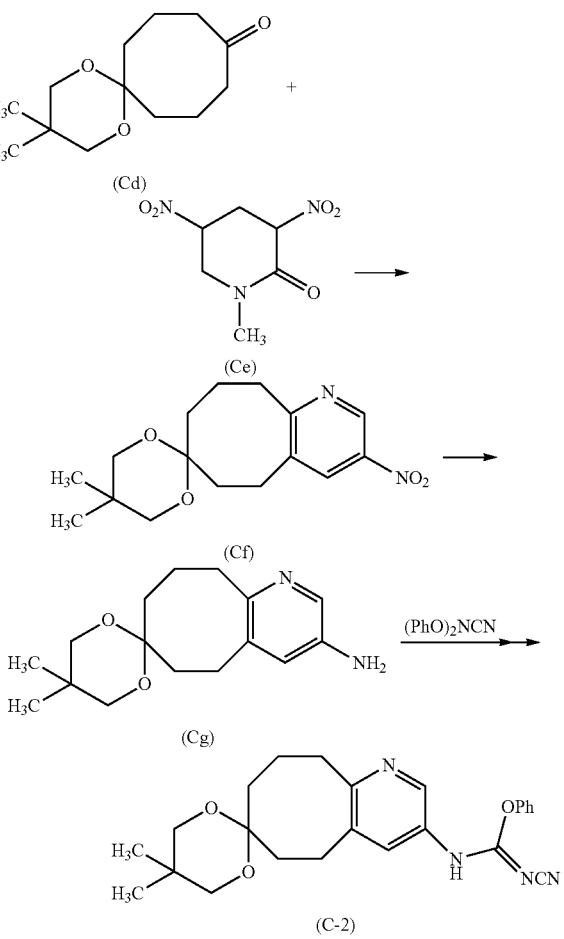

Compounds of formula (Cd) and (Ce) are commercially available or can be prepared according to methods known to one skilled in the art.

In general, compounds of formula (C-2) are prepared, as set forth above in Reaction Scheme 4, by first heating a mixture of the compound of formula (Cd) (1.0 equiv) and a compound of formula (Ce) (0.96 equiv) and ammonia in an protic solvent, such a methanol, to reflux temperature. The compound of formula (Cf) is then isolated from the reaction mixture by standard isolation techniques.

The compound of formula (Cf) is then reduced under standard reduction conditions known to one skilled in the art to yield the compound of formula (Cg).

A mixture of molar equivalent amounts of the compound of formula (Cg), diphenylcyanocarboimidate and diisopropylethylamine in a protic solvent, such as isopropyl alcohol, is stirred at ambient temperature for a period of time of between 8 hours and 16 hours, preferably for about 16 hours, to form the compound of formula (C-2), which is isolated from the reaction mixture by standard isolation techniques known to one skilled in the art.

All compounds of the invention which exist in free base or acid form can be converted to their pharmaceutically acceptable salts by treatment with the appropriate inorganic or organic base or acid by methods known to one of ordinary skill in the art. Salts of the compounds of the invention can be converted to their free base or acid form by standard techniques known to one skilled in the art.

The following specific Synthetic Preparations (for intermediates) and Synthetic Examples (for compounds of the invention) are provided as a guide to assist in the practice of the invention, and are not intended as a limitation on the scope of the invention. The number following each compound below refers to its number in Table 1 and Table 2, as discussed in more detail below.

SYNTHETIC PREPARATION 1

Synthesis of 8,9-dihydro-5H-benzo[7]annulen-7(6H)-one

Compound of Formula (Ca)

A. Sodium methoxide (9.4 g, 174.2 mmol) was added to a 250 mL of flask with dry methanol (100 mL) at 0° C. After the solid was dissolved, the resulting solution was warmed to ambient temperature and was added to a solution of dimethyl acetone-1,3-dicarboxylate (15.2 g, 87.1 mmol) and o-xylylene dibromide (20 g, 75.7 mmol) in 100 mL of dry THF at 0° C. dropwise within 30 min. After the addition, the reaction mixture was warmed to ambient temperature and stirred overnight. The volatiles were evaporated, the residue was poured into 40 mL of 10% HCl solution and extracted with ethyl acetate (EtOAc) (200 mL×2). The combined extracts were washed with water, saturated NaHCO$_3$ solution and brine. After evaporation, the residual oil was used for next step directly.

B. The crude dimethyl 7-oxo-6,7,8,9-tetrahydro-5H-benzo[7]annulene-6,8-dicarboxylate was dissolved in 200 mL of ethanol (EtOH) and then 100 mL of 2 N KOH. The resulting mixture was refluxed at 85° C. for 17 h. After cooling to ambient temperature, the volatiles were evaporated. To the residue was added 120 mL of 2N HCl at 0° C., the crude product was extracted by EtOAc (200 mL×2). The combined extracts were washed with brine. After being dried (MgSO$_4$), filtered, and concentrated, the residue was purified by flash column chromatography on silica gel (hexanes/EtOAc 8:1) to afford 6.6 g (57%) of 8,9-dihydro-5H-benzo[7]annulen-7(6H)-one as a white solid: mp 40-41° C.; $^1$H NMR (300 MHz, CDCl$_3$) δ: 7.21 (m, 4H), 2.94-2.90 (m, 4H), 2.63-2.60 (m, 4H); LC-MS: 161 (M+H)$^+$.

SYNTHETIC PREPARATION 2

Synthesis of 2-nitro-8,9-dihydro-5H-benzo[7]annulen-7(6H)-one

Compound of formula (Cb1)

To a solution of cold (0° C.) concentrated sulfuric acid (15 mL) was added 70% nitric acid (15 mL) dropwise over 30 min. The addition was controlled to maintain the internal reaction temperature below 5° C. After the addition, the resulting solution was transferred into an addition funnel and was added dropwise to a solution of 8,9-dihydro-5H-benzo[7]annulen-7(6H)-one (14 g, 87.5 mmol) in nitromethane (80 mL) at 0° C. over a period of 40 min. After the addition, the reaction mixture was stirred at 0° C. for 2 h. Then ice water (~80 mL) was added to the reaction mixture, and the mixture was stirred for additional 30 min. Then the mixture was transferred to a separatory funnel where the layers were separated. The aqueous layer was extracted with ethyl acetate (3×80 mL). The combined layers were washed with cold water, sat. NaHCO$_3$ solution and brine. After being dried (MgSO$_4$), filtered, and concentrated, the residue was purified by flash column chromatography on silica gel (hexanes/EtOAc=3:1 to 2:1) to afford the mixture of nitro regioisomers (~15 g), which was then purified by recrystallization from MTBE (tert-butyl methyl ether, 180 mL) to yield 7.3 g of 2-nitro-8,9-dihydro-5H-benzo[7]annulen-7(6H)-one (40% yield) as a yellow solid: $^1$H NMR (300 MHz, CDCl$_3$) δ: 8.10-8.06 (m, 2H), 7.40-7.37 (m, 1H), 3.04-3.00 (m, 4H), 2.67-2.65 (m, 4H); LC-MS: 206 (M+H)$^+$.

SYNTHETIC PREPARATION 3

Synthesis of 1-(2-nitro-6,7,8,9-tetrahydro-5H-benzo[7]annulen-7-yl)pyrrolidine

Compound of Formula (Cc)

Pyrrolidine (0.85 g, 12 mmol) and 2-nitro-5,6,8,9-tetrahydro-benzocyclohepten-7-one (2.05 g, 10 mmol) were mixed in 1,2-dichloroethane (35 mL) and then treated with NaBH(OAc)$_3$ (3.18 g, 15 mmol) and AcOH (0.60 g, 10 mmol). The mixture was stirred at ambient temperature under a N$_2$ atmosphere overnight. The reaction mixture was quenched with saturated NaHCO$_3$, and the product was extracted with EtOAc (3×30 mL). The organic layers were combined and dried over NaSO$_4$. The solvent was evaporated and the residue was purified by flash column chromatography eluting with CH$_2$Cl$_2$/DMA=1/1 (DMA=CH$_2$Cl$_2$/MeOH/30% NH$_3$=80/19/1) to afford 1-(2-nitro-6,7,8,9-tetrahydro-5H-benzo[7]annulen-7-yl)pyrrolidine, a yellow oil (2.2 g, 85%); MS (m/e): 261 (M+H$^+$).

SYNTHETIC PREPARATION 4

Synthesis of 7-(pyrrolidin-1-yl)-6,7,8,9-tetrahydro-5H-benzo[7]annulen-2-amine

Compound of Formula (Ba)

A mixture of 1-(2-nitro-6,7,8,9-tetrahydro-5H-benzo[7]annulen-7-yl)pyrrolidine (2.0 g; 7.69 mmol) and 10% palladium on carbon (0.2 g, ~50% water) in methanol (150 mL) was shaken under hydrogen (40 psi) for 1 h. After this time the reaction mixture was filtered through diatomaceous earth and the filtrate was concentrated under reduced pressure to afford 7-(pyrrolidin-1-yl)-6,7,8,9-tetrahydro-5H-benzo[7]annulen-2-amine as an oil (quantitative yield); MS (m/e): 231 (M+H$^+$).

SYNTHETIC PREPARATION 5

Synthesis of Phenyl N'-cyano-N-(7-(pyrrolidin-1-yl)-6,7,8,9-tetrahydro-5H-benzo[7]annulene-2-yl)carbamimidate Compound of formula (C-1)

A mixture of 7-(pyrrolidin-1-yl)-6,7,8,9-tetrahydro-5H-benzo[7]annulen-2-amine (1.7 g; 7.39 mmo) and diphenyl cyanocarboimidate (1.76 g, 7.39 mmol) in 20 mL of isopropanol was stirred at ambient temperature overnight. The solid was filtered, washed with isopropanol and ether and dried to give phenyl N'-cyano-N-(7-(pyrrolidin-1-yl)-6,7,8,9-tetrahydro-5H-benzo[7]annulene-2-yl)carbamimidate, as a white solid (2.2 g, 80%). MS (m/e): 375 (M+H$^+$).

SYNTHETIC PREPARATION 6

Isolation of Phenyl (S)—N'-cyano-N-(7-(pyrrolidin-1-yl)-6,7,8,9-tetrahydro-5H-benzo[7]annulene-2-yl) carbamimidate and Phenyl (R)—N'-cyano-N-(7-(pyrrolidin-1-yl)-6,7,8,9-tetrahydro-5H-benzo[7]annulene-2-yl)carbamimidate Enantiomers of the Compound of Formula (C-1)

Phenyl N'-cyano-N-(7-(pyrrolidin-1-yl)-6,7,8,9-tetrahydro-5H-benzo[7]annulen-2-yl)carbamimidate (0.43 g, racemic) was eluted on a chiral column chromatography mobile phase; ethanol/MeOH/triethyl amine=1/1/0.2% to afford phenyl (S)—N'-cyano-N-(7-(pyrrolidin-1-yl)-6,7,8,9-tetrahydro-5H-benzo[7]annulene-2-yl)carbamimidate and phenyl (R)—N'-cyano-N-(7-(pyrrolidin-1-yl)-6,7,8,9-tetrahydro-5H-benzo[7]annulene-2-yl)carbamimidate: Chiral column: Chiralcel O J, 21.2×250 mm. 10 µM; packing material: cellulose tris-(4-methylbenzoate) coated on 10 µm silica gel substrate. Flow rate 9.9 mL/min, sample solubility 30 mg/mL in methanol. Single enantiomers were isolated in 170 mg and 190 mg quantities, respectively. Absolute configuration of each enantiomer was not determined at this time.

SYNTHETIC PREPARATION 7

Synthesis of ethyl 2-(5-oxo-6,7,8,9-tetrahydro-5H-benzo[7]annulen-6-yl)acetate

Compound of Formula (Db)

To a mixture of 1-benzosuberone (5.0 g, 31.2 mmol, Aldrich) in dry tetrahydrofuran (THF) (20 mL) was added hexamethylphosphoramide (6.5 mL, 37.5 mmol) (99%, Aldrich). The resulting mixture was stirred at ambient temperature for 10 min and then cooled to 0° C. with a ice-water bath, 1.0 M solution of lithium bis(trimethylsilyl)-amide in THF (32.7 mL, 32.7 mmol) was added dropwise in 30 min. After the addition, the reaction mixture was stirred at 0° C. for 30 min. Ethyl bromoacetate (8.7 mL, 78.1 mmol) was then added. After stirring for a further 10 min, the reaction mixture was warmed to ambient temperature and stirred for 2 h. Solvent was evaporated, the residue was diluted with ethyl acetate (EtOAc) (300 mL), and washed with water and brine. After being dried (MgSO$_4$), filtered, and concentrated, the residue was purified by flash column chromatography eluting with hexanes-ethyl acetate 6:1→4:1) to afford 6.6 g of the compound of formula (Db), ethyl 2-(5-oxo-6,7,8,9-tetrahydro-5H-benzo[7]annulen-6-yl)acetate, as an orange oil (84%), $^1$H NMR (300 MHz, CDCl$_3$) δ: 7.69-7.21 (m, 4H), 4.22-4.05 (m, 2H), 3.40-3.30 (m, 1H), 3.12-2.92 (m, 3H), 2.52-2.43 (m, 1H), 2.20-1.58 (m, 4H), 1.28-1.21 (m, 3H); LC-MS: purity: 91.8%; MS (m/e): 247 (MH$^+$).

SYNTHETIC PREPARATION 8

Synthesis of 2-(5-oxo-6,7,8,9-tetrahydro-5H-benzo[7]annulen-6-yl)acetic acid

Compound of Formula (Dc)

The compound of formula (Db), ethyl 2-(5-oxo-6,7,8,9-tetrahydro-5H-benzo[7]annulen-6-yl)acetate, (6.6 g, 26.8 mmol) was dissolved in ethanol (EtOH) (30 mL), then 10% potassium hydroxide (KOH) aqueous solution (37.5 mL, 67 mmol) was added and the resulting mixture was refluxed for 2 h. After cooling to ambient temperature, the EtOH was removed by evaporation. The residue was extracted with EtOAc twice (15 mL×2). The aqueous layer was then transferred into a flask and cooled with an ice-water bath, con. HCl was added dropwise to adjust pH to about 2.0. EtOAc (60 mL) was then added, the layers were separated, and the aqueous layer was extracted with EtOAc. The combined extracts were washed with brine. After being dried (MgSO$_4$), filtered, and concentrated, the compound of formula (Dc), 2-(5-oxo-6,7,8,9-tetrahydro-5H-benzo[7]annulen-6-yl)acetic acid, was obtained as an orange oil (5.7 g, 97%); $^1$H NMR (300 MHz, CDCl$_3$) δ: 7.71-7.68 (m, 1H), 7.41-7.20 (m, 3H), 3.37-3.31 (m, 1H), 3.12-2.91 (m, 3H), 2.57-2.49 (m, 1H), 2.15-1.90 (m, 2H), 1.75-1.62 (m, 2H); LC-MS: purity: 100%; MS (m/e): 219 (MH$^+$).

SYNTHETIC PREPARATION 9

Synthesis of 4a,5,6,7-tetrahydro-2H-benzo[6,7]cyclohepta[c]pyridazin-3(4H)-one

Compound of Formula (Dd)

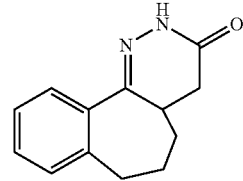 [SMILES: O=C1CC2CCCc3ccccc3C2=NN1]

A. A mixture of the compound of formula (Dc), 2-(5-oxo-6,7,8,9-tetrahydro-5H-benzo[7]annulen-6-yl)acetic acid, (5.7 g, 26.1 mmol) and hydrazine hydrate (1.6 mL, 32.7 mmol) in 20 mL of ethanol was refluxed for 2 h, cooled and filtered (washed with small amount of EtOH) to give the compound of formula (Dd), 4a,5,6,7-tetrahydro-2H-benzo[6,7]cyclohepta[c]pyridazin-3(4H)-one, as a white solid (4.7 g, 84%); $^1$H NMR (300 MHz, CDCl$_3$) δ: 8.61 (bs, 1H), 7.53-7.14 (m, 4H), 2.98-2.75 (m, 3H), 2.58 (dd, J=15.3, 16.8 Hz, 1H), 2.31 (dd, J=12.0, 16.8 Hz, 1H), 1.96-1.59 (m, 4H); LC-MS: purity: 100%; MS (m/e): 215 (MH$^+$).

B. Alternatively, a mixture of benzosuberone (10.6 g, 66.2 mmol), glyoxylic acid monohydrate (6.08 g, 66.2 mMol), sodium hydroxide (10.6 g, 265 mmol), ethanol (40 mL) and water (100 mL) were stirred overnight at ambient temperature, and then heated under reflux for 1 h. The mixture was cooled, then diluted with water and extracted twice with dichloromethane (subsequently discarded). The aqueous layer was then acidified with 10% aqueous hydrochloric acid. Ice was added for cooling. The mixture was then filtered to give a pale yellow solid, 10.5 g (after air drying). The crude solid was then heated at 100° C. for 1 h with a mixture of acetic acid (60 mL), water (30 mL) and zinc dust (6 g). The reaction mixture was cooled to ambient temperature and filtered. The filtrate was extracted with ethyl acetate. The organic layer was washed three times with saturated sodium chloride solution, then dried over anhydrous sodium sulfate and concentrated under vacuum. The crude residue was heated with ethanol (25 mL) and hydrazine monohydrate (10 mL) under reflux for 3 h. The solvent was removed under vacuum and the residue was crystallized from benzene/ethanol, 1/1, to give 4a,5,6,7-tetrahydro-2H-benzo[6,7]cyclohepta[c]pyridazin-3(4H)-one as a white solid, 2.31 g; $^1$H NMR (CDCl$_3$, 300 MHz) 8.66 (s, 1H), 7.52 (d, 1H), 7.24-7.50 (m, 2H), 7.16 (d, 2H), 2.75-3.00 (m, 3H), 2.56 (dd, 1H), 2.31 (dd, 1H), 1.60-1.90 (m, 4H) ppm; MS (ES) 215 (M+H). This procedure followed that reported by V. Peesapati and S. C. Venkata, *Indian J. Chem.*, 41B, 839 (2002).

SYNTHETIC PREPARATION 10

Synthesis of 3-oxo-6,7-dihydro-5H-benzo[6,7]cyclohepta[1,2-c]pyridazine

Compound of Formula (De)

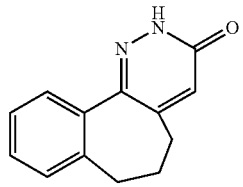 [SMILES: O=c1cc2c(n[nH]1)-c1ccccc1CCC2]

A. A mixture of the compound of formula (Dd), 4a,5,6,7-tetrahydro-2H-benzo[6,7]cyclohepta[c]pyridazin-3(4H)-one (4.7 g, 22 mmol) and anhydrous copper(II) chloride (6 g, 44 mmol) was refluxed in acetonitrile (45 mL) for 2 hours. After cooling to ambient temperature, the mixture was poured into ice-water (200 g) and the solid obtained was washed with 10% HCl solution twice (about 20 mL×2) and cold water twice (about 20 mL×2). After freeze-drying, the compound of formula (De), 3-oxo-6,7-dihydro-5H-benzo[6,7]cyclohepta[1,2-c]pyridazine (4.2 g, 90%) was obtained as a white solid, $^1$H NMR (300 MHz, CDCl$_3$) δ: 10.80 (bs, 1H), 7.53-7.21 (m, 4H), 6.77 (s, 1H), 2.66 (t, J=6.9 Hz, 2H), 2.45 (t, J=6.9 Hz, 2H), 2.14 (quant, J=6.9 Hz, 2H); LC-MS: purity: 100%; MS (m/e): 213 (MH$^+$).

B. Alternatively, a solution of 4a,5,6,7-tetrahydro-2H-benzo[6,7]cyclohepta[c]pyridazin-3(4H)-one (2.31 g, 10.74 mmol), sodium m-nitrobenzenesulfonate (2.48 g, 11 mmol), sodium hydroxide (1.86 g, 46.5 mmol) in water (80 mL) was heated under reflux for 1.5 h. The solution was cooled to ambient temperature, and then acidified with concentrated hydrochloric acid. The solid which precipitated was filtered off, washed with water and crystallized from ethanol to give 3-oxo-6,7-dihydro-5H-benzo[6,7]cyclohepta[1,2-c]pyridazine as tan crystals, 1.46 g; $^1$H NMR (DMSO-d$_6$, 300 MHz) 13.04 (s, 1H), 7.25-7.45 (m, 4H), 6.78 (s, 1H), 2.49 (m, 2H), 2.35 (m, 2H), 2.04 (m, 2H) ppm; MS (ES) 213 (M+H).

SYNTHETIC PREPARATION 11

Synthesis of 3-chloro-6,7-dihydro-5H-benzo[6,7]cyclohepta[1,2-c]pyridazine

Compound of Formula (Df)

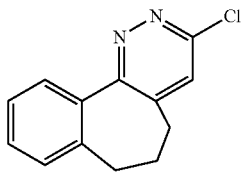 [SMILES: Clc1cc2c(nn1)-c1ccccc1CCC2]

A. A mixture of the compound of formula (De), 3-oxo-6,7-dihydro-5H-benzo[6,7]cyclohepta[1,2-c]pyridazine (4.0 g, 19.3 mmol) and POCl$_3$ (20 mL) was refluxed for 2 h. After cooling to ambient temperature, the volatiles were evaporated. The residue was poured into a mixture of ice water and sodium bicarbonate, CH$_2$Cl$_2$ (200 mL) was added to dissolve the solid. The layers were separated, and the aqueous layer was extracted with CH$_2$Cl$_2$ one more time. The combined organic layers were washed with brine. After being dried (MgSO$_4$), filtered, and concentrated, the compound of formula (Df), 3-chloro-6,7-dihydro-5H-benzo[6,7]cyclohepta[1,2-c]pyridazine was obtained as a yellow solid (4.3 g, 99%), $^1$H NMR (300 MHz, CDCl$_3$) δ: 7.82 (m, 1H), 7.45-7.24 (m, 4H), 2.59-2.51 (m, 4H), 2.27 (quant, J=6.9 Hz, 2H); LC-MS: purity: 100%; MS (m/e): 231 (MH$^+$).

B. Alternatively, 3-Oxo-6,7-dihydro-5H-benzo[6,7]cyclohepta[1,2-c]pyridazine was heated with 20 mL of phosphorus (III) oxychloride at 100° C. for 4.75 h. The solvent was removed under vacuum. The residue was treated with ice and saturated sodium bicarbonate solution. The solid which formed was filtered off, washed well with water and air-dried to yield the corresponding 3-chloro-6,7-dihydro-5H-benzo[6,7]cyclohepta[1,2-c]pyridazine (1.6 g); $^1$H NMR (CDCl$_3$, 300 MHz) 7.82 (m, 1H), 7.44 (m, 2H), 7.39 (s, 1H), 7.27 (m, 1H), 2.55 (m, 4H), 2.32 (m, 2H) ppm; MS (ES) 231/233 (M+H).

SYNTHETIC PREPARATION 12

Synthesis of 3-hydrazino-6,7-dihydro-5H-benzo[6,7]cyclohepta[1,2-c]pyridazine

Compound of Formula (D-1)

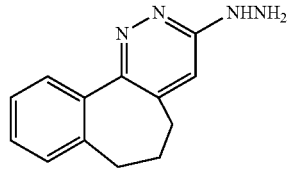 [SMILES: NNc1cc2c(nn1)-c1ccccc1CCC2]

A. A mixture of the compound of formula (Of), 3-chloro-6,7-dihydro-5H-benzo[6,7]cyclohepta[1,2-c]pyridazine, (4.3 g, 18.6 mmol) and anhydrous hydrazine (11.7 mL, 370 mmol) in 45 mL of ethanol was refluxed for 16 h. After cooling to ambient temperature, 5 mL of water was added and the volatiles were then evaporated. To the solid residue was added cold water (about 80 mL). After sonication for 10 min, the resulting solid was collected by filtration and washed with cold water three times. After freeze-drying, the compound of formula (D-1), 3-hydrazino-6,7-dihydro-5H-benzo[6,7]cyclohepta[1,2-c]pyridazine, (4.14 g, 98%) was obtained as a slight yellow solid, $^1$H NMR (300 MHz, CD$_3$OD) δ: 7.59 (m, 1H), 7.39-7.26 (m, 3H), 7.04 (s, 1H), 2.54 (t, J=6.9 Hz, 2H), 2.47 (t, J=6.9 Hz, 2H), 2.18 (quant, J=6.9 Hz, 2H); LC-MS: purity: 100%; MS (m/e): 227 (MH$^+$).

B. Alternatively, 3-chloro-6,7-dihydro-5H-benzo[6,7]cyclohepta[1,2-c]pyridazine (1.6 g) was heated with anhydrous hydrazine (4 mL) in ethanol (50 mL) at 100° C. for 4.75 h. The solvent was removed under vacuum. The residue was partitioned between chloroform and 1M saturated aqueous potassium carbonate. The organic layer was dried over anhydrous sodium sulfate and concentrated under vacuum to give 3-hydrazino-6,7-dihydro-5H-benzo[6,7]cyclohepta[1,2-c]pyridazine as a brown solid; $^1$H NMR (CDCl$_3$, 300 MHz) 7.74 (m, 1H), 7.30 (m, 2H), 7.17 (m, 1H), 6.92 (s, 1H), 2.49 (m, 2H), 2.39 (m, 2H), 2.12 (m, 2H) ppm; MS (ES) 227 (M+H).

SYNTHETIC EXAMPLE 1

Synthesis of 1-(6,7-Dihydro-5H-benzo[6,7]cyclohepta[1,2-c]pyridazin-3-yl)-N$^3$-(4-(2-(pyrrolidin-1-yl)ethoxy)phenyl)-1H-1,2,4-triazole-3,5-diamine

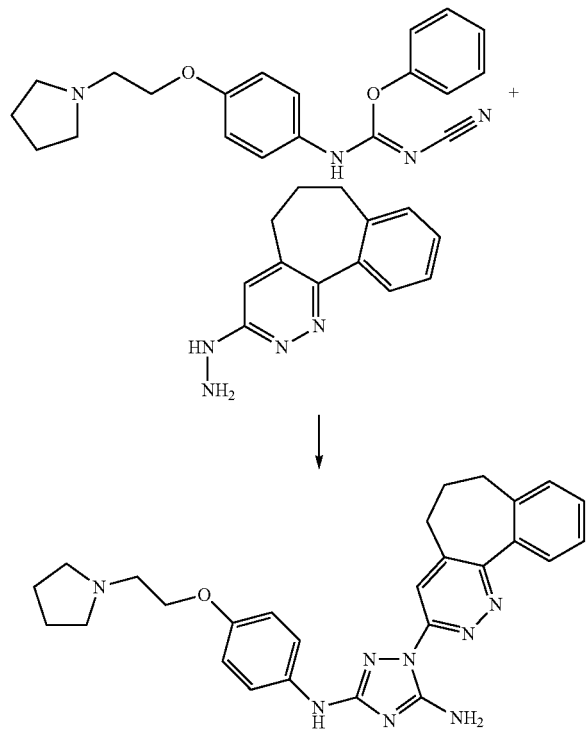

Diphenylcyanocarbonimidate (1.1 equiv) and 4-(2-(pyrrolidin-1-yl)ethoxy)aniline (1 equiv) were stirred in iso-propyl alcohol at ambient temperature overnight. The resulting white precipitate was filtered and washed with iso-propyl alcohol and dried to yield (Z)-phenyl N'-cyano-N-(4-(2-(pyrrolidin-1-yl)ethoxy)phenyl)carbamimidate. 3-Hydrazino-6,7-dihydro-5H-benzo[6,7]cyclohepta[1,2-c]pyridazine (82 mg, 0.36 mMol) and (Z)-phenyl N'-cyano-N-(4-(2-(pyrrolidin-1-yl)ethoxy)phenyl)carbamimidate (128 mg, 0.36 mMol) were suspended in isopropanol (3 mL) and subjected to microwave irradiation (150° C., 20 min). The precipitate which formed in the microwave vial was re-dissolved in hot isopropanol. The mixture was cooled to ambient temperature and then filtered to give 1-(6,7-dihydro-5H-benzo[6,7]cyclohepta[1,2-c]pyridazin-3-yl)-N$^3$-(4-(2-(pyrrolidin-1-yl)ethoxy)phenyl)-1H-1,2,4-triazole-3,5-diamine, compound #1, as a yellow solid, 23 mg. $^1$H NMR (CDCl$_3$, 300 MHz) 7.90 (s, 1H), 7.83 (t, 1H), 7.43 (m, 3H), 7.29 (t, 1H), 6.93 (d, 1H), 6.83 (br s, 2H), 6.39 (s, 1H), 4.17 (m, 2H), 2.98 (m, 2H), 2.60-2.80 (m, 8H), 2.32 (m, 2H), 1.87 (m, 4H) ppm; MS (ES) 483.16 (M+H).

SYNTHETIC EXAMPLE 2

Synthesis of 1-(6,7-dihydro-5H-benzo[6,7]cyclohepta[1,2-c]pyridazin-3-yl)-N$^3$-(7-(S)-(pyrrolidin-1-yl)-6,7,8,9-tetrahydro-5H-benzo[7]annulene-2-yl)-1H-1,2,4-triazole-3,5-diamine and 1-(6,7-dihydro-5H-benzo[6,7]cyclohepta[1,2-c]pyridazin-3-yl)-N$^3$-(7-(R)-(pyrrolidin-1-yl)-6,7,8,9-tetrahydro-5H-benzo[7]annulene-2-yl)-1H-1,2,4-triazole-3,5-diamine Phenyl (S)—N'-cyano-N-(7-(pyrrolidin-1-yl)-6,7,8,9-tetrahydro-5H-benzo[7]annulene-2-yl)carbamimidate and phenyl (R)—N'-cyano-N-(7-(pyrrolidin-1-yl)-6,7,8,9-tetrahydro-5H-benzo[7]annulene-2-yl)carbamimidate were treated with 3-hydrazino-6,7-dihydro-5H-benzo[6,7]cyclohepta[1,2-c]pyridazine in a similar manner as described above in Synthetic Example 2 to yield 1-(6,7-dihydro-5H-benzo[6,7]cyclohepta[1,2-c]pyridazin-3-yl)-N$^3$-(7-(S)-(pyrrolidin-1-yl)-6,7,8,9-tetrahydro-5H-benzo[7]annulene-2-yl)-1H-1,2,4-triazole-3,5-diamine and 1-(6,7-dihydro-5H-benzo[6,7]cyclohepta[1,2-c]pyridazin-3-yl)-N$^3$-(7-(R)-(pyrrolidin-1-yl)-6,7,8,9-tetrahydro-5H-benzo[7]annulene-2-yl)-1H-1,2,4-triazole-3,5-diamine. For example, a suspension of a single enantiomer of phenyl N'-cyano-N-(7-(pyrrolidin-1-yl)-6,7,8,9-tetrahydro-5H-benzo[7]annulen-2-yl)carbamimidate (0.06 g, 0.16 mmol) and 3-hydrazino-6,7-dihydro-5H-benzo[6,7]cyclohepta[1,2-c]pyridazine (0.036 g, 0.16 mmol) in 1 mL of IPA was stirred at 90° C. for 18 h. After cooling to ambient temperature, the solvent was evaporated and the residue was purified by HPLC to provide enantiomerically pure 1-(6,7-dihydro-5H-benzo[6,7]cyclohepta[1,2-c]pyridazin-3-yl)-N$^3$-(7-(R)-(pyrrolidin-1-yl)-6,7,8,9-tetrahydro-5H-benzo[7]annulene-2-yl)-1H-1,2,4-triazole-3,5-diamine as a yellow solid (0.04 g, 50%). $^1$H NMR (DMSO-d$_6$, 300 MHz) 9.11 (s, 1H), 7.94 (s, 1H), 7.85 (br s, 2H), 7.72 (m, 1H), 7.46 (m, 3H), 7.37 (m, 2H), 7.06 (m, 1H), 3.46 (m, 4H), 3.12 (m, 2H), 2.72 (m, 4H), 2.61 (m, 3H), 2.25 (m, 5H), 2.09-1.82 (m, 5H) ppm; MS (ES) 507 (M+H).

SYNTHETIC EXAMPLE 3

1-(6,7-dihydro-5H-benzo[6,7]cyclohepta[1,2-c]pyridazin-3-yl)-N$^3$-(5',5'-dimethyl-6,8,9,10-tetrahydro-5H-spiro[cycloocta[b]pyridine-7,2'-[1,3]dioxane]-3-yl)-1H-1,2,4-triazole-3,5-diamine, compound #247

A mixture of N'-cyano-N-(5',5'-dimethyl-6,8,9,10-tetrahydro-5H-spiro[cycloocta[b]pyridine-7,2'-[1,3]dioxane]-3-yl)carbamimidate (120 mg, 0.286 mmol) and (6,7-dihydro-5H-benzo[6,7]cyclohepta[1,2-c]pyridazin-3-yl)hydrazine (65 mg, 0.286 mmol) in isopropyl alcohol (2 mL) was heated in microwave at 150° C. for 20 min, filtered, and washed with isopropanol to give 1-(6,7-dihydro-5H-benzo[6,7]cyclohepta[1,2-c]pyridazin-3-yl)-N$^3$-(5',5'-dimethyl-6,8,9,10-tetrahydro-5H-spiro[cycloocta[b]pyridine-7,2'-[1,3]dioxane]-3-yl)-1H-1,2,4-triazole-3,5-diamine, compound #247 (55 mg, 35%); $^1$H NMR (DMSO-d$_6$, 300 MHz) 9.22 (s, 1H), 8.72 (d, 1H), 7.94 (s, 1H), 7.88 (s, 2H), 7.13 (m, 1H), 7.62 (d, 1H), 7.44 (m, 2H), 7.36 (m, 1H), 3.42 (s, 4H), 2.82 (t, 2H), 2.71 (m, 2H), 2.25 (m, 2H), 1.97 (d, 2H), 1.69 (m, 2H), 1.52 (m, 2H), 1.02 (d, 4H), 0.88 (d, 6H) ppm; MS (ES) 553.28 (M+H).

SYNTHETIC EXAMPLE 4

In a similar manner as described above utilizing the appropriately substituted starting materials and reagents, the following compounds of formula (Ia) were prepared:

N³-(4-(4-cyclohexanylpiperazin-1-yl)phenyl)-1-(6,7-dihydro-5H-benzo[6,7]cyclohepta[1,2-c]pyridazin-3-yl)-1H-1,2,4-triazole-3,5-diamine, compound #3, ¹H NMR (CDCl₃, 300 MHz) 7.89 (s, 1H), 7.81 (t, 1H), 7.58 (d, 1H), 7.42 (d, 2H), 7.30 (m, 1H), 6.97 (d, 2H), 6.80 (br s, 2H), 6.33 (s, 1H), 3.24 (m, 3H), 2.80 (m, 2H), 2.60 (M, 6H), 2.31 (m, 2H), 1.85 (m, 4H), 1.55-1.70 (m, 4H), 1.30 (m, 4H) ppm; MS (ES) 536.29 (M+H);

1-(6,7-dihydro-5H-benzo[6,7]cyclohepta[1,2-c]pyridazin-3-yl)-N³-(3-fluoro-4-(4-(pyrrolidin-1-yl)piperidin-1-yl)-1H-1,2,4-triazole-3,5-diamine, compound #4, ¹H NMR (300 MHz, DMSO): 9.19 (br. s, 1H), 7.91 (s, 1H), 7.86 (br. s, 2H), 7.72-7.69 (m, 1H), 7.45-7.43 (m, 2H), 7.38-7.33 (m, 3H), 6.96 (t, J=9.3 Hz, 1H), 3.23-3.19 (m, 4H), 2.65-2.58 (m, 5H), 2.56-2.53 (m, 2H), 2.10-2.00 (m, 1H), 1.94-1.90 (m, 3H), 1.67 (br. s, 6H), 1.60-1.48 (m, 2H), MS (ES): 540.33 (M+H);

1-(6,7-dihydro-5H-benzo[6,7]cyclohepta[1,2-c]pyridazin-3-yl)-N³-(3-fluoro-4-(4-(pyrrolidin-1-yl)piperidin-1-yl)-1H-1,2,4-triazole-3,5-diamine formic acid salt (formic acid salt of compound #4);

1-(6,7-dihydro-5H-benzo[6,7]cyclohepta[1,2-c]pyridazin-3-yl)-N-3-(3-fluoro-4-(4-methyl-3-phenylpiperazin-1-yl)phenyl)-1H-1,2,4-triazole-3,5-diamine, compound #5, ¹H NMR (DMSO-d₆, 300 MHz) 9.19 (s, 2H), 8.13 (s, 1H), 7.90 (s, 1H), 7.83 (s, 1H), 7.71-7.67 (m, 1H), 7.46-7.41 (m, 2H), 7.38-7.35 (m, 1H), 7.29 (d, 2H), 7.19-7.07 (m, 3H), 6.96 (t, 1H), 4.24 (d, 2H), 3.11 (d, 2H), 2.92-2.88 (m, 4H), 2.59-2.48 (m, 2H), 2.30-2.20 (m, 5H), 2.00 (t, 2H) ppm; MS (ES) 562.45 (M+H);

1-(6,7-dihydro-5H-benzo[6,7]cyclohepta[1,2-c]pyridazin-3-yl)-N³-(3-fluoro-(4-(4-piperidin-1-yl)piperidin-1-yl)phenyl)-1H-1,2,4-triazole-3,5-diamine, compound #6, ¹H NMR (DMSO-d₆, 300 MHz) 9.19 (s, 1H), 7.88 (d, 2H), 7.70 (s, 1H), 7.45-7.20 (m, 4H), 6.96 (t, 1H), 3.30 (s, 4H), 2.62-2.40 (m, 9H), 2.20-2.16 (m, 2H), 1.87-1.80 (m, 2H), 1.59-1.48 (m, 8H) ppm; MS (ES) 554.20 (M+H);

1-(6,7-dihydro-5H-benzo[6,7]cyclohepta[1,2-c]pyridazin-3-yl)-N³-(3-fluoro-4-(4-(indolin-2-on-1-yl)piperidin-1-yl)phenyl)-1H-1,2,4-triazole-3,5-diamine, compound #7, ¹H NMR (DMSO-d₆, 300 MHz) 9.22 (s, 1H), 7.91 (s, 1H), 7.86 (s, 2H), 7.71-7.67 (m, 1H), 7.45-7.35 (m, 4H), 7.28-7.15 (m, 3H), 7.08-6.94 (m, 2H), 4.26-4.18 (m, 1H), 3.55 (s, 2H), 2.85-2.76 (m, 2H), 2.61-2.46 (m, 4H), 2.30-2.20 (m, 2H), 2.75-2.48 (m, 2H) ppm; MS (ES) 602.48 (M+H);

1-(6,7-dihydro-5H-benzo[6,7]cyclohepta[1,2-c]pyridazin-3-yl)-N³-(6-(4-(bicyclo[2.2.1]heptan-2-yl)piperazin-1-yl)pyridin-3-yl)-1H-1,2,4-triazole-3,5-diamine, compound #8, ¹H NMR (DMSO-d₆, 300 MHz) 9.77 (s, 1H), 8.53 (s, 1H), 7.92 (s, 1H), 7.86 (s, 1H), 7.75-7.69 (m, 1H), 7.48-7.35 (m, 2H), 6.96 (d, 1H), 4.27-4.14 (m, 2H), 3.60-3.41 (m, 2H), 3.23-3.10 (m, 3H), 2.60-2.40 (m, 10H), 2.39-2.31 (m, 2H), 2.08-1.95 (m, 1H), 1.63-1.51 (m, 2H), 1.39 (s, 1H), 1.22-1.18 (m, 1H) ppm; MS (ES) 549.15 (M+H);

1-(6,7-dihydro-5H-benzo[6,7]cyclohepta[1,2-c]pyridazin-3-yl)-N³-(3-fluoro-4-(4-(morpholin-4-yl)piperidin-1-yl)phenyl)-1H-1,2,4-triazole-3,5-diamine, compound #9, ¹H NMR (DMSO-d₆, 300 MHz) 9.79 (s, 1H), 9.23 (s, 1H), 7.90 (s, 1H), 7.86 (s, 1H), 7.77-7.68 (m, 1H), 7.45-7.38 (m, 4H), 7.00 (t, 1H), 4.01 (d, 2H), 3.72 (t, 2H), 3.50 (d, 2H), 3.47 (d, 2H), 3.20-3.08 (m, 2H), 2.70-2.57 (m, 6H), 2.25-2.09 (m, 4H), 1.80-1.76 (m, 2H) ppm; MS (ES) 556.17 (M+H);

1-(6,7-dihydro-5H-benzo[6,7]cyclohepta[1,2-c]pyridazin-3-yl)-N³-(4-(4-(cyclopentyl)piperazin-1-ylcarbonyl)phenyl)-1H-1,2,4-triazole-3,5-diamine, compound #10, ¹H NMR (DMSO-d₆, 300 MHz) 9.51 (s, 1H), 7.99 (s, 1H), 7.90 (br s, 2H), 7.69 (m, 6H), 7.41 (m, 2H), 3.48 (m, 8H), 2.58 (m, 3H), 2.22 (m, 4H), 1.75-1.32 (m, 8H) ppm; MS (ES) 550.2 (M+H);

1-(6,7-dihydro-5H-benzo[6,7]cyclohepta[1,2-c]pyridazin-3-yl)-N³-(4,5-dihydro-1H-benzo[b]azepin-2(3H)-on-8-yl)-1H-1,2,4-triazole-3,5-diamine, compound #11, ¹H NMR (DMSO-d₆, 300 MHz) 9.51 (s, 1H), 9.22 (s, 1H), 7.99 (s, 1H), 7.85 (br s, 2H), 7.71 (m, 1H), 7.40 (m, 4H), 7.22 (m, 1H), 7.08 (m, 1H), 2.59 (m, 5H), 2.25-2.06 (m, 7H) ppm; MS (ES) 453.1 (M+H);

1-(6,7-dihydro-5H-benzo[6,7]cyclohepta[1,2-c]pyridazin-3-yl)-N³-(44(2-pyrrolidin-1-ylethyl)aminocarbonyl)phenyl)-1H-1,2,4-triazole-3,5-diamine, compound #12, ¹H NMR (DMSO-d₆, 300 MHz) 9.56 (s, 1H), 7.99 (s, 1H), 7.90 (br s, 2H), 7.78 (m, 2H), 7.69 (m, 3H), 7.45 (m, 2H), 7.39 (m, 2H), 3.35 (m, 2H), 2.59 (m, 10H), 2.24 (m, 2H), 1.68 (m, 4H) ppm; MS (ES) 510.3 (M+H);

1-(6,7-dihydro-5H-benzo[6,7]cyclohepta[1,2-c]pyridazin-3-yl)-N³-(2-(dimethylaminomethyl)-1H-benzo[d]imidazol-5-yl)-1H-1,2,4-triazole-3,5-diamine, compound #13, ¹H NMR (DMSO-d₆, 300 MHz) 9.11 (s, 1H), 8.02 (s, 1H), 7.94 (m, 1H), 7.84 (br s, 2H), 7.72 (m, 2H), 7.40 (m, 5H), 3.60 (m, 2H), 2.53 (m, 4H), 2.21 (m, 8H) ppm; MS (ES) 467.1 (M+H);

1-(6,7-dihydro-5H-benzo[6,7]cyclohepta[1,2-c]pyridazin-3-yl)-N³-(4-(2,2,6,6-tetramethylpiperidin-1-yl)ethoxyphenyl)-1H-1,2,4-triazole-3,5-diamine, compound #14; ¹H NMR (DMSO-d₆, 300 MHz) 8.96 (s, 1H), 7.93 (s, 1H), 7.82 (br s, 2H), 7.63 (m, 2H), 7.55 (m, 2H), 7.45 (m, 2H), 7.37 (m, 2H), 3.78 (m, 2H), 2.78 (m, 2H), 2.59 (m, 3H), 2.22 (m, 3H), 1.49 (m, 2H), 1.38 (m, 4H), 1.01 (s, 12H) ppm; MS (ES) 553.2 (M+H);

1-(6,7-dihydro-5H-benzo[6,7]cyclohepta[1,2-c]pyridazin-3-yl)-N³-(7-(pyrrolidin-1-yl)-6,7,8,9-tetrahydro-5H-benzo[7]annulen-2-yl)-1H-1,2,4-triazole-3,5-diamine, compound #15, ¹H NMR (DMSO-d₆, 300 MHz) 9.19 (s, 1H), 7.84 (br s, 2H), 7.69 (m, 4H), 7.05 (m, 4H), 2.71-2.55 (m, 11H), 2.20 (m, 5H), 1.80 (m, 4H), 1.44 (m, 3H) ppm; MS (ES) 507.6 (M+H);

1-(6,7-dihydro-5H-benzo[6,7]cyclohepta[1,2-c]pyridazin-3-yl)-N³-(7-(S)-(pyrrolidin-1-yl)-6,7,8,9-tetrahydro-5H-benzo[7]annulen-2-yl)-1H-1,2,4-triazole-3,5-diamine, enantiomer of compound #15; ¹H NMR (DMSO-d₆, 300 MHz) 9.11 (s, 1H), 7.93 (s, 1H), 7.85 (br s, 2H), 7.71 (m, 1H), 7.45 (m, 3H), 7.38 (m, 2H), 7.05 (m, 1H), 2.76-2.46 (m, 10H), 2.23-1.76 (m, 13H) ppm; MS (ES) 507.3 (M+H);

1-(6,7-dihydro-5H-benzo[6,7]cyclohepta[1,2-c]pyridazin-3-yl)-N³-(7-(R)-(pyrrolidin-1-yl)-6,7,8,9-tetrahydro-5H-benzo[7]annulen-2-yl)-1H-1,2,4-triazole-3,5-diamine, enantiomer of compound #15; ¹H NMR (DMSO-d₆, 300 MHz) 9.11 (s, 1H), 7.93 (s, 1H), 7.85 (br s, 2H), 7.71 (m, 1H), 7.45 (m, 3H), 7.38 (m, 2H), 7.05 (m, 1H), 2.76-2.46 (m, 10H), 2.23-1.76 (m, 13H) ppm; MS (ES) 507.3 (M+H);

1-(6,7-dihydro-5H-benzo[6,7]cyclohepta[1,2-c]pyridazin-3-yl)-N³-(4-(4-cyclopentyl-2-methylpiperazin-1-yl)phenyl)-1H-1,2,4-triazole-3,5-diamine, compound #16, ¹H NMR (DMSO-d₆, 300 MHz) 8.92 (s, 1H), 7.82 (br s, 2H), 7.71 (m, 2H), 7.50 (m, 3H), 7.45 (m, 2H), 6.87 (m, 2H), 3.68 (d, 1H), 3.14-2.12 (m, 12H), 1.53 (m, 7H), 0.92 (d, 3H) ppm; MS (ES) 536.7 (M+H);

1-(6,7-dihydro-5H-benzo[6,7]cyclohepta[1,2-c]pyridazin-3-yl)-N³-(4-(3,5-dimethylpiperazin-1-yl)phenyl)-1H-1,2,4-triazole-3,5-diamine, compound #17, ¹H NMR (DMSO-d₆, 300 MHz) 8.93 (s, 1H), 7.92 (s, 1H), 7.82 (br s, 2H), 7.71 (m, 1H), 7.52 (m, 2H), 7.45 (m, 2H), 7.37 (m, 1H), 6.90 (m, 2H), 3.47 (m, 2H), 3.07 (m, 2H), 2.55 (m, 4H), 2.26 (m, 5H), 1.11 (d, 6H) ppm; MS (ES) 482.1 (M+H);

1-(6,7-dihydro-5H-benzo[6,7]cyclohepta[1,2-c]pyridazin-3-yl)-N$^3$-(4-(4-(pyrrolidin-1-yl)piperidin-1-yl)-3-cyanophenyl)-1H-1,2,4-triazole-3,5-diamine, compound #18, $^1$H NMR (DMSO-d$_6$, 300 MHz) 9.38 (s, 1H), 7.91 (br s, 2H), 7.77 (m, 3H), 7.41 (m, 3H), 7.16 (m, 2H), 2.77-2.43 (m, 11H), 2.18-1.88 (m, 8H), 1.64 (m, 4H) ppm; MS (ES) 547.2 (M+H);

1-(6,7-dihydro-5H-benzo[6,7]cyclohepta[1,2-c]pyridazin-3-yl)-N$^3$-(4-((2-(dimethylamino)ethyl)aminocarbonyl)phenyl)-1H-1,2,4-triazole-3,5-diamine, compound #19, $^1$H NMR (DMSO-d$_6$, 300 MHz) 9.55 (s, 1H), 7.99 (s, 1H), 7.89 (br s, 2H), 7.78 (m, 2H), 7.68 (m, 3H), 7.45 (m, 2H), 7.38 (m, 2H), 3.33 (m, 2H), 2.61 (m, 2H), 2.37 (m, 2H), 2.23 (m, 4H), 2.15 (s, 6H) ppm; MS (ES) 484.6 (M+H);

1-(6,7-dihydro-5H-benzo[6,7]cyclohepta[1,2-c]pyridazin-3-yl)-N$^3$-(44(2-(methoxy)ethyl)aminocarbonyl)phenyl)-1H-1,2,4-triazole-3,5-diamine, compound #20, $^1$H NMR (DMSO-d$_6$, 300 MHz) 9.55 (s, 1H), 7.99 (s, 1H), 7.89 (br s, 2H), 7.79 (m, 2H), 7.70 (m, 3H), 7.45 (m, 2H), 7.37 (m, 2H), 3.38 (m, 4H), 3.25 (s, 3H), 2.55 (m, 4H), 2.26 (m, 2H) ppm; MS (ES) 471.1 (M+H);

1-(6,7-dihydro-5H-benzo[6,7]cyclohepta[1,2-c]pyridazin-3-yl)-N$^3$-(4-((2-(pyrrolidin-1-yl)ethyl)aminocarbonyl)phenyl)-1H-1,2,4-triazole-3,5-diamine, compound #21, $^1$H NMR (DMSO-d$_6$, 300 MHz) 9.39 (s, 1H), 8.41 (m, 1H), 7.99 (s, 1H), 7.88 (br s, 2H), 7.71 (m, 2H), 7.48-7.24 (m, 7H), 3.40 (m, 2H), 2.59 (m, 10H), 2.24 (m, 2H), 1.68 (m, 4H) ppm; MS (ES) 510.2 (M+H);

1-(6,7-dihydro-5H-benzo[6,7]cyclohepta[1,2-c]pyridazin-3-yl)-N$^3$-(44(4-(pyrrolidin-1-yl)piperidin-1-yl)carbonyl)phenyl)-1H-1,2,4-triazole-3,5-diamine, compound #22, $^1$H NMR (DMSO-d$_6$, 300 MHz) 9.50 (s, 1H), 7.99 (s, 1H), 7.90 (br s, 2H), 7.68 (m, 3H), 7.45 (m, 2H), 7.33 (m, 3H), 2.99 (m, 4H), 2.55 (m, 4H), 2.23 (m, 4H), 1.80-1.34 (m, 10H) ppm; MS (ES) 550.3 (M+H);

1-(6,7-dihydro-5H-benzo[6,7]cyclohepta[1,2-c]pyridazin-3-yl)-N$^3$-(7-((bicyclo[2.2.1]heptan-2-yl)amino)-6,7,8,9-tetrahydro-5H-benzo[7]annulen-2-yl)-1H-1,2,4-triazole-3,5-diamine, compound #23, $^1$H NMR (DMSO-d$_6$, 300 MHz) 9.09 (s, 1H), 7.84 (br s, 2H), 7.73 (m, 2H). 7.45 (m, 4H), 7.31 (s, 1H), 7.04 (m, 1H), 3.41 (m, 1H), 3.23 (m, 1H), 2.75 (m, 4H), 2.53 (m, 4H), 2.25 (m, 4H), 1.73-1.11 (m, 13H) ppm; MS (ES) 547.3 (M+H);

1-(6,7-dihydro-5H-benzo[6,7]cyclohepta[1,2-c]pyridazin-3-yl)-N$^3$-(7-((bicyclo[2.2.1]heptan-2-yl)(methyl)amino)-6,7,8,9-tetrahydro-5H-benzo[7]annulen-2-yl)-1H-1,2,4-triazole-3,5-diamine, compound #24, $^1$H NMR (DMSO-d$_6$, 300 MHz) 9.09 (s, 1H), 7.84 (br s, 2H), 7.72 (m, 2H). 7.40 (m, 5H), 7.05 (m, 1H), 3.84 (m, 1H), 3.54 (m, 1H), 3.25 (m, 1H), 2.77 (m, 3H), 2.53 (m, 7H), 2.30 (m, 6H), 1.73-1.12 (m, 10H) ppm; MS (ES) 561.3 (M+H);

1-(6,7-dihydro-5H-benzo[6,7]cyclohepta[1,2-c]pyridazin-3-yl)-M-(6-(4-cyclopentyl-1,4-diazepan-1-yl)pyridin-3-yl)-1H-1,2,4-triazole-3,5-diamine, compound #25, $^1$H NMR (DMSO-d$_6$, 300 MHz) 8.32 (s, 1H), 8.17 (br s, 2H), 7.86 (m, 1H), 7.80 (s, 1H), 7.72 (m, 1H). 7.44 (m, 2H), 7.36 (m, 2H), 6.63 (m, 1H), 3.71 (m, 2H), 3.59 (m, 2H), 2.98 (m, 1H), 2.83 (m, 2H), 2.66 (m, 2H), 2.53 (m, 4H), 2.19 (m, 2H), 1.82 (m, 4H), 1.47 (m, 6H) ppm; MS (ES) 537.1 (M+H);

1-(6,7-dihydro-5H-benzo[6,7]cyclohepta[1,2-c]pyridazin-3-yl)-N$^3$-(7-cyclopentyl-6,7,8,9-tetrahydro-5H-pyrido[3,2-d]azepin-3-yl)-1H-1,2,4-triazole-3,5-diamine, compound #26, $^1$H NMR (DMSO-d$_6$, 300 MHz) 9.73 (s, 1H), 8.68 (s, 1H), 8.37 (m, 1H), 8.08 (s, 1H), 7.94 (br s, 2H), 7.72 (m, 1H), 7.46 (m, 2H), 7.39 (m, 1H), 3.54 (m, 3H), 3.16 (m, 3H), 2.54 (m, 5H), 2.25 (m, 2H), 1.85 (m, 2H), 1.69 (m, 4H), 1.49 (m, 4H) ppm; MS (ES) 508.2 (M+H);

1-(6,7-dihydro-5H-benzo[6,7]cyclohepta[1,2-c]pyridazin-3-yl)-N$^3$-(6-(4-methylpiperazin-1-yl)pyridin-3-yl)-1H-1,2,4-triazole-3,5-diamine, compound #27, $^1$H NMR (CDCl$_3$, 300 MHz) 8.55 (d, 1H), 7.89 (s, 1H), 7.82 (m, 1H), 7.65 (m, 1H), 7.44 (m, 2H), 7.30 (m, 1H), 6.84 (br s, 2H), 6.72 (d, 1H), 6.26 (s, 1H), 3.50 (m, 4H), 2.68-2.54 (m, 8H), 2.36 (s, 3H), 2.31 (m, 2H) ppm; MS (ES) 469.04 (M+H);

1-(6,7-dihydro-5H-benzo[6,7]cyclohepta[1,2-c]pyridazin-3-yl)-N$^3$-(6-methyl-5,6,7,8-tetrahydro-1,6-naphthyridin-3-yl)-1H-1,2,4-triazole-3,5-diamine, compound #28, $^1$H NMR (DMSO-d$_6$, 300 MHz) 9.27 (s, 1H), 8.60 (s, 1H), 7.94 (d, 1H), 7.88 (br s, 2H), 7.67 (m, 2H), 7.43 (m, 2H), 7.36 (m, 1H), 3.52 (s, 2H), 2.79 (m, 2H), 2.64 (m, 4H), 2.53 (m, 2H), 2.36 (s, 3H), 2.24 (m, 2H) ppm; MS (ES) 440.42 (M+);

1-(6,7-dihydro-5H-benzo[6,7]cyclohepta[1,2-c]pyridazin-3-yl)-N$^3$-(6-(4-(pyrrolidin-1-yl)piperidin-1-yl)pyridine-3-yl)-1H-1,2,4-triazole-3,5-diamine, compound #29, $^1$H NMR (DMSO-d$_6$, 300 MHz) 8.88 (s, 1H), 8.46 (s, 1H), 7.92 (s, 1H), 7.82 (s, 2H), 7.79 (d, 1H), 7.70 (m, 1H), 7.43 (t, 2H), 7.36 (m, 1H), 6.80 (d, 1H), 4.05 (m, 2H), 3.15 (d, 1H), 2.77 (m, 2H), 2.60 (m, 2H), 2.55 (m, 2H), 2.25-2.10 (m, 4H), 1.87 (d, 2H), 1.66 (m, 4H), 1.40 (m, 4H) ppm; MS (ES) 523.47 (M+H);

1-(6,7-dihydro-5H-benzo[6,7]cyclohepta[1,2-c]pyridazin-3-yl)-N$^3$-(6-(4-(4-methylpiperazin-1-yl)piperidin-1-yl)pyridine-3-yl)-1H-1,2,4-triazole-3,5-diamine, compound #30, $^1$H NMR (DMSO-d$_6$, 300 MHz) 8.89 (s, 1H), 8.46 (s, 1H), 7.90 (d, 1H), 7.81 (s, 2H), 7.77 (s, 1H), 7.69 (m, 1H), 7.44 (d, 2H), 7.37 (t, 1H), 6.80 (d, 1H), 4.15 (d, 2H), 2.72-2.53 (m, 5H), 2.41 (s, 6H), 2.23 (d, 2H), 2.19 (s, 3H), 1.80 (m, 4H), 1.38 (m, 4H) ppm; MS (ES) 552.28 (M+H);

1-(6,7-dihydro-5H-benzo[6,7]cyclohepta[1,2-c]pyridazin-3-yl)-N$^3$-(6-(4-methylpiperazin-1-yl)carbonyl-5,6,7,8-tetrahydroquinolin-3-yl)-1H-1,2,4-triazole-3,5-diamine, compound #31, 1H-1,2,4-triazole-3,5-diamine; $^1$H NMR (DMSO-d$_6$, 300 MHz) 9.24 (s, 1H), 8.58 (s, 1H), 7.94 (s, 1H), 7.87 (s, 2H), 7.71 (s, 2H), 7.44 (m, 2H), 7.36 (m, 1H), 3.52 (m, 4H), 2.78 (m, 2H), 2.61 (t, 2H), 2.42 (d, 2H), 2.32 (s, 2H), 2.25 (m, 4H), 2.18 (s, 3H), 1.95 (m, 2H), 1.75 (m, 2H) ppm; MS (ES) 551.54 (M+);

1-(6,7-dihydro-5H-benzo[6,7]cyclohepta[1,2-c]pyridazin-3-yl)-N$^3$-(3-fluoro-4-(3-(diethylamino)pyrrolidin-1-yl)phenyl)-1H-1,2,4-triazole-3,5-diamine, compound #32, $^1$H NMR (DMSO-d$_6$, 300 MHz) 9.06 (s, 1H), 7.89 (s, 1H), 8.84 (s, 2H), 7.69 (d, 1H), 7.47 (m, 3H), 7.38 (m, 1H), 7.30 (d, 1H), 6.74 (t, 1H), 3.24 (m, 4H), 3.15 (d, 2H), 2.60-2.54 (m, 8H), 2.23 (t, 2H), 2.10 (m, 2H), 1.80 (s, 1H), 1.01 (s, 6H) ppm; MS (ES) 528.10 (M+H);

1-(6,7-dihydro-5H-benzo[6,7]cyclohepta[1,2-c]pyridazin-3-yl)-N$^3$-(4-(4-(bicyclo[2.2.1]heptan-2-yl)piperazin-1-yl)phenyl)-1H-1,2,4-triazole-3,5-diamine, compound #33, $^1$H-NMR (DMSO-d$_6$, 300 MHz) 10.69 (s, 1H), 8.87 (s, 1H), 7.92 (s, 1H), 7.80 (m, 1H), 7.71 (m, 1H), 7.35-7.57 (m, 4H), 6.91 (d, 1H), 6.85 (d, 1H), 3.03 (m, 4H), 2.43 (m, 10H), 2.20 (m, 4H), 1.69 (m, 2H), 1.17-1.40 (m, 5H) ppm; MS (ES) 548.20 (M+H);

1-(6,7-dihydro-5H-benzo[6,7]cyclohepta[1,2-c]pyridazin-3-yl)-N$^3$-(4-(4-methylpiperazin-1-yl)phenyl)-1H-1,2,4-triazole-3,5-diamine, compound #34, $^1$H-NMR (CDCl$_3$, 300 MHz) 7.89 (s, 1H), 7.81 (m, 1H), 7.75 (m, 1H), 7.43 (m, 7.29 (m, 1H), 6.89-6.99 (m, 4H), 3.22 (m, 4H), 2.78 (m, 4H), 2.58-2.79 (m, 4H), 2.46 (s, 3H), 2.32 (m, 2H) ppm; MS (ES) 468 (M+H);

1-(6,7-dihydro-5H-benzo[6,7]cyclohepta[1,2-c]pyridazin-3-yl)-N$^3$-(4-((4-methylpiperazin-yl)methyl)phenyl)-1H-1,2,4-triazole-3,5-diamine, compound #35, $^1$H-NMR (CDCl$_3$, 300 MHz) 7.91 (s, 1H), 7.81 (m, 1H), 7.44 (m, 3H), 7.26 (m, 4H), 6.85 (s, 2H), 6.59 (s, 1H), 3.51 (s, 2H), 2.59-2.69 (m, 9H), 2.34 (m, 8H)ppm; MS (ES) 482 (M+H);

1-(6,7-dihydro-5H-benzo[6,7]cyclohepta[1,2-c]pyridazin-3-yl)-N$^3$-(3-fluoro-4-(4-(diethylamino)piperidin-1-yl)phenyl)-1H-1,2,4-triazole-3,5-diamine, compound #36, $^1$H-NMR (CDCl$_3$, 300 MHz) 7.88 (s, 1H), 7.82 (m, 1H), 7.44 (m, 3H), 7.40 (m, 1H), 7.03 (m, 1H), 6.95 (m, 1H), 6.79 (s, 2H), 6.42 (s, 1H), 3.46 (m, 2H), 2.98 (m, 1H), 2.88 (q, 4H), 2.40-2.75 (m, 9H), 2.36 (m, 2H), 1.91-2.05 (m, 5H), 1.25 (t, 6H)ppm; MS (ES) 540 (M+H);

1-(6,7-dihydro-5H-benzo[6,7]cyclohepta[1,2-d]pyrimidin-4-yl)-N$^3$-(4-(2-(pyrrolidin-1-yl)ethoxy)phenyl)-1H-1,2,4-triazole-3,5-diamine, compound #37, $^1$H-NMR (CDCl$_3$, 300 MHz) 8.88 (s, 1H), 8.36 (s, 1H), 7.84 (m, 1H), 7.41 (m, 4H), 7.30 (m, 1H), 6.86 (d, 2H), 4.24 (t, 2H), 3.17 (t, 2H), 3.03 (m, 4H), 2.67 (m, 2H), 2.55 (m, 4H), 1.97 (m, 4H)ppm; MS (ES) 483 (M+H);

1-(6,7-dihydro-5H-benzo[6,7]cyclohepta[1,2-c]pyrimidin-4-yl)-N$^3$-(4-(4-(bicyclo[2.2.1]heptan-2-yl)piperazin-1-yl)phenyl)-1H-1,2,4-triazole-3,5-diamine, compound #38, $^1$H-NMR (CDCl$_3$, 300 MHz) 8.88 (s, 1H), 8.03 (s, 1H), 7.85 (m, 1H), 7.43 (m, 3H), 7.29 (m, 3H), 6.90 (d, 1H), 6.62 (s, 1H), 6.63 (s, 1H), 3.22 (m, 2H), 3.06 (m, 2H), 2.55-2.70 (m, 6H), 2.38 (m, 1H), 2.24 (m, 1H), 1.73 (m, 11H), 1.40 (m, 4H)ppm; MS (ES) 548 (M+H);

1-(6,7-dihydro-5H-benzo[6,7]cyclohepta[1,2-c]pyrimidin-4-yl)-N$^3$-(3-fluoro-4-(4-(diethylamino)piperidin-1-yl)phenyl)-1H-1,2,4-triazole-3,5-diamine, compound #39, $^1$H-NMR (DMSO-d$_6$, 300 MHz) 8.92 (m, 1H), 7.76 (d, 1H), 7.42-7.53 (m, 4H), 7.37 (m, 1H), 7.14 (d, 1H), 6.90 (t, 1H), 3.26 (m, 2H), 3.13 (m, 2H), 2.88 (m, 2H), 2.49-2.62 (m, 9H), 1.73 (m, 2H), 1.60 (m, 2H), 0.99 (m, 6H)ppm; MS (ES) 542.28 (M+H);

1-(6,7-dihydro-5H-benzo[6,7]cyclohepta[1,2-d]pyrimidin-2-yl)-N$^3$-(4-(N-methylpiperazin-1-yl)phenyl)-1H-1,2,4-triazole-3,5-diamine, compound #40, $^1$H-NMR (CDCl$_3$, 300 MHz) 8.47 (s, 1H), 7.69 (d, 1H), 7.35 (m, 4H), 7.25 (m, 3H), 7.08 (s, 1H), 6.85 (d, 2H), 3.07 (m, 4H), 2.55 (m, 6H), 2.47 (m, 2H), 2.31 (s, 3H), 2.24 (m, 2H)ppm; MS (ES) 468.15 (M+H);

1-(7-methyl-6,7-dihydro-5H-benzo[2,3]azepino[4,5-c]pyridazin-3-yl)-N$^3$-(4-(N-methylpiperazin-1-yl)phenyl)-1H-1,2,4-triazole-3,5-diamine, compound #41, $^1$H-NMR (CDCl$_3$, 300 MHz) 7.89 (s, 1H), 7.78 (d, 1H), 7.43 (m, 3H), 7.18 (t, 1H), 7.01 (broad s, 2H), 6.95 (d, 2H), 6.87 (s, 1H), 3.49 (m, 2H), 3.16 (m, 4H), 2.85 (m, 2H), 2.79 (s, 3H), 2.61 (m, 4H), 2.37 (s, 3H)ppm; MS (ES) 483.25 (M+H);

1-(7-methyl-6,7-dihydro-5H-benzo[2,3]azepino[4,5-c]pyridazin-3-yl)-N$^3$-(3-fluoro-4-(2-(pyrrolidin-1-yl)ethoxy)phenyl)-1H-1,2,4-triazole-3,5-diamine, compound #42, $^1$H-NMR (CDCl$_3$, 300 MHz) 7.86 (s, 1H), 7.78 (m, 1H), 7.58 (m, 1H), 7.45 (m, 1H), 7.25 (broad s, 2H), 7.18 (t, 1H), 7.08 (d, 1H), 6.97 (d, 1H), 6.90 (t, 1H), 4.10 (m, 2H), 3.48 (m, 2H), 2.89 (m, 4H), 2.78 (s, 3H), 2.63 (m, 4H), 1.80 (m, 4H)ppm; MS (ES) 483.19 (M+H);

1-(7-methyl-6,7-dihydro-5H-benzo[2,3]azepino[4,5-c]pyridazin-3-yl)-N$^3$-(3-fluoro-4-(4-cyclohexylpiperazinyl)phenyl)-1H-1,2,4-triazole-3,5-diamine, compound #43, $^1$H-NMR (CDCl$_3$/MeOH-d$_4$, 300 MHz) 7.83 (s, 1H), 7.69 (d, 1H), 7.37 (m, 2H), 7.05-7.15 (m, 3H), 6.90 (t, 1H), 3.44 (m, 2H), 3.00-3.10 (m, 6H), 2.82 (m, 2H), 2.74 (m, 2H), 2.27 (m, 1H), 1.91 (m, 2H), 1.77 (m, 2H), 1.60 (m, 2H), 1.10-1.20 (m, 6H)ppm; MS (ES) 569.25 (M+H);

1-(6,7-dihydro-5H-benzo[6,7]cyclohepta[1,2-d]pyrimidin-2-yl)-N$^3$-(3-fluoro-4-(2-(pyrrolidin-1-yl)ethoxy)phenyl)-1H-1,2,4-triazole-3,5-diamine, compound #44, $^1$H-NMR (CDCl$_3$, 300 MHz) 8.53 (s, 1H), 7.24 (d, 1H), 7.43 (m, 2H), 7.31 (d, 1H), 7.04 (d, 1H), 6.90 (m, 3H), 4.20 (t, 2H), 3.08 (t, 2H), 2.89 (m, 4H), 2.59 (m, 2H), 2.52 (m, 2H), 2.32 (m, 2H), 1.89 (m, 4H)ppm; MS (ES) 501.30 (M+H);

1-(6,7-dihydro-5H-benzo[6,7]cyclohepta[1,2-d]pyrimidin-2-yl)-N$^3$-(3-fluoro-4-(4-cyclohexylpiperazinyl)phenyl)-1H-1,2,4-triazole-3,5-diamine, compound #45, $^1$H-NMR (CDCl$_3$, 300 MHz) 8.55 (s, 1H), 8.46 (s, 1H), 7.74 (m, 1H), 7.43 (m, 2H), 7.31 (m, 1H), 7.06 (m, 1H), 6.97 (m, 1H), 6.86 (m, 3H), 3.26 (m, 4H), 2.98 (m, 4H), 2.95 (m, 1H), 2.60 (m, 2H), 2.52 (m, 2H), 2.32 (m, 2H), 2.13 (m, 2H), 1.91 (m, 2H), 1.39 (m, 4H), 1.16 (m, 1H)ppm; MS (ES) 554.25 (M+H);

1-(6,7-dihydro-5H-benzo[6,7]cyclohepta[1,2-d]pyrimidin-2-yl)-N$^3$-(4-(4-(2S)-bicyclo[2.2.1]heptan-2-yl)-piperazinylphenyl)-1H-1,2,4-triazole-3,5-diamine, compound #46, $^1$H-NMR (CDCl$_3$, 300 MHz) 8.54 (s, 1H), 7.74 (m, 1H), 7.43 (m, 2H), 7.36 (d, 2H), 7.30 (m, 1H), 6.90 (d, 2H), 6.78 (broad s, 2H), 6.46 (s, 1H), 3.12 (m, 4H), 2.45-2.60 (m, 6H), 2.32 (m, 4H), 2.19 (m, 1H), 2.05 (m, 2H), 1.78 (m, 2H), 1.51 (m, 1H), 1.30-1.40 (m, 4H), 0.98 (m, 1H)ppm; MS (ES) 547.28 (M+H);

1-(6,7-dihydro-5H-benzo[6,7]cyclohepta[1,2-c]pyridazin-3-yl)-N$^3$-(3-chloro-4-(2-(pyrrolidin-1-yl)ethoxy)phenyl)-1H-1,2,4-triazole-3,5-diamine, compound #47, $^1$H-NMR (CDCl$_3$, 300 MHz) 7.84 (m, 1H), 7.75 (m, 1H), 7.60 (m, 1H), 7.38-7.48 (m, 3H), 7.27 (m, 1H), 6.93 (m, 1H), 4.33 (m, 2H), 3.42 (m, 2H), 2.60 (m, 8H), 2.28 (m, 2H), 2.01 (m, 4H)ppm; MS (ES) 517.15 (M+H);

1-(6,7-dihydro-5H-benzo[6,7]cyclohepta[1,2-c]pyridazin-3-yl)-N$^3$-(3-fluoro-4-(2-(pyrrolidin-1-yl)ethoxy)phenyl)-1H-1,2,4-triazole-3,5-diamine, compound #48, $^1$H-NMR (CDCl$_3$, 300 MHz) 7.65 (m, 1H), 7.56 (m, 1H), 7.34 (m, 2H), 7.20 (m, 1H), 7.13 (m, 1H), 6.89 (t, 1H), 4.08 (t, 2H), 2.89 (t, 2H), 2.64 (m, 4H), 2.50 (m, 4H), 2.19 (m, 2H), 1.76 (m, 4H)ppm; MS (ES) 501.17 (M+H); 14(Z)-dibenzo[b,f][1,4]thiazepin-11-yl)-N$^3$-(4-(2-(pyrrolidin-1-yl)ethoxy)phenyl)-1H-1,2,4-triazole-3,5-diamine, compound #49, $^1$H-NMR (CDCl$_3$, 300 MHz) 11.15 (s, 1H), 7.62 (m, 1H), 7.48-7.58 (m, 4H), 7.42 (m, 1H), 7.36 (m, 1H), 7.33 (m, 1H), 7.29 (m, 1H), 7.11 (m, 1H), 6.93 (d, 2H), 4.16 (broad s, 2H), 4.12 (t, 2H), 2.92 (t, 2H), 2.66 (m, 4H), 1.83 (m, 4H)ppm; MS (ES) 498.17 (M+H);

1-((Z)-dibenzo[b,f][1,4]thiazepin-11-yl)-N$^3$-(4-(4-N-methylpiperazinyl)phenyl)-1H-1,2,4-triazole-3,5-diamine, compound #50, $^1$H-NMR (CDCl$_3$, 300 MHz) 11.10 (s, 1H), 7.61 (m, 1H), 7.48-7.55 (m, 4H), 7.42 (m, 1H), 7.35 (m, 1H), 7.30 (m, 1H), 7.24 (m, 1H), 7.10 (m, 1H), 6.95 (d, 2H), 4.24 (broad s, 2H), 3.19 (m, 4H), 2.60 (m, 4H), 2.36 (s, 3H)ppm; MS (ES) 483.09 (M+H);

1-((Z)-dibenzo[b,f][1,4]thiazepin-11-yl)-N$^3$-(3-fluoro-4-(4-diethylaminopiperidin-1-yl)phenyl)-1H-1,2,4-triazole-3,5-diamine, compound #51, $^1$H-NMR (CDCl$_3$, 300 MHz) 11.26 (s, 1H), 7.59 (m, 1H), 7.45-7.55 (m, 3H), 7.42 (m, 1H), 7.27-7.38 (m, 2H), 7.18-7.25 (m, 2H), 7.11 (t, 1H), 6.94 (t, 1H), 4.62 (s, 2H), 3.45 (m, 1H), 2.62 (m, 8H), 1.84 (m, 4H), 1.08 (t, 6H)ppm; MS (ES) 557.15 (M+H);

1-(6,7-dihydro-5H-9-methoqbenzo[6,7]cyclohepta[1,2-c]pyridazin-3-yl)-N$^3$-(3-fluoro-4-(4-(pyrrolidin-1-yppiperidin-1-Aphenyl)-1H-1,2,4-triazole-3,5-diamine, compound #52, $^1$H-NMR (CDCl$_3$, 300 MHz) 7.61 (s, 1H), 7.52 (d, 1H), 7.46 (m, 1H), 7.28 (m, 1H), 6.83-6.90 (m, 2H), 6.74 (m, 1H), 3.80 (s, 3H), 3.68 (m, 4H), 3.31 (m, 2H), 2.72

(m, 2H), 2.56 (m, 4H), 2.38 (m, 1H), 2.07 (m, 2H), 1.94 (m, 2H), 1.71-1.80 (m, 5H)ppm; MS (ES) 570.30 (M+H);

1-(6,7-dihydro-5H-10-fluorobenzo[6,7]cyclohepta[1,2-c]pyridazin-3-yl)-$N^3$-(3-fluoro-4-(4-(pyrrolidin-1-yl)piperidin-1-yl)phenyl)-1H-1,2,4-triazole-3,5-diamine, compound #53, $^1$H-NMR (CDCl$_3$, 300 MHz) 10.89 (s, 1H), 7.83 (s, 1H), 7.64 (dd, 1H), 7.54 (dd, 1H), 7.21-7.27 (m, 2H), 7.12 (dt, 1H), 6.92 (t, 1H), 4.28 (br s, 2H), 3.45 (m, 4H), 2.84 (m, 2H), 2.46-2.75 (m, 5H), 2.26 (m, 2H), 2.03 (m, 2H), 1.90 (m, 6H)ppm; MS (ES) 558.38 (M+H);

1-(6,7-dihydro-5H-10-fluorobenzo[6,7]cyclohepta[1,2-c]pyridazin-3-yl)-$N^3$-(3-fluoro-4-(2-(pyrrolidin-1-yl)ethoxy)phenyl)-1H-1,2,4-triazole-3,5-diamine, compound #54, $^1$H-NMR (CDCl$_3$/MeOD$_4$, 300 MHz) 8.40 (s, 1H), 7.83 (s, 1H), 7.39-7.46 (m, 2H), 7.16 (m, 1H), 7.04 (m, 2H), 6.93 (t, 1H), 4.15 (m, 2H), 3.07 (m, 2H), 2.89 (m, 4H), 2.58 (m, 2H), 2.49 (m, 2H), 2.23 (m, 2H), 1.85 (m, 4H)ppm; MS (ES) 519.37 (M+H);

1-(6,7-dihydro-5H-10-fluorobenzo[6,7]cyclohepta[1,2-c]pyridazin-3-yl)-$N^3$-(3-fluoro-4-(4-(cyclohexyl)piperazin-1-yl)phenyl)-1H-1,2,4-triazole-3,5-diamine, compound #55, $^1$H-NMR (CDCl$_3$, 300 MHz) 10.91 (s, 1H), 7.83 (s, 1H), 7.64 (m, 1H), 7.54 (m, 1H), 7.27 (m, 1H), 7.05-7.20 (m, 2H), 6.95 (m, 1H), 4.29 (s, 1H), 3.15 (m, 4H), 2.88 (m, 4H), 2.47-2.70 (m, 5H), 2.26 (m, 2H), 1.85-1.90 (m, 4H), 1.66 (m, 1H), 1.10-1.35 (m, 6H)ppm; MS (ES) 572.28 (M+H);

1-(6,7-dihydro-5H-9-methoxybenzo[6,7]cyclohepta[1,2-c]pyridazin-3-yl)-$N^3$-(3-fluoro-4-(2-(pyrrolidin-1-ypethoxy)phenyl)-1H-1,2,4-triazole-3,5-diamine, compound #56, $^1$H-NMR (CDCl$_3$, 300 MHz) 8.52 (broad s, 1H), 7.77 (d, 1H), 7.71 (s, 1H), 7.62 (d, 1H), 7.33 (m, 1H), 6.90-7.00 (m, 2H), 6.83 (s, 1H), 4.29 (m, 2H), 3.89 (s, 3H), 3.23 (m, 2H), 3.05 (m, 4H), 2.62 (m, 4H), 2.16 (m, 2H), 1.97 (m, 4H)ppm; MS (ES) 531.21 (M+H);

1-(6,7-dihydro-5H-9-methoxybenzo[6,7]cyclohepta[1,2-c]pyridazin-3-yl)-$N^3$-(3-fluoro-4-(4-(cyclohexyl)piperazin-1-yl)phenyl)-1H-1,2,4-triazole-3,5-diamine, compound #57, $^1$H-NMR (CDCl$_3$/MeOD$_4$, 300 MHz) 7.71 (s, 1H), 7.61 (s, 1H), 7.43-7.53 (m, 2H), 6.99-7.08 (m, 2H), 6.78 (m, 2H), 6.67 (m, 2H), 3.70 (s, 3H), 2.95 (m, 4H), 2.71 (m, 4H), 2.25-2.50 (m, 4H), 2.12 (m, 1H), 1.82 (m, 2H), 1.62 (m, 2H), 1.49 (m, 2H), 0.95-1.15 (m, 6H)ppm; MS (ES) 584.14 (M+H);

1-(6,7-dihydro-5H-benzo[6,7]cyclohepta[1,2-c]pyridazin-3-yl)-$N^3$-(3-fluoro-4-(4-(4-methylpiperazin-1-yl)piperidin-1-yl)phenyl)-1H-1,2,4-triazole-3,5-diamine, compound #58, $^1$H-NMR (CDCl$_3$, 300 MHz) 7.87 (s, 1H), 7.81 (m, 1H), 7.61 (broad s, 1H), 7.49 (m, 1H), 7.42 (m, 2H), 7.26 (m, 2H), 7.01 (m, 1H), 6.87 (t, 1H), 3.46 (m, 2H), 2.40-2.65 (m, 14H), 2.95-3.25 (m, 3H), 2.30 (s, 3H), 1.89 (m, 2H), 1.75 (m, 2H)ppm; MS (ES) 634 (M+H);

1-(6,7-dihydro-5H-benzo[6,7]cyclohepta[1,2-c]pyridazin-3-yl)-$N^3$-(3-fluoro-4-(4-(4-methylpiperazin-1-yl)piperidin-1-yl)phenyl)-1H-1,2,4-triazole-3,5-diamine, benzene sulfonic acid salt, (benzene sulfonic acid salt of compound #58);

1-(6,7-dihydro-5H-benzo[6,7]cyclohepta[1,2-c]pyridazin-3-yl)-$N^3$-(3-fluoro-4-(4-(4-methylpiperidin-1-yppiperidin-1-yl)phenyl)-1H-1,2,4-triazole-3,5-diamine, compound #59, $^1$H-NMR (CDCl$_3$/MeOD$_4$, 300 MHz) 7.70 (s, 1H), 7.51 (m, 1H), 7.21-7.27 (m, 3H), 7.08 (m, 1H), 6.95 (m, 1H), 6.74 (t, 1H), 3.19 (m, 2H), 2.73 (m, 2H), 2.30-2.45 (m, 5H), 2.00-2.25 (m, 5H), 1.72 (m, 2H), 1.40-1.60 (m, 4H), 1.00-1.20 (m, 4H), 0.72 (d, 3H)ppm; MS (ES) 634 (M+H);

1-(6,7-dihydro-5H-benzo[6,7]cyclohepta[1,2-c]pyridazin-3-yl)-$N^3$-(4-(2-(N-methylcyclopentylamino)ethoxy)phenyl)-1H-1,2,4-triazole-3,5-diamine, compound #60, $^1$H-NMR (CDCl$_3$/MeOD$_4$, 300 MHz) 7.77 (s, 1H), 7.61 (m, 1H), 7.25-7.35 (m, 3H), 7.15 (m, 1H), 7.76 (d, 2H), 3.97 (m, 2H), 2.76 (m, 2H), 2.40-2.80 (m, 4H), 2.26 (s, 3H), 2.20 (m, 2H), 1.76 (m, 1H), 1.57 (m, 2H), 1.30-1.50 (m, 5H)ppm; MS (ES) 511.24 (M+H);

1-(6,7-dihydro-5H-benzo[6,7]cyclohepta[1,2-c]pyridazin-3-yl)-$N^3$-(3-fluoro-4-(4-dimethylaminopiperidin-1-yl)phenyl)-1H-1,2,4-triazole-3,5-diamine, compound #61, $^1$H-NMR (CDCl$_3$, 300 MHz) 7.87 (m, 1H), 7.94 (m, 1H), 7.64 (m, 1H), 7.42 (m, 3H), 7.25 (m, 2H), 7.00 (m, 1H), 6.90 (m, 1H), 3.40 (m, 2H), 2.57-2.70 (m, 6H), 2.33 (s, 6H), 2.25.2.30 (m, 2H), 2.19 (m, 1H), 1.90 (m, 2H), 1.72 (m, 2H)ppm; MS (ES) 514.42 (M+H);

1-(6,7-dihydro-5H-benzo[6,7]cyclohepta[1,2-c]pyridazin-3-yl)-$N^3$-(3-chloro-4-(4-pyrrolidin-1-yl-piperidin-1-yl)phenyl)-1H-1,2,4-triazole-3,5-diamine, compound #62, $^1$H-NMR (CDCl$_3$, 300 MHz) 7.86 (s, 1H), 7.80 (m, 1H), 7.61 (m, 1H), 7.43 (m, 2H), 7.29 (m, 2H), 7.16 (broad s, 2H), 7.05 (m, 1H), 6.99 (m, 1H), 3.31 (m, 2H), 2.55-2.65 (m, 9H), 2.30 (m, 2H), 2.18 (m, 2H), 1.98 (m, 2H), 1.82 (m, 6H)ppm; MS (ES) 556.13 (M+H);

1-(6,7-dihydro-5H-benzo[6,7]cyclohepta[1,2-c]pyridazin-3-yl)-$N^3$-(3-trifluoromethyl-4-(4-pyrrolidin-1-yl-piperidin-1-yl)phenyl)-1H-1,2,4-triazole-3,5-diamine, compound #63, $^1$H-NMR (CDCl$_3$/MeOD$_4$, 300 MHz) 7.73-7.80 (m, 2H), 7.50-7.60 (m, 2H), 7.10-7.35 (m, 4H), 3.98 (m, 2H), 2.88 (m, 2H), 2.40-2.55 (m, 8H), 2.16 (m, 2H), 2.06 (m, 2H), 1.83 (m, 2H), 1.50-1.75 (m, 5H)ppm; MS (ES) 590.29 (M+H);

1-(6,7-dihydro-5H-9,10-dimethoxybenzo[6,7]cyclohepta[1,2-c]pyridazin-3-yl)-$N^3$-(3-fluoro-4-(4-pyrrolidin-1-yl-piperidin-1-yl)phenyl)-1H-1,2,4-triazole-3,5-diamine, compound #64, $^1$H-NMR (CDCl$_3$, 300 MHz) 7.81 (s, 1H), 7.65 (m, 1H), 7.37 (s, 1H), 7.25 (m, 1H), 6.88 (t, 1H), 6.79 (s, 1H), 3.96 (m, 6H), 3.80 (m, 2H), 3.51 (m, 2H), 3.17 (m, 2H), 2.93 (m, 2H), 2.73 (m, 2H), 2.45-2.73 (m, 4H), 2.00-2.35 (m, 9H)ppm; MS (ES) 600.21 (M+H);

1-(6,7-dihydro-5H-9,10,11-trimethoxybenzo[6,7]cyclohepta[1,2-c]pyridazin-3-yl)-$N^3$-(3-fluoro-4-(4-pyrrolidin-1-yl-piperidin-1-yl)phenyl)-1H-1,2,4-triazole-3,5-diamine, compound #65, $^1$H-NMR (CDCl$_3$/MeOD$_4$, 300 MHz) 7.77 (s, 1H), 7.36 (m, 1H), 7.03 (m, 1H), 6.83 (m, 1H), 6.51 (s, 1H), 3.82 (m, 9H), 3.68 (m, 2H), 3.37 (m, 2H), 3.22 (m, 4H), 3.00 (m, 1H), 2.57 (m, 4H), 1.96 (m, 9H)ppm; MS (ES) 631.00 (M+H);

1-(6,7-dihydro-5H-benzo[6,7]cyclohepta[1,2-c]pyridazin-3-yl)-$N^3$-(3-fluoro-4-(5-methyloctahydropyrrolo[3,4-c]pyrrolyl)phenyl)-1H-1,2,4-triazole-3,5-diamine, compound #66, $^1$H-NMR (CDCl$_3$/MeOD$_4$, 300 MHz) 7.81 (s, 1H), 7.67 (m, 1H), 7.40 (m, 1H), 7.36 (m, 2H), 7.20 (m, 1H), 7.05 (m, 1H), 6.74 (t, 1H), 3.70 (m, 1H), 3.26 (m, 2H), 3.04 (m, 2H), 2.84 (m, 2H), 2.72 (s, 3H), 2.70-2.75 (m, 3H), 2.58 (m, 2H), 2.53 (m, 2H), 2.24 (m, 2H)ppm; MS (ES) 512.21 (M+H);

1-(6,7-dihydro-5H-benzo[6,7]cyclohepta[1,2-c]pyridazin-3-yl)-$N^3$-(3-fluoro-4-(N-methylpiperidin-4-yl-N-methylamino)phenyl)-1H-1,2,4-triazole-3,5-diamine, compound #67, $^1$H-NMR (CDCl$_3$/MeOD$_4$, 300 MHz) 7.87 (s, 1H), 7.71 (m, 1H), 7.36-7.48 (m, 3H), 7.26 (m, 1H), 7.12 (m, 1H), 7.02 (m, 1H), 3.31 (m, 3H), 2.80 (m, 2H), 2.55-2.70 (m, 9H), 2.30 (m, 2H), 1.94 (m, 4H)ppm; MS (ES) 514.24 (M+H);

1-(6,7-dihydro-5H-benzo[6,7]cyclohepta[1,2-c]pyridazin-3-yl)-$N^3$-(3-fluoro-4-(3-pyrrolidin-1-yl-piperidin-1-yl)phenyl)-1H-1,2,4-triazole-3,5-diamine, compound #68, $^1$H-NMR (CDCl$_3$/MeOD$_4$, 300 MHz) 7.88 (s, 1H), 7.70

(m, 1H), 7.35-7.45 (m, 3H), 7.26 (m, 1H), 7.16 (m, 1H), 6.99 (t, 1H), 3.55 (m, 1H), 3.31 (m, 4H), 3.17 (m, 2H), 3.02 (t, 1H), 2.55-2.80 (m, 6H), 2.30 (m, 2H), 2.05-2.15 (m, 4H), 1.92 (m, 1H), 1.79 (m, 1H)ppm; MS (ES) 540.29 (M+H);

1-(6,7-dihydro-5H-benzo[6,7]cyclohepta[1,2-c]pyridazin-3-yl)-$N^3$-(3-fluoro-4-(3-pyrrolidin-1-yl-azepan-1-yl)phenyl)-1H-1,2,4-triazole-3,5-diamine, compound #69, $^1$H-NMR (CDCl$_3$/MeOD$_4$, 300 MHz) 7.88 (s, 1H), 7.70 (m, 1H), 7.37-7.46 (m, 3H), 7.27 (m, 1H), 7.12-7.22 (m, 1H), 7.00 (m, 1H), 3.40-3.55 (m, 4H), 3.30 (m, 4H), 3.10 (m, 1H), 2.57 (m, 4H), 2.28 (m, 2H), 2.05 (m, 4H), 1.60-2.00 (m, 6H)ppm; MS (ES) 554.38 (M+H);

1-(6,7-dihydro-5H-benzo[6,7]cyclohepta[1,2-c]pyridazin-3-yl)-$N^3$-(3-fluoro-4-(4-N-methylpiperidin-4-yl-piperidin-1-yl)phenyl)-1H-1,2,4-triazole-3,5-diamine, compound #70, $^1$H-NMR (CDCl$_3$/MeOD$_4$, 300 MHz) 7.84 (s, 1H), 7.22 (m, 1H), 7.64 (m, 1H), 7.35-7.45 (m, 2H), 7.29 (m, 1H), 7.24 (m, 1H), 7.16 (m, 1H), 3.45 (m, 2H), 3.30 (m, 1H), 2.90 (m, 1H), 2.74 (s, 3H), 2.61 (m, 4H), 2.29 (m, 1H), 2.13 (m, 1H), 1.55-1.95 (m, 10H), 1.34 (m, 3H)ppm; MS (ES) 568.18 (M+H);

1-(6,7-dihydro-5H-benzo[6,7]cyclohepta[4,5-c]pyridazin-2-yl)-$N^3$-(3-fluoro-4-(4-(pyrrolidinyl)piperidinyl)phenyl)-1H-1,2,4-triazole-3,5-diamine, compound #71, $^1$H-NMR (DMSO-d$_6$, 300 MHz) 8.97 (s, 1H), 7.80 (m, 1H), 7.68 (s, 1H), 7.58 (m, 1H), 7.38-7.48 (m, 3H), 7.25 (m, 1H), 6.93 (t, 1H), 3.22 (m, 1H), 2.82 (m, 2H), 2.55-2.70 (m, 6H), 2.49 (m, 4H), 2.28 (m, 2H), 1.92 (m, 2H), 1.73 (m, 4H), 1.61 (m, 2H)ppm; MS (ES) 540.23 (M+H);

1-(6,7-dihydro-5H-benzo[6,7]cyclohepta[1,2-c]pyridazin-3-yl)-$N^3$-(3-fluoro-4-(decahydropyrazino[1,2-a]azepin-2-yl)phenyl)-1H-1,2,4-triazole-3,5-diamine, compound #73, $^1$H-NMR (CDCl$_3$/MeOD$_4$, 300 MHz) 7.85 (s, 1H), 7.72 (m, 1H), 7.39 (m, 2H), 7.30 (m, 1H), 7.24 (m, 1H), 7.19 (m, 1H), 6.95 (t, 1H), 3.17-3.55 (m, 12H), 2.57-2.65 (m, 4H), 2.27 (m, 2H), 1.65-2.10 (m, 4H)ppm; MS (ES) 540.53 (M+H);

1-(6,7-dihydro-5H-benzo[6,7]cyclohepta[4,5-c]pyridazin-2-yl)-$N^3$-(3-fluoro-4-(4-(pyrrolidinyl)piperidinyl)phenyl)-1H-1,2,4-triazole-3,5-diamine, formic acid salt (formic acid salt of compound #71);

1-(6,7-dihydro-5H-benzo[6,7]cyclohepta[1,2-c]pyridazin-3-yl)-$N^3$-(3-fluoro-4-(5-cyclopentyloctahydropyrrolo[3,4-c]pyrrolyl)phenyl)-1H-1,2,4-triazole-3,5-diamine, compound #75, $^1$H-NMR (DMSO-d$_6$, 300 MHz) 9.09 (s, 1H), 7.90 (s, 1H), 7.84 (s, 1H), 7.70 (m, 1H), 7.43 (m, 1H), 7.37 (m, 1H), 7.30 (m, 1H), 6.78 (m, 1H), 3.19 (m, 2H), 2.89 (m, 2H), 2.48-2.68 (m, 9H), 2.32 (m, 4H), 1.35-1.70 (m, 9H)ppm; MS (ES) 566.17 (M+H);

1-(6,7-dihydro-5H-benzo[6,7]cyclohepta[1,2-c]pyridazin-3-yl)-$N^3$-(3-fluoro-4-(3-(pyrrolidin-1-yl)-8-azabicyclo[3.2.1]oct-8-yl)phenyl)-1H-1,2,4-triazole-3,5-diamine, compound #76, $^1$H-NMR (DMSO-d$_6$, 300 MHz) 9.38 (broad s, 1H), 9.15 (s, 1H), 7.88 (s, 1H), 7.70 (m, 1H), 7.43 (m, 2H), 7.38 (m, 1H), 7.29 (m, 1H), 6.90 (t, 1H), 4.08 (m, 2H), 3.48 (m, 1H), 3.22 (m, 1H), 2.97 (m, 2H), 2.40-2.60 (m, 2H), 2.23 (m, 4H), 1.96 (m, 4H), 1.79 (m, 1H), 1.63 (m, 2H), 1.48 (m, 2H)ppm; MS (ES) 566.41 (M+H);

1-(6,7-dihydro-5H-benzo[6,7]cyclohepta[1,2-c]pyridazin-3-yl)-$N^3$-(3-fluoro-4-(4-pyrrolidin-1-yl-azepan-1-yl)phenyl)-1H-1,2,4-triazole-3,5-diamine, compound #77, $^1$H-NMR (CDCl$_3$/MeOD$_4$, 300 MHz) 7.88 (s, 1H), 7.70 (m, 1H), 7.43 (m, 2H), 7.35 (m, 1H), 7.26 (m, 1H), 7.12 (m, 1H), 6.93 (t, 1H), 3.39 (m, 1H), 3.15-3.45 (m, 4H), 2.95 (m, H), 2.66 (m, 1H), 2.58 (m, 4H), 2.32 (m, 4H), 1.80-2.20 (m, 9H)ppm; MS (ES) 554.54 (M+H);

1-(6,7-dihydro-5H-benzo[6,7]cyclohepta[1,2-c]pyridazin-3-yl)-$N^3$-(3-fluoro-4-(4-(4-methylpiperazin-1-yl)piperidin-1-yl)phenyl)-1H-1,2,4-triazole-3,5-diamine, compound #78;

1-(6,7-dihydro-5H-benzo[6,7]cyclohepta[1,2-c]pyridazin-3-yl)-$N^3$-(3-fluoro-4-(4-(4-isopropylpiperazin-1-yl)piperidin-1-yl)phenyl)-1H-1,2,4-triazole-3,5-diamine, compound #80, $^1$H-NMR (DMSO-d$_6$, 300 MHz) 9.24 (s, 1H), 7.91 (s, 1H), 7.71 (m, 1H), 7.46 (m, 3H), 7.34 (m, 2H), 7.00 (t, 1H), 3.53 (m, 2H), 3.37 (m, 2H), 3.10 (m, 4H), 2.40-2.60 (m, 8H), 2.24 (m, 2H), 2.06 (m, 2H), 1.75 (m, 2H), 1.24 (d, 6H)ppm; MS (ES) 597.17 (M+H);

1-(6,7-dihydro-5H-benzo[6,7]cyclohepta[1,2-c]pyridazin-3-yl)-$N^3$-(3-fluoro-4-(1-methyloctahydropyrrolo[3,4-b]pyrrol-5-yl)phenyl)-1H-1,2,4-triazole-3,5-diamine, compound #81, $^1$H-NMR (CDCl$_3$/MeOD$_4$, 300 MHz) 7.80 (s, 1H), 7.62 (m, 1H), 7.35 (m, 3H), 7.20 (m, 1H), 7.05 (m, 1H), 6.73 (t, 1H), 3.80-3.85 (m, 2H), 3.30 (m, 1H), 2.90-3.20 (m, 4H), 2.83 (s, 3H), 2.56 (m, 2H), 2.51 (m, 4H), 2.24 (m, 2H), 1.95 (m, 1H)ppm; MS (ES) 512.15 (M+H);

1-(6,7-dihydro-5H-benzo[6,7]cyclohepta[1,2-c]pyridazin-3-yl)-$N^3$-(3-fluoro-4-(4-(N-methylcyclopentylamino)piperidinyl)phenyl)-1H-1,2,4-triazole-3,5-diamine, compound #82, $^1$H-NMR (CDCl$_3$/MeOD$_4$, 300 MHz) 7.91 (s, 1H), 7.71 (m, 1H), 7.41 (m, 3H), 7.29 (m, 1H), 7.16 (m, 1H), 6.92 (t, 1H), 3.40 (m, 2H), 3.31 (m, 1H), 3.05 (m, 1H), 2.90 (m, 1H), 2.50-2.70 (m, 6H), 2.34 (s, 3H), 2.29 (m, 1H), 1.87 (m, 6H), 1.73 (m, 2H), 1.55 (m, 4H)ppm; MS (ES) 597.17 (M+H);

1-(6,7-dihydro-5H-benzo[6,7]cyclohepta[1,2-c]pyridazin-3-yl)-$N^3$-(3-fluoro-4-(4-(dipropylamino)piperidin-1-yl)phenyl)-1H-1,2,4-triazole-3,5-diamine, compound #83, $^1$H-NMR (CDCl$_3$/MeOD$_4$, 300 MHz) 7.67 (s, 1H), 7.59 (m, 1H), 7.48 (m, 1H), 7.29 (m, 2H), 7.12 (m, 2H), 6.81 (t, 1H), 3.37 (m, 2H), 3.27 (m, 1H), 2.96 (m, 2H), 2.85 (m, 2H), 2.64 (t, 2H), 2.46 (m, 4H), 2.14 (m, 2H), 1.99 (m, 2H), 1.84 (m, 2H), 1.68 (m, 4H)ppm; MS (ES) 570.38 (M+H);

1-(6,7-dihydro-5H-benzo[6,7]cyclohepta[1,2-c]pyridazin-3-yl)-$N^3$-(3-fluoro-4-(1-propyloctahydro-1H-pyrrolo[3,2-c]pyridine-5-yl)phenyl)-1H-1,2,4-triazole-3,5-diamine, compound #84, $^1$H-NMR (CDCl$_3$/MeOD$_4$, 300 MHz) 7.78 (s, 1H), 7.61 (m, 1H), 7.32 (m, 2H), 7.24 (m, 1H), 7.18 (m, 1H), 7.05 (m, 1H), 6.83 (m, 1H), 3.97 (m, 1H), 3.50 (m, 1H), 3.19 (m, 2H), 2.80-3.05 (m, 4H), 2.45-2.65 (m, 7H), 2.23 (m, 2H), 2.19 (m, 2H), 1.65-1.80 (m, 3H), 0.90 (m, 3H)ppm; MS (ES) 555.40 (M+H);

1-(6,7-dihydro-5H-benzo[6,7]cyclohepta[4,5-c]pyridazin-2-yl)-$N^3$-(3-fluoro-4-(4-(N-methylpiperazin-1-yl)piperidin-1-yl)phenyl)-1H-1,2,4-triazole-3,5-diamine, compound #85, $^1$H-NMR (DMSO-d$_6$, 300 MHz) 9.16 (s, 1H), 7.80 (s, 1H), 7.59 (m, 1H), 7.48 (m, 2H), 7.42 (m, 2H), 7.25 (m, 1H), 6.92 (t, 1H), 2.80 (m, 1H), 2.40-2.50 (m, 12H), 2.28 (m, 6H), 2.13 (s, 3H), 1.76 (m, 2H), 1.53 (m, 2H)ppm; MS (ES) 569 (M+H);

1-(6,7-dihydro-5H-benzo[6,7]cyclohepta[1,2-c]pyridazin-3-yl)-M-(3-fluoro-4-(4-(tert-butyloxycarbonylamino)piperidin-1-yl)phenyl)-1H-1,2,4-triazole-3,5-diamine, compound #86, $^1$H-NMR (CDCl$_3$/MeOD$_4$, 300 MHz) 7.76 (s, 1H), 7.58 (m, 1H), 7.42 (m, 1H), 7.27 (m, 2H), 7.16 (m, 3H), 3.41 (m, 3H), 3.16 (m, 2H), 2.54 (m, 2H), 2.46 (m, 2H), 2.18 (m, 2H), 1.97 (m, 2H), 1.95 (m, 2H), 1.76 (m, 2H), 1.28 (s, 9H)ppm; MS (ES) 586.19 (M+H);

1-(6,7-dihydro-5H-benzo[6,7]cyclohepta[1,2-c]pyridazin-3-yl)-$N^3$-(3-fluoro-4-(4-aminopiperidin-1-yl)phenyl)-1H-1,2,4-triazole-3,5-diamine, compound #87, $^1$H-NMR (CDCl$_3$/MeOD$_4$, 300 MHz) 7.83 (s, 1H), 7.65 (m, 1H), 7.36 (m, 3H), 7.21 (m, 1H), 7.12 (m, 1H), 6.98 (t, 1H), 3.36 (m, 2H), 3.13 (m, 1H), 2.79 (m, 2H), 2.60 (m, 2H), 2.53 (m, 2H), 2.28 (m, 2H), 2.04 (m, 2H), 1.83 (m, 2H)ppm; MS (ES) 486.15 (M+H);

1-(6,7-dihydro-5H-benzo[6,7]cyclohepta[1,2-c]pyridazin-3-yl)-M-(3-fluoro-4-(4-(5-cyclohexyloctahydropyrrolo[3,4-c]pyrrolyl)piperidin-1-yl)phenyl)-1H-1,2,4-triazole-3,5-diamine, compound #88, $^1$H-NMR (CDCl$_3$/MeOD$_4$, 300 MHz) 7.83 (s, 1H), 7.68 (m, 1H), 7.40 (m, 2H), 7.24 (m, 2H), 7.07 (m, 1H), 6.86 (t, 1H), 3.30 (m, 4H), 3.08 (m, 2H), 2.88 (m, 2H), 2.45-2.65 (m, 8H), 2.26 (m, 2H), 1.97 (m, 8H), 1.82 (m, 2H), 1.61 (m, 2H), 1.45 (m, 2H), 1.18 (m, 4H)ppm; MS (ES) 666.30 (M+H);

1-(6,7-dihydro-5H-benzo[6,7]cyclohepta[1,2-c]pyridazin-3-yl)-$N^3$-(2,3,4,5-tetrahydrobenzo[b]oxepin-7-yl)-1H-1,2,4-triazole-3,5-diamine, compound #89, $^1$H NMR (CDCl$_3$, 300 MHz) 7.61 (d, 1H), 7.34 (s, 1H), 7.28 (t, 1H), 7.24 (d, 1H), 7.21 (t, 1H), 7.18 (s, 1H), 6.87 (d, 1H), 6.78 (d, 1H), 5.42 (s, 2H), 4.05 (t, 2H), 3.31 (t, 2H), 2.85-2.60 (m, 4H), 2.05 (m, 2H), 1.71-1.55 (m, 2H), 1.45 (m, 2H) ppm; MS (ES) 440.07 (M+H);

1-(6,7-dihydro-5H-benzo[6,7]cyclohepta[1,2-c]pyridazin-3-yl)-$N^3$-(44(N-butyl-N-acetoamino)methyl)phenyl)-1H-1,2,4-triazole-3,5-diamine, compound #90, $^1$H NMR (CDCl$_3$, 300 MHz) 7.85 (s, 1H), 7.60 (d, 2H), 7.55-7.19 (m, 6H), 5.55 (s, 2H), 4.61 (s, 1H), 3.34 (m, 2H), 2.76 (d, 2H), 2.1 (s, 2H), 2.05-1.85 (m, 2H), 1.42 (m, 2H), 1.12 (m, 3H) ppm, MS (ES) 497.53 (M+H);

1-(6,7-dihydro-5H-benzo[6,7]cyclohepta[1,2-c]pyridazin-3-yl)-$N^3$-(4-((5-fluoroindolin-2-on-3-yl)methyl)phenyl)-1H-1,2,4-triazole-3,5-diamine, compound #91, $^1$H NMR (CDCl$_3$, 300 MHz) 7.66 (d, 2H), 7.59 (d, 2H), 7.31 (s, 1H), 7.30-7.18 (m, 3H), 7.11 (d, 1H), 7.08-7.03 (m, 3H), 7.00 (t, 1H), 5.93 (s, 2H), 3.71 (s, 1H), 3.58 (d, 1H), 3.33-3.18 (m, 2H), 3.14 (m, 2H), 2.55 (m, 2H), 2.10-1.96 (m, 2H) ppm; MS (ES) 533.14 (M+H);

1-(6,7-dihydro-5H-benzo[6,7]cyclohepta[1,2-c]pyridazin-3-yl)-$N^3$-(6-iodopyridin-3-yl)-1H-1,2,4-triazole-3,5-diamine, compound #92, $^1$H NMR (CDCl$_3$, 300 MHz) 8.73 (s, 1H), 7.61 (d, 1H), 7.49 (d, 1H), 7.38 (s, 1H), 7.28-7.17 (m, 4H), 5.81 (s, 2H), 2.89 (m, 2H), 2.38 (m, 2H), 2.10-1.89 (m, 2H) ppm; MS (ES) 497.09 (M+H);

1-(6,7-dihydro-5H-benzo[6,7]cyclohepta[1,2-c]pyridazin-3-yl)-$N^3$-(pyridin-3-yl)-1H-1,2,4-triazole-3,5-diamine, compound #93, $^1$H NMR (CDCl$_3$, 300 MHz) 8.77 (s, 1H), 8.13 (d, 1H), 7.67 (d, 1H), 7.46 (d, 1H), 7.35 (s, 1H), 7.22-7.13 (m, 4H), 5.62 (s, 2H), 2.79 (m, 2H), 2.29 (m, 2H), 2.05-1.83 (m, 2H) ppm; MS (ES) 371.07 (M+H);

1-(6,7-dihydro-5H-benzo[6,7]cyclohepta[1,2-c]pyridazin-3-yl)-$N^3$-(6-(6-aminopyridin-3-yl)pyridine-3-yl)-1H-1,2,4-triazole-3,5-diamine, compound #94, $^1$H NMR (CDCl$_3$, 300 MHz); 8.98 (s, 1H), 8.88 (s, 1H), 8.09 (d, 1H), 7.69 (d, 1H), 7.59 (d, 1H), 7.53 (s, 1H), 7.29-7.18 (m, 2H), 6.51 (s, 2H), 5.38 (s, 2H), 2.93 (m, 2H), 2.42 (m, 2H), 2.11-1.92 (m, 2H) ppm; MS (ES) 463.11 (M+H);

1-(6,7-dihydro-5H-benzo[6,7]cyclohepta[1,2-c]pyridazin-3-yl)-$N^3$-(6-(3-aminophenyl)pyridine-3-yl)-1H-1,2,4-triazole-3,5-diamine, compound #95, $^1$H NMR (CDCl$_3$, 300 MHz); 8.75 (s, 1H), 7.96 (d, 1H), 7.73 (d, 1H), 7.56 (d, 1H), 7.51 (s, 1H), 7.31-7.13 (m, 6H), 6.79 (d, 1H), 5.91 (s, 2H), 5.23 (s, 2H), 2.83 (m, 2H), 2.38-2.29 (m, 2H), 2.04-1.96 (m, 2H) ppm; MS (ES) 462.14 (M+H);

1-(6,7-dihydro-5H-benzo[6,7]cyclohepta[1,2-c]pyridazin-3-yl)-$N^3$-(6-(3-cyanophenyl)pyridine-3-yl)-1H-1,2,4-triazole-3,5-diamine, compound #96, $^1$H NMR (CDCl$_3$, 300 MHz) 8.75 (s, 1H), 8.06 (d, 1H), 7.93 (d, 1H), 7.66 (d, 1H), 7.52 (d, 1H), 7.36 (m, 1H), 7.31-7.17 (m, 6H), 5.73 (s, 2H), 2.79 (m, 2H), 2.31 (m, 2H), 2.06 (m, 2H) ppm; MS (ES) 472.08 (M+H);

1-(6,7-dihydro-5H-benzo[6,7]cyclohepta[1,2-c]pyridazin-3-yl)-$N^3$-(64 benzo[d][1,3]dioxole-6-yhpyridine-3-O-1H-1,2,4-triazole-3,5-diamine, compound #97, $^1$H NMR (CDCl$_3$, 300 MHz) 8.89 (s, 1H), 8.02 (m, 1H), 7.57 (d, 1H), 7.38 (s, 1H), 7.34-7.17 (m, 4H), 6.83 (d, 1H), 5.98 (s, 2H), 5.88-5.83 (m, 3H), 2.88 (m, 2H), 2.45 (m, 2H), 1.98 (m, 2H) ppm; MS (ES) 491.10 (M+H);

1-(6,7-dihydro-5H-benzo[6,7]cyclohepta[1,2-c]pyridazin-3-yl)-$N^3$-(6-(3-methylsulfonamidylphenyl)pyridine-3-yl)-1H-1,2,4-triazole-3,5-diamine, compound #98, $^1$H NMR (CDCl$_3$, 300 MHz) 8.88 (s, 1H), 8.02 (d, 1H), 7.91 (d, 1H), 7.63 (d, 1H), 7.49 (d, 1H), 7.34 (m, 1H), 7.29-7.15 (m, 6H), 5.53 (s, 2H), 3.08 (s, 3H), 2.83 (m, 2H), 2.29 (m, 2H), 1.97 (m, 2H) ppm; MS (ES) 540.01 (M+H);

1-(6,7-dihydro-5H-benzo[6,7]cyclohepta[1,2-c]pyridazin-3-yl)-$N^3$-(4-(methylpiperidin-4-yl)phenyl)-1H-1,2,4-triazole-3,5-diamine, compound #99, $^1$H NMR (DMSO-d$_6$, 300 MHz) 9.11 (br s, 1H), 7.95 (s, 1H), 7.84 (br s, 2H), 7.72-7.69 (m, 1H), 7.56 (d, 2H), 7.46-7.43 (m, 2H), 7.34-7.32 (m, 1H), 7.12 (d, 2H), 3.01-2.92 (m, 4H), 2.62-2.59 (m, 1H), 2.47 (s, 3H), 2.43-2.24 (m, 4H), 1.76-1.67 (m, 6H) ppm; MS (ES) 467.17 (M+H);

1-(6,7-dihydro-5H-benzo[6,7]cyclohepta[1,2-c]pyridazin-3-yl)-$N^3$-(3,4-dihydro-2H-benzo[b][1,4]dioxepin-7-yl)-1H-1,2,4-triazole-3,5-diamine, compound #100, $^1$H NMR (DMSO-d$_6$, 300 MHz) 9.05 (s, 1H), 7.83 (br s, 2H), 7.72-7.67 (m, 1H), 7.46-7.43 (m, 2H), 7.38-7.34 (m, 1H), 7.25-7.18 (m, 3H), 6.85 (d, 2H), 4.08 (m, 2H), 4.01 (m, 2H), 2.59-2.52 (m, 4H), 2.25-2.23 (m, 2H), 2.05 (m, 2H) ppm; MS (ES) 442.52 (M+H);

1-(6,7-dihydro-5H-benzo[6,7]cyclohepta[1,2-c]pyridazin-3-yl)-$N^3$-(4-(4-pyrrolidin-1-ylpiperidinyl)phenyl)-1H-1,2,4-triazole-3,5-diamine, compound #101, $^1$H NMR (DMSO-d$_6$, 300 MHz) 9.05 (br s, 1H), 8.88 (s, 1H), 7.99 (s, 1H), 7.92 (s, 1H), 7.81 (s, 1H), 7.67 (br s, 2H), 7.50-7.43 (m, 2H), 7.36-7.34 (m, 1H), 6.93-6.86 (m, 2H), 2.61 (m, 4H), 2.56 (m, 1H), 2.42 (m, 4H), 2.25-2.20 (m, 4H), 2.08-2.04 (m, 2H), 1.97-1.92 (m, 2H), 1.70 (m, 4H), 1.55-1.51 (m, 2H) ppm; MS (ES) 522.37 (M+H);

1-(6,7-dihydro-5H-benzo[6,7]cyclohepta[1,2-c]pyridazin-3-yl)-$N^3$-(4-((4-pyrrolidin-1-ylpiperidinyl)methyl)phenyl)-1H-1,2,4-triazole-3,5-diamine, compound #103, $^1$H NMR (DMSO-d$_6$, 300 MHz) 9.17 (br s, 1H), 7.96 (s, 1H), 7.84 (br s, 2H), 7.72-7.69 (m, 1H), 7.57 (d, 2H), 7.45-7.43 (m, 2H), 7.36-7.35 (m, 1H), 7.15 (d, 2H), 3.37 (s, 2H), 2.81-2.78 (m, 2H), 2.66 (m, 4H), 2.46 (m, 2H), 2.21-2.20 (m, 4H), 2.09-2.07 (m, 1H), 1.93-1.81 (m, 4H), 1.71 (m, 4H), 1.50-1.38 (m, 2H) ppm; MS (ES) 536.45 (M+H);

1-(6,7-dihydro-5H-benzo[6,7]cyclohepta[1,2-c]pyridazin-3-yl)-$N^3$-(4-((4-cyclopentylpiperazinyl)methyl)phenyl)-1H-1,2,4-triazole-3,5-diamine, compound #104, $^1$H NMR (DMSO-d$_6$, 300 MHz) 9.16 (br s, 1H), 7.96 (s, 1H), 7.84 (br s, 2H), 7.72-7.65 (m, 1H), 7.57 (d, 2H), 7.45-7.43 (m, 2H), 7.37-7.35 (m, 1H), 7.15 (d, 2H), 3.36 (s, 2H), 2.62 (m, 1H), 2.53 (m, 4H), 2.43-2.38 (m, 4H), 2.26-2.23 (m, 4H), 1.73 (m, 2H), 1.58-1.46 (m, 6H), 1.30-1.24 (m, 2H) ppm; MS (ES) 536.59 (M+H);

1-(6,7-dihydro-5H-benzo[6,7]cyclohepta[1,2-c]pyridazin-3-yl)-N³-(3-fluoro-4-(4-pyrrolidin-1-ylpiperidinyl)phenyl)-1H-1,2,4-triazole-3,5-diamine, compound #105, ¹H NMR (DMSO-d₆, 300 MHz) 10.22 (br s, 1H), 9.25 (br s, 1H), 7.91 (s, 1H), 7.87 (br s, 2H), 7.70 (dd, 1H), 7.46-7.42 (m, 3H), 7.37-7.35 (m, 2H), 6.99 (t, 1H), 3.56-3.51 (m, 2H), 3.21-3.18 (m, 1H), 3.07 (m, 2H), 2.66-2.59 (m, 4H), 2.54 (m, 4H), 2.26-2.22 (m, 2H), 2.15-2.11 (m, 2H), 1.99-1.98 (m, 2H), 1.86-1.79 (m, 4H) ppm; MS (ES) 540.29 (M+H);

1-(6,7-dihydro-5H-benzo[6,7]cyclohepta[1,2-c]pyridazin-3-yl)-N³-(3-methyl-4-(4-pyrrolidin-1-ylpiperidinyl)phenyl)-1H-1,2,4-triazole-3,5-diamine, compound #106, ¹H NMR (DMSO-d₆, 300 MHz) 8.92 (br s, 1H), 7.91 (s, 1H), 7.82 (br s, 2H), 7.70 (dd, 1H), 7.53 (m, 1H), 7.45-7.43 (m, 2H), 7.38-7.35 (m, 1H), 7.26 (d, 1H), 6.94 (d, 1H), 2.98-2.94 (m, 2H), 2.61-2.59 (m, 3H), 2.55 (m, 4H), 2.54 (m, 4H), 2.26 (M, 1H), 2.22 (s, 3H), 2.04 (m, 1H), 1.93-1.89 (m, 2H), 1.68 (m, 4H), 1.55-1.50 (m, 2H) ppm; MS (ES) 536.09 (M+H);

1-(6,7-dihydro-5H-benzo[6,7]cyclohepta[1,2-c]pyridazin-3-yl)-N³-(3-methyl-4-(4-pyrrolidin-1-ylpiperidinyl)phenyl)-1H-1,2,4-triazole-3,5-diamine, formic acid (formic acid salt of compound #106, ¹H NMR (DMSO-d₆, 300 MHz) 8.93 (br s, 1H), 7.91 (s, 1H), 7.82 (br s, 2H), 7.72-7.68 (m, 1H), 7.56-7.52 (m, 1H), 7.45-7.42 (m, 2H), 7.38-7.34 (m, 1H), 7.25-7.27 (m, 1H), 6.95 (d, 2H), 2.95-2.93 (m, 4H), 2.59 (m, 4H), 2.56-2.46 (m, 5H), 2.28-1.96 (m, 2H), 2.22 (s, 3H), 1.95-1.91 (m, 2H), 1.72 (m, 2H), 1.70 (m, 4H), 1.60-1.50 (m, 2H) ppm; MS (ES) 536.57 (M+H);

1-(6,7-dihydro-5H-benzo[6,7]cyclohepta[1,2-c]pyridazin-3-yl)-N³-(3-fluoro-4-(4-cyclopentylpiperazinyl)phenyl)-1H-1,2,4-triazole-3,5-diamine, compound #107, ¹H NMR (DMSO-d₆, 300 MHz) 9.33 (br s, 1H), 7.92 (s, 1H), 7.88 (br s, 2H), 7.71 (m, 1H), 7.51-7.38 (m, 5H), 7.04 (t, 1H), 3.37 (m, 4H), 3.24-3.22 (m, 2H), 3.01-2.97 (m, 2H), 2.60 (m, 1H), 2.49 (m, 4H), 2.25 (m, 2H), 2.03 (m, 2H), 1.71 (m, 4H), 1.57 (m, 2H) ppm; MS (ES) 540.24 (M+H);

1-(6,7-dihydro-5H-benzo[6,7]cyclohepta[1,2-c]pyridazin-3-yl)-N³-(44(4-isopropylpiperazinyl)methyl)phenyl)-1H-1,2,4-triazole-3,5-diamine, compound #108, ¹H NMR (DMSO-d₆, 300 MHz) 9.32 (br s, 1H), 7.96 (s, 1H), 7.87 (br s, 2H), 7.74-7.69 (m, 1H), 7.64 (d, 2H), 7.45 (d, 2H), 7.38-7.36 (m, 1H), 7.27 (m, 2H), 3.45 (s, 2H), 3.05 (m, 4H), 2.72 (m, 2H), 2.55 (m, 4H), 2.40 (m, 4H), 2.26 (m, 2H), 1.22 (d, 6H) ppm; MS (ES) 510.29 (M+H);

1-(6,7-dihydro-5H-benzo[6,7]cyclohepta[1,2-c]pyridazin-3-yl)-N³-(3-fluoro-4-(4-N-methylpiperidin-4-ylpiperazinyl)phenyl)-1H-1,2,4-triazole-3,5-diamine, compound #109, ¹H NMR (DMSO-d₆, 300 MHz) 9.33 (br s, 1H), 7.91 (s, 1H), 7.88 (br s, 2H), 7.70 (dd, 1H), 7.51-7.35 (m, 5H), 7.04 (t, 1H), 3.25 (m, 4H), 3.02-2.96 (m, 4H), 2.78 (s, 3H), 2.62-2.58 (m, 1H), 2.56-2.52 (m, 4H), 2.43-2.42 (m, 4H), 2.36-2.33 (m, 2H), 2.26-2.22 (m, 2H), 1.86-1.81 (m, 2H) ppm; MS (ES) 569.27 (M+H);

1-(6,7-dihydro-5H-benzo[6,7]cyclohepta[1,2-c]pyridazin-3-yl)-N³-(3-fluoro-4-(7-methyl-2,7-diazaspiro[4.4]nonan-2-yl)phenyl)-1H-1,2,4-triazole-3,5-diamine, compound #110, ¹H NMR (DMSO-d₆, 300 MHz) 9.06 (br s, 1H), 7.86 (s, 1H), 7.83 (br s, 2H), 7.70-7.68 (m, 1H), 7.44-7.42 (m, 2H), 7.37-7.35 (m, 2H), 7.29-7.26 (m, 1H), 6.69 (t, 1H), 3.61-3.57 (m, 4H), 3.30 (m, 4H), 3.15-3.00 (m, 4H), 2.84 (s, 3H), 2.24-2.13 (m, 4H), 2.01-1.90 (m, 2H) ppm; MS (ES) 525.55 (M+H);

1-(6,7-dihydro-5H-benzo[6,7]cyclohepta[1,2-c]pyridazin-3-yl)-N³-(3-fluoro-4-(N-isopropylpiperazin-1-yl)phenyl)-1H-1,2,4-triazole-3,5-diamine, compound #111, ¹H NMR (DMSO-d₆, 300 MHz) 9.31 (br s, 1H), 7.91 (s, 1H), 7.87 (br s, 2H), 7.71-7.68 (m, 1H), 7.50-7.36 (m, 5H), 7.04 (t, 1H), 3.51-3.47 (m, 3H), 3.41-3.38 (m, 2H), 3.19 (q, 2H), 2.99 (t, 2H), 2.59 (m, 4H), 2.24-2.20 (m, 2H), 1.28 (d, 6H) ppm; MS (ES) 514.26 (M+H);

1-(6,7-dihydro-5H-benzo[6,7]cyclohepta[1,2-c]pyridazin-3-yl)-N³-(3-fluoro-4-(4-pyrrolidin-1-ylpiperidinyl)phenyl)-1H-1,2,4-triazole-3,5-diamine, benzenesulfonic acid salt, (benzene sulfonic acid salt of compound #4), ¹H NMR (DMSO-d₆, 300 MHz) 9.24 (br s, 1H), 7.91 (s, 1H), 7.86 (br s, 2H), 7.72-7.69 (m, 1H), 7.58-7.54 (m, 2H), 7.47-7.42 (m, 3H), 7.38-7.34 (dd, 2H), 7.31-7.27 (m, 3H), 6.99 (t, 1H), 3.54 (m, 2H), 3.36-3.30 (m, 4H), 3.10 (m, 2H), 2.69-2.67 (m, 1H), 2.63-2.60 (m, 2H), 2.54-2.52 (m, 2H), 2.26-2.22 (m, 2H), 2.15-2.11 (m, 2H), 2.02 (m, 2H), 1.88-1.82 (m, 2H), 1.78-1.70 (m, 2H) ppm; MS (ES) 538.37 (M+H);

1-(6,7-dihydro-5H-benzo[6,7]cyclohepta[1,2-c]pyridazin-3-yl)-N³-(3-fluoro-4-(3-pyrrolidin-1-ylazetidinyl)phenyl)-1H-1,2,4-triazole-3,5-diamine, compound #113, ¹H NMR (DMSO-d₆, 300 MHz) 9.16 (br s, 1H), 7.90 (s, 1H), 7.85 (br s, 2H), 7.72-7.68 (m, 1H), 7.49-7.47 (m, 1H), 7.45-7.43 (m, 2H), 7.38-7.29 (m, 2H), 6.59 (t, 1H), 4.15-4.07 (m, 2H), 3.94-3.92 (m, 2H), 3.80-3.76 (m, 2H), 3.60 (m, 2H), 2.03 (m, 1H), 2.60-2.54 (m, 4H), 2.26-2.22 (m, 2H), 2.05 (m, 2H), 1.89 (m, 2H) ppm; MS (ES) 512.50 (M+H);

1-(6,7-dihydro-5H-benzo[6,7]cyclohepta[1,2-c]pyridazin-3-yl)-N³-(3-methyl-4-(4-(N-methylpiperazin-4-yl)piperidin-1-yl)phenyl)-1H-1,2,4-triazole-3,5-diamine, compound #114, ¹H NMR (DMSO-d₆, 300 MHz) 9.02 (br s, 1H), 7.91 (s, 1H), 7.84 (br s, 2H), 7.72-7.69 (m, 1H), 7.55 (d, 1H), 7.46-7.43 (m, 2H), 7.38-7.35 (m, 1H), 7.31 (m, 1H), 7.02-6.99 (m, 1H), 4.07 (m, 2H), 3.64 (m, 2H), 3.52 (m, 2H), 3.12-2.95 (m, 4H), 2.78 (s, 3H), 2.71 (m, 1H), 2.61 (t, 2H), 2.56-2.54 (m, 2H), 2.43-2.41 (m, 2H), 2.25 (s, 3H), 2.24 (m, 2H), 2.02-2.00 (m, 2H), 1.72-1.68 (m, 2H) ppm; MS (ES) 565.29 (M+H);

1-(6,7-dihydro-5H-benzo[6,7]cyclohepta[1,2-c]pyridazin-3-yl)-N³-(3-fluoro-4-((S)-3-(pyrrolidin-1-ylmethyl)pyrrolidinyl)phenyl)-1H-1,2,4-triazole-3,5-diamine, compound #115, ¹H NMR (DMSO-d₆, 300 MHz) 9.18 (br s, 1H), 7.88 (s, 1H), 7.85 (br s, 2H), 7.72-7.68 (m, 1H), 7.53-7.51 (m, 1H), 7.46-7.43 (m, 2H), 7.39-7.35 (m, 1H), 7.31 (dd, 1H), 6.94 (t, 1H), 3.99 (m, 2H), 3.13 (m, 4H), 3.01 (m, 4H), 2.60-2.52 (m, 2H), 2.43 (m, 2H), 2.26-2.22 (m, 4H), 2.20-2.10 (m, 1H), 1.93-1.90 (m, 4H) ppm; MS (ES) 540.28 (M+H);

1-(6,7-dihydro-5H-benzo[2,3]oxepino[4,5-c]pyridazin-3-yl)-N³-(4-(4-pyrrolidin-1-ylpiperidinyl)phenyl)-1H-1,2,4-triazole-3,5-diamine, compound #116, ¹H NMR (CD₃OD, 300 MHz) 9.04 (d, 1H), 8.03 (s, 1H), 7.84 (m, 2H), 7.60 (m, 2H), 7.35 (t, 1H), 7.20 (d, 1H), 6.99 (t, 2H), 4.57 (t, 2H), 4.47 (t, 2H), 3.70 (t, 4H), 3.40 (m, 4H), 2.99 (m, 2H), 2.73 (m, 2H), 2.23 (m, 2H), 2.09 (br s, 4H), 1.84 (m, 2H); MS (ES) 524.12 (M+H);

1-(6,7-dihydro-5H-benzo[2,3]oxepino[4,5-c]pyridazin-3-yl)-N³-(3-fluoro-4-(4-pyrrolidin-1-ylpiperidinyl)phenyl)-1H-1,2,4-triazole-3,5-diamine, compound #117, ¹H NMR (CD₃OD, 300 MHz) 8.24 (s, 1H), 8.00 (s, 1H), 7.82 (m, 1H), 7.48 (m, 2H), 7.35 (m, 1H), 7.20 (m, 1H), 6.98 (m, 1H), 4.61 (m, 4H), 3.48 (m, 4H), 3.02 (m, 4H), 2.76 (m, 4H), 2.21 (m, 2H), 2.10 (br s, 3H), 1.89 (m, 2H); MS (ES) 542.13 (M+H);

1-(6,7-dihydro-5H-benzo[2,3]oxepino[4,5-c]pyridazin-3-yl)-N³-(2-(pyrrolidin-1-ylmethyl)benzo[d]oxazol-5-yl)-1H-1,2,4-triazole-3,5-diamine, compound #118, ¹H NMR (CD₃OD, 300 MHz) 8.13 (s, 1H), 7.84 (m, 1H), 7.69 (m, 1H), 7.53 (m, 1H), 7.38 (m, 1H), 7.20 (m, 2H), 6.95 (d, 1H), 4.60 (m, 4H), 3.74 (s, 2H), 3.05 (m, 4H), 2.12 (m, 4H); MS (ES) 496.08 (M+H);

1-(6,7-dihydro-5H-benzo[2,3]thiepino[4,5-c]pyridazin-3-yl)-N³-(3-fluoro-4-(4-pyrrolidin-1-ylpiperidinyl)phenyl)-1H-1,2,4-triazole-3,5-diamine, compound #119, ¹H NMR (CD₃OD, 300 MHz) 8.05 (s, 1H), 7.78 (m, 1H), 7.70 (m, 1H), 7.61 (m, 1H), 7.53 (m, 2H), 7.25 (m, 1H), 7.02 (m, 1H), 3.70 (t, 2H), 3.47 (m, 4H), 3.20 (m, 4H), 2.97 (m, 2H), 2.80 (t, 2H), 2.30-1.80 (m, 8H); MS (ES) 558.18 (M+H);

1-(6,7-dihydro-5H-benzo[2,3]thiepino[4,5-c]pyridazin-3-yl)-N³-(4-(4-pyrrolidin-1-ylpiperidinyl)phenyl)-1H-1,2,4-triazole-3,5-diamine, compound #120, ¹H NMR (CD₃OD, 300 MHz) 8.07 (s, 1H), 7.80-7.48 (m, 6H), 7.39 (m, 2H), 3.78 (t, 2H), 3.46 (m, 4H), 3.24 (m, 4H), 2.95 (m, 2H), 2.43 (m, 2H), 2.26-2.02 (m, 8H); MS (ES) 540.16 (M+H);

1-(6,7-dihydro-5H-benzo[6,7]cyclohepta[1,2-c]pyridazin-3-yl)-N³-(4-(2-dimethylaminoethyl)-(3,4-dihydro-2H-benzo[b][1,4]oxazin-7-yl))—1H-1,2,4-triazole-3,5-diamine, compound #121, ¹H NMR (CD₃OD, 300 MHz) 8.41 (m, 1H), 7.93 (m, 1H), 7.73 (m, 1H), 7.52-7.23 (m, 3H), 7.20 (m, 1H), 7.02 (m, 1H), 6.79 (m, 1H), 4.24 (t, 3H), 3.53 (t, 2H), 3.29 (m, 6H), 2.93 (s, 3H), 2.92 (s, 3H), 2.60 (m, 4H), 2.28 (m, 2H); MS (ES) 498.18 (M+H);

1-(6,7-dihydro-5H-benzo[2,3]oxepino[4,5-c]pyridazin-3-yl)-N³-(4-(2-dimethylaminoethyl)-(3,4-dihydro-2H-benzo[b][1,4]oxazin-7-yl))-1H-1,2,4-triazole-3,5-diamine, compound #122, ¹H NMR (CD₃OD, 300 MHz) 8.38 (m, 1H), 7.98 (m, 1H), 7.80 (m, 1H), 7.49 (m, 1H), 7.31 (m, 1H), 7.18 (m, 1H), 6.97 (m, 1H), 6.76 (m, 1H), 4.60 (t, 2H), 4.23 (br s, 2H), 3.53 (br s, 2H), 3.28 (m, 6H), 2.94 (s, 3H), 2.92 (s, 3H); MS (ES) 500.13 (M+H);

1-(6,7-dihydro-5H-benzo[2,3]thiepino[4,5-c]pyridazin-3-yl)-N³-(3-fluoro-4-(isoindolin-2-yl)phenyl)-1H-1,2,4-triazole-3,5-diamine, compound #123, ¹H NMR (CD₃OD, 300 MHz) 8.03 (s, 1H), 7.80-7.21 (m, 11H), 3.42 (t, 2H), 3.37 (s, 4H), 3.01 (t, 2H); MS (ES) 523.08 (M+H);

1-(6,7-dihydro-5H-benzo[6,7]cyclohepta[1,2-c]pyridazin-3-yl)-N³-(3-fluoro-4-(4-(pyrrolidinylmethyl)piperidinyl) phenyl)-1H-1,2,4-triazole-3,5-diamine, compound #124, ¹H NMR (CD₃OD, 300 MHz) 7.88 (s, 1H), 7.70 (m, 1H), 7.45 (m, 1H), 7.38 (m, 2H), 7.25 (m, 1H), 7.16 (m, 1H), 7.02 (m, 1H), 3.78 (m, 2H), 3.36 (m, 2H), 2.88 (m, 2H), 2.77 (t, 2H), 2.65*m, 2H), 2.57 (m, 2H), 2.30 (m, 2H), 2.07 (m, 4H), 1.90 (m, 3H), 1.56 (m, 2H); MS (ES) 554.22 (M+H);

1-(6,7-dihydro-5H-benzo[2,3]thiepino[4,5-c]pyridazin-3-yl)-N³-(3-fluoro-4-(4-(pyrrolidinylmethyl)piperidinyl) phenyl)-1H-1,2,4-triazole-3,5-diamine, compound #125, ¹H NMR (CD₃OD, 300 MHz) 7.93 (s, 1H), 7.74 (m, 1H), 7.65 (m, 1H), 7.54 (m, 2H), 7.46 (m, 1H), 7.17 (m, 1H), 7.10 (m, 1H), 3.74 (m, 2H), 3.43 (m, 4H), 3.07 (m, 2H), 2.94 (m, 6H), 2.08 (m, 4H), 1.94 (m, 2H), 1.63 (m, 2H); MS (ES) 572.22 (M+H);

1-(6,7-dihydro-5H-benzo[2,3]thiepino[4,5-c]pyridazin-3-yl)-N³-(3-fluoro-4-((4aR,8aS)-decahydroisoquinolin-2-yl)phenyl)-1H-1,2,4-triazole-3,5-diamine, compound #126, ¹H NMR (CD₃OD, 300 MHz) 8.02 (s, 1H), 7.80-7.32 (m, 7H), 3.62 (m, 1H), 3.44 (m, 4H), 3.14 (t, 1H), 2.96 (t, 2H), 2.64 (m, 1H), 2.02 (m, 1H), 1.95-1.58 (m, 6H), 1.36 (m, 2H), 1.11 (m, 2H); MS (ES) 543.17 (M+H);

1-(6,7-dihydro-5H-benzo[6,7]cyclohepta[1,2-c]pyridazin-3-yl)-N³-(3-fluoro-4-((4aR,8aS)-decahydroisoquinolin-2-yl)phenyl)-1H-1,2,4-triazole-3,5-diamine, compound #127, ¹H NMR (CD₃OD, 300 MHz) 8.07 (s, 1H), 7.84 (m, 1H), 7.80 (m, 1H), 7.70 (m, 1H), 7.58 (m, 1H), 7.46 (m, 2H), 7.37 (m, 1H), 3.67 (m, 2H), 3.53 (m, 1H), 3.37 (m, 2H), 2.65 (m, 4H), 2.33 (t, 2H), 1.95 (m, 1H), 1.74 (m, 6H), 1.40 (m, 3H), 1.15 (m, 1H); MS (ES) 525.16 (M+H);

1-(6,7-dihydro-5H-benzo[6,7]cyclohepta[1,2-c]pyridazin-3-yl)-N³-(3-fluoro-4-(octahydro-1H-pyrido[1,2-a]pyrazin-2-yl)phenyl)-1H-1,2,4-triazole-3,5-diamine, compound #128, ¹H NMR (CD₃OD, 300 MHz) 8.31 (s, 1H), 7.92 (s, 1H), 7.70 (m, 1H), 7.44 (m, 2H), 7.32 (m, 2H), 3.31 (m, 4H), 3.05 (m, 3H), 2.60 (m, 6H), 2.35 (t, 2H), 1.90 (m, 4H), 1.50 (m, 2H); MS (ES) 526.20 (M+H);

1-(6,7-dihydro-5H-benzo[2,3]thiepino[4,5-c]pyridazin-3-yl)-N³-(3-fluoro-4-(octahydro-1H-pyrido[1,2-a]pyrazin-2-yl)phenyl)-1H-1,2,4-triazole-3,5-diamine, compound #129, ¹H NMR (CD₃OD, 300 MHz) 8.38 (s, 1H), 7.97 (s, 1H), 7.77-7.40 (m, 4H), 7.23 (m, 1H), 6.99 (m, 1H), 3.42 (m, 7H), 3.20-2.78 (m, 6H), 1.92 (m, 4H), 1.60 (m, 2H); MS (ES) 544.14 (M+H);

1-(6,7-dihydro-5H-benzo[6,7]cyclohepta[1,2-c]pyridazin-3-yl)-N³-(6-(2-diethylaminomethyl)pyrrolidin-1-ylpyridin-3-yl)-1H-1,2,4-triazole-3,5-diamine, compound #130; ¹H NMR (CD₃OD, 300 MHz) 8.44 (m, 1H), 8.28 (m, 1H), 7.93 (m, 2H), 7.75 (m, 2H), 7.45 (m, 2H), 6.82 (m, 2H), 4.39 (m, 1H), 3.60-3.30 (m, 4H), 2.66-1.85 (m, 13H), 1.40 (m, 8H); MS (ES) 525.25 (M+H);

1-(6,7-dihydro-5H-benzo[2,3]thiepino[4,5-c]pyridazin-3-yl)-N³-(2-(1-(4-(2-(dimethylamino)ethyl)piperazin-1-yl) oxomethyl)benzo[b]thiophen-5-yl)-1H-1,2,4-triazole-3,5-diamine, compound #131; ¹H NMR (CD₃OD, 300 MHz) 8.30 (s, 2H), 7.92-7.45 (m, 8H), 3.82 (m, 5H), 3.41 (m, 4H), 3.22 (s, 3H), 2.92 (m, 7H), 2.65 (m, 5H); MS (ES) 627.16 (M+H);

1-(6,7-dihydro-5H-benzo[6,7]cyclohepta[1,2-c]pyridazin-3-yl)-N³-(3-fluoro-(4-(3-pyrrolidin-1-yl)pyrrolidin-1-yl) phenyl)-1H-1,2,4-triazole-3,5-diamine, trifluoroacetic acid salt, compound #132; ¹H-NMR (DMSO-d₆, 300 MHz) 9.17 (s, 1H), 7.89 (s, 1H), 7.86 (br. s, 2H), 7.73-7.69 (m, 1H), 7.50-7.32 (m, 5H), 6.84 (t, J=9.9 Hz, 1H), 4.00-3.90 (m, 4H), 3.45-3.40 (m, 4H), 3.19-3.10 (m, 4H), 2.71 (m, 1H), 2.62-2.58 (m, 2H), 2.26-2.24 (m, 2H), 2.06-2.02 (m, 2H), 1.89-1.85 (m, 2H) ppm; MS (ES) 525.43 (M);

1-(6,7-dihydro-5H-benzo[6,7]cyclohepta[1,2-c]pyridazin-3-yl)-N³-(6-(3-diethylaminopyrrolidin-1-yl)pyridin-3-yl)-1H-1,2,4-triazole-3,5-diamine, formic acid salt, compound #133;

1-(6,7-dihydro-5H-benzo[6,7]cyclohepta[1,2-c]pyridazin-3-yl)-N³-(3-fluoro-4-(4-(5-methyloctahydropyrrolo[3,4-c] pyrrolyl)piperidin-1-yl)phenyl)-1H-1,2,4-triazole-3,5-diamine, formic acid salt, compound #134;

1-(6,7-dihydro-5H-benzo[6,7]cyclohepta[1,2-c]pyridazin-3-yl)-N³-(6-(3-(4-(N-methylpiperazin-4-yl)piperidin-1-yl)-(E)-propenyl)pyridin-3-yl)-1H-1,2,4-triazole-3,5-diamine, compound #135; ¹H NMR (CDCl₃, 300 MHz) 8.81 (s, 1H), 8.51 (s, 1H), 7.91-7.73 (m, 4H), 7.40 (m, 2H), 7.21 (m, 3H), 6.51 (m, 2H), 3.25-2.81 (m, 9H), 2.65 (m, 4H), 2.45 (s, 3H), 2.32 (m, 2H), 2.15 (m, 6H), 1.97 (m, 2H), 1.82 (m, 2H), 1.51 (m, 2H) ppm; MS (ES) 592.55 (M+H), 590.30 (M−H);

1-(6,7-dihydro-5H-benzo[6,7]cyclohepta[1,2-c]pyridazin-3-yl)-N³-(6-(4-(pyrrolidin-1-yl)piperidin-1-yl)-5-methylpyridin-3-yl)-1H-1,2,4-triazole-3,5-diamine, trifluoroacetic acid salt, compound #136; ¹H-NMR (DMSO-d₆, 300 MHz) 9.23 (s, 1H), 8.54 (s, 1H), 7.94 (s, 1H), 7.88 (br. s, 2H), 7.72-7.68 (m, 2H), 7.46-7.42 (m, 2H), 7.39-7.35 (m, 1H), 3.54 (m, 2H), 3.39-3.35 (m, 2H), 3.10-3.06 (m, 4H), 2.75-2.71 (m, 1H), 2.63-2.60 (m, 2H), 2.54-2.52 (m, 2H), 2.26 (s, 3H), 2.26-2.22 (m, 2H), 2.15-2.11 (m, 2H), 2.02 (m, 2H), 1.88-1.82 (m, 2H), 1.76-1.72 (m, 2H) ppm; MS (ES) 537.31 (M+H);

1-(6,7-dihydro-5H-benzo[6,7]cyclohepta[1,2-c]pyridazin-3-yl)-$N^3$-(3-fluoro-4-(octahydropyrrolo[3,4-c]pyrrolyl)phenyl)-1H-1,2,4-triazole-3,5-diamine, trifluoroacetic acid salt, compound #137;

1-(6,7-dihydro-5H-benzo[6,7]cyclohepta[1,2-c]pyridazin-3-yl)-$N^3$-(6-(3-piperidin-1-yl-(E)-propenyl)pyridin-3-yl)-1H-1,2,4-triazole-3,5-diamine, compound #138; $^1$H NMR (CDCl$_3$, 300 MHz) 8.85 (s, 1H), 8.53 (s, 1H), 7.95-7.77 (m, 4H), 7.42 (m, 2H), 7.25 (m, 3H), 6.56 (m, 2H), 3.05 (m, 2H), 2.54 (m, 4H), 2.24 (m, 4H), 1.94 (m, 2H), 1.52 (m, 6H) ppm; MS (ES) 494.38 (M+H), 492.29 (M−H);

1-(6,7-dihydro-5H-benzo[6,7]cyclohepta[1,2-c]pyridazin-3-yl)-$N^3$-(6-cyclopentyl-6,7,8,9-tetrahydro-5H-pyrido[3,2-c]azepin-3-yl)-1H-1,2,4-triazole-3,5-diamine, compound #139; $^1$H NMR (DMSO-d$_6$, 300 MHz) 10.96 (s, 1H), 9.94 (m, 1H), 9.08 (m, 1H), 8.18 (m, 1H), 7.86 (m, 1H), 7.72 (m, 1H), 7.40 (m, 4H), 4.54 (m, 3H), 3.16 (m, 2H), 2.49 (m, 2H), 2.25-1.51 (m, 16H) ppm; MS (ES) 508.4 (M+H);

1-(6,7-dihydro-5H-benzo[6,7]cyclohepta[1,2-c]pyridazin-3-yl)-$N^3$-(6-(4-(bicyclo[2.2.1]heptan-2-yl)-1,4-diazepan-1-yl)pyridin-3-yl)-1H-1,2,4-triazole-3,5-diamine, compound #140; $^1$H NMR (DMSO-d$_6$, 300 MHz) 9.40 (s, 1H), 8.72 (m, 1H), 7.97 (m, 4H), 7.71 (m, 1H), 7.41 (m, 3H), 7.14 (m, 1H), 4.13 (m, 1H), 3.86 (m, 1H), 3.57 (m, 4H), 3.19 (m, 2H), 2.60 (m, 6H), 2.24 (m, 5H), 1.97 (m, 1H), 1.54 (m, 3H), 1.37 (m, 3H), 1.20 (m, 1H) ppm; MS (ES) 563.3 (M+H);

1-(6,7-dihydro-5H-benzo[6,7]cyclohepta[1,2-c]pyridazin-3-yl)-$N^3$-(6-(3-(4-(pyrrolidin-1-yl)piperidin-1-yl)-(E)-propenyl)pyridin-3-yl)-1H-1,2,4-triazole-3,5-diamine, compound #141; $^1$H NMR (CDCl$_3$, 300 MHz) 8.91 (s, 1H), 8.33 (s, 2H), 7.97 (s, 1H), 7.83 (m, 2H), 7.61 (s, 1H), 7.50-7.23 (m, 3H), 7.13 (s, 1H), 6.72-6.41 (m, 2H), 3.37 (m, 1H), 3.22 (m, 6H), 3.05 (m, 2H), 2.76-2.51 (m, 5H), 2.33 (m, 4H), 2.03 (m, 6H) ppm; MS (ES) 563.25 (M+H), 561.68 (M−H);

1-(6,7-dihydro-5H-benzo[6,7]cyclohepta[1,2-c]pyridazin-3-yl)-$N^3$-(6-(3-piperidin-1-yl)-propanylpyridin-3-yl)-1H-1,2,4-triazole-3,5-diamine, compound #142; $^1$H NMR (CDCl$_3$, 300 MHz) 8.85 (s, 1H), 8.53 (s, 1H), 7.95-7.77 (m, 4H), 7.42 (m, 2H), 7.25 (m, 3H), 3.05 (m, 2H), 2.54 (m, 4H), 2.24 (m, 4H), 1.94 (m, 2H), 1.52 (m, 6H), 1.42 (m, 4H) ppm; MS (ES) 496.13 (M+H), 494.17 (M−H);

1-(6,7-dihydro-9-chloro-5H-benzo[6,7]cyclohepta[1,2-c]pyridazin-3-yl)-$N^3$-(3-fluoro-4-(4-pyrrolidin-1-ylpiperidin-1-yl)phenyl)-1H-1,2,4-triazole-3,5-diamine, formic acid salt, compound #143;

1-(6,7-dihydro-9-chloro-5H-benzo[6,7]cyclohepta[1,2-c]pyridazin-3-yl)-$N^3$-(3-fluoro-4-(4-(N-methylpiperazin-1-yl)piperidin-1-yl)phenyl)-1H-1,2,4-triazole-3,5-diamine, formic acid salt, compound #144;

1-(6,7-dihydro-5H-benzo[6,7]cyclohepta[1,2-c]pyridazin-3-yl)-$N^3$-(6-(3-(4-(piperidin-1-yl)piperidin-1-yl)-(E)-propenyl)pyridin-3-yl)-1H-1,2,4-triazole-3,5-diamine, compound #145; $^1$H NMR (CDCl$_3$, 300 MHz) 8.85 (s, 1H), 8.53 (s, 1H), 7.95-7.77 (m, 4H), 7.42 (m, 2H), 7.25 (m, 3H), 6.56 (m, 2H), 3.29-2.82 (m, 9H), 2.61 (m, 4H), 2.3 (m, 2H), 2.17 (m, 2H), 1.99 (m, 2H), 1.86 (m, 6H), 1.54 (m, 2H) ppm; MS (ES) 577.27 (M+H), 575.40 (M−H);

1-(6,7-dihydro-5H-benzo[6,7]cyclohepta[1,2-c]pyridazin-3-yl)-$N^3$-(6-(3-(4-dimethylaminopiperidin-1-yl)-(E)-propenyl)pyridin-3-yl)-1H-1,2,4-triazole-3,5-diamine, compound #146; $^1$H NMR (CDCl$_3$, 300 MHz) 8.85 (s, 1H), 7.97-7.73 (m, 4H), 7.53-7.21 (m, 6H), 6.53 (m, 2H), 3.22-2.95 (m, 4H), 2.66-2.47 (m, 4H), 2.37 (s, 6H), 2.29 (m, 2H), 2.05 (m, 2H), 1.87 (m, 2H), 1.62 (m, 3H) ppm; MS (ES) 537.51 (M+H), 535.33 (M−H);

1-(6,7-dihydro-5H-benzo[6,7]cyclohepta[1,2-c]pyridazin-3-yl)-$N^3$-(2-(4-pyrrolidin-1-ylpiperidin-1-yl)pyrimidin-5-yl)-1H-1,2,4-triazole-3,5-diamine, compound #147; $^1$H NMR (CD$_3$OD, 300 MHz) 8.62 (s, 2H), 8.19 (s, 1H), 7.83 (s, 1H), 7.70 (m, 1H), 7.40 (m, 5H), 7.49 (s, 1H), 4.78 (m, 2H), 4.03 (s, 3H), 3.30 (m, 4H), 3.18 (m, 4H), 2.86 (m, 2H), 2.60-1.70 (m, 13H); MS (ES) 524.25 (M+H);

1-(6,7-dihydro-5H-benzo[6,7]cyclohepta[1,2-c]pyridazin-3-yl)-$N^3$-(2-(4-(piperidin-1-ylmethyl)piperidin-1-yl)pyrimidin-5-yl)-1H-1,2,4-triazole-3,5-diamine, compound #148; $^1$H NMR (CD$_3$OD, 300 MHz) 8.71 (s, 1H), 8.59 (s, 1H), 7.91 (s, 1H), 7.81 (s, 1H), 7.70 (m, 2H), 7.42 (m, 2H), 7.30 (m, 2H), 4.72 (m, 2H), 3.59 (m, 2H), 3.00-2.52 (m, 10H), 2.38-1.80 (m, 9H), 1.50-1.23 (m, 4H); MS (ES) 552.27 (M+H);

1-(6,7-dihydro-5H-benzo[6,7]cyclohepta[1,2-c]pyridazin-3-yl)-$N^3$-(6(4(4-piperidin-1-ylpiperidin-1-yl)carbonyl)pyridin-3-yl)-1H-1,2,4-triazole-3,5-diamine, formic acid salt, compound #149; $^1$H NMR (DMSO-d$_6$, 300 MHz) 9.45 (s, 1H), 7.95 (s, 1H), 7.91 (s, 2H), 7.75-7.55 (m, 2H), 7.41 (m, 4H), 3.61 (m, 2H), 3.37 (m, 2H), 2.94 (m, 4H), 2.65-2.38 (m, 5H), 2.38-2.14 (m, 4H), 1.99-1.50 (m, 6H), 1.34 (m, 2H) ppm; MS (ES) 565.21 (M+H);

1-(6,7-dihydro-5H-benzo[6,7]cyclohepta[1,2-c]pyridazin-3-yl)-$N^3$-((7-piperidin-1-yl)-6,7,8,9-tetrahydro-5H-benzo[7]annulene-2-yl)-1H-1,2,4-triazole-3,5-diamine, compound #150; $^1$H NMR (DMSO-d$_6$, 300 MHz) 9.03 (m, 1H), 8.20 (m, 1H), 7.91 (m, 1H), 7.84 (br s, 2H), 7.70 (m, 1H), 7.37 (m, 5H), 6.99 (m, 1H), 2.54 (m, 6H), 2.22 (m, 5H), 2.03 (m, 4H), 1.36 (m, 10H) ppm; MS (ES) 521.3 (M+H);

1-(6,7-dihydro-5H-benzo[6,7]cyclohepta[1,2-c]pyridazin-3-yl)-$N^3$-((7-azetidin-1-yl)-6,7,8,9-tetrahydro-5H-benzo[7]annulene-2-yl)-1H-1,2,4-triazole-3,5-diamine, compound #151; $^1$H NMR (DMSO-d$_6$, 300 MHz) 9.21 (m, 1H), 8.03 (m, 1H), 7.70 (m, 1H), 7.60 (br s, 2H), 7.44 (m, 5H), 7.03 (m, 1H), 2.77 (m, 3H), 2.55 (m, 6H), 1.98 (m, 8H), 1.12 (m, 4H) ppm; MS (ES) 493.6 (M+H);

1-(6,7-dihydro-5H-benzo[6,7]cyclohepta[1,2-c]pyridazin-3-yl)-$N^3$-((7-pyrrolidin-1-yl)-6,7,8,9-tetrahydro-5H-cyclohepta[b]pyridine-3-yl)-1H-1,2,4-triazole-3,5-diamine, trifluoroacetic acid salt, compound #152; $^1$H-NMR (DMSO-d$_6$, 300 MHz) 8.87 (br. s, 1H), 8.04 (m, 2H), 7.99 (br. s, 2H), 7.72-7.70 (m, 1H), 7.46-7.44 (m, 3H), 7.38-7.36 (m, 1H), 3.50-3.46 (m, 4H), 3.18-3.16 (m, 1H), 3.14-3.00 (m, 4H), 2.71-2.55 (m, 4H), 2.26 (m, 4H), 1.98 (m, 2H), 1.84 (m, 2H), 1.59-1.53 (m, 2H) ppm; MS (ES) 508.19 (M+H);

1-(6,7-dihydro-5H-benzo[6,7]cyclohepta[1,2-c]pyridazin-3-yl)-$N^3$ (2-cyclopentyl-1,2,3,4-tetrahydroisoquinolin-7-yl)-1H-1,2,4-triazole-3,5-diamine, compound #153;

1-(6,7-dihydro-5H-benzo[6,7]cyclohepta[1,2-c]pyridazin-3-yl)-$N^3$-(4-iodophenyl)-1H-1,2,4-triazole-3,5-diamine, compound #156; $^1$H NMR (DMSO-d$_6$, 300 MHz) 9.40 (s, 1H), 7.97 (s, 1H), 7.89 (s, 2H), 7.70 (m, 1H), 7.61-7.31 (m, 7H), 2.69-2.43 (m, 4H), 2.22 (m, 2H) ppm; MS (ES) 496.07 (M+H);

1-(spiro[chromeno[4,3-c]pyridazine-5,1'-cyclopentane]-3-yl)-$N^3$-(3-fluoro-4-(4-(4-methylpiperazin-1-yl)piperidin-1-yl)phenyl)-1H-1,2,4-triazole-3,5-diamine, compound #175; $^1$H-NMR (DMSO-d$_6$, 300 MHz) 9.28 (s, 1H), 8.27 (d, 1H), 7.74 (s, 1H), 7.40-7.52 (m, 2H), 7.26 (m, 1H), 7.17 (t, 1H), 6.95-7.05 (m, 2H), 3.47 (m, 3H), 3.34 (m, 3H), 2.99 (m, 2H), 2.78 (m, 2H), 2.65 (m, 2H), 2.12 (m, 2H), 1.80-2.10 (m, 9H), 1.68 (m, 2H); MS (ES) 611.30 (M+H);

1-(spiro[chromeno[4,3-c]pyridazine-5,1'-cyclopentane]-3-yl)-N³-(3-fluoro-4-(4-(pyrrolidin-1-yl)piperidin-1-yl)phenyl)-1H-1,2,4-triazole-3,5-diamine, compound #176; ¹H-NMR (DMSO-d₆, 300 MHz) 9.68 (broad s, 1H), 9.28 (s, 1H), 8.27 (d, 1H), 7.74 (s, 1H), 7.40-7.53 (m, 2H), 7.26 (m, 1H), 7.17 (t, 1H), 6.95-7.03 (m, 2H), 3.54 (m, 2H), 3.32 (m, 2H), 3.22 (m, 1H), 3.10 (m, 2H), 2.64 (m, 2H), 1.65-2.30 (m, 16H); MS (ES) 582.31 (M+H);

1-(6,7-dihydro-5H-benzo[6,7]cyclohepta[1,2-c]pyridazin-3-yl)-N³-(3-fluoro-4-(4-pyrrolidin-1-ylpiperidin-1-yl)phenyl)-1H-1,2,4-triazole-3,5-diamine (formic acid salt), compound #177;

1-(6,7-dihydro-5H-benzo[6,7]cyclohepta[4,5-c]pyridazin-2-yl)-N³-(3-fluoro-4-(4-pyrrolidin-1-ylpiperidin-1-yl)phenyl)-1H-1,2,4-triazole-3,5-diamine (formic acid salt), compound #178; ¹H-NMR (DMSO-d₆, 300 MHz) 10.76 (s, 1H), 8.21 (s, 1H), 7.77 (m, 1H), 7.76 (broad s, 1H), 7.54 (m, 1H), 7.46 (m, 2H), 7.39 (m, 1H), 7.24 (m, 1H), 7.02 (t, 1H), 3.28 (m, 2H), 2.82 (m, 2H), 2.70 (m, 2H), 2.45-2.60 (m, 6H), 2.15-2.35 (m, 3H), 1.93 (m, 2H), 1.70 (m, 4H), 1.61 (m, 2H); MS (ES) 540.0 (M+H);

1-(6,7-dihydro-5H-benzo[6,7]cyclohepta[1,2-c]pyridazin-3-yl)-N³-(3-fluoro-4-(4-(4-methylpiperazin-1-yl)piperidin-1-yl)phenyl)-1H-1,2,4-triazole-3,5-diamine (benzene sulfonic acid salt), compound #179;

1-(6,7-dihydro-5H-benzo[6,7]cyclohepta[1,2-c]pyridazin-3-yl)-N³-(3-fluoro-4-(3-(3R)-dimethylaminopyrrolidin-1-yl)phenyl)-1H-1,2,4-triazole-3,5-diamine (formic acid salt), compound #180; ¹H-NMR (DMSO-d₆, 300 MHz) 9.66 (s, 1H), 9.15 (s, 1H), 7.90 (s, 1H), 7.86 (s, 1H), 7.73-7.70 (m, 1H), 7.49-7.42 (m, 2H), 7.38-7.31 (m, 2H), 6.87 (t, 1H), 3.52-3.38 (m, 2H), 3.26-3.19 (m, 1H), 2.84 (s, 3H), 2.63-2.58 (m, 3H), 2.57 (s, 6H), 2.40-2.20 (m, 4H) ppm; MS (ES) 500.71 (M+H);

1-(6,7-dihydro-5H-benzo[6,7]cyclohepta[1,2-c]pyridazin-3-yl)-N-3-((7-pyrrolidin-1-yl)-6,7,8,9-tetrahydro-5H-benzo[7]annulene-2-yl)-1H-1,2,4-triazole-3,5-diamine, compound #181; ¹H NMR (DMSO-d₆, 300 MHz) 9.11 (s, 1H), 7.93 (s, 1H), 7.85 (br s, 2H), 7.71 (m, 1H), 7.45 (m, 3H), 7.38 (m, 2H), 7.05 (m, 1H), 2.76-2.46 (m, 10H), 2.22-1.76 (m, 13H) ppm; MS (ES) 507.6 (M+H);

1-(6,7-dihydro-5H-benzo[6,7]cyclohepta[4,5-c]pyridazin-2-yl)-N³-(3-methyl-4-(4-pyrrolidin-1-ylpiperidin-1-yl)phenyl)-1H-1,2,4-triazole-3,5-diamine (formic acid salt), compound #182;

1-(6,7-dihydro-5H-benzo[6,7]cyclohepta[4,5-c]pyridazin-2-yl)-N³-(3-fluoro-4-(4-pyrrolidin-1-ylpiperidin-1-yl)phenyl)-1H-1,2,4-triazole-3,5-diamine (benzene sulfonic acid salt), compound #183;

1-(6,7-dihydro-5H-benzo[6,7]cyclohepta[1,2-c]pyridazin-3-yl)-N³-((7-(R)-pyrrolidin-1-yl)-6,7,8,9-tetrahydro-5H-benzo[7]annulene-2-yl)-1H-1,2,4-triazole-3,5-diamine, compound #184; ¹H NMR (DMSO-d₆, 300 MHz) 9.11 (s, 1H), 7.93 (s, 1H), 7.85 (br s, 2H), 7.71 (m, 1H), 7.45 (m, 3H), 7.38 (m, 2H), 7.05 (m, 1H), 2.76-2.46 (m, 10H), 2.23-1.76 (m, 13H) ppm; MS (ES) 507.3 (M+H);

1-(6,7-dihydro-5H-benzo[6,7]cyclohepta[1,2-c]pyridazin-3-yl)-N³-(7-diethylamino-6,7,8,9-tetrahydro-5H-benzo[7]annulene-2-yl)-1H-1,2,4-triazole-3,5-diamine, compound #185; ¹H NMR (DMSO-d₆, 300 MHz) 9.10 (s, 1H), 7.94 (s, 1H), 7.87 (br s, 2H), 7.70 (m, 1H), 7.44 (m, 3H), 7.37 (m, 2H), 7.06 (m, 1H), 2.88 (m, 2H), 2.55 (m, 8H), 2.25 (m, 3H), 1.92-1.24 (m, 12H) ppm; MS (ES) 509.3 (M+H);

1-(6,7-dihydro-5H-benzo[6,7]cyclohepta[1,2-c]pyridazin-3-yl)-N³-(7-cyclopentylamino-6,7,8,9-tetrahydro-5H-benzo[7]annulene-2-yl)-1H-1,2,4-triazole-3,5-diamine, compound #186; ¹H NMR (DMSO-d₆, 300 MHz) 9.11 (s, 1H), 7.93 (s, 1H), 7.85 (br s, 2H), 7.71 (m, 1H), 7.45 (m, 3H), 7.35 (m, 2H), 7.04 (m, 1H), 3.66 (m, 1H), 3.34 (m, 1H), 2.74 (m, 4H), 2.57 (m, 7H), 2.25 (m, 4H), 1.99 (m, 2H), 1.71 (m, 4H), 1.54 (m, 4H) ppm; MS (ES) 521.3 (M+H);

1-(6,7-dihydro-5H-benzo[6,7]cyclohepta[1,2-c]pyridazin-3-yl)-N³-(2-(4-cyclopropylmethylpiperazin-1-yl)pyridine-5-yl)-1H-1,2,4-triazole-3,5-diamine, compound #187; ¹H NMR (DMSO-d₆, 300 MHz) 9.45 (s, 1H), 8.41 (m, 1H), 8.02 (m, 1H), 7.93 (s, 1H), 7.95 (br s, 2H), 7.71 (m, 1H), 7.45 (m, 2H), 7.37 (m, 1H), 7.08 (m, 1H), 3.61 (m, 2H), 3.40 (m, 2H), 3.17 (m, 6H), 2.55 (m, 4H), 2.25 (m, 2H), 1.08 (m, 1H), 0.65 (m, 2H), 0.38 (m, 2H) ppm; MS (ES) 509.3 (M+H);

1-(6,7-dihydro-5H-benzo[6,7]cyclohepta[1,2-c]pyridazin-3-yl)-N³-(7-pyrrolidin-1-yl)-6,7,8,9-tetrahydro-5H-benzo[7]annulene-2-yl)-1H-1,2,4-triazole-3,5-diamine, compound #188; ¹H NMR (DMSO-d₆, 300 MHz) 9.06 (s, 1H), 7.93 (s, 1H), 7.84 (br s, 2H), 7.71 (m, 1H), 7.45 (m, 3H), 7.35 (m, 2H), 7.02 (m, 1H), 2.86 (m, 2H), 2.55 (m, 8H), 2.22 (m, 3H), 1.89 (m, 3H), 1.68 (m, 4H), 1.50 (m, 3H) ppm; MS (ES) 507.3 (M+H); [α]²=+11.3 (c=0.84, CH₃OH);

1-(6,7-dihydro-5H-benzo[6,7]cyclohepta[1,2-c]pyridazin-3-yl)-N³-(6-(pyrrolidin-1-yl)-5,6,7,8-tetrahydroquinolin-3-yl)-1H-1,2,4-triazole-3,5-diamine (formic acid salt), compound #189; ¹H NMR (DMSO-d₆, 300 MHz) 9.27 (s, 1H), 8.63 (s, 1H), 8.10 (s, 1H), 7.98 (s, 1H), 7.89 (s, 2H), 7.67 (m, 2H), 7.43 (m, 2H), 7.36 (m, 1H), 3.38 (s, 2H), 3.02 (s, 2H), 2.75 (s, 4H), 2.60 (t, 1H), 2.23 (m, 4H), 1.73 (s, 4H), 1.48 (m, 1H), 1.21 (m, 2H), 0.83 (s, 1H) ppm; MS (ES) 494.22 (M+H);

1-(6,7-dihydro-5H-benzo[6,7]cyclohepta[1,2-c]pyridazin-3-yl)-N³-(6-cyclopentyl-5,6,7,8-tetrahydro-1,6-naphthyridine-3-yl)-1H-1,2,4-triazole-3,5-diamine (formic acid salt), compound #190; ¹H NMR (DMSO-d₆, 300 MHz) 9.28 (s, 1H), 8.62 (s, 1H), 8.13 (s, 1H), 7.95 (s, 1H), 7.89 (s, 2H), 7.69 (m, 1H), 7.64 (s, 1H), 7.43 (m, 2H), 7.37 (m, 1H), 3.64 (s, 2H), 2.78 (s, 4H), 2.69 (t, 1H), 2.61 (t, 2H), 2.53 (t, 2H), 2.23 (t, 2H), 1.89 (s, 2H), 1.63 (d, 2H), 1.49 (m, 4H) ppm; MS (ES) 494.19 (M+H);

1-(6,7-dihydro-5H-benzo[6,7]cyclohepta[1,2-c]pyridazin-3-yl)-N³—(S)-7-(pyrrolidin-1-yl)-6,7,8,9-tetrahydro-5H-cyclohepta[b]pyridine-3-yl)-1H-1,2,4-triazole-3,5-diamine, compound #191; ¹H-NMR (CDCl₃/MeOD-4, 300 MHz) 8.55 (s, 1H), 7.88 (s, 1H), 7.70 (m, 1H), 7.62 (m, 1H), 7.40 (m, 1H), 7.26 (m, 1H), 3.03 (m, 1H), 2.54-2.87 (m, 12H), 2.26 (m, 4H), 1.80 (m, 4H), 1.49 (m, 2H); MS (ES) 508.27 (M+H);

1-(4-phenyl-6,7-dihydro-5H-benzo[6,7]cyclohepta[1,2-b]pyridin-2-yl)-N³-(3-fluoro-4-(4-cyclohexylpiperazin-1-yl)phenyl)-1H-1,2,4-triazole-3,5-diamine, compound #192; ¹H-NMR (DMSO-d₆, 300 MHz) 8.86 (s, 1H), 7.67 (m, 1H), 7.36-7.56 (m, 10H), 7.22 (m, 1H), 6.89 (t, 1H), 2.88 (m, 4H), 2.62 (m, 6H), 2.46 (m, 2H), 2.17-2.27 (m, 4H), 1.73 (m, 4H), 1.55 (m, 1H), 1.19 (m, 4H); MS (ES) 629.27 (M+H);

1-(4-phenyl-6,7-dihydro-5H-benzo[6,7]cyclohepta[1,2-b]pyridin-2-yl)-N³-(4-(4-methylpiperazin-1-yl)phenyl)-1H-1,2,4-triazole-3,5-diamine, compound #193; ¹H-NMR (DMSO-d₆, 300 MHz) 8.50 (s, 1H), 7.68 (m, 1H), 7.34-7.52 (m, 11H), 6.80 (d, 2H), 3.00 (m, 3H), 2.65 (m, 2H), 2.49 (m, 1H), 2.43 (m, 4H), 2.14-2.26 (m, 4H), 2.21 (s, 3H); MS (ES) 543.16 (M+H);

1-(6,7-dihydro-5H-benzo[6,7]cyclohepta[1,2-c]pyridazin-3-yl)-N³-((7-(2-(S)-methyloxycarbonyl)pyrrolidin-1-yl)-6,7,8,9-tetrahydro-5H-benzo[7]annulene-2-yl)-1H-1,2,4-triazole-3,5-diamine, compound #194; ¹H-NMR (CDCl₃/MeOD-4, 300 MHz) 7.78 (s, 1H), 7.62 (m, 1H), 7.29 (m, 3H), 7.16 (m, 1H), 7.05 (m, 1H), 6.93 (d, 1H), 3.96 (s, 1H), 3.58 (s, 3H), 3.40 (m, 1H), 2.89 (m, 1H), 2.63 (m, 3H), 2.44-2.58 (m, 7H), 2.19 (m, 2H), 1.93 (m, 2H), 1.65-1.80 (m, 3H), 1.27 (m, 2H); MS (ES) 565.33 (M+H);

1-(6,7-dihydro-5H-benzo[6,7]cyclohepta[1,2-c]pyridazin-3-yl)-N³-(7-(2-(S)-carboxy)pyrrolidin-1-yl)-6,7,8,9-tetrahydro-5H-benzo[7]annulen-2-yl)-1H-1,2,4-triazole-3,5-diamine (hydrochloric acid salt), compound #195; ¹H-NMR (DMSO-d₆, 300 MHz) 8.83 (s, 1H), 7.89 (s, 1H), 7.72 (m 2H), 7.44 (m, 3H), 7.33 (m, 2H), 7.02 (d, 1H), 4.15 (m, 1H), 3.48 (m, 2H), 3.15 (m, 1H), 2.53-2.80 (m, 9H), 2.24 (m, 4H), 2.02 (m, 1H), 1.89 (m, 1H), 1.79 (m, 1H), 1.42 (m, 2H); MS (ES) 551.25 (M+H);

1-(6,7-dihydro-5H-benzo[6,7]cyclohepta[1,2-c]pyridazin-3-yl)-N³-(4-(4-(4-methylpiperazin-1-yl)piperidin-1-ylprop-1-enyl)phenyl)-1H-1,2,4-triazole-3,5-diamine (bis trifluoroacetic acid salt), compound #196; ¹H NMR (DMSO-d₆, 300 MHz) 9.47 (s, 1H), 7.97 (s, 1H), 7.91 (s, 2H), 7.77-7.59 (m, 3H), 7.52-7.30 (m, 5H), 6.72 (d, 1H), 6.14 (m, 1H), 3.83 (m, 2H), 3.55 (m, 2H), 3.21 (m, 3H), 3.01-2.69 (m, 9H), 2.66-2.41 (m, 6H), 2.35-1.96 (m, 4H), 1.67 (m, 2H) ppm; MS (ES) 591.31 (M+H), 589.53 (M−H);

1-(6,7-dihydro-5H-benzo[6,7]cyclohepta[1,2-c]pyridazin-3-yl)-N³-(4-(4-(piperidin-1-yl)piperidin-1-ylprop-1-enyl)phenyl)-1H-1,2,4-triazole-3,5-diamine (bis trifluoroacetic acid salt), compound #197; ¹H NMR (DMSO-d₆, 300 MHz) 9.47 (s, 1H), 7.97 (s, 1H), 7.91 (s, 2H), 7.75-7.58 (m, 3H), 7.41 (m, 4H), 6.75 (d, 1H), 6.13 (m, 1H), 3.86 (m, 2H), 3.61 (m, 2H), 3.37 (m, 2H), 2.94 (m, 4H), 2.65-2.38 (m, 5H), 2.33-2.14 (m, 4H), 1.99-1.52 (m, 6H), 1.36 (m, 2H) ppm; MS (ES) 576.32 (M+H), 574.51 (M−H);

1-(6,7-dihydro-5H-benzo[6,7]cyclohepta[1,2-c]pyridazin-3-yl)-N³-(4-(piperidin-1-ylprop-1-enyl)phenyl)-1H-1,2,4-triazole-3,5-diamine (bis trifluoroacetic acid salt); compound #198; ¹H NMR (DMSO-d₆, 300 MHz) 9.46 (s, 1H), 8.03-7.84 (m, 3H), 7.77-7.59 (m, 3H), 7.40 (m, 4H), 6.73 (d, 1H), 6.14 (m, 1H), 3.79 (s, 2H), 3.42 (d, 2H), 2.86 (d, 2H), 2.66-2.41 (m, 4H), 2.23 (m, 2H), 1.80 (m, 2H), 1.63 (m, 2H), 1.37 (m, 2H) ppm; MS (ES) 493.24 (M+H), 491.34 (M−H);

1-(6,7-dihydro-5H-benzo[6,7]cyclohepta[1,2-c]pyridazin-3-yl)-N³-(4-(pyrrolidin-1-ylprop-1-enyl)phenyl)-1H-1,2,4-triazole-3,5-diamine (bis trifluoroacetic acid salt), compound #199; ¹H NMR (DMSO-d₆, 300 MHz) 9.38 (s, 1H), 8.09-7.81 (m, 3H), 7.71-7.43 (m, 3H), 7.34 (m, 4H), 6.69 (d, 1H), 6.08 (m, 1H), 3.74 (s, 2H), 3.33 (d, 2H), 2.85-2.41 (m, 6H), 2.28 (m, 2H), 1.74 (m, 2H), 1.59 (m, 2H) ppm; MS (ES) 479.22 (M+H), 477.45 (M−H);

1-(6,7-dihydro-5H-benzo[6,7]cyclohepta[1,2-c]pyridazin-3-yl)-N³-(4-(3-dimethylaminopyrrolidin-1-ylprop-1-enyl)phenyl)-1H-1,2,4-triazole-3,5-diamine (bis trifluoroacetic acid salt), compound #200; ¹H NMR (DMSO-d₆, 300 MHz) 9.31 (s, 1H), 7.88 (s, 1H), 7.81 (s, 2H), 7.72 (m, 3H), 7.42 (m, 5H), 6.73 (d, 1H), 6.18 (m, 1H), 3.90 (m, 2H), 3.64 (m, 2H), 3.17 (m, 5H), 2.74-2.42 (m, 8H), 2.18 (m, 2H), 1.07 (m, 2H) ppm; MS (ES) 522.30 (M+H), 520.51 (M−H);

1-(6,7-dihydro-5H-benzo[6,7]cyclohepta[1,2-c]pyridazin-3-yl)-N³-(4-(3-diethylaminopyrrolidin-1-ylprop-1-enyl)phenyl)-1H-1,2,4-triazole-3,5-diamine (bis trifluoroacetic acid salt), compound #201; ¹H NMR (DMSO-d₆, 300 MHz) 9.48 (s, 1H), 7.97 (s, 1H), 7.92 (s, 2H), 7.71 (m, 3H), 7.40 (m, 5H), 6.75 (d, 1H), 6.14 (m, 1H), 3.95 (m, 2H), 3.69 (m, 2H), 3.18 (m, 5H), 2.70-2.41 (m, 8H), 2.23 (m, 2H), 1.17 (m, 6H) ppm; MS (ES) 550.31 (M+H), 548.55 (M−H);

1-(6,7-dihydro-5H-benzo[6,7]cyclohepta[1,2-c]pyridazin-3-yl)-N³-(2-(3-(S)-methyl-4-cyclopropylmethylpiperazin-1-yl)pyridine-5-yl)-1H-1,2,4-triazole-3,5-diamine (bis trifluoroacetic acid salt), compound #202; ¹H NMR (DMSO-d₆, 300 MHz) 9.42 (s, 1H), 8.77 (s, 1H), 8.52 (s, 2H), 8.19-7.63 (m, 3H), 7.49-7.29 (m, 2H), 7.05 (d, 1H), 4.31 (m, 2H), 4.08 (m, 1H), 3.78 (m, 1H), 3.54-2.87 (m, 4H), 2.67-2.38 (m, 5H), 2.27-1.97 (m, 2H), 1.28 (m, 3H), 1.08 (m, 1H), 0.65 (m, 2H), 0.38 (m, 2H) ppm; MS (ES) 523.27 (M+H), 521.39 (M−H);

1-(6,7-dihydro-5H-benzo[6,7]cyclohepta[1,2-c]pyridazin-3-yl)-N³-(4-(4-pyrrolidin-1-ylpiperidin-1-ylprop-1-enyl)phenyl)-1H-1,2,4-triazole-3,5-diamine (bis formic acid salt), compound #203; ¹H NMR (DMSO-d₆, 300 MHz) 9.31 (s, 1H), 8.22 (s, 1H), 8.06-7.81 (m, 3H), 7.70 (m, 1H), 7.58 (d, 1H), 7.53-7.28 (m, 4H), 6.42 (d, 1H), 6.09 (m, 1H), 3.04 (d, 2H), 2.88 (m, 2H), 2.71-2.31 (m, 5H), 2.23 (m, 4H), 2.01-1.76 (m, 5H), 1.69 (m, 5H), 1.44 (m, 2H) ppm; MS (ES) 562.28 (M+H), 560.52 (M−H);

1-(6,7-dihydro-5H-benzo[6,7]cyclohepta[1,2-c]pyridazin-3-yl)-N³-(4-(4-methylpiperazin-1-ylprop-1-enyl)phenyl)-1H-1,2,4-triazole-3,5-diamine (bis formic acid salt), compound #204; ¹H NMR (DMSO-d₆, 300 MHz) 9.28 (s, 1H), 8.15 (s, 1H), 8.12-7.89 (m, 3H), 7.75 (m, 1H), 7.52 (d, 1H), 7.55-7.22 (m, 4H), 6.45 (d, 1H), 6.05 (m, 1H), 3.04 (d, 2H), 2.26 (m, 4H), 2.46 (m, 4H), 2.27 (s, 3H), 1.95 (m, 2H) ppm; MS (ES) 506.42 (M−H);

1-(6,7-dihydro-5H-benzo[6,7]cyclohepta[1,2-c]pyridazin-3-yl)-N³-(4-(4-isopropylpiperazin-1-ylprop-1-enyl)phenyl)-1H-1,2,4-triazole-3,5-diamine (bis formic acid salt), compound #205; ¹H NMR (DMSO-d₆, 300 MHz) 9.21 (s, 1H), 8.19 (s, 1H), 8.12-7.79 (m, 3H), 7.69 (m, 1H), 7.61 (d, 1H), 7.50-7.23 (m, 4H), 6.40 (d, 1H), 6.14 (m, 1H), 3.14 (d, 2H), 2.97 (m, 1H), 2.58 (m, 4H), 2.46-2.37 (m, 4H), 1.88 (m, 2H), 1.06 (m, 6H) ppm; MS (ES) 534.43 (M−H);

1-(6,7-dihydro-5H-benzo[6,7]cyclohepta[1,2-c]pyridazin-3-yl)-N³-(4-(4-cyclopentylpiperazin-1-ylprop-1-enyl)phenyl)-1H-1,2,4-triazole-3,5-diamine (bis formic acid salt), compound #206; ¹H NMR (DMSO-d₆, 300 MHz) 9.24 (s, 1H), 8.11 (s, 1H), 8.12-7.85 (m, 3H), 7.74 (m, 1H), 7.51 (d, 1H), 7.53-7.21 (m, 4H), 6.39 (d, 1H), 6.12 (m, 1H), 3.23 (d, 2H), 2.81 (m, 2H), 2.78-2.22 (m, 5H), 2.12 (m, 4H), 2.05-1.68 (m, 5H), 1.62 (m, 5H), 1.41 (m, 2H) ppm; MS (ES) 562.28 (M+H), 560.32 (M−H);

1-(6,7-dihydro-5H-benzo[6,7]cyclohepta[1,2-c]pyridazin-3-yl)-N³-(4-(morpholin-4-ylprop-1-enyl)phenyl)-1H-1,2,4-triazole-3,5-diamine (bis formic acid salt), compound #207; ¹H NMR (DMSO-d₆, 300 MHz) 9.46 (s, 1H), 8.03-7.84 (m, 3H), 7.77-7.59 (m, 3H), 7.40 (m, 4H), 6.73 (d, 1H), 6.14 (m, 1H), 3.82 (m, 4H), 3.65 (m, 2H), 2.64 (m, 4H): 2.37 (m, 4H), 1.87 (m, 2H) ppm; MS (ES) 495.21 (M+H), 493.36 (M−H);

1-(6,7-dihydro-5H-benzo[6,7]cyclohepta[1,2-c]pyridazin-3-yl)-N³-(8-diethylaminoethyl-9-hydroxy-6,7,8,9-tetrahydro-5H-benzo[7]annulen-2-yl)-1H-1,2,4-triazole-3,5-diamine (trifluoroacetic acid salt), compound #208; ¹H NMR (DMSO-d₆, 300 MHz) 9.35 (s br, 2H), 9.15 (s, 1H), 7.96-7.79 (m, 2H), 7.77-7.58 (m, 3H), 7.53-7.23 (m, 4H), 7.02 (d, 1H), 4.46 (m, 1H), 3.82-3.49 (m, 2H), 3.40-3.08 (m, 3H), 2.82 (m, 1H), 2.71-2.38 (m, 6H), 2.22 (m, 3H), 2.02-1.64 (m, 4H), 1.52 (m, 2H), 1.17 (m, 6H) ppm; MS (ES) 553.31 (M+H), 551.44 (M−H);

1-(6,7-dihydro-5H-benzo[6,7]cyclohepta[1,2-c]pyridazin-3-yl)-N³-(3-fluoro-4-(4-methylpiperazin-1-yl)phenyl)-1H-1,2,4-triazole-3,5-diamine (trifluoroacetic acid salt), compound #209; ¹H-NMR (DMSO-d₆, 300 MHz) 9.31 (br. s, 1H), 7.91 (s, 1H), 7.88 (br. s, 2H), 7.72-7.69 (m, 1H), 7.51 (s, 1H), 7.46-7.43 (m, 2H), 7.39-7.36 (m, 2H), 7.04 (t, J=8.7 Hz, 1H), 3.52-3.47 (m, 2H), 3.39-3.35 (m, 2H), 3.25-3.15 (m, 2H), 2.98-2.94 (m, 2H), 2.85 (s, 3H), 2.60-2.54 (m, 4H), 2.26-2.22 (m, 2H) ppm; MS (ES) 485.57 (M+H);

1-(6,7-dihydro-5H-benzo[6,7]cyclohepta[1,2-c]pyridazin-3-yl)-$N^3$-(4-(1-methylpiperidin-3-yl-oxy)phenyl)-1H-1,2,4-triazole-3,5-diamine (trifluoroacetic acid salt), compound #210; $^1$H-NMR (DMSO-$d_6$, 300 MHz) 9.09 (br. s, 1H), 7.92 (s, 1H), 7.84 (br. s, 2H), 7.72-7.69 (m, 1H), 7.59-7.57 (m, 2H), 7.45-7.42 (m, 2H), 7.37-7.35 (m, 1H), 6.99-6.97 (m, 2H), 6.93-6.91 (m, 1H), 3.62-3.58 (m, 1H), 3.37-3.26 (m, 2H), 2.98-2.94 (m, 2H), 2.78 (s, 3H), 2.60-2.54 (m, 4H), 2.25-2.22 (m, 2H), 1.94-1.89 (m, 2H), 1.72-1.57 (m, 2H) ppm; MS (ES) 483.61 (M+H);

1-(6,7-dihydro-5H-benzo[6,7]cyclohepta[1,2-c]pyridazin-3-yl)-$N^3$-(4-(1-bicyclo[2.2.1]heptan-2-yl)-piperidin-4-ylphenyl)-1H-1,2,4-triazole-3,5-diamine (trifluoroacetic acid salt), compound #211; $^1$H-NMR (DMSO-$d_6$, 300 MHz) 9.08 (br. s, 1H), 7.94 (s, 1H), 7.83 (br. s, 2H), 7.71-7.67 (m, 1H), 7.54 (d, J=8.4 Hz, 2H), 7.45-7.43 (m, 2H), 7.37-7.35 (m, 1H), 7.12 (d, J=8.4 Hz, 2H), 3.02-2.98 (m, 4H), 2.92-2.58 (m, 2H), 2.29-2.23 (m, 4H), 2.13 (m, 1H), 1.89-1.87 (m, 2H), 1.73-1.69 (m, 6H), 1.46-1.18 (m, 5H), 0.88-0.85 (m, 2H) ppm; MS (ES) 547.36 (M+H);

1-(6,7-dihydro-5H-benzo[6,7]cyclohepta[1,2-c]pyridazin-3-yl)-$N^3$-(4-(1-cyclopropylmethylpiperidin-4-yl)phenyl)-1H-1,2,4-triazole-3,5-diamine (trifluoroacetic acid salt), compound #212; $^1$H-NMR (DMSO-$d_6$, 300 MHz) 9.18 (br. s, 1H), 7.95 (s, 1H), 7.85 (br. s, 2H), 7.72-7.69 (m, 1H), 7.59 (d, J=8.4 Hz, 2H), 7.46-7.43 (m, 2H), 7.38-7.35 (m, 1H), 7.12 (d, J=8.7 Hz, 2H), 3.64-3.61 (m, 4H), 3.07-3.00 (m, 3H), 2.61-2.54 (m, 4H), 2.25-2.22 (m, 2H), 2.03-1.98 (m, 2H), 1.86-1.82 (m, 2H), 1.11-1.07 (m, 1H), 0.66 (d, J=7.2 Hz, 2H), 0.38 (d, J=5.1 Hz, 2H) ppm; MS (ES) 507.27 (M+H);

1-(6,7-dihydro-5H-benzo[6,7]cyclohepta[1,2-c]pyridazin-3-yl)-$N^3$-(1,2,3,4-tetrahydroisoquinolin-7-yl)-1H-1,2,4-triazole-3,5-diamine (trifluoroacetic acid salt), compound #213; $^1$H-NMR (DMSO-$d_6$, 300 MHz) 9.28 (br. s, 1H), 7.94 (s, 1H), 7.87 (br. s, 2H), 7.71-7.69 (m, 1H), 7.53-7.51 (m, 1H), 7.45-7.43 (m, 3H), 7.38-7.35 (m, 1H), 7.09 (d, J=8.4 Hz, 1H), 4.18 (m, 2H), 3.36 (m, 2H), 3.00 (m, 2H), 2.61 (m, 2H), 2.52 (m, 2H), 2.25-2.20 (m, 2H) ppm; MS (ES) 425.50 (M+H);

1-(6,7-dihydro-5H-benzo[6,7]cyclohepta[1,2-c]pyridazin-3-yl)-$N^3$-(3-fluoro-4-(4-cyclopropylmethylpiperazin-1-yl)phenyl)-1H-1,2,4-triazole-3,5-diamine (trifluoroacetic acid salt), compound #214; $^1$H-NMR (DMSO-$d_6$, 300 MHz) 9.31 (br. s, 1H), 7.91 (s, 1H), 7.87 (br. s, 2H), 7.72-7.69 (m, 1H), 7.50-7.38 (m, 5H), 7.05 (t, J=10.2 Hz, 1H), 3.63 (m, 4H), 3.59 (m, 4H), 3.41-3.37 (m, 1H), 3.21-3.17 (m, 1H), 3.08-3.01 (m, 2H), 2.62-2.58 (m, 2H), 2.26-2.22 (m, 2H), 1.09 (m, 1H), 0.66 (d, J=8.1 Hz, 2H), 0.39 (d, J=4.5 Hz, 2H) ppm; MS (ES) 526.32 (M+H), 524.33 (M−H);

1-(6,7-dihydro-5H-benzo[6,7]cyclohepta[1,2-c]pyridazin-3-yl)-$N^3$-(2-(1-methylpiperidin-4-yl)-1,2,3,4-tetrahydroisoquinolin-7-yl)-1H-1,2,4-triazole-3,5-diamine (bis trifluoroacetic acid salt), compound #215; $^1$H-NMR (DMSO-$d_6$, 300 MHz) 9.34 (br. s, 1H), 7.95 (s, 1H), 7.87 (br. s, 2H), 7.72-7.69 (m, 1H), 7.57-7.55 (m, 1H), 7.50 (s, 1H), 7.46-7.44 (m, 2H), 7.38-7.36 (m, 1H), 7.12 (d, J=8.4 Hz, 1H), 4.42-4.37 (m, 2H), 3.62 (m, 4H), 3.58 (m, 4H), 3.45-3.35 (m, 2H), 3.14 (m, 2H), 3.04-3.02 (m, 1H), 2.78 (s, 3H), 2.62 (m, 2H), 2.26-2.23 (m, 2H), 1.93-1.90 (m, 2H) ppm; MS (ES) 522.30 (M+H), 520.12 (M−H);

1-(6,7-dihydro-5H-benzo[6,7]cyclohepta[1,2-c]pyridazin-3-yl)-$N^3$-(2-(cyclopropylmethyl)-1,2,3,4-tetrahydroisoquinolin-7-yl)-1H-1,2,4-triazole-3,5-diamine (formic acid salt), compound #216; $^1$H-NMR (DMSO-$d_6$, 300 MHz) 9.05 (br. s, 1H), 7.91 (s, 1H), 7.84 (br. s, 2H), 7.72-7.68 (m, 1H), 7.44-7.31 (m, 5H), 6.93 (d, J=8.1 Hz, 1H), 3.59 (m, 2H), 2.82-2.75 (m, 4H), 2.60-2.58 (m, 2H), 2.40-2.36 (m, 4H), 2.25-2.23 (m, 2H), 0.93 (m, 1H), 0.66 (d, J=8.1 Hz, 2H), 0.39 (d, J=4.5 Hz, 2H) ppm; MS (ES) 479.22 (M+H);

1-(6,7-dihydro-5H-benzo[6,7]cyclohepta[1,2-c]pyridazin-3-yl)-$N^3$-(7-(3-(S)-fluoropyrrolidin-1-yl)-6,7,8,9-tetrahydro-5H-benzo[7]annulene-2-yl)-1H-1,2,4-triazole-3,5-diamine (trifluoroacetic acid salt), compound #217; $^1$H-NMR (DMSO-$d_6$, 300 MHz) 9.11 (br. s, 1H), 7.93 (s, 1H), 7.84 (br. s, 2H), 7.71-7.69 (m, 1H), 7.46-7.42 (m, 3H), 7.37-7.35 (m, 2H), 7.05 (d, J=8.4 Hz, 1H), 3.42-3.32 (m, 4H), 2.75-2.71 (m, 4H), 2.63-2.61 (m, 4H), 2.30-2.26 (m, 6H), 1.40 (m, 4H) ppm; MS (ES) 525.51 (M+H);

1-(6,7-dihydro-5H-benzo[6,7]cyclohepta[1,2-c]pyridazin-3-yl)-$N^3$-(7-(2-(S)-methylpyrrolidin-1-yl)-6,7,8,9-tetrahydro-5H-benzo[7]annulene-2-yl)-1H-1,2,4-triazole-3,5-diamine (trifluoroacetic acid salt), compound #218; $^1$H-NMR (DMSO-$d_6$, 300 MHz) 9.10 (br. s, 1H), 7.92 (s, 1H), 7.84 (s, 1H), 7.71-7.69 (m, 1H), 7.46-7.42 (m, 2H), 7.37-7.33 (m, 2H), 7.04 (d, J=8.4 Hz, 1H), 3.28 (m, 2H), 3.16-3.15 (m, 2H), 2.78-2.70 (m, 4H), 2.63-2.59 (m, 2H), 2.56-2.52 (m, 2H), 2.26-2.12 (m, 6H), 1.88-1.83 (m, 2H), 1.61-1.40 (m, 2H), 1.34 (d, J=5.7 Hz, 3H) ppm; MS (ES) 521.82 (M+H);

1-(6,7-dihydro-5H-benzo[6,7]cyclohepta[1,2-c]pyridazin-3-yl)-$N^3$-(7-(3-(R)-hydroxypyrrolidin-1-yl)-6,7,8,9-tetrahydro-5H-benzo[7]annulene-2-yl)-1H-1,2,4-triazole-3,5-diamine (trifluoroacetic acid salt), compound #219; $^1$H-NMR (DMSO-$d_6$, 300 MHz 9.08 (br. s, 1H), 7.92 (s, 4H), 7.83 (m, 1H), 7.72-7.69 (m, 1H), 7.46-7.44 (m, 2H), 7.36-7.34 (m, 2H), 7.03 (d, 1H), 3.42-3.32 (m, 4H), 2.75-2.71 (m, 4H), 2.63-2.61 (m, 4H), 2.30-2.26 (m, 6H), 1.40 (m, 4H) ppm; MS (ES) 523.73 (M+H);

1-(6,7-dihydro-5H-benzo[6,7]cyclohepta[1,2-c]pyridazin-3-yl)-$N^3$-(7-(2-(R)-methylpyrrolidin-1-yl)-6,7,8,9-tetrahydro-5H-benzo[7]annulene-2-yl)-1H-1,2,4-triazole-3,5-diamine (trifluoroacetic acid salt), compound #220; $^1$H-NMR (DMSO-$d_6$, 300 MHz) 9.08 (br. s, 1H), 7.92 (s, 1H), 7.83 (s, 1H), 7.71-7.69 (m, 1H), 7.46-7.42 (m, 2H), 7.37-7.33 (m, 2H), 7.04 (d, J=8.4 Hz, 1H), 3.28 (m, 2H), 3.16-3.15 (m, 2H), 2.78-2.70 (m, 4H), 2.63-2.59 (m, 2H), 2.56-2.52 (m, 2H), 2.26-2.12 (m, 6H), 1.88-1.83 (m, 2H), 1.61-1.40 (m, 2H), 1.35 (d, J=5.7 Hz, 3H) ppm; MS (ES) 521.34 (M+H);

1-(6,7-dihydro-5H-benzo[6,7]cyclohepta[1,2-c]pyridazin-3-yl)-$N^3$-(7-(3-(S)-hydroxypyrrolidin-1-yl)-6,7,8,9-tetrahydro-5H-benzo[7]annulene-2-yl)-1H-1,2,4-triazole-3,5-diamine (trifluoroacetic acid salt), compound #221; $^1$H-NMR (DMSO-$d_6$, 300 MHz) 9.08 (br. s, 1H), 7.92 (s, 1H), 7.83 (s, 1H), 7.70-7.69 (m, 1H), 7.46-7.43 (m, 2H), 7.36-7.34 (m, 2H), 7.03 (d, 1H), 3.42-3.32 (m, 4H), 2.75-2.71 (m, 4H), 2.63-2.61 (m, 4H), 2.30-2.26 (m, 6H), 1.40 (m, 4H) ppm; MS (ES) 523.73 (M+H);

1-(6,7-dihydro-5H-benzo[6,7]cyclohepta[1,2-c]pyridazin-3-yl)-$N^3$-(7-(3-(R)-fluoropyrrolidin-1-yl)-6,7,8,9-tetrahydro-5H-benzo[7]annulene-2-yl)-1H-1,2,4-triazole-3,5-diamine (formic acid salt), compound #222; $^1$H-NMR (DMSO-$d_6$, 300 MHz) 8.99 (br. s, 1H), 7.91 (s, 1H), 7.83 (br. s, 2H), 7.71-7.69 (m, 1H), 7.46-7.42 (m, 3H), 7.37-7.35 (m, 1H), 7.25 (s, 1H), 6.98 (d, J=8.4 Hz, 1H), 3.42-3.32 (m, 4H), 2.75-2.71 (m, 4H), 2.63-2.61 (m, 4H), 2.30-2.26 (m, 6H), 1.40 (m, 4H) ppm; MS (ES) 525.15 (M+H);

1-(6,7-dihydro-5H-benzo[6,7]cyclohepta[1,2-c]pyridazin-3-yl)-$N^3$-(7-oxo-6,7,8,9-tetrahydro-5H-benzo[7]annulene- 2-yl)-1H-1,2,4-triazole-3,5-diamine (trifluoroacetic acid salt), compound #223; $^1$H NMR (CDCl$_3$, 300 MHz) 7.90 (s, 1H), 7.81 (m, 2H), 7.47-6.88 (m, 8H), 2.89 (m, 4H), 2.63 (m, 8H), 2.35 (m, 2H); MS (ES) 452.22 (M+H);

1-(6,7-dihydro-5H-benzo[6,7]cyclohepta[1,2-c]pyridazin-3-yl)-N$^3$-(7-cyclohexylamino-6,7,8,9-tetrahydro-5H-benzo[7]annulene-2-yl)-1H-1,2,4-triazole-3,5-diamine (bis trifluoroacetic acid salt), compound #224; $^1$H NMR (CDCl$_3$, 300 MHz) 8.39 (s, 2H), 7.87 (s, 1H), 7.79 (m, 1H), 7.58 (m, 1H), 7.51 (m, 1H), 7.42 (m, 2H), 7.34 (m, 1H), 7.05 (m, 2H), 3.28 (m, 1H), 3.03 (m, 1H), 2.61 (m, 8H), 2.30 (m, 4H), 2.05 (m, 2H), 1.83 (m, 2H), 1.57-1.23 (m, 8H); MS (ES) 535.36 (M+H);

1-(6,7-dihydro-5H-benzo[6,7]cyclohepta[1,2-c]pyridazin-3-yl)-N$^3$-(7-cyclopropylamino-6,7,8,9-tetrahydro-5H-benzo[7]annulene-2-yl)-1H-1,2,4-triazole-3,5-diamine (bis trifluoroacetic acid salt), compound #225; $^1$H NMR (CDCl$_3$, 300 MHz) 8.28 (s, 1H), 7.90 (s, 1H), 7.81 (m, 1H), 7.45-7.07 (m, 9H), 3.48 (m, 4H), 2.62 (m, 6H), 2.35 (m, 4H), 1.57 (m, 2H), 0.90 (m, 2H), 0.71 (d, J=6.3 Hz, 1H); MS (ES) 493.31 (M+H);

1-(6,7-dihydro-5H-benzo[6,7]cyclohepta[1,2-c]pyridazin-3-yl)-N$^3$-(7-hydroxy-6,7,8,9-tetrahydro-5H-benzo[7]annulene-2-yl)-1H-1,2,4-triazole-3,5-diamine (trifluoroacetic acid salt), compound #226; $^1$H NMR (CDCl$_3$, 300 MHz) 7.92 (s, 1H), 7.75 (m, 1H), 7.44 (m, 4H), 7.36 (m, 2H), 7.32 (m, 1H), 7.17 (m, 1H), 7.10 (m, 1H), 3.88 (m, 1H), 3.35 (m, 1H), 2.82 (m, 2H), 2.63 (m, 6H), 2.33 (m, 2H), 2.07 (m, 2H), 1.51 (m, 2H); MS (ES) 454.24 (M+H);

1-(6,7-dihydro-5H-benzo[6,7]cyclohepta[1,2-c]pyridazin-3-yl)-N$^3$-(7-(4-methylpiperazin-1-yl)-6,7,8,9-tetrahydro-5H-benzo[7]annulene-2-yl)-1H-1,2,4-triazole-3,5-diamine (bis trifluoroacetic acid salt), compound #227; $^1$H NMR (CDCl$_3$, 300 MHz) 7.89 (s, 1H), 7.81 (m, 1H), 7.44 (m, 2H), 7.35 (m, 1H), 7.31 (m, 1H), 7.20 (m, 1H), 7.07 (m, 1H), 7.00 (m, 1H), 6.91 (m, 1H), 2.98 (m, 8H), 2.86-2.58 (m, 8H), 2.55 (s, 3H), 2.33 (m, 5H), 1.44 (m, 2H); MS (ES) 536.28 (M+H);

1-(6,7-dihydro-5H-benzo[6,7]cyclohepta[1,2-c]pyridazin-3-yl)-N$^3$-(7-(tetrahydrofuran-2-ylmethyl)amino-6,7,8,9-tetrahydro-5H-benzo[7]annulene-2-yl)-1H-1,2,4-triazole-3,5-diamine (bis trifluoroacetic acid salt), compound #228; $^1$H NMR (CDCl$_3$, 300 MHz) 8.41 (s, 1H), 7.87 (m, 1H), 7.80 (m, 1H), 7.44-7.04 (m, 9H), 4.46 (m, 6H), 3.87 (m, 2H), 3.25 (m, 2H), 2.63 (m, 6H), 2.33 (m, 3H), 2.10 (m, 1H), 1.95 (m, 2H), 1.58 (m, 2H); MS (ES) 507.27 (M+H);

1-(6,7-dihydro-5H-benzo[6,7]cyclohepta[1,2-c]pyridazin-3-yl)-N$^3$-(7-cyclobutylamino-6,7,8,9-tetrahydro-5H-benzo[7]annulene-2-yl)-1H-1,2,4-triazole-3,5-diamine (bis trifluoroacetic acid salt), compound #229; $^1$H NMR (CDCl$_3$, 300 MHz) 8.42 (s, 1H), 7.90 (s, 1H), 7.81 (m, 1H), 7.53 (m, 1H), 7.43 (m, 2H), 7.29 (m, 4H), 7.07 (m, 1H), 6.98 (m, 1H), 3.71 (m, 1H), 3.12 (m, 2H), 2.80 (m, 1H), 2.62 (m, 7H), 2.30 (m, 7H), 1.80 (m, 2H), 1.56 (m, 2H); MS (ES) 537.30 (M+H);

1-(6,7-dihydro-5H-benzo[6,7]cyclohepta[1,2-c]pyridazin-3-yl)-N$^3$-(7-(cyclopropylmethyl)amino-6,7,8,9-tetrahydro-5H-benzo[7]annulene-2-yl)-1H-1,2,4-triazole-3,5-diamine (bis trifluoroacetic acid salt), compound #230; $^1$H NMR (CDCl$_3$, 300 MHz) 8.40 (m, 2H), 7.88 (s, 1H), 7.79 (m, 1H), 7.43 (m, 4H), 7.26 (m, 2H), 7.05 (m, 2H), 3.29 (m, 1H), 2.65 (m, 10H), 2.31 (m, 6H), 1.57 (m, 2H), 1.31 (m, 1H), 0.61 (m, 2H), 0.33 (m, 2H); MS (ES) 507.28 (M+H);

1-(6,7-dihydro-5H-benzo[6,7]cyclohepta[1,2-c]pyridazin-3-yl)-N$^3$-(7-(2-(diethylamino)ethyl)methylamino-6,7,8,9-tetrahydro-5H-benzo[7]annulene-2-yl)-1H-1,2,4-triazole-3,5-diamine (bis trifluoroacetic acid salt), compound #231; $^1$H NMR (CDCl$_3$, 300 MHz) 8.38 (m, 1H), 7.92 (m, 1H), 7.76 (m, 1H), 7.46-7.10 (m, 8H), 4.04 (m, 8H), 3.02 (m, 6H), 2.72 (m, 6H), 2.42 (m, 2H), 2.20 (m, 2H), 1.43 (m, 2H), 1.25 (m, 6H); MS (ES) 566.31 (M+H);

1-(6,7-dihydro-5H-benzo[6,7]cyclohepta[1,2-c]pyridazin-3-yl)-N$^3$-(7-(4-pyrrolidin-1-ylpiperidin-1-yl)-6,7,8,9-tetrahydro-5H-benzo[7]annulene-2-yl)-1H-1,2,4-triazole-3,5-diamine (bis trifluoroacetic acid salt), compound #232; $^1$H NMR (CDCl$_3$+CD$_3$OD, 300 MHz) 7.93 (s, 1H), 7.76 (m, 1H), 7.47 (m, 4H), 7.36 (m, 2H), 7.25 (m, 1H), 7.14 (m, 1H), 3.35 (m, 10H), 2.64 (m, 8H), 2.39-2.09 (m, 11H), 1.55 (m, 3H); MS (ES) 590.36 (M+H);

1-(6,7-dihydro-5H-benzo[6,7]cyclohepta[1,2-c]pyridazin-3-yl)-N$^3$-(7-(4-(piperidin-1-ylmethyl)piperidin-1-yl)-6,7,8,9-tetrahydro-5H-benzo[7]annulene-2-yl)-1H-1,2,4-triazole-3,5-diamine (bis trifluoroacetic acid salt), compound #233; $^1$H NMR (CDCl$_3$+CD$_3$OD, 300 MHz) 7.95 (s, 1H), 7.78 (m, 1H), 7.44 (m, 3H), 7.30-7.12 (m, 6H), 3.35 (m, 6H), 3.12-2.47 (m, 12H), 2.39 (m, 6H), 2.10-1.40 (m, 12H); MS (ES) 618.38 (M+H);

1-(6,7-dihydro-5H-benzo[6,7]cyclohepta[1,2-c]pyridazin-3-yl)-N$^3$-(7-amino-6,7,8,9-tetrahydro-5H-benzo[7]annulene-2-yl)-1H-1,2,4-triazole-3,5-diamine (bis trifluoroacetic acid salt), compound #234; $^1$H NMR (CD$_3$OD, 300 MHz) 8.42 (m, 1H), 7.98 (s, 1H), 7.72 (m, 1H), 7.46 (m, 3H), 7.36 (m, 1H), 7.27 (m, 1H), 7.08 (m, 1H), 3.42 (m, 1H), 2.85 (m, 4H), 2.65 (m, 4H), 2.30 (m, 4H), 1.46 (m, 2H); MS (ES) 453.25 (M+H);

1-(6,7-dihydro-5H-benzo[6,7]cyclohepta[1,2-c]pyridazin-3-yl)-N$^3$-(7-(2-(dimethylamino)ethyl)amino-6,7,8,9-tetrahydro-5H-benzo[7]annulene-2-yl)-1H-1,2,4-triazole-3,5-diamine (bis trifluoroacetic acid salt), compound #235; $^1$H NMR (CD$_3$OD, 300 MHz) 8.00 (m, 1H), 7.78 (m, 1H), 7.46 (m, 3H), 7.38 (m, 1H), 7.26 (m, 1H), 7.15 (m, 1H), 3.55 (m, 5H), 2.98 (m, 6H), 2.86 (m, 4H), 2.64 (m, 4H), 2.31 (m, 4H), 1.49 (m, 2H); MS (ES) 524.31 (M+H);

1-(6,7-dihydro-5H-benzo[2,3]thiepino[4,5-c]pyridazin-3-yl)-N$^3$-(4-(1-bicyclo[2.2.1]heptan-2-yl)-piperidin-4-ylphenyl)-1H-1,2,4-triazole-3,5-diamine (bis trifluoroacetic acid salt), compound #236; $^1$H NMR (CD$_3$OD, 300 MHz) 8.06 (m, 1H), 7.77-7.51 (m, 7H), 7.16 (m, 2H), 3.68 (m, 2H), 3.44 (m, 4H), 2.96 (m, 4H), 2.69 (s, 1H), 2.39 (s, 1H), 2.08 (m, 4H), 1.55 (m, 6H), 1.29 (m, 2H); MS (ES) 565.33 (M+H);

1-(6,7-dihydro-5H-benzo[6,7]cyclohepta[1,2-c]pyridazin-3-yl)-N$^3$-(7-(carboxymethyl)amino-6,7,8,9-tetrahydro-5H-benzo[7]annulene-2-yl)-1H-1,2,4-triazole-3,5-diamine, compound #237; $^1$H NMR (CDCl$_3$+CD$_3$OD, 300 MHz) 8.09 (s, 1H), 7.95 (s, 1H), 7.43 (m, 3H), 7.33 (m, 2H), 7.09 (m, 2H), 3.48 (m, 1H), 2.83 (m, 4H), 2.61 (m, 4H), 2.33 (m, 4H), 1.47 (m, 4H); MS (ES) 511.18 (M+H);

1-(4-phenyl-6,7-dihydro-5H-benzo[6,7]cyclohepta[1,2-b]pyridin-2-yl)-N$^3$-(3-fluoro-4-(4-pyrrolidin-1-ylpiperidin-1-yl)phenyl)-1H-1,2,4-triazole-3,5-diamine, compound #238; $^1$H-NMR (DMSO-d$_6$, 300 MHz) 8.85 (s, 1H), 7.68 (m, 1H), 7.41-7.55 (m, 9H), 7.36 (m, 1H), 7.22 (m, 1H), 6.91 (t, 2H), 2.63 (m, 4H), 2.48-2.55 (m, 6H), 2.26 (m, 2H), 2.18 (m, 3H), 1.88 (m, 2H), 1.69 (m, 4H), 1.54 (m, 2H); MS (ES) 615.54 (M+H);

1-(6,7-dimethoxy-quinazolin-4-yl)-N$^3$-(5,7,8,9-tetrahydrospiro[cyclohepta[b]pyridine-6,2'-[1,3]dioxolane]-3-yl)-1H-1,2,4-triazole-3,5-diamine (trifluoroacetic acid salt), compound #239; $^1$H-NMR (DMSO-d$_6$, 300 MHz) 9.28 (br. s, 1H), 9.06 (s, 1H), 8.81 (d, J=12.9 Hz, 1H), 8.18 (br. s, 2H), 7.53 (d, J=17.4 Hz, 1H), 7.37 (d, J=12.9 Hz, 1H), 3.99 (s, 3H), 3.94 (s, 3H), 3.88-3.86 (m, 4H), 2.93 (m, 2H), 2.89 (m, 2H), 1.89 (m, 2H), 1.62 (m, 2H) ppm; MS (ES) 491.19 (M+H);

1-(2-chloro-7-methylthieno[3,2-d]pyrimidin-4-yl)-N$^3$-(5,7,8,9-tetrahydrospiro[cyclohepta[b]pyridine-6,2'-[1,3]dioxolane]-3-yl)-1H-1,2,4-triazole-3,5-diamine (trifluoroacetic acid salt), compound #240; $^1$H-NMR (DMSO-d$_6$, 300 MHz) 10.37 (br. s, 1H), 8.77 (s, 1H), 8.27 (s, 1H), 8.24 (s, 1H), 8.09 (br. s, 2H), 3.95-3.88 (m, 4H), 3.23 (s, 2H), 3.12-3.10 (m, 2H), 2.39 (s, 3H), 1.98-1.96 (m, 2H), 1.74 (m, 2H) ppm; MS (ES) 485.66 (M+H);

1-(2-chloro-7-methylthieno[3,2-d]pyrimidin-4-yl)-N$^3$-(5,6,8,9-tetrahydrospiro[cyclohepta[b]pyridine-7,2'-[1,3]dioxolane]-3-yl)-1H-1,2,4-triazole-3,5-diamine (trifluoroacetic acid salt), compound #241; $^1$H-NMR (DMSO-d$_6$, 300 MHz) 10.35 (br. s, 1H), 8.83 (s, 1H), 8.27 (s, 1H), 8.18 (s, 1H), 8.08 (br. s, 2H), 3.95-3.94 (m, 4H), 3.04 (m, 2H), 3.90 (m, 2H), 2.39 (s, 3H), 1.84 (m, 4H) ppm; MS (ES) 485.05 (M+H), 483.15 (M−H);

1-(2-chloro-7-methylthieno[3,2-d]pyrimidin-4-yl)-N$^3$-(5',5'-dimethyl-6,8,9,10-9tetrahydro-5H-spiro[cycloocta[b]pyridine-7,2'-[1,3]dioxane]-3-yl)-1H-1,2,4-triazole-3,5-diamine, compound #246;

1-(6,7-dihydro-5H-benzo[6,7]cyclohepta[1,2-c]pyridazin-3-yl)-N$^3$-(5',5'-dimethyl-6,8,9,10-tetrahydro-5H-spiro[cycloocta[b]pyridine-7,2''-[1,3]dioxane]-3-yl)-1H-1,2,4-triazole-3,5-diamine compound #247;

SYNTHETIC EXAMPLE 5

In a similar manner as described above utilizing the appropriately substituted starting materials and reagents, the following compounds of formula (Ib) were prepared:

1-(6,7-dihydro-5H-benzo[6,7]cyclohepta[1,2-c]pyridazin-3-yl)-N$^5$-(3-fluoro-4-(4-(indolin-2-on-1-yl)piperidin-1-yl)phenyl)-1H-1,2,4-triazole-3,5-diamine, compound #157, $^1$H NMR (DMSO-d$_6$, 300 MHz) 10.90 (s, 1H), 7.93-7.81 (m, 2H), 7.77-7.71 (m, 1H), 7.52-6.98 (m, 9H), 5.91 (s, 2H), 4.30-4.19 (m, 2H), 3.48-3.38 (m, 2H), 2.82 (t, 2H), 2.63-2.41 (m, 4H), 2.24-2.19 (m, 3H), 1.72 (d, 2H) ppm; MS (ES) 602.39 (M+H);

1-(6,7-dihydro-5H-benzo[6,7]cyclohepta[1,2-c]pyridazin-3-yl)-N$^5$-(3-fluoro-4-(4-(morpholin-4-yl)piperidin-1-yl)phenyl)-1H-1,2,4-triazole-3,5-diamine, compound #158, $^1$H NMR (DMSO-d$_6$, 300 MHz) 10.95 (s, 1H), 7.84-7.80 (m, 2H), 7.75-7.70 (m, 1H), 7.47-7.41 (m, 2H), 7.38-7.35 (m, 1H), 7.12 (d, 1H), 7.01 (t, 1H), 5.96 (s, 2H), 3.58-3.55 (m, 4H), 3.38-3.23 (m, 4H), 2.68-2.42 (m, 7H), 2.29-2.18 (m, 4H), 1.86 (d, 2H), 1.61-1.49 (m, 2H) ppm; MS (ES) 556.55 (M+H);

1-(6,7-dihydro-5H-benzo[6,7]cyclohepta[1,2-c]pyridazin-3-yl)-N$^5$-(2-((dimethylamino)methyl)-1H-benzo[d]imidazol-5-yl)-1H-1,2,4-triazole-3,5-diamine, compound #159, $^1$H NMR (DMSO-d$_6$, 300 MHz) 10.5 (s, 1H), 8.05 (s, 1H), 7.90 (m, 1H), 7.80 (br s, 2H), 7.70 (m, 5H), 3.64 (m, 2H), 2.56 (m, 4H), 2.15 (m, 8H) ppm; MS (ES) 467.1 (M+H);

1-(6,7-dihydro-5H-benzo[6,7]cyclohepta[1,2-c]pyridazin-3-yl)-N$^5$-(4-(3,5-dimethylpiperazin-1-yl)phenyl)-1H-1,2,4-triazole-3,5-diamine, compound #160, $^1$H NMR (DMSO-d$_6$, 300 MHz) 10.7 (s, 1H), 7.82 (br s, 2H), 7.72 (m, 1H), 7.58-7.36 (m, 6H), 6.96 (m, 2H), 3.55 (m, 5H), 2.99 (m, 3H), 2.21 (m, 5H), 1.08 (d, 6H) ppm; MS (ES) 482.1 (M+H);

1-(6,7-dihydro-5H-benzo[6,7]cyclohepta[1,2-c]pyridazin-3-yl)-N$^5$-(7-((bicyclo[2.2.1]heptan-2-yl)(methyl)amino)-6,7,8,9-tetrahydro-5H-benzo[7]annulene-2-yl)-1H-1,2,4-triazole-3,5-diamine, compound #161, $^1$H NMR (DMSO-d$_6$, 300 MHz) 10.9 (s, 1H), 7.84 (br s, 2H), 7.72 (m, 2H). 7.42 (m, 5H), 7.16 (m, 1H), 3.88 (m, 1H), 3.55 (m, 1H), 3.23 (m, 1H), 2.77 (m, 3H), 2.57 (m, 7H), 2.25 (m, 6H), 1.74-1.13 (m, 10H) ppm; MS (ES) 561.3 (M+H);

1-(7-methyl-6,7-dihydro-5H-benzo[2,3]azepino[4,5-c]pyridazin-3-yl)-N$^5$-(4-(N-methylpiperazin-1-yl)phenyl)-1H-1,2,4-triazole-3,5-diamine, compound #162, $^1$H-NMR (CDCl$_3$, 300 MHz) 10.78 (s, 1H), 7.74 (m, 2H), 7.55 (d, 2H), 7.45 (t, 1H), 7.19 (t, 1H), 6.94 (d, 1H), 4.28 (s, 2H), 3.44 (m, 2H), 3.16 (m, 4H), 2.78 (m, 5H), 2.59 (m, 4H), 2.36 (s, 3H)ppm; MS (ES) 483.21 (M+H);

1-(6,7-dihydro-5H-benzo[6,7]cyclohepta[1,2-c]pyridazin-3-yl)-N$^5$-(4-((5-fluoroindolin-2-on-yl)methyl)phenyl)-1H-1,2,4-triazole-3,5-diamine, compound #163, MS (ES) 533.08 (M+H);

1-(6,7-dihydro-5H-benzo[6,7]cyclohepta[1,2-c]pyridazin-3-yl)-N$^5$-(4-(4-pyrrolidin-1-ylpiperidinyl)phenyl)-1H-1,2,4-triazole-3,5-diamine, compound #164, $^1$H NMR (DMSO-d$_6$, 300 MHz) 10.71 (br s, 1H), 7.81 (s, 1H), 7.74-7.72 (m, 1H), 7.55 (d, 2H), 7.45-7.43 (m, 2H), 7.38-7.35 (m, 1H), 6.94 (d, 2H), 5.84 (br s, 2H), 3.61-3.57 (m, 4H), 2.67 (m, 4H), 2.62-2.60 (m, 1H), 2.57-2.52 (m, 4H), 2.22-2.18 (m, 2H), 1.97-1.92 (m, 2H), 1.72 (m, 4H), 1.60-1.50 (m, 2H) ppm; MS (ES) 522.66 (M+H);

1-(6,7-dihydro-5H-benzo[6,7]cyclohepta[1,2-c]pyridazin-3-yl)-N$^5$-(44(4-pyrrolidin-1-ylpiperidinyl)methyl)phenyl)-1H-1,2,4-triazole-3,5-diamine, compound #165, $^1$H NMR (DMSO-d$_6$, 300 MHz) 10.95 (br s, 1H), 7.84 (s, 1H), 7.72 (t, 1H), 7.67 (d, 2H), 7.57 (d, 1H), 7.45 (m, 1H), 7.36-7.35 (m, 1H), 7.25 (d, 2H), 7.15 (d, 1H), 5.89 (br s, 2H), 3.40 (s, 2H), 2.80-2.76 (m, 2H), 2.61 (m, 4H), 2.56 (m, 2H), 2.42 (m, 1H), 2.25-2.21 (m, 4H), 1.98-1.80 (m, 4H), 1.69 (m, 4H), 1.40-1.36 (m, 2H) ppm; MS (ES) 536.47 (M+H);

1-(6,7-dihydro-5H-benzo[6,7]cyclohepta[1,2-c]pyridazin-3-yl)-N$^5$-(4-((4-cyclopentylpiperazinyl)methyl)phenyl)-1H-1,2,4-triazole-3,5-diamine, compound #166, $^1$H NMR (DMSO-d$_6$, 300 MHz) 10.94 (br s, 1H), 7.84 (s, 1H), 7.73 (m, 1H), 7.66 (d, 2H), 7.45 (m, 2H), 7.36 (m, 1H), 7.24 (d, 2H), 5.89 (br s, 2H), 3.32 (s, 2H), 3.30 (m, 4H), 2.71 (m, 1H), 2.46 (m, 4H), 1.73 (m, 2H), 1.57-1.46 (m, 6H), 1.29 (m, 2H) ppm; MS (ES) 536.44 (M+H);

1-(6,7-dihydro-5H-benzo[6,7]cyclohepta[1,2-c]pyridazin-3-yl)-N$^5$-(4-((4-isopropylpiperazinyl)methyl)phenyl)-1H-1,2,4-triazole-3,5-diamine, compound #167, $^1$H NMR (DMSO-d$_6$, 300 MHz) 11.01 (br s, 1H), 7.85 (s, 1H), 7.78-7.70 (m, 2H), 7.48-7.44 (m, 2H), 7.40-7.30 (m, 4H), 5.95 (br s, 2H), 3.45 (s, 2H), 3.08 (m, 4H), 2.72 (m, 1H), 2.56 (m, 4H), 2.42 (m, 4H), 2.26-2.22 (m, 2H), 1.21 (d, 6H) ppm; MS (ES) 510.18 (M+H);

1-(6,7-dihydro-5H-benzo[6,7]cyclohepta[1,2-c]pyridazin-3-yl)-N$^5$-(3-fluoro-4-(4-N-methylpiperid-4-ylpiperazinyl)phenyl)-1H-1,2,4-triazole-3,5-diamine, compound #168, $^1$H NMR (DMSO-d$_6$, 300 MHz) 10.92 (br s, 1H), 7.95 (d, 1H), 7.84 (s, 1H), 7.71 (dd, 1H), 7.48-7.44 (m, 2H), 7.38-7.32 (m, 2H), 7.10 (t, 1H), 3.61-3.58 (m, 4H), 3.27 (m, 2H), 3.10-3.00 (m, 2H), 2.78 (s, 3H), 2.72 (m, 1H), 2.59 (m, 4H), 2.43-2.41 (m, 4H), 2.40-2.36 (m, 2H), 2.26-2.20 (m, 2H), 1.92-1.82 (m, 2H) ppm; MS (ES) 569.22 (M+H);

1-(6,7-dihydro-5H-benzo[6,7]cyclohepta[1,2-c]pyridazin-3-yl)-$N^5$-(3-fluoro-4-(7-methyl-2,7-diazaspiro[4.4]nonan-2-yl)phenyl)-1H-1,2,4-triazole-3,5-diamine, compound #169, $^1$H NMR (DMSO-$d_6$, 300 MHz) 10.73 (br s, 1H), 7.81 (s, 1H), 7.76 (d, 1H), 7.73-7.70 (m, 1H), 7.45-7.42 (m, 2H), 7.36-7.34 (m, 1H), 7.17 (d, 1H), 6.68 (t, 1H), 5.87 (br s, 2H), 3.19-3.16 (m, 4H), 2.56-2.53 (m, 4H), 2.43-2.40 (m, 4H), 2.26 (s, 3H), 2.21-2.17 (m, 2H), 1.92-1.77 (m, 4H) ppm; MS (ES) 526.26 (M+H);

1-(6,7-dihydro-5H-benzo[6,7]cyclohepta[1,2-c]pyridazin-3-yl)-$N^5$-(3-fluoro-4-(3-pyrrolidin-1-ylazetidinyl)phenyl)-1H-1,2,4-triazole-3,5-diamine, compound #170, $^1$H NMR (DMSO-$d_6$, 300 MHz) 10.82 (br s, 1H), 7.85 (m, 1H), 7.83 (br s, 2H), 7.70-7.66 (m, 1H), 7.46-7.44 (m, 2H), 7.38-7.36 (m, 1H), 7.28 (d, 1H), 7.65 (t, 1H), 5.89 (br s, 2H), 4.20-4.18 (m, 2H), 4.00-3.98 (m, 2H), 3.56-3.54 (m, 4H), 3.03 (m, 1H), 2.55 (m, 2H), 2.44-2.42 (m, 2H), 2.25-2.20 (m, 2H), 2.05 (m, 2H), 1.89 (m, 2H) ppm; MS (ES) 512.21 (M+H);

1-(6,7-dihydro-5H-benzo[6,7]cyclohepta[1,2-c]pyridazin-3-yl)-$N^5$-(3-methyl-4-(4-(N-methylpiperazin-4-yl)piperidin-1-yl)phenyl)-1H-1,2,4-triazole-3,5-diamine, compound #171, $^1$H NMR (DMSO-$d_6$, 300 MHz) 10.83 (br s, 1H), 7.83 (s, 1H), 7.72 (dd, 1H), 7.55-7.51 (m, 2H), 7.46-7.44 (m, 2H), 7.38-7.35 (m, 1H), 7.03 (d, 1H), 5.90 (br s, 2H), 3.48 (m, 4H), 3.13-3.11 (m, 2H), 3.00 (m, 2H), 2.78 (s, 3H), 2.71-2.69 (m, 1H), 2.63-2.55 (m, 4H), 2.42 (m, 4H), 2.27 (s, 3H), 2.23-2.21 (m, 2H), 2.01 (m, 2H), 1.72-1.68 (m, 2H) ppm; MS (ES) 565.32 (M+H);

1-(6,7-dihydro-5H-benzo[2,3]thiepino[4,5-c]pyridazin-3-yl)-$N^5$-(4-(4-pyrrolidin-1-ylpiperidinyl)phenyl)-1H-1,2,4-triazole-3,5-diamine, compound #172, $^1$H NMR (CD3OD, 300 MHz) 8.01 (s, 1H), 7.80-7.51 (m, 6H), 7.18 (m, 2H), 3.82 (m, 2H), 3.70 (m, 2H), 3.39 (m, 2H), 3.23 (m, 2H), 2.94 (m, 4H), 2.34-1.91 (m, 8H); MS (ES) 540.16 (M+H);

1-(6,7-dihydro-5H-benzo[6,7]cyclohepta[1,2-c]pyridazin-3-yl)-$N^5$-(6-(4-(pyrrolidin-1-yl)piperidin-1-yl)-5-methylpyridin-3-yl)-1H-1,2,4-triazole-3,5-diamine, trifluoroacetic acid salt, compound #173; $^1$H-NMR (DMSO-$d_6$, 300 MHz) 10.67 (br s, 1H), 8.45 (s, 1H), 7.97 (s, 1H), 7.83 (s, 1H), 7.75-7.70 (m, 1H), 7.47-7.44 (m, 2H), 7.38-7.35 (m, 1H), 5.82 (br s, 2H), 3.60-3.40 (m, 4H), 3.12-3.08 (m, 2H), 2.78-2.71 (m, 3H), 2.55-2.52 (m, 2H), 2.27 (s, 3H), 2.21-2.11 (m, 4H), 2.02 (m, 2H), 1.85-1.72 (m, 4H) ppm; MS (ES) 537.57 (M+H);

1-(6,7-dihydro-5H-benzo[6,7]cyclohepta[1,2-c]pyridazin-3-yl)-$N^5$-(3-fluoro-(4-(3-pyrrolidin-1-yl)pyrrolidin-1-yl)phenyl)-1H-1,2,4-triazole-3,5-diamine, trifluoroacetic acid salt, compound #174; $^1$H-NMR (DMSO-$d_6$, 300 MHz) 10.81 (s, 1H), 7.87 (s, 1H), 7.83 (s, 1H), 7.72-7.70 (m, 1H), 7.45-7.43 (m, 2H), 7.37-7.35 (m, 1H), 7.28-7.26 (m, H), 6.85 (t, J=10.2 Hz), 5.93 (br. s, 2H), 4.00-3.92 (m, 4H), 3.60 (m, 2H), 3.52-3.48 (m, 4H), 2.28-2.26 (m, 1H), 3.12 (m, 2H), 2.40-2.36 (m, 2H), 2.26-2.20 (m, 2H), 2.08-2.04 (m, 2H), 1.89-1.85 (m, 2H) ppm; MS (ES) 526.34 (M+H);

1-(6,7-dihydro-5H-benzo[6,7]cyclohepta[1,2-c]pyridazin-3-yl)-$N^5$-(3-fluoro-4-(4-methylpiperazin-1-yl)phenyl)-1H-1,2,4-triazole-3,5-diamine (trifluoroacetic acid salt), compound #242; $^1$H-NMR (DMSO-$d_6$, 300 MHz) 10.92 (br. s, 1H), 7.92 (d, J=16.5 Hz, 1H), 7.84 (s, 1H), 7.74-7.71 (m, 1H), 7.46-7.44 (m, 2H), 7.37-7.30 (m, 2H), 7.11 (t, J=9.6 Hz, 1H), 3.53-3.42 (m, 4H), 3.24-3.18 (m, 2H), 3.01-2.93 (m, 2H), 2.86 (s, 3H), 2.59-2.54 (m, 4H), 2.25-2.19 (m, 2H) ppm; MS (ES) 485.57 (M+H);

1-(6,7-dihydro-5H-benzo[6,7]cyclohepta[1,2-c]pyridazin-3-yl)-$N^5$-(1,2,3,4-tetrahydroisoquinolin-7-yl)-1H-1,2,4-triazole-3,5-diamine (trifluoroacetic acid salt), compound #243; $^1$H-NMR (DMSO-$d_6$, 300 MHz) 11.03 (br. s, 1H), 7.85 (s, 1H), 7.70-7.67 (m, 2H), 7.58 (s, 1H), 7.47-7.43 (m, 2H), 7.38-7.36 (m, 1H), 7.21-7.19 (d, J=8.7 Hz, 1H), 5.95 (br. s, 2H), 4.25-4.21 (m, 2H), 3.39-3.36 (m, 2H), 3.02-2.98 (m, 2H), 2.58-2.55 (m, 4H), 2.26-2.22 (m, 2H) ppm; MS (ES) 425.50 (M+H);

1-(6,7-dihydro-5H-benzo[6,7]cyclohepta[1,2-c]pyridazin-3-yl)-$N^5$-(3-fluoro-4-(4-cyclopropylmethylpiperazin-1-yl)phenyl)-1H-1,2,4-triazole-3,5-diamine (trifluoroacetic acid salt), compound #244; $^1$H-NMR (DMSO-$d_6$, 300 MHz) 10.91 (br. s, 1H), 7.95-7.91 (m, 1H), 7.84 (s, 1H), 7.71 (m, 1H), 7.45-7.31 (m, 4H), 7.11 (t, J=9.0 Hz, 1H), 5.90 (br. s, 2H), 3.64-3.60 (m, 2H), 3.21-3.17 (m, 4H), 3.08-3.04 (m, 4H), 2.51 (m, 4H), 2.24-2.21 (m, 2H), 1.10-1.08 (m, 1H), 0.66 (d, J=8.1 Hz, 2H), 0.39 (d, J=4.5 Hz, 2H) ppm; MS (ES) 526.32 (M+H);

1-(6,7-dihydro-5H-benzo[6,7]cyclohepta[1,2-c]pyridazin-3-yh-$N^5$-(2-(1-methylpiperidin-4-yl)-1,2,3,4-tetrahydroisoquinolin-7-yl)-1H-1,2,4-triazole-3,5-diamine (bis trifluoroacetic acid salt), compound #245; $^1$H-NMR (DMSO-$d_6$, 300 MHz) 11.07 (br. s, 1H), 7.85 (s, 1H), 7.73-7.71 (m, 2H), 7.65 (s, 1H), 7.46-7.44 (m, 2H), 7.39-7.37 (m, 1H), 7.22 (d, J=9.0 Hz, 1H), 5.92 (br. s, 2H), 4.47-4.43 (m, 2H), 3.45-3.35 (m, 4H), 3.14 (m, 2H), 3.02 (m, 2H), 2.78 (s, 3H), 2.59 (m, 4H), 2.45-2.35 (m, 1H), 2.23-2.21 (m, 4H), 1.94 (m, 2H) ppm; MS (ES) 522.30 (M+H);

1-(6,7-dihydro-5H-benzo[6,7]cyclohepta[1,2-c]pyridazin-3-yl)-$N^5$-(5,7,8,9-tetrahydrospiro[cyclohepta[b]pyridine-6,2"[1,3]dioxolane]-3-yl)-1H-1,2,4-triazole-3,5-diamine (trifluoroacetic acid salt), compound #248; $^1$H-NMR (DMSO-$d_6$, 300 MHz) 11.14 (br. s, 1H), 9.04 (s, 1H), 8.41 (s, 1H), 7.88 (s, 1H), 7.75-7.71 (m, 1H), 7.47-7.44 (m, 2H), 7.38-7.36 (m, 1H), 5.98 (br. s, 2H), 3.98-3.94 (m, 2H), 3.87-3.83 (m, 2H), 3.19 (s, 2H), 3.09-3.07 (m, 2H), 2.60-2.53 (m, 4H), 2.24-2.20 (m, 2H), 197-1.95 (m, 2H), 1.75-1.71 (m, 2H) ppm; MS (ES) 497.51 (M+H); and 1-(6,7-dihydro-5H-benzo[6,7]cyclohepta[1,2-c]pyridazin-3-yl)-$N^5$-(7-(S)-pyrrolidin-1-yl-6,7,8,9-tetrahydro-5H-benzo[7]annulene-2-yl)-1H-1,2,4-triazole-3,5-diamine, compound #249; $^1$H NMR (DMSO-$d_6$, 300 MHz) 10.90 (s, 1H, NH), 7.83 (s, 1H), 7.73 (s, 1H), 7.53-7.28 (m, 5H), 7.07 (d, 1H), 5.89 (s, 2H), 3.31 (s, 4H), 2.91 (m, 2H), 2.66-2.36 (m, 7H), 2.19 (m, 2H), 1.87 (m, 2H), 1.68 (s, 4H), 1.52 (m, 2H) ppm; MS (ES) 507.32 (M+H).

Testing of the Compounds of the Invention

The compounds of the invention were tested in the following assay for their ability to inhibit Axl activity.

Phospho-AKT in-Cell Western Assay

Reagents and Buffers:

Cell culture plate: 96 well assay plate (Corning 3610), white, clear bottom, tissue-culture treated.

Cells: Hela cells.

Starvation medium: For Axl stimulation: 0.5% FCS (fetal calf serum) in DMEM, plus Axl/Fc (extracellular domain of AXL fused to immunoglobulin Fc region) (R&D, 154-AL) 500 ng/mL.

For EGF (epidermal growth factor) stimulation: 0.5% FCS in DMEM (Dulbecco's modified Eagles medium).

Poly-L-Lysine 0.01% solution (the working solution): 10 μg/ml, dilute In PBS (phosphate buffered saline).

Axl antibody cross-linking:

$1^{st}$: Mouse anti-Axl (R&D, MAB154).

$2^{nd}$: Biotin-SP-conjugated AffiniPure goat anti-mouse IgG (H+ L) (Jackson ImmunoResearch #115-065-003).

Fixing buffer: 4% formaldehyde in PBS.

Wash buffer: 0.1% TritonX-100 in PBS.

Quenching buffer: 3% $H_2O_2$, 0.1% Azide in wash buffer, Azide and hydrogen peroxide ($H_2O_2$) are added fresh.

Blocking buffer: 5% BSA in TBST (tris buffered saline plus 0.1% Tween 20).

Primary antibody: Rabbit anti-human Phospho-Akt antibody (Cell Signaling 9271): 1×250 diluted in blocking buffer.

Secondary antibody: HRP (horse radish peroxidase)-conjugated Goat anti-Rabbit secondary, stock solution: Jackson ImmunoResearch (Goat anti-Rabbit HRP, #111-035-144) 1:1 diluted in glycerol, store at −20° C. The working solution: 1×2000 dilution of stock in blocking buffer.

Chemiluminescent working solution (Pierce, 37030): SuperSignal ELISA (enzyme linked immunosorbant assay) Pico Chemiluminescent substrate.

Crystal Violet solution: Stock: 2.5% Crystal violet in methanol, filtered and kept at ambient temperature. The working solution: dilute the stock 1:20 with PBS immediately before use.

10% SDS: working solution: 5% SDS (sodium dodecylsulfate), diluted in PBS

Methods:

Day 1:

A 96 well TC (tissue culture treated) plate was coated with 10 μg/mL poly-L-Lysine at 37° C. for 30 min, washed twice with PBS, and air-dried for 5 minutes before cells were added. Hela cells were seeded at 10,000 cells/well and the cells were starved in 100 μL starvation medium containing Axl/Fc for 24 hrs.

Day 2:

The cells were pre-treated with test compounds by adding 100 μL of 2× test compound to the starvation medium on the cells. The cells were incubated at 37° C. for 1 hr before stimulation.

The cells were stimulated by Axl-antibody cross-linking as follows: A 5×$1^{st}$/$2^{nd}$ Axl antibody mixture was made (37.5 μg/mL $1^{st}$/100 μg/mL $2^{nd}$) in starvation medium and nutated at 4° C. with thorough mixing for 1-2 hours for clustering. The resulting mix was warmed to 37° C. 50 μL of 5×Axl $1^{st}$/$2^{nd}$ of antibody cluster was added to the cells and the cells were incubated at 37° C. for 5 min.

After 5 minutes stimulation, the plate was flicked to remove medium and the plate was tapped onto paper towels. Formaldehyde (4.0% in PBS, 100 μL) was added to fix the cells and the cells were incubated at ambient temperature for 20 min without shaking.

The cells were washed with a plate washer buffer to remove the formaldehyde solution. The plate was flicked to removed excess wash buffer and tapped onto paper towels. Quenching buffer (100 μL) was added to each well and the cells were incubated at ambient temperature for 20 minutes without shaking.

The cells were washed with a plate washer buffer to remove the quenching buffer. Blocking buffer (100 μL) was added and the cells were incubated at ambient temperature for at least an hour with gentle shaking.

The cells were washed with a plate washer buffer and diluted primary antibody (50 μL) was added to each well (blocking buffer was added to the negative control wells instead). The plates were incubated overnight at 4° C. with gentle shaking.

Day 3:

The wash buffer was removed, diluted secondary antibody (100 μL) was added, and the cells were incubated at ambient temperature for 1 hour with gentle shaking. During the incubation, the chemiluminescent reagent was brought to ambient temperature.

The secondary antibody was removed by washing the cells 1× with wash buffer, 1× with PBS by plate washer. The PBS was removed from the plate and the chemiluminescent reagent (80 μL: 40 μL A and 40 μL B) was added to each well at ambient temperature.

The resulting chemiluminescence was read with a Luminomitor within 10 minutes to minimize changes in signal intensity. After reading the chemiluminescence, the cells were washed 1× with wash buffer and 1× with PBS by plate washer. The plate was tapped onto paper towels to remove excess liquid from wells and air-dried at ambient temperature for 5 minutes.

Crystal Violet working solution (60 μL) was added to each well and the cells were incubated at ambient temperature for 30 min. The crystal violet solution was removed, and the wells were rinsed with PBS, then washed 3× with PBS (200 μL) for 5 minutes each.

5% SDS solution (70 μL) was added to each well and the cells were incubated on a shaker for 30 min at ambient temperature.

The absorbance was read at 590 nM on a Wallac photospec. The 590 nM readings indicated the relative cell number in each well. This relative cell number was then used to normalize each luminescence reading.

The results of the ability of the compounds of the invention to inhibit Axl activity, when tested in the above assay, are shown in the following Tables 1-2 wherein the level of activity (i.e., the $IC_{50}$) for each compound is indicated in each Table. The compound numbers in the Tables referred to the compounds disclosed herein as being prepared by the methods disclosed herein:

TABLE 1

(Ia)

| Cpd # | Compound Name | R¹ | R² | R³ | R⁴ | R⁵ | IC$_{50}$ |
|---|---|---|---|---|---|---|---|
| 1 | 1-(6,7-dihydro-5H-benzo[6,7]cyclohepta[1,2-c]pyridazin-3-yl)-N³-(4-(2-(pyrrolidin-1-yl)ethoxy)phenyl)-1H-1,2,4-triazole-3,5-diamine | H | [pyrrolidinyl-ethoxy-phenyl] | [benzo[6,7]cyclohepta[1,2-c]pyridazinyl] | H | H | A |
| 3 | N³-(4-(4-cyclohexanylpiperazin-1-yl)phenyl)-1-(6,7-dihydro-5H-benzo[6,7]cyclohepta[1,2-c]pyridazin-3-yl)-1H-1,2,4-triazole-3,5-diamine | H | [4-cyclohexylpiperazinyl-phenyl] | [benzo[6,7]cyclohepta[1,2-c]pyridazinyl] | H | H | A |
| 4 | 1-(6,7-dihydro-5H-benzo[6,7]cyclohepta[1,2-c]pyridazin-3-yl)-N³-(3-fluoro-4-(4-(pyrrolidin-1-yl)piperidin-1-yl)-1H-1,2,4-triazole-3,5-diamine | H | [3-fluoro-4-(4-pyrrolidinylpiperidinyl)-phenyl] | [benzo[6,7]cyclohepta[1,2-c]pyridazinyl] | H | H | A |

TABLE 1-continued (Ia)

| Cpd # | Compound Name | R¹ | R² | R³ | R⁴ | R⁵ | IC$_{50}$ |
|---|---|---|---|---|---|---|---|
| 5 | 1-(6,7-dihydro-5H-benzo[6,7]cyclohepta[1,2-c]pyridazin-3-yl)-N³-(3-fluoro-4-(4-methyl-3-phenylpiperazin-1-yl)phenyl)-1H-1,2,4-triole-3,5-diamine | H | 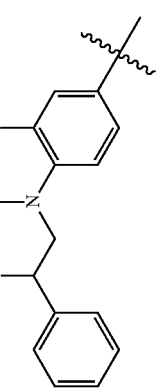 | 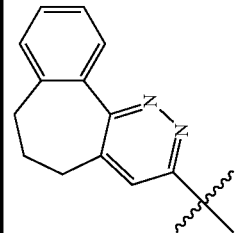 | H | H | D |
| 6 | 1-(6,7-dihydro-5H-benzo[6,7]cyclohepta[1,2-c]pyridazin-3-yl)-N³-(3-fluoro-4-(4-piperidin-1-yl)phenyl)-1H-1,2,4-triazole-3,5-diamine | H | 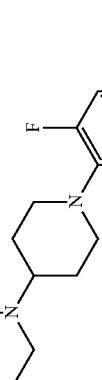 | 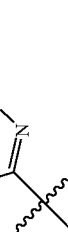 | H | H | A |
| 7 | 1-(6,7-dihydro-5H-benzo[6,7]cyclohepta[1,2-c]pyridazin-3-yl)-N³-(3-fluoro-4-(4-(indolin-2-on-1-yl)piperidin-1-yl)phenyl)-1H-1,2,4-triazole-3,5-diamine | H | 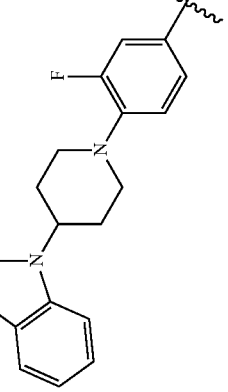 | 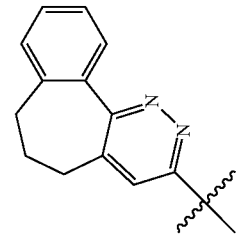 | H | H | D |

TABLE 1-continued (Ia) structure with R1, R2, R3, R4, R5 substituents on triazole-diamine core

| Cpd # | Compound Name | R1 | R2 | R3 | R4 | R5 | IC50 |
|---|---|---|---|---|---|---|---|
| 8 | 1-(6,7-dihydro-5H-benzo[6,7]cyclohepta[1,2-c]pyridazin-3-yl)-N³-(6-(4-(bicyclo[2.2.1]heptan-2-yl)piperazin-1-yl)pyridin-3-yl)-1H-1,2,4-triazole-3,5-diamine | H | [bicycloheptyl-piperazinyl-pyridinyl group] | [dihydrobenzocycloheptapyridazinyl group] | H | H | B |
| 9 | 1-(6,7-dihydro-5H-benzo[6,7]cyclohepta[1,2-c]pyridazin-3-yl)-N³-(3-fluoro-4-(morpholin-4-yl)piperidin-1-yl)phenyl)-1H-1,2,4-triazole-3,5-diamine | H | [fluoro-morpholino-piperidinyl-phenyl group] | [dihydrobenzocycloheptapyridazinyl group] | H | H | B |
| 10 | 1-(6,7-dihydro-5H-benzo[6,7]cyclohepta[1,2-c]pyridazin-3-yl)-N³-(4-(4-(cyclopentyl)piperazin-1-ylcarbonyl)phenyl)-1H-1,2,4-triazole-3,5-diamine | H | [cyclopentyl-piperazinyl-carbonyl-phenyl group] | [dihydrobenzocycloheptapyridazinyl group] | H | H | B |

TABLE 1-continued (Ia)
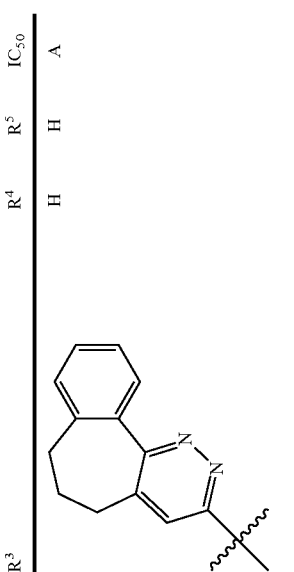

| Cpd # | Compound Name | R¹ | R² | R³ | R⁴ | R⁵ | IC₅₀ |
|---|---|---|---|---|---|---|---|
| 11 | 1-(6,7-dihydro-5H-benzo[6,7]cyclohepta[1,2-c]pyridazin-3-yl)-N³-(4,5-dihydro-1H-benzo[b]azepin-2(3H)-on-8-yl)-1H-1,2,4-triazole-3,5-diamine | H | 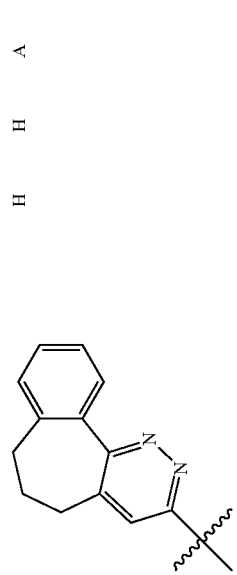 | 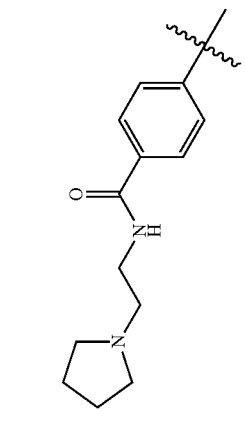 | H | H | A |
| 12 | 1-(6,7-dihydro-5H-benzo[6,7]cyclohepta[1,2-c]pyridazin-3-yl)-N³-(4-((2-pyrrolidin-1-yl)ethyl)aminocarbonyl)phenyl)-1H-1,2,4-triazole-3,5-diamine | H | 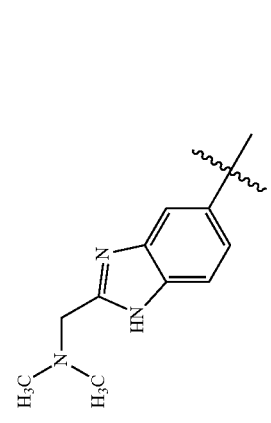 | 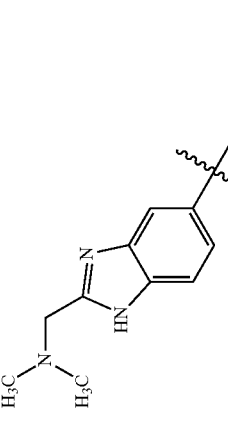 | H | H | A |
| 13 | 1-(6,7-dihydro-5H-benzo[6,7]cyclohepta[1,2-c]pyridazin-3-yl)-N³-((dimethylamino)methyl)-1H-benzo[d]imidazol-5-yl)-1H-1,2,4-triazole-3,5-diamine | H |  | 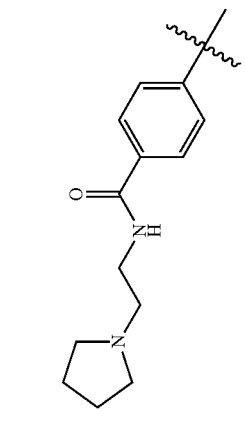 | H | H | B |

TABLE 1-continued

| Cpd # | Compound Name | R¹ | R² | R³ | R⁴ | R⁵ | IC₅₀ |
|---|---|---|---|---|---|---|---|
| 14 | 1-(6,7-dihydro-5H-benzo[6,7]cyclohepta[1,2-c]pyridazin-3-yl)-N³-(4-(2,2,6,6-tetramethylpiperidin-1-yl)ethoxyphenyl)-1H-1,2,4-triazole-3,5-diamine | H | H₃C CH₃ structure with piperidine and phenoxyethyl | 6,7-dihydro-5H-benzo[6,7]cyclohepta[1,2-c]pyridazin-3-yl | H | H | B |
| 15 | 1-(6,7-dihydro-5H-benzo[6,7]cyclohepta[1,2-c]pyridazin-3-yl)-N³-(7-(pyrrolidin-1-yl)-6,7,8,9-tetrahydro-5H-benzo[7]annulene-2-yl)-1H-1,2,4-triazole-3,5-diamine | H | pyrrolidinyl-tetrahydrobenzannulene structure | 6,7-dihydro-5H-benzo[6,7]cyclohepta[1,2-c]pyridazin-3-yl | H | H | A |
| 16 | 1-(6,7-dihydro-5H-benzo[6,7]cyclohepta[1,2-c]pyridazin-3-yl)-N³-(4-(4-cyclopentyl-2-methylpiperazin-1-yl)phenyl)-1H-1,2,4-triazole-3,5-diamine | H | cyclopentyl-methylpiperazinyl-phenyl structure | 6,7-dihydro-5H-benzo[6,7]cyclohepta[1,2-c]pyridazin-3-yl | H | H | A |

TABLE 1-continued

| Cpd # | Compound Name | R¹ | R² | R³ | R⁴ | R⁵ | IC₅₀ |
|---|---|---|---|---|---|---|---|
| 17 | 1-(6,7-dihydro-5H-benzo[6,7]cyclohepta[1,2-c]pyridazin-3-yl)-N³-(4-(3,5-dimethylpiperazin-1-yl)phenyl)-1H-1,2,4-triazole-3,5-diamine | H | (2,6-dimethylpiperazin-1-yl)phenyl group | 6,7-dihydro-5H-benzo[6,7]cyclohepta[1,2-c]pyridazin-3-yl | H | H | A |
| 18 | 1-(6,7-dihydro-5H-benzo[6,7]cyclohepta[1,2-c]pyridazin-3-yl)-N³-(4-(4-(pyrrolidin-1-yl)piperidin-1-yl)-3-cyanophenyl)-1H-1,2,4-triazole-3,5-diamine | H | 4-(4-(pyrrolidin-1-yl)piperidin-1-yl)-3-cyanophenyl | 6,7-dihydro-5H-benzo[6,7]cyclohepta[1,2-c]pyridazin-3-yl | H | H | A |
| 19 | 1-(6,7-dihydro-5H-benzo[6,7]cyclohepta[1,2-c]pyridazin-3-yl)-N³-(4-((2-(dimethylamino)ethyl)-aminocarbonyl)phenyl)-1H-1,2,4-triazole-3,5-diamine | H | 4-((2-(dimethylamino)ethyl)aminocarbonyl)phenyl | 6,7-dihydro-5H-benzo[6,7]cyclohepta[1,2-c]pyridazin-3-yl | H | H | B |

TABLE 1-continued

| Cpd # | Compound Name | R¹ | R² | R³ | R⁴ | R⁵ | IC$_{50}$ |
|---|---|---|---|---|---|---|---|
| 20 | 1-(6,7-dihydro-5H-benzo[6,7]cyclohepta[1,2-c]pyridazin-3-yl)-N³-(4-((2-(methoxy)ethyl)amino-carbonyl)phenyl)-1H-1,2,4-triazole-3,5-diamine | H | CH₃ | | H | H | B |
| 21 | 1-(6,7-dihydro-5H-benzo[6,7]cyclohepta[1,2-c]pyridazin-3-yl)-N³-(4-((2-(pyrrolidin-1-yl)ethyl)aminocarbonyl)-phenyl)-1H-1,2,4-triazole-3,5-diamine | H | | | H | H | A |
| 22 | 1-(6,7-dihydro-5H-benzo[6,7]cyclohepta[1,2-c]pyridazin-3-yl)-N³-(4-((4-(pyrrolidin-1-yl)piperidin-1-yl)carbonyl)phenyl)-1H-1,2,4-triazole-3,5-diamine | H | | | H | H | A |

TABLE 1-continued

| Cpd # | Compound Name | R¹ | R² | R³ | R⁴ | R⁵ | IC$_{50}$ |
|---|---|---|---|---|---|---|---|
| 23 | 1-(6,7-dihydro-5H-benzo[6,7]cyclohepta[1,2-c]pyridazin-3-yl)-N³-(7-((bicyclo[2.2.1]heptan-2-yl)amino)-6,7,8,9-tetrahydro-5H-benzo[7]annulene-2-yl)-1H-1,2,4-triazole-3,5-diamine | H | | | H | H | A |
| 24 | 1-(6,7-dihydro-5H-benzo[6,7]cyclohepta[1,2-c]pyridazin-3-yl)-N³-(7-((bicyclo[2.2.1]heptan-2-yl)(methyl)amino)-6,7,8,9-tetrahydro-5H-benzo[7]annulene-2-yl)-1H-1,2,4-triazole-3,5-diamine | H | | | H | H | B |
| 25 | 1-(6,7-dihydro-5H-benzo[6,7]cyclohepta[1,2-c]pyridazin-3-yl)-N³-(6-(4-cyclopentyl-1,4-diazepan-1-yl)pyridin-3-yl)-1H-1,2,4-triazole-3,5-diamine | H | | | H | H | A |

TABLE 1-continued (Ia)

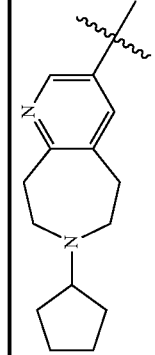

| Cpd # | Compound Name | R¹ | R² | R³ | R⁴ | R⁵ | IC₅₀ |
|---|---|---|---|---|---|---|---|
| 26 | 1-(6,7-dihydro-5H-benzo[6,7]cyclohepta[1,2-c]pyridazin-3-yl)-N³-(7-cyclopentyl-6,7,8,9-tetrahydro-5H-pyrido[3,2-d]azepin-3-yl)-1H-1,2,4-triazole-3,5-diamine | H | 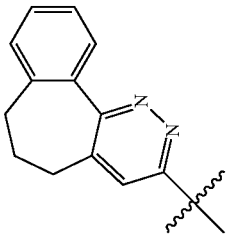 | 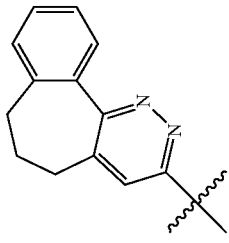 | H | H | B |
| 27 | 1-(6,7-dihydro-5H-benzo[6,7]cyclohepta[1,2-c]pyridazin-3-yl)-N³-(6-(4-methylpiperazin-1-yl)pyridin-3-yl)-1H-1,2,4-triazole-3,5-diamine | H | 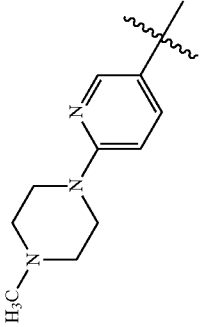 | 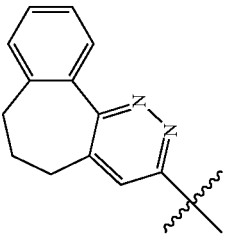 | H | H | A |
| 28 | 1-(6,7-dihydro-5H-benzo[6,7]cyclohepta[1,2-c]pyridazin-3-yl)-N³-(6-methyl-5,6,7,8-tetrahydro-1,6-naphthyridin-3-yl)-1H-1,2,4-triazole-3,5-diamine | H | 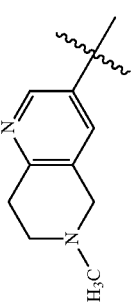 | 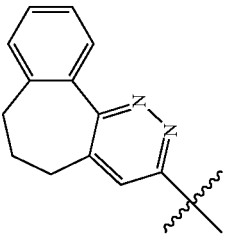 | H | H | A |

TABLE 1-continued (Ia)

| Cpd # | Compound Name | R¹ | R² | R³ | R⁴ | R⁵ | IC$_{50}$ |
|---|---|---|---|---|---|---|---|
| 29 | 1-(6,7-dihydro-5H-benzo[6,7]cyclohepta[1,2-c]pyridazin-3-yl)-N³-(6-(4-(pyrrolidin-1-yl)piperidin-1-yl)pyridine-3-yl)-1H-1,2,4-triazole-3,5-diamine | H | 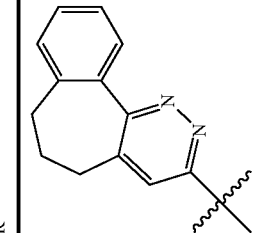 |  | H | H | B |
| 30 | 1-(6,7-dihydro-5H-benzo[6,7]cyclohepta[1,2-c]pyridazin-3-yl)-N³-(6-(4-(4-methylpiperazin-1-yl)piperidin-1-yl)pyridine-3-yl)-1H-1,2,4-triazole-3,5-diamine | H | 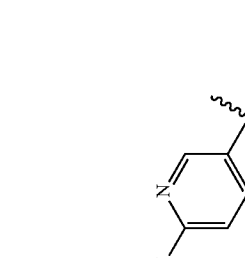 | 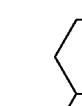 | H | H | A |
| 31 | 1-(6,7-dihydro-5H-benzo[6,7]cyclohepta[1,2-c]pyridazin-3-yl)-N³-(6-(4-methylpiperazin-1-yl)carbonyl-5,6,7,8-tetrahydroquinolin-3-yl)-1H-1,2,4-triazole-3,5-diamine | H | 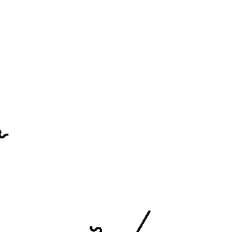 |  | H | H | A |

TABLE 1-continued

| Cpd # | Compound Name | R¹ | R² | R³ | R⁴ | R⁵ | IC₅₀ |
|---|---|---|---|---|---|---|---|
| 32 | 1-(6,7-dihydro-5H-benzo[6,7]cyclohepta[1,2-c]pyridazin-3-yl)-N³-(3-fluoro-4-(3-(diethylamino)pyrrolidin-1-yl)phenyl)-1H-1,2,4-triazole-3,5-diamine | H |  |  | H | H | A |
| 33 | 1-(6,7-dihydro-5H-benzo[6,7]cyclohepta[1,2-c]pyridazin-3-yl)-N³-(4-(4-(bicyclo[2.2.1]heptan-2-yl)piperazin-1-yl)phenyl)-1H-1,2,4-triazole-3,5-diamine | H |  |  | H | H | B |
| 34 | 1-(6,7-dihydro-5H-benzo[6,7]cyclohepta[1,2-c]pyridazin-3-yl)-N³-(4-(4-methylpiperazin-1-yl)phenyl)-1H-1,2,4-triazole-3,5-diamine | H |  |  | H | H | A |

TABLE 1-continued (Ia)

| Cpd # | Compound Name | $R^1$ | $R^2$ | $R^3$ | $R^4$ | $R^5$ | $IC_{50}$ |
|---|---|---|---|---|---|---|---|
| 35 | 1-(6,7-dihydro-5H-benzo[6,7]cyclohepta[1,2-c]pyridazin-3-yl)-$N^3$-(4-((4-methylpiperazin-1-yl)methyl)phenyl)-1H-1,2,4-triazole-3,5-diamine | H | 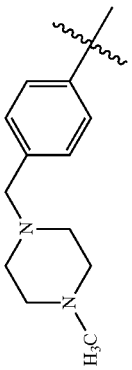 | 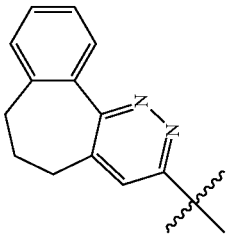 | H | H | A |
| 36 | 1-(6,7-dihydro-5H-benzo[6,7]cyclohepta[1,2-c]pyridazin-3-yl)-$N^3$-(3-fluoro-4-(diethylamino)piperidin-1-yl)phenyl)-1H-1,2,4-triazole-3,5-diamine | H | 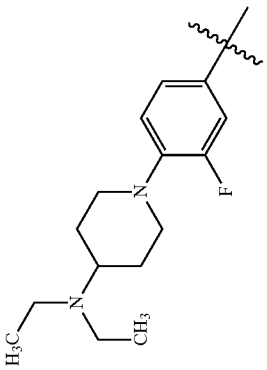 | 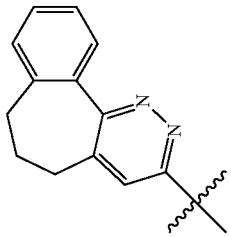 | H | H | A |
| 37 | 1-(6,7-dihydro-5H-benzo[6,7]cyclohepta[1,2-d]pyrimidin-4-yl)-$N^3$-(4-(2-(pyrrolidin-1-yl)ethoxy)phenyl)-1H-1,2,4-triazole-3,5-diamine | H | 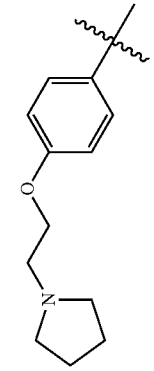 | 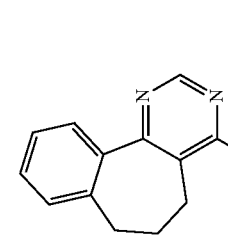 | H | H | A |

TABLE 1-continued

| Cpd # | Compound Name | R¹ | R² | R³ | R⁴ | R⁵ | IC$_{50}$ |
|---|---|---|---|---|---|---|---|
| 38 | 1-(6,7-dihydro-5H-benzo[6,7]cyclohepta[1,2-d]pyrimidin-4-yl)-N3-(4-(4-(bicyclo[2.2.1]heptan-2-yl)piperazin-1-yl)phenyl)-1H-1,2,4-triazole-3,5-diamine | H | 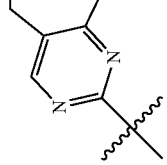 |  | H | H | A |
| 39 | 1-(6,7-dihydro-5H-benzo[6,7]cyclohepta[1,2-d]pyrimidin-4-yl)-N³-(3-fluoro-4-(4-(diethylamino)piperidin-1-yl)phenyl)-1H-1,2,4-triazole-3,5-diamine | H |  | 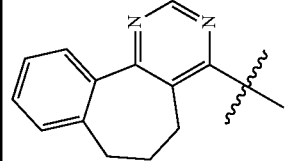 | H | H | A |
| 40 | 1-(6,7-dihydro-5H-benzo[6,7]cyclohepta[1,2-d]pyrimidin-2-yl)-N³-(4-(N-methylpiperazin-1-yl)phenyl)-1H-1,2,4-triazole-3,5-diamine | H | 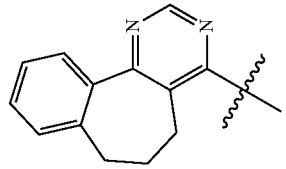 | 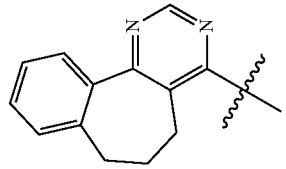 | H | H | B |

TABLE 1-continued

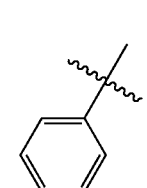

| Cpd # | Compound Name | R¹ | R² | R³ | R⁴ | R⁵ | IC₅₀ |
|---|---|---|---|---|---|---|---|
| 41 | 1-(7-methyl-6,7-dihydro-5H-benzo[2,3]azepino[4,5-c]pyridazin-3-yl)-N³-(4-(N-methylpiperazin-1-yl)phenyl)-1H-1,2,4-triazole-3,5-diamine | H |  | 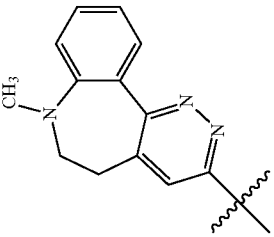 | H | H | B |
| 42 | 1-(7-methyl-6,7-dihydro-5H-benzo[2,3]azepino[4,5-c]pyridazin-3-yl)-N³-(3-fluoro-4-(2-(pyrrolidin-1-yl)ethoxy)phenyl)-1H-1,2,4-triazole-3,5-diamine | H | 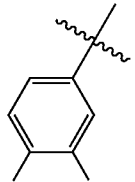 | 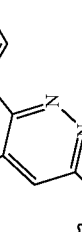 | H | H | A |
| 43 | 1-(7-methyl-6,7-dihydro-5H-benzo[2,3]azepino[4,5-c]pyridazin-3-yl)-N³-(3-fluoro-4-(4-cyclohexylpiperazinyl)phenyl)-1H-1,2,4-triazole-3,5-diamine | H |  | 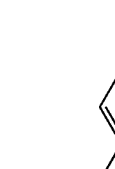 | H | H | B |

TABLE 1-continued (Ia)

| Cpd # | Compound Name | R¹ | R² | R³ | R⁴ | R⁵ | IC₅₀ |
|---|---|---|---|---|---|---|---|
| 44 | 1-(6,7-dihydro-5H-benzo[6,7]cyclohepta[1,2-d]pyrimidin-2-yl)-N³-(3-fluoro-4-(2-(pyrrolidin-1-yl)ethoxy)phenyl)-1H-1,2,4-triazole-3,5-diamine | H | | | H | H | A |
| 45 | 1-(6,7-dihydro-5H-benzo[6,7]cyclohepta[1,2-d]pyrimidin-2-yl)-N³-(3-fluoro-4-(4-cyclohexylpiperazinyl)phenyl)-1H-1,2,4-triazole-3,5-diamine | H | | | H | H | A |
| 46 | 1-(6,7-dihydro-5H-benzo[6,7]cyclohepta[1,2-d]pyrimidin-2-yl)-N³-(4-(4-(2S)-bicyclo[2.2.1]heptan-2-yl)-piperazinyl)phenyl)-1H-1,2,4-triazole-3,5-diamine | H | | | H | H | A |

TABLE 1-continued

| Cpd # | Compound Name | R¹ | R² | R³ | R⁴ | R⁵ | IC$_{50}$ |
|---|---|---|---|---|---|---|---|
| 47 | 1-(6,7-dihydro-5H-benzo[6,7]cyclohepta[1,2-c]pyridazin-3-yl)-N³-(3-chloro-4-(2-(pyrrolidin-1-yl)ethoxyphenyl)-1H-1,2,4-triazole-3,5-diamine | H | (3-chloro-4-(2-(pyrrolidin-1-yl)ethoxy)phenyl) | (6,7-dihydro-5H-benzo[6,7]cyclohepta[1,2-c]pyridazin-3-yl) | H | H | B |
| 48 | 1-(6,7-dihydro-5H-benzo[6,7]cyclohepta[1,2-c]pyridazin-3-yl)-N³-(3-fluoro-4-(2-(pyrrolidin-1-yl)ethoxyphenyl)-1H-1,2,4-triazole-3,5-diamine | H | (3-fluoro-4-(2-(pyrrolidin-1-yl)ethoxy)phenyl) | (6,7-dihydro-5H-benzo[6,7]cyclohepta[1,2-c]pyridazin-3-yl) | H | H | B |
| 49 | 1-((Z)-dibenzo[b,f][1,4]thiazepin-11-yl)-N³-(4-(2-(pyrrolidin-1-yl)ethoxyphenyl)-1H-1,2,4-triazole-3,5-diamine | H | (4-(2-(pyrrolidin-1-yl)ethoxy)phenyl) | (Z)-dibenzo[b,f][1,4]thiazepin-11-yl | H | H | B |

TABLE 1-continued
(Ia)
| Cpd # | Compound Name | R¹ | R² | R³ | R⁴ | R⁵ | IC₅₀ |
|---|---|---|---|---|---|---|---|
| 50 | 1-((Z)-dibenzo[b,f][1,4]thiazepin-11-yl)-N³-(4-(N-methylpiperazin-1-yl)phenyl)-1H-1,2,4-triazole-3,5-diamine | H | 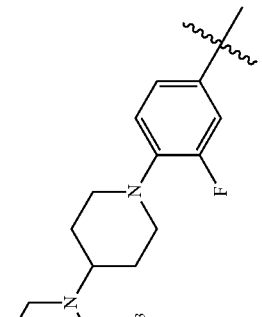 | 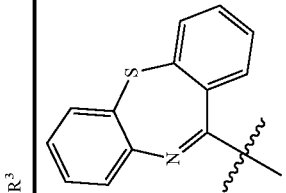 | H | H | B |
| 51 | 1-((Z)-dibenzo[b,f][1,4]thiazepin-11-yl)-N³-(3-fluoro-4-(4-diethylaminopiperidin-1-yl)phenyl)-1H-1,2,4-triazole-3,5-diamine | H | 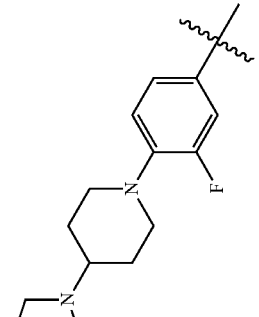 | 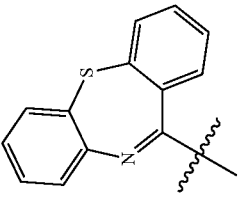 | H | H | B |
| 52 | 1-(6,7-dihydro-5H-9-methoxybenzo[6,7]cyclohepta[1,2-c]pyridazin-3-yl)-N³-(3-fluoro-4-(4-(pyrrolidin-1-yl)piperidin-1-yl)phenyl)-1H-1,2,4-triazole-3,5-diamine | H | 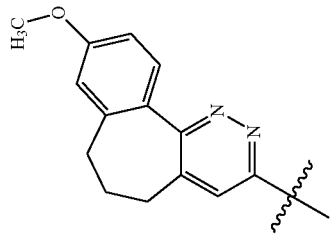 | 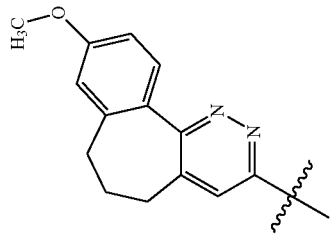 | H | H | A |

TABLE 1-continued (Ia)

| Cpd # | Compound Name | R¹ | R² | R³ | R⁴ | R⁵ | IC$_{50}$ |
|---|---|---|---|---|---|---|---|
| 53 | 1-(6,7-dihydro-5H-10-fluorobenzo[6,7]cyclohepta[1,2-c]pyridazin-3-yl)-N³-(3-fluoro-4-(4-(pyrrolidin-1-yl)piperidin-1-yl)phenyl)-1H-1,2,4-triazole-3,5-diamine | H | | | H | H | A |
| 54 | 1-(6,7-dihydro-5H-10-fluorobenzo[6,7]cyclohepta[1,2-c]pyridazin-3-yl)-N³-(3-fluoro-4-(2-(pyrrolidin-1-yl)ethoxy)phenyl)-1H-1,2,4-triazole-3,5-diamine | H | | | H | H | A |
| 55 | 1-(6,7-dihydro-5H-10-fluorobenzo[6,7]cyclohepta[1,2-c]pyridazin-3-yl)-N³-(3-fluoro-4-(4-(cyclohexyl)piperazin-1-yl)phenyl)-1H-1,2,4-triazole-3,5-diamine | H | | | H | H | C |

TABLE 1-continued
(Ia)
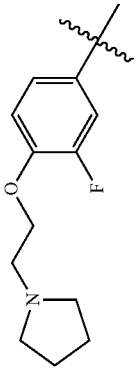
| Cpd # | Compound Name | R[1] | R[2] | R[3] | R[4] | R[5] | IC$_{50}$ |
|---|---|---|---|---|---|---|---|
| 56 | 1-(6,7-dihydro-5H-9-methoxybenzo[6,7]cyclohepta[1,2-c]pyridazin-3-yl)-N[3]-(3-fluoro-4-(2-(pyrrolidin-1-yl)ethoxy)phenyl)-1H-1,2,4-triazole-3,5-diamine | H | 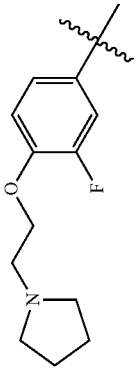 |  | H | H | B |
| 57 | 1-(6,7-dihydro-5H-9-methoxybenzo[6,7]cyclohepta[1,2-c]pyridazin-3-yl)-N[3]-(3-fluoro-4-(4-(cyclohexyl)piperazin-1-yl)phenyl)-1H-1,2,4-triazole-3,5-diamine | H |  |  | H | H | D |

TABLE 1-continued

| Cpd # | Compound Name | R¹ | R² | R³ | R⁴ | R⁵ | IC₅₀ |
|---|---|---|---|---|---|---|---|
| 58 | 1-(6,7-dihydro-5H-benzo[6,7]cyclohepta[1,2-c]pyridazin-3-yl)-N³-(3-fluoro-4-(4-(4-methylpiperazin-1-yl)piperidin-1-yl)phenyl)-1H-1,2,4-triazole-3,5-diamine | H | 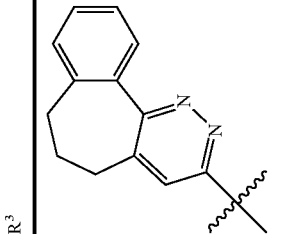 | 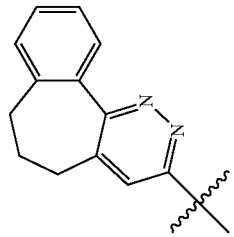 | H | H | A |
| 59 | 1-(6,7-dihydro-5H-benzo[6,7]cyclohepta[1,2-c]pyridazin-3-yl)-N³-(4-(4-methylpiperidin-1-yl)phenyl)-1H-1,2,4-triazole-3,5-diamine | H | 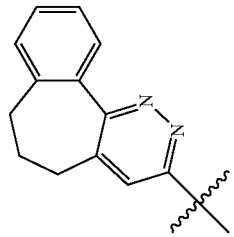 | 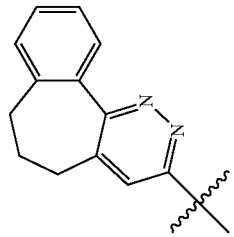 | H | H | A |
| 60 | 1-(6,7-dihydro-5H-benzo[6,7]cyclohepta[1,2-c]pyridazin-3-yl)-N³-(4-(2-(N-methylcyclopentylamino)ethoxy)phenyl)-1H-1,2,4-triazole-3,5-diamine | H | 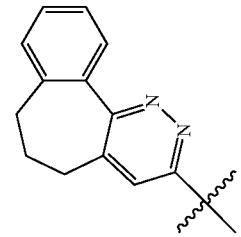 | 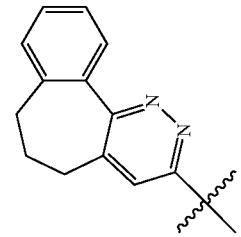 | H | H | A |

TABLE 1-continued

| Cpd # | Compound Name | R¹ | R² | R³ | R⁴ | R⁵ | IC₅₀ |
|---|---|---|---|---|---|---|---|
| 61 | 1-(6,7-dihydro-5H-benzo[6,7]cyclohepta[1,2-c]pyridazin-3-yl)-N³-(3-fluoro-4-(4-dimethylaminopiperidin-1-yl)phenyl)-1H-1,2,4-triazole-3,5-diamine | H |  |  | H | H | A |
| 62 | 1-(6,7-dihydro-5H-benzo[6,7]cyclohepta[1,2-c]pyridazin-3-yl)-N³-(3-chloro-4-(4-pyrrolidin-1-yl-piperidin-1-yl)phenyl)-1H-1,2,4-triazole-3,5-diamine | H |  |  | H | H | A |
| 63 | 1-(6,7-dihydro-5H-benzo[6,7]cyclohepta[1,2-c]pyridazin-3-yl)-N³-(3-trifluoromethyl-4-(4-pyrrolidin-1-yl-piperidin-1-yl)phenyl)-1H-1,2,4-triazole-3,5-diamine | H |  |  | H | H | B |

TABLE 1-continued
| Cpd # | Compound Name | R¹ | R² | R³ | R⁴ | R⁵ | IC$_{50}$ |
|---|---|---|---|---|---|---|---|
| 64 | 1-(6,7-dihydro-5H-9,10-dimethoxybenzo[6,7]cyclohepta[1,2-c]pyridazin-3-yl)-N³-(3-fluoro-4-(4-pyrrolidin-1-yl)piperidin-1-yl)phenyl)-1H-1,2,4-triazole-3,5-diamine | H |  |  | H | H | B |
| 65 | 1-(6,7-dihydro-5H-9,10,11-trimethoxybenzo[6,7]cyclohepta[1,2-c]pyridazin-3-yl)-N³-(3-fluoro-4-(4-pyrrolidin-1-yl)piperidin-1-yl)phenyl)-1H-1,2,4-triazole-3,5-diamine | H |  | 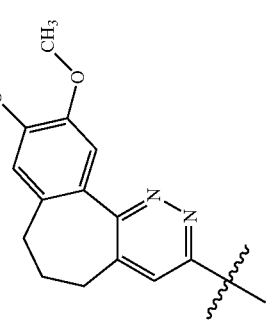 | H | H | A |

TABLE 1-continued (Ia)

| Cpd # | Compound Name | R¹ | R² | R³ | R⁴ | R⁵ | IC₅₀ |
|---|---|---|---|---|---|---|---|
| 66 | 1-(6,7-dihydro-5H-benzo[6,7]cyclohepta[1,2-c]pyridazin-3-yl)-N³-(3-fluoro-4-(5-methyloctahydro-pyrrolo[3,4-c]pyrrolyl)phenyl)-1H-1,2,4-triazole-3,5-diamine | H | H₃C-pyrrolopyrrole-fluorophenyl | benzocycloheptapyridazinyl | H | H | A |
| 67 | 1-(6,7-dihydro-5H-benzo[6,7]cyclohepta[1,2-c]pyridazin-3-yl)-N³-(3-fluoro-4-(N-methylpiperidin-4-yl-N-methylamino)phenyl)-1H-1,2,4-triazole-3,5-diamine | H | N-methylpiperidinyl-N-methyl-fluorophenyl | benzocycloheptapyridazinyl | H | H | A |
| 68 | 1-(6,7-dihydro-5H-benzo[6,7]cyclohepta[1,2-c]pyridazin-3-yl)-N³-(3-fluoro-4-(3-pyrrolidin-1-yl-piperidin-1-yl)phenyl)-1H-1,2,4-triazole-3,5-diamine | H | pyrrolidinyl-piperidinyl-fluorophenyl | benzocycloheptapyridazinyl | H | H | A |

TABLE 1-continued

| Cpd # | Compound Name | R¹ | R² | R³ | R⁴ | R⁵ | IC₅₀ |
|---|---|---|---|---|---|---|---|
| 69 | 1-(6,7-dihydro-5H-benzo[6,7]cyclohepta[1,2-c]pyridazin-3-yl)-N³-(3-fluoro-4-(3-pyrrolidin-1-yl-azepan-1-yl)phenyl)-1H-1,2,4-triazole-3,5-diamine | H | 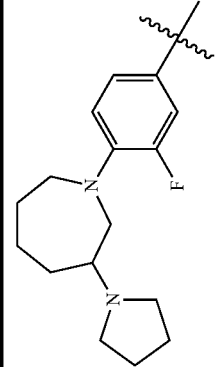 | 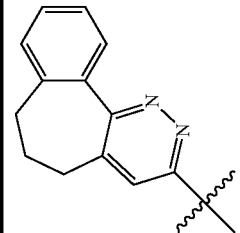 | H | H | A |
| 70 | 1-(6,7-dihydro-5H-benzo[6,7]cyclohepta[1,2-c]pyridazin-3-yl)-N³-(3-fluoro-4-(4-N-methylpiperidin-4-yl-piperidin-1-yl)phenyl)-1H-1,2,4-triazole-3,5-diamine | H | 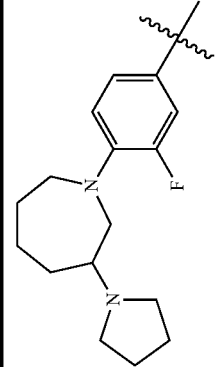 | 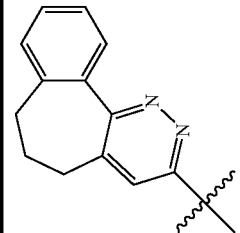 | H | H | A |
| 71 | 1-(6,7-dihydro-5H-benzo[4,5-c]pyridazin-2-yl)-N³-(3-fluoro-4-(4-(pyrrolidinyl)piperidinyl)phenyl)-1H-1,2,4-triazole-3,5-diamine | H | 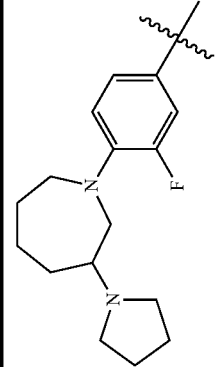 | 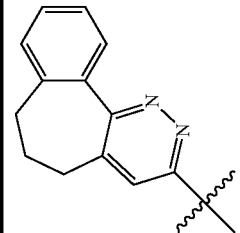 | H | H | A |

TABLE 1-continued

| Cpd # | Compound Name | R¹ | R² | R³ | R⁴ | R⁵ | IC₅₀ |
|---|---|---|---|---|---|---|---|
| 72 | 1-(6,7-dihydro-5H-benzo[6,7]cyclohepta[1,2-c]pyridazin-3-yl)-N³-(3-fluoro-4-(5-propyl-octahydropyrrolo[3,4-c]pyrrolyl)phenyl)-1H-1,2,4-triazole-3,5-diamine | H | H₃C— (propyl-octahydropyrrolo[3,4-c]pyrrolyl-fluorophenyl group) | (6,7-dihydro-5H-benzo[6,7]cyclohepta[1,2-c]pyridazin-3-yl) | H | H | A |
| 73 | 1-(6,7-dihydro-5H-benzo[6,7]cyclohepta[1,2-c]pyridazin-3-yl)-N³-(3-fluoro-4-(decahydropyrazino[1,2-a]azepin-2-yl)phenyl)-1H-1,2,4-triazole-3,5-diamine | H | (decahydropyrazino[1,2-a]azepin-2-yl-fluorophenyl group) | (6,7-dihydro-5H-benzo[6,7]cyclohepta[1,2-c]pyridazin-3-yl) | H | H | A |
| 75 | 1-(6,7-dihydro-5H-benzo[6,7]cyclohepta[1,2-c]pyridazin-3-yl)-N³-(3-fluoro-4-(5-cyclopentyloctahydropyrrolo[3,4-c]pyrrolyl)phenyl)-1H-1,2,4-triazole-3,5-diamine | H | (5-cyclopentyloctahydropyrrolo[3,4-c]pyrrolyl-fluorophenyl group) | (6,7-dihydro-5H-benzo[6,7]cyclohepta[1,2-c]pyridazin-3-yl) | H | H | A |

TABLE 1-continued

| Cpd # | Compound Name | R¹ | R² | R³ | R⁴ | R⁵ | IC₅₀ |
|---|---|---|---|---|---|---|---|
| 76 | 1-(6,7-dihydro-5H-benzo[6,7]cyclohepta[1,2-c]pyridazin-3-yl)-N³-(3-fluoro-4-(3-(pyrrolidin-1-yl)-8-azabicyclo[3.2.1]oct-8-yl)phenyl)-1H-1,2,4-triazole-3,5-diamine | H | | | H | H | A |
| 77 | 1-(6,7-dihydro-5H-benzo[6,7]cyclohepta[1,2-c]pyridazin-3-yl)-N³-(3-fluoro-4-(4-pyrrolidin-1-yl-azepan-1-yl)phenyl)-1H-1,2,4-triazole-3,5-diamine | H | | | H | H | A |
| 78 | 1-(6,7-dihydro-5H-benzo[6,7]cyclohepta[1,2-c]pyridazin-3-yl)-N³-(3-fluoro-4-(4-(4-methylpiperazin-1-yl)piperidin-1-yl)phenyl)-1H-1,2,4-triazole-3,5-diamine | H | | | H | H | A |

TABLE 1-continued

| Cpd # | Compound Name | R¹ | R² | R³ | R⁴ | R⁵ | IC₅₀ |
|---|---|---|---|---|---|---|---|
| 80 | 1-(6,7-dihydro-5H-benzo[6,7]cyclohepta[1,2-c]pyridazin-3-yl)-N³-(3-fluoro-4-(4-(4-isopropylpiperazin-1-yl)piperidin-1-yl)phenyl)-1H-1,2,4-triazole-3,5-diamine | H | 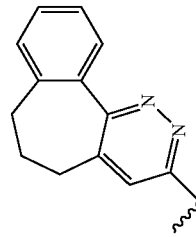 |  | H | H | A |
| 81 | 1-(6,7-dihydro-5H-benzo[6,7]cyclohepta[1,2-c]pyridazin-3-yl)-N³-(3-fluoro-4-(1-methyl-octahydropyrrolo[3,4-b]pyrrol-5-yl)phenyl)-1H-1,2,4-triazole-3,5-diamine | H |  | 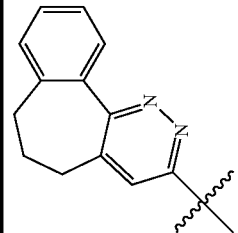 | H | H | A |
| 82 | 1-(6,7-dihydro-5H-benzo[6,7]cyclohepta[1,2-c]pyridazin-3-yl)-N³-(3-fluoro-4-(N-methyl-cyclopentylamino)-piperidinyl)phenyl)-1H-1,2,4-triazole-3,5-diamine | H | 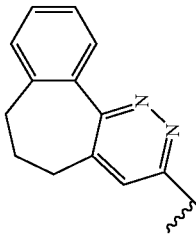 | 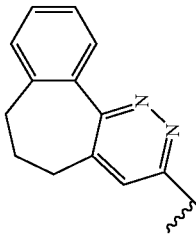 | H | H | A |

TABLE 1-continued

| Cpd # | Compound Name | R¹ | R² | R³ | R⁴ | R⁵ | IC$_{50}$ |
|---|---|---|---|---|---|---|---|
| 83 | 1-(6,7-dihydro-5H-benzo[6,7]cyclohepta[1,2-c]pyridazin-3-yl)-N³-(3-fluoro-4-(4-(dipropylamino)piperidin-1-yl)phenyl)-1H-1,2,4-triazole-3,5-diamine | H | (dipropylaminopiperidinyl-fluorophenyl group) | (benzocycloheptapyridazinyl group) | H | H | B |
| 84 | 1-(6,7-dihydro-5H-benzo[6,7]cyclohepta[1,2-c]pyridazin-3-yl)-N³-(3-fluoro-4-(1-propyloctahydro-1H-pyrrolo[3,2-c]pyridine-5-yl)phenyl)-1H-1,2,4-triazole-3,5-diamine | H | (propyl-octahydropyrrolopyridinyl-fluorophenyl group) | (benzocycloheptapyridazinyl group) | H | H | A |
| 85 | 1-(6,7-dihydro-5H-benzo[4,5]cyclohepta[1,2-c]pyridazin-2-yl)-N³-(3-fluoro-4-(4-(N-methylpiperazin-1-yl)phenyl)-1H-1,2,4-triazole-3,5-diamine | H | (methylpiperazinyl-fluorophenyl group) | (benzocycloheptapyridazinyl group) | H | H | A |

TABLE 1-continued (Ia)

| Cpd # | Compound Name | R¹ | R² | R³ | R⁴ | R⁵ | IC$_{50}$ |
|---|---|---|---|---|---|---|---|
| 86 | 1-(6,7-dihydro-5H-benzo[6,7]cyclohepta[1,2-c]pyridazin-3-yl)-N³-(3-fluoro-4-(4-((tert-butyloxycarbonylamino)-piperidin-1-yl)phenyl)-1H-1,2,4-triazole-3,5-diamine | H | (piperidinyl-phenyl with tert-butylcarbamate) | (dihydrobenzocycloheptapyridazine) | H | H | B |
| 87 | 1-(6,7-dihydro-5H-benzo[6,7]cyclohepta[1,2-c]pyridazin-3-yl)-N³-(3-fluoro-4-(4-aminopiperidin-1-yl)phenyl)-1H-1,2,4-triazole-3,5-diamine | H | (4-aminopiperidinyl-fluorophenyl) | (dihydrobenzocycloheptapyridazine) | H | H | A |
| 88 | 1-(6,7-dihydro-5H-benzo[6,7]cyclohepta[1,2-c]pyridazin-3-yl)-N³-(3-fluoro-4-(4-(5-cyclohexyl-octahydropyrrolo[3,4-c]pyrrolyl)piperidin-1-yl)phenyl)-1H-1,2,4-triazole-3,5-diamine | H | (cyclohexyl-octahydropyrrolopyrrolyl-piperidinyl-fluorophenyl) | (dihydrobenzocycloheptapyridazine) | H | H | A |

TABLE 1-continued

| Cpd # | Compound Name | R¹ | R² | R³ | R⁴ | R⁵ | IC$_{50}$ |
|---|---|---|---|---|---|---|---|
| 89 | 1-(6,7-dihydro-5H-benzo[6,7]cyclohepta[1,2-c]pyridazin-3-yl)-N³-(2,3,4,5-tetrahydrobenzo[b]oxepin-7-yl)-1H-1,2,4-triazole-3,5-diamine | H | | | H | H | B |
| 90 | 1-(6,7-dihydro-5H-benzo[6,7]cyclohepta[1,2-c]pyridazin-3-yl)-N³-(4-((N-butyl)-N-acetoamino)methyl)phenyl)-1H-1,2,4-triazole-3,5-diamine | H | | | H | H | B |
| 91 | 1-(6,7-dihydro-5H-benzo[6,7]cyclohepta[1,2-c]pyridazin-3-yl)-N³-(4-((5-fluoroindolin-2-on-3-yl)methyl)phenyl)-1H-1,2,4-triazole-3,5-diamine | H | | | H | H | D |

TABLE 1-continued

| Cpd # | Compound Name | R¹ | R² | R³ | R⁴ | R⁵ | IC$_{50}$ |
|---|---|---|---|---|---|---|---|
| 92 | 1-(6,7-dihydro-5H-benzo[6,7]cyclohepta[1,2-c]pyridazin-3-yl)-N³-(6-iodopyridin-3-yl)-1H-1,2,4-triazole-3,5-diamine | H | (5-iodopyridin-2-yl) | (6,7-dihydro-5H-benzo[6,7]cyclohepta[1,2-c]pyridazin-3-yl) | H | H | D |
| 93 | 1-(6,7-dihydro-5H-benzo[6,7]cyclohepta[1,2-c]pyridazin-3-yl)-N³-(pyridin-3-yl)-1H-1,2,4-triazole-3,5-diamine | H | (pyridin-3-yl) | (6,7-dihydro-5H-benzo[6,7]cyclohepta[1,2-c]pyridazin-3-yl) | H | H | D |
| 94 | 1-(6,7-dihydro-5H-benzo[6,7]cyclohepta[1,2-c]pyridazin-3-yl)-N³-(6-aminopyridin-3-yl)pyridine-3-yl)-1H-1,2,4-triazole-3,5-diamine | H | (6-aminopyridin-3-yl)pyridin-3-yl | (6,7-dihydro-5H-benzo[6,7]cyclohepta[1,2-c]pyridazin-3-yl) | H | H | D |

TABLE 1-continued

| Cpd # | Compound Name | R¹ | R² | R³ | R⁴ | R⁵ | IC$_{50}$ |
|---|---|---|---|---|---|---|---|
| 95 | 1-(6,7-dihydro-5H-benzo[6,7]cyclohepta[1,2-c]pyridazin-3-yl)-N³-(6-(3-aminophenyl)pyridine-3-yl)-1H-1,2,4-triazole-3,5-diamine | H | 3-aminophenyl-pyridinyl | 6,7-dihydro-5H-benzo[6,7]cyclohepta[1,2-c]pyridazin-3-yl | H | H | D |
| 96 | 1-(6,7-dihydro-5H-benzo[6,7]cyclohepta[1,2-c]pyridazin-3-yl)-N³-(6-(3-cyanophenyl)pyridine-3-yl)-1H-1,2,4-triazole-3,5-diamine | H | 3-cyanophenyl-pyridinyl | 6,7-dihydro-5H-benzo[6,7]cyclohepta[1,2-c]pyridazin-3-yl | H | H | D |
| 97 | 1-(6,7-dihydro-5H-benzo[6,7]cyclohepta[1,2-c]pyridazin-3-yl)-N³-(6-(benzo[d][1,3]dioxole-6-yl)pyridine-3-yl)-1H-1,2,4-triazole-3,5-diamine | H | benzo[d][1,3]dioxole-pyridinyl | 6,7-dihydro-5H-benzo[6,7]cyclohepta[1,2-c]pyridazin-3-yl | H | H | D |

TABLE 1-continued

| Cpd # | Compound Name | R¹ | R² | R³ | R⁴ | R⁵ | IC₅₀ |
|---|---|---|---|---|---|---|---|
| 98 | 1-(6,7-dihydro-5H-benzo[6,7]cyclohepta[1,2-c]pyridazin-3-yl)-N³-(6-(3-methylsulfonamidylphenyl)-pyridine-3-yl)-1H-1,2,4-triazole-3,5-diamine | H | (3-methylsulfonamido phenyl)pyridinyl group | (6,7-dihydro-5H-benzo[6,7]cycloheptapyridazinyl) | H | H | D |
| 99 | 1-(6,7-dihydro-5H-benzo[6,7]cyclohepta[1,2-c]pyridazin-3-yl)-N³-(4-(methylpiperidin-4-yl)phenyl)-1H-1,2,4-triazole-3,5-diamine | H | (4-(1-methylpiperidin-4-yl)phenyl) | (6,7-dihydro-5H-benzo[6,7]cycloheptapyridazinyl) | H | H | A |
| 100 | 1-(6,7-dihydro-5H-benzo[6,7]cyclohepta[1,2-c]pyridazin-3-yl)-N³-(3,4-dihydro-2H-benzo[b][1,4]dioxepin-7-yl)-1H-1,2,4-triazole-3,5-diamine | H | (3,4-dihydro-2H-benzo[b][1,4]dioxepin-7-yl) | (6,7-dihydro-5H-benzo[6,7]cycloheptapyridazinyl) | H | H | B |

TABLE 1-continued

| Cpd # | Compound Name | R¹ | R² | R³ | R⁴ | R⁵ | IC₅₀ |
|---|---|---|---|---|---|---|---|
| 101 | 1-(6,7-dihydro-5H-benzo[6,7]cyclohepta[1,2-c]pyridazin-3-yl)-N³-(4-(4-pyrrolidin-1-yl)piperidinyl)phenyl)-1H-1,2,4-triazole-3,5-diamine | H | 4-(4-(pyrrolidin-1-yl)piperidin-1-yl)phenyl | 6,7-dihydro-5H-benzo[6,7]cyclohepta[1,2-c]pyridazin-3-yl | H | H | A |
| 103 | 1-(6,7-dihydro-5H-benzo[6,7]cyclohepta[1,2-c]pyridazin-3-yl)-N³-(4-((4-pyrrolidin-1-yl)piperidinyl)methyl)phenyl)-1H-1,2,4-triazole-3,5-diamine | H | 4-((4-(pyrrolidin-1-yl)piperidin-1-yl)methyl)phenyl | 6,7-dihydro-5H-benzo[6,7]cyclohepta[1,2-c]pyridazin-3-yl | H | H | A |
| 104 | 1-(6,7-dihydro-5H-benzo[6,7]cyclohepta[1,2-c]pyridazin-3-yl)-N³-(4-((4-cyclopentylpiperazinyl)-methyl)phenyl)-1H-1,2,4-triazole-3,5-diamine | H | 4-((4-cyclopentylpiperazin-1-yl)methyl)phenyl | 6,7-dihydro-5H-benzo[6,7]cyclohepta[1,2-c]pyridazin-3-yl | H | H | A |

TABLE 1-continued

| Cpd # | Compound Name | R¹ | R² | R³ | R⁴ | R⁵ | IC$_{50}$ |
|---|---|---|---|---|---|---|---|
| 105 | 1-(6,7-dihydro-5H-benzo[6,7]cyclohepta[1,2-c]pyridazin-3-yl)-N³-(3-fluoro-4-(4-pyrrolidin-1-yl)piperidinyl)phenyl)-1H-1,2,4-triazole-3,5-diamine | H |  |  | H | H | A |
| 106 | 1-(6,7-dihydro-5H-benzo[6,7]cyclohepta[1,2-c]pyridazin-3-yl)-N³-(3-methyl-4-(4-pyrrolidin-1-yl)piperidinyl)phenyl)-1H-1,2,4-triazole-3,5-diamine | H |  | 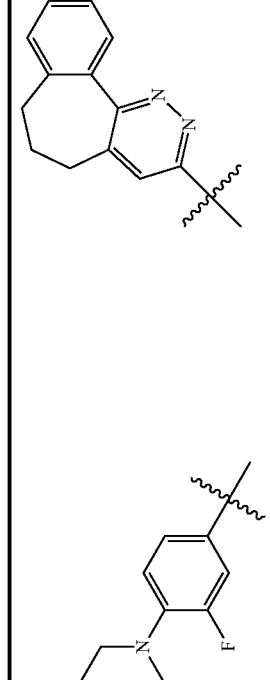 | H | H | A |
| 107 | 1-(6,7-dihydro-5H-benzo[6,7]cyclohepta[1,2-c]pyridazin-3-yl)-N³-(3-fluoro-4-(4-cyclopentylpiperazinyl)phenyl)-1H-1,2,4-triazole-3,5-diamine | H |  |  | H | H | A |

TABLE 1-continued

| Cpd # | Compound Name | R¹ | R² | R³ | R⁴ | R⁵ | IC₅₀ |
|---|---|---|---|---|---|---|---|
| 108 | 1-(6,7-dihydro-5H-benzo[6,7]cyclohepta[1,2-c]pyridazin-3-yl)-N³-(4-((4-isopropylpiperazinyl)methyl)phenyl)-1H-1,2,4-triazole-3,5-diamine | H | 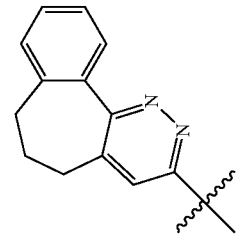 | 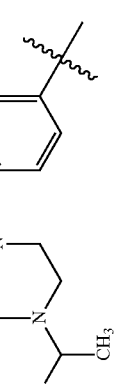 | H | H | A |
| 109 | 1-(6,7-dihydro-5H-benzo[6,7]cyclohepta[1,2-c]pyridazin-3-yl)-N³-(3-fluoro-4-(4-N-methylpiperidin-4-yl)piperazinyl)phenyl)-1H-1,2,4-triazole-3,5-diamine | H | 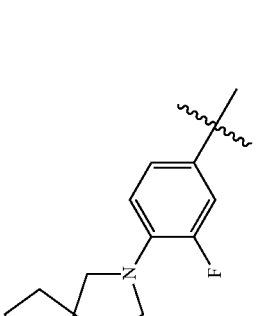 | 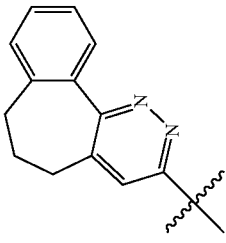 | H | H | A |
| 110 | 1-(6,7-dihydro-5H-benzo[6,7]cyclohepta[1,2-c]pyridazin-3-yl)-N³-(3-fluoro-4-(7-methyl-2,7-diazaspiro[4.4]nonan-2-yl)phenyl)-1H-1,2,4-triazole-3,5-diamine | H | 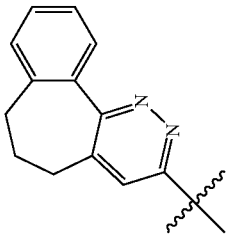 | 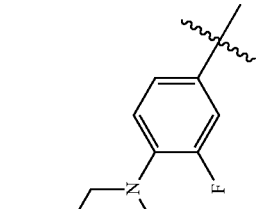 | H | H | A |

TABLE 1-continued

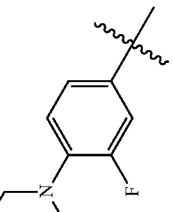

| Cpd # | Compound Name | R¹ | R² | R³ | R⁴ | R⁵ | IC₅₀ |
|---|---|---|---|---|---|---|---|
| 111 | 1-(6,7-dihydro-5H-benzo[6,7]cyclohepta[1,2-c]pyridazin-3-yl)-N³-(3-fluoro-4-(N-isopropylpiperazin-1-yl)phenyl)-1H-1,2,4-triazole-3,5-diamine | H | 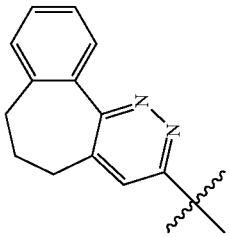 |  | H | H | A |
| 113 | 1-(6,7-dihydro-5H-benzo[6,7]cyclohepta[1,2-c]pyridazin-3-yl)-N³-(3-fluoro-4-(3-pyrrolidin-1-ylazetidinyl)phenyl)-1H-1,2,4-triazole-3,5-diamine | H |  | 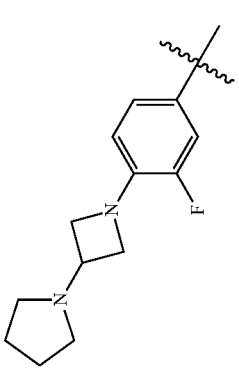 | H | H | A |
| 114 | 1-(6,7-dihydro-5H-benzo[6,7]cyclohepta[1,2-c]pyridazin-3-yl)-N³-(3-methyl-4-(4-(N-methylpiperazin-4-yl)piperidin-1-yl)phenyl)-1H-1,2,4-triazole-3,5-diamine | H | 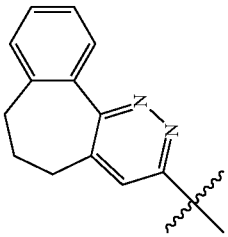 |  | H | H | A |

TABLE 1-continued

| Cpd # | Compound Name | R¹ | R² | R³ | R⁴ | R⁵ | IC₅₀ |
|---|---|---|---|---|---|---|---|
| 115 | 1-(6,7-dihydro-5H-benzo[6,7]cyclohepta[1,2-c]pyridazin-3-yl)-N³-(3-fluoro-4-((S)-3-(pyrrolidin-1-ylmethyl)pyrrolidinyl)phenyl)-1H-1,2,4-triazole-3,5-diamine | H | | | H | H | B |
| 116 | 1-(6,7-dihydro-5H-benzo[2,3]oxepino[4,5-c]pyridazin-3-yl)-N³-(4-(4-pyrrolidin-1-yl)piperidinyl)phenyl)-1H-1,2,4-triazole-3,5-diamine | H | | | H | H | B |
| 117 | 1-(6,7-dihydro-5H-benzo[2,3]oxepino[4,5-c]pyridazin-3-yl)-N³-(3-fluoro-4-(4-pyrrolidin-1-yl)piperidinyl)phenyl)-1H-1,2,4-triazole-3,5-diamine | H | | | H | H | A |

TABLE 1-continued

| Cpd # | Compound Name | R¹ | R² | R³ | R⁴ | R⁵ | IC$_{50}$ |
|---|---|---|---|---|---|---|---|
| 118 | 1-(6,7-dihydro-5H-benzo[2,3]oxepino[4,5-c]pyridazin-3-yl)-N³-(2-(pyrrolidin-1-ylmethyl)benzo[d]oxazol-5-yl)-1H-1,2,4-triazole-3,5-diamine | H | | | H | H | B |
| 119 | 1-(6,7-dihydro-5H-benzo[2,3]thiepino[4,5-c]pyridazin-3-yl)-N³-(3-fluoro-4-(4-pyrrolidin-1-yl)piperidinyl)phenyl)-1H-1,2,4-triazole-3,5-diamine | H | | | H | H | A |
| 120 | 1-(6,7-dihydro-5H-benzo[2,3]thiepino[4,5-c]pyridazin-3-yl)-N³-(4-(4-pyrrolidin-1-ylpiperidinyl)phenyl)-1H-1,2,4-triazole-3,5-diamine | H | | | H | H | A |

TABLE 1-continued

| Cpd # | Compound Name | R¹ | R² | R³ | R⁴ | R⁵ | IC$_{50}$ |
|---|---|---|---|---|---|---|---|
| 121 | 1-(6,7-dihydro-5H-benzo[6,7]cyclohepta[1,2-c]pyridazin-3-yl)-N³-(4-(2-dimethylaminoethyl)-(3,4-dihydro-2H-benzo[b][1,4]oxazin-7-yl))-1H-1,2,4-triazole-3,5-diamine | H | | | H | H | A |
| 122 | 1-(6,7-dihydro-5H-benzo[2,3]oxepino[4,5-c]pyridazin-3-yl)-N³-(4-(2-dimethylaminoethyl)-(3,4-dihydro-2H-benzo[b][1,4]oxazin-7-yl))-1H-1,2,4-triazole-3,5-diamine | H | | | H | H | A |
| 123 | 1-(6,7-dihydro-5H-benzo[2,3]thiepino[4,5-c]pyridazin-3-yl)-N³-(3-fluoro-4-(isoindolin-2-yl)phenyl)-1H-1,2,4-triazole-3,5-diamine | H | | | H | H | D |

TABLE 1-continued (Ia)

| Cpd # | Compound Name | R¹ | R² | R³ | R⁴ | R⁵ | IC₅₀ |
|---|---|---|---|---|---|---|---|
| 124 | 1-(6,7-dihydro-5H-benzo[6,7]cyclohepta[1,2-c]pyridazin-3-yl)-N³-(3-fluoro-4-(4-(pyrrolidinylmethyl)-piperidinyl)phenyl)-1H-1,2,4-triazole-3,5-diamine | H | 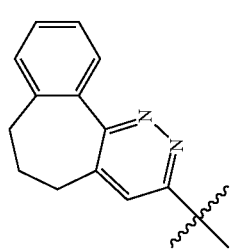 |  | H | H | A |
| 125 | 1-(6,7-dihydro-5H-benzo[2,3]thiepino[4,5-c]pyridazin-3-yl)-N³-(3-fluoro-4-(4-(pyrrolidinylmethyl)-piperidinyl)phenyl)-1H-1,2,4-triazole-3,5-diamine | H | 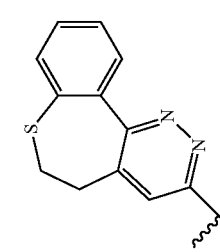 | 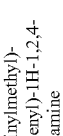 | H | H | A |
| 126 | 1-(6,7-dihydro-5H-benzo[2,3]thiepino[4,5-c]pyridazin-3-yl)-N³-(3-fluoro-4-((4aR,8aS)-decahydroisoquinolin-2-yl)phenyl)-1H-1,2,4-triazole-3,5-diamine | H | 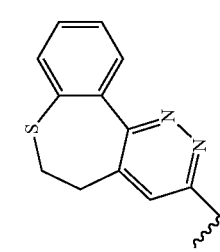 | 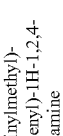 | H | H | D |

TABLE 1-continued (Ia)

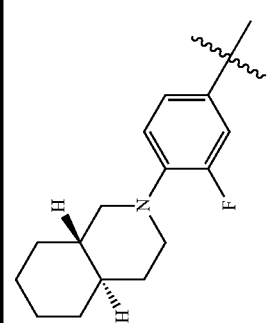

| Cpd # | Compound Name | R¹ | R² | R³ | R⁴ | R⁵ | IC₅₀ |
|---|---|---|---|---|---|---|---|
| 127 | 1-(6,7-dihydro-5H-benzo[6,7]cyclohepta[1,2-c]pyridazin-3-yl)-N³-(3-fluoro-4-((4aR,8aS)-decahydroisoquinolin-2-yl)phenyl)-1H-1,2,4-triazole-3,5-diamine | H | 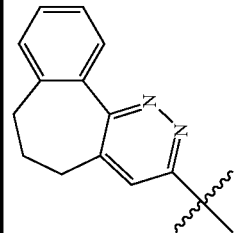 | 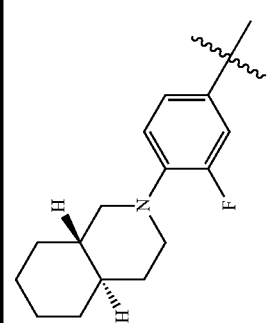 | H | H | B |
| 128 | 1-(6,7-dihydro-5H-benzo[6,7]cyclohepta[1,2-c]pyridazin-3-yl)-N³-(3-fluoro-4-(octahydro-1H-pyrido[1,2-a]pyrazin-2-yl)phenyl)-1H-1,2,4-triazole-3,5-diamine | H | 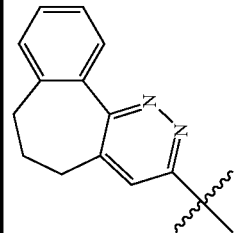 | 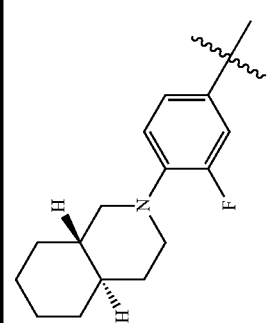 | H | H | B |
| 129 | 1-(6,7-dihydro-5H-benzo[2,3]thiepino[4,5-c]pyridazin-3-yl)-N³-(3-fluoro-4-(octahydro-1H-pyrido[1,2-a]pyrazin-2-yl)phenyl)-1H-1,2,4-triazole-3,5-diamine | H | 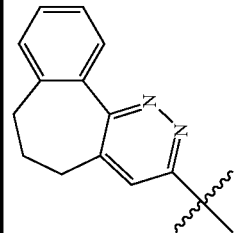 |  | H | H | A |

TABLE 1-continued (Ia)

| Cpd # | Compound Name | R¹ | R² | R³ | R⁴ | R⁵ | IC₅₀ |
|---|---|---|---|---|---|---|---|
| 130 | 1-(6,7-dihydro-5H-benzo[6,7]cyclohepta[1,2-c]pyridazin-3-yl)-N³-(6-(2-diethylaminomethyl)pyrrolidin-1-yl)pyridin-3-yl)-1H-1,2,4-triazole-3,5-diamine | H | | | H | H | B |
| 131 | 1-(6,7-dihydro-5H-benzo[2,3]thiepino[4,5-c]pyridazin-3-yl)-N³-(2-(1-(4-(2-(dimethylamino)ethyl)piperazin-1-yl)oxomethyl)benzo[b]thiophen-5-yl)-1H-1,2,4-triazole-3,5-diamine | H | | | H | H | B |
| 132 | 1-(6,7-dihydro-5H-benzo[6,7]cyclohepta[1,2-c]pyridazin-3-yl)-N³-(3-fluoro-4-(3-pyrrolidin-1-yl)pyrrolidin-1-yl)phenyl)-1H-1,2,4-triazole-3,5-diamine | H | | | H | H | A |

TABLE 1-continued

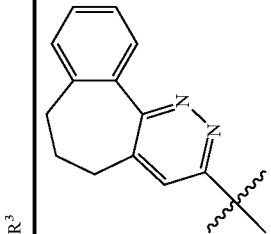

| Cpd # | Compound Name | R¹ | R² | R³ | R⁴ | R⁵ | IC₅₀ |
|---|---|---|---|---|---|---|---|
| 133 | 1-(6,7-dihydro-5H-benzo[6,7]cyclohepta[1,2-c]pyridazin-3-yl)-N³-(6-(3-diethylaminopyrrolidin-1-yl)pyridin-3-yl)-1H-1,2,4-triazole-3,5-diamine | H |  | 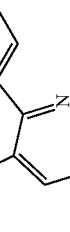 | H | H | A |
| 134 | 1-(6,7-dihydro-5H-benzo[6,7]cyclohepta[1,2-c]pyridazin-3-yl)-N³-(3-fluoro-4-(5-methyloctahydropyrrolo[3,4-c]pyrrolyl)piperidin-1-yl)phenyl)-1H-1,2,4-triazole-3,5-diamine | H |  | 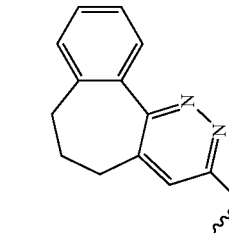 | H | H | A |
| 135 | 1-(6,7-dihydro-5H-benzo[6,7]cyclohepta[1,2-c]pyridazin-3-yl)-N³-(6-(3-(4-(N-methylpiperazin-4-yl)piperidin-1-yl)-(E)-propenyl)pyridin-3-yl)-1H-1,2,4-triazole-3,5-diamine | H | 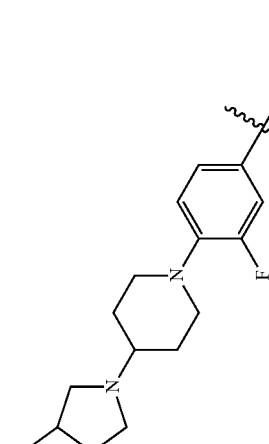 |  | H | H | A |

TABLE 1-continued (Ia)

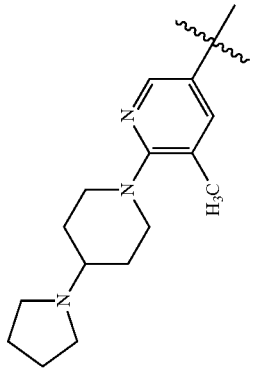

| Cpd # | Compound Name | R¹ | R² | R³ | R⁴ | R⁵ | IC₅₀ |
|---|---|---|---|---|---|---|---|
| 136 | 1-(6,7-dihydro-5H-benzo[6,7]cyclohepta[1,2-c]pyridazin-3-yl)-N³-(6-(4-(pyrrolidin-1-yl)piperidin-1-yl)-5-methylpyridin-3-yl)-1H-1,2,4-triazole-3,5-diamine | H | 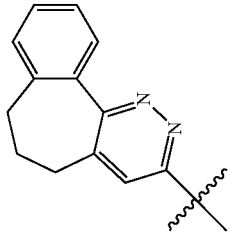 | 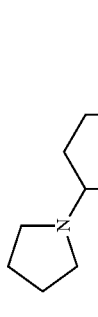 | H | H | A |
| 137 | 1-(6,7-dihydro-5H-benzo[6,7]cyclohepta[1,2-c]pyridazin-3-yl)-N³-(3-fluoro-4-(octahydropyrrolo[3,4-c]pyrrolyl)phenyl)-1H-1,2,4-triazole-3,5-diamine | H | 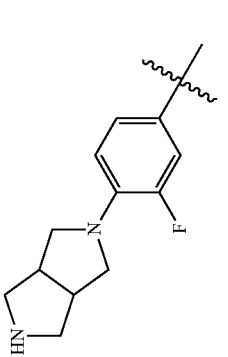 | 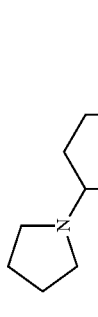 | H | H | A |
| 138 | 1-(6,7-dihydro-5H-benzo[6,7]cyclohepta[1,2-c]pyridazin-3-yl)-N³-(6-(3-piperidin-1-yl-(E)-propenyl)pyridin-3-yl)-1H-1,2,4-triazole-3,5-diamine | H | 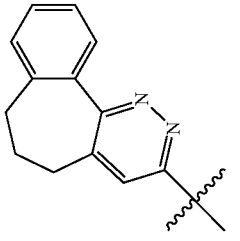 | 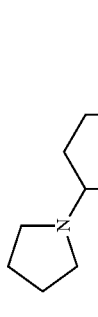 | H | H | A |

TABLE 1-continued

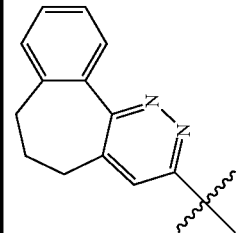
(Ia)

| Cpd # | Compound Name | R¹ | R² | R³ | R⁴ | R⁵ | IC₅₀ |
|---|---|---|---|---|---|---|---|
| 139 | 1-(6,7-dihydro-5H-benzo[6,7]cyclohepta[1,2-c]pyridazin-3-yl)-N³-(6-cyclopentyl-6,7,8,9-tetrahydro-5H-pyrido[3,2-c]azepin-3-yl)-1H-1,2,4-triazole-3,5-diamine | H | 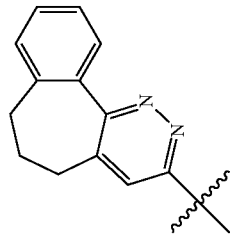 | 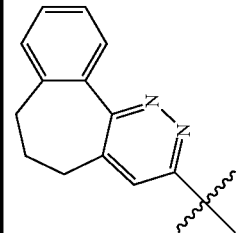 | H | H | D |
| 140 | 1-(6,7-dihydro-5H-benzo[6,7]cyclohepta[1,2-c]pyridazin-3-yl)-N³-(6-(4-(bicyclo[2.2.1]heptan-2-yl)-1,4-diazepan-1-yl)pyridin-3-yl)-1H-1,2,4-triazole-3,5-diamine | H | 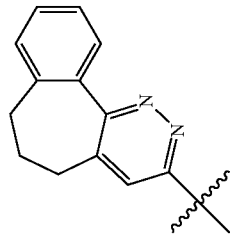 | 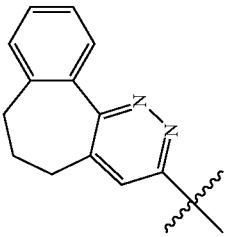 | H | H | A |
| 141 | 1-(6,7-dihydro-5H-benzo[6,7]cyclohepta[1,2-c]pyridazin-3-yl)-N³-(6-(3-(4-(pyrrolidin-1-yl)piperidin-1-yl)-(E)-propenyl)pyridin-3-yl)-1H-1,2,4-triazole-3,5-diamine | H | 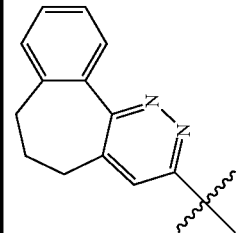 | 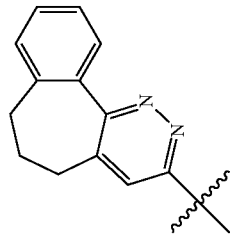 | H | H | B |

TABLE 1-continued (Ia)

| Cpd # | Compound Name | R¹ | R² | R³ | R⁴ | R⁵ | IC$_{50}$ |
|---|---|---|---|---|---|---|---|
| 142 | 1-(6,7-dihydro-5H-benzo[6,7]cyclohepta[1,2-c]pyridazin-3-yl)-N³-(6-(3-piperidin-1-yl)-propanylpyridin-3-yl)-1H-1,2,4-triazole-3,5-diamine | H | 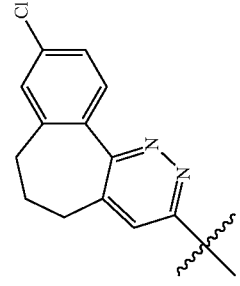 | 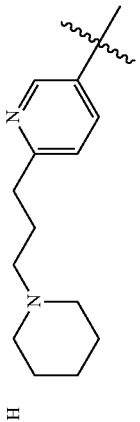 | H | H | A |
| 143 | 1-(6,7-dihydro-9-chloro-5H-benzo[6,7]cyclohepta[1,2-c]pyridazin-3-yl)-N³-(3-fluoro-4-(4-pyrrolidin-1-yl)piperidin-1-yl)phenyl)-1H-1,2,4-triazole-3,5-diamine | H | 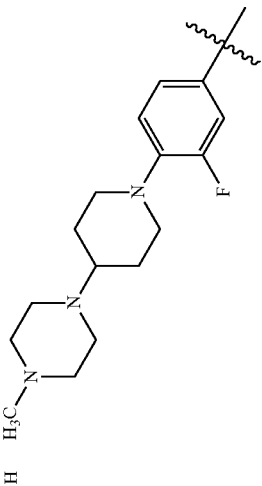 | 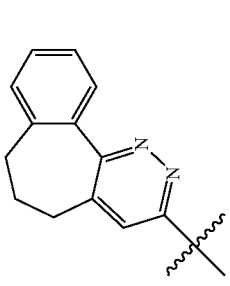 | H | H | A |
| 144 | 1-(6,7-dihydro-9-chloro-5H-benzo[6,7]cyclohepta[1,2-c]pyridazin-3-yl)-N³-(3-fluoro-4-(4-(N-methylpiperazin-1-yl)piperidin-1-yl)phenyl)-1H-1,2,4-triazole-3,5-diamine | H | 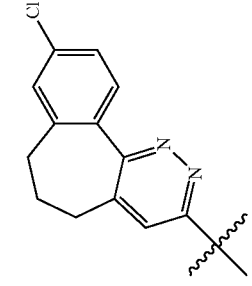 | 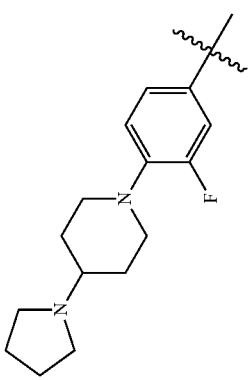 | H | H | B |

TABLE 1-continued (Ia)

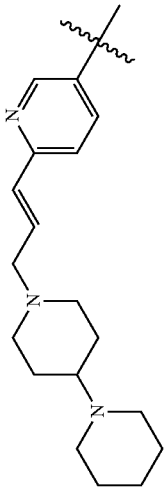

| Cpd # | Compound Name | R¹ | R² | R³ | R⁴ | R⁵ | IC$_{50}$ |
|---|---|---|---|---|---|---|---|
| 145 | 1-(6,7-dihydro-5H-benzo[6,7]cyclohepta[1,2-c]pyridazin-3-yl)-N³-(6-(3-(4-(piperidin-1-yl)piperidin-1-yl)-(E)-propenyl)pyridin-3-yl)-1H-1,2,4-triazole-3,5-diamine | H | 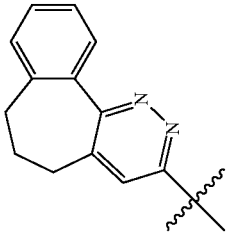 | 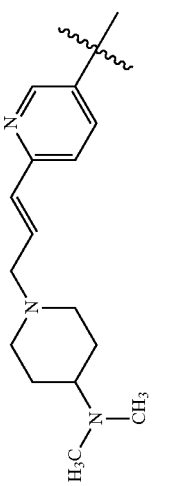 | H | H | A |
| 146 | 1-(6,7-dihydro-5H-benzo[6,7]cyclohepta[1,2-c]pyridazin-3-yl)-N³-(6-(3-(4-dimethylaminopiperidin-1-yl)-(E)-propenyl)pyridin-3-yl)-1H-1,2,4-triazole-3,5-diamine | H | 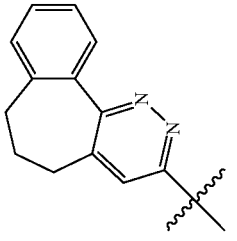 | 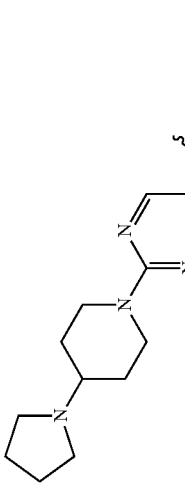 | H | H | A |
| 147 | 1-(6,7-dihydro-5H-benzo[6,7]cyclohepta[1,2-c]pyridazin-3-yl)-N³-(2-(4-pyrrolidin-1-yl)piperidin-1-yl)pyrimidin-5-yl)-1H-1,2,4-triazole-3,5-diamine | H | 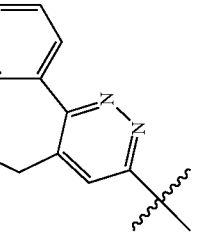 | 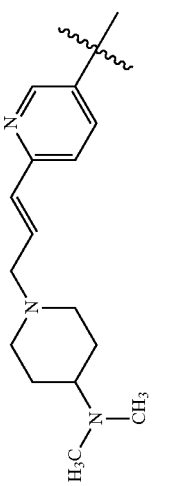 | H | H | A |

TABLE 1-continued

| Cpd # | Compound Name | R¹ | R² | R³ | R⁴ | R⁵ | IC₅₀ |
|---|---|---|---|---|---|---|---|
| 148 | 1-(6,7-dihydro-5H-benzo[6,7]cyclohepta[1,2-c]pyridazin-3-yl)-N³-(2-(4-(piperidin-1-ylmethyl)piperidin-1-yl)pyrimidin-5-yl)-1H-1,2,4-triazole-3,5-diamine | H | (pyrimidine-piperidine-piperidine-methyl group) | (6,7-dihydro-5H-benzo[6,7]cyclohepta[1,2-c]pyridazin-3-yl) | H | H | B |
| 149 | 1-(6,7-dihydro-5H-benzo[6,7]cyclohepta[1,2-c]pyridazin-3-yl)-N³-(6-((4-piperidin-1-ylpiperidin-1-yl)carbonyl)pyridin-3-yl)-1H-1,2,4-triazole-3,5-diamine | H | (pyridine-carbonyl-piperidine-piperidine group) | (6,7-dihydro-5H-benzo[6,7]cyclohepta[1,2-c]pyridazin-3-yl) | H | H | B |
| 150 | 1-(6,7-dihydro-5H-benzo[6,7]cyclohepta[1,2-c]pyridazin-3-yl)-N³-((7-piperidin-1-yl)-6,7,8,9-tetrahydro-5H-benzo[7]annulene-2-yl)-1H-1,2,4-triazole-3,5-diamine | H | (tetrahydrobenzoannulene-piperidine group) | (6,7-dihydro-5H-benzo[6,7]cyclohepta[1,2-c]pyridazin-3-yl) | H | H | A |

TABLE 1-continued (Ia)

| Cpd # | Compound Name | R¹ | R² | R³ | R⁴ | R⁵ | IC₅₀ |
|---|---|---|---|---|---|---|---|
| 151 | 1-(6,7-dihydro-5H-benzo[6,7]cyclohepta[1,2-c]pyridazin-3-yl)-N³-((7-azetidin-1-yl)-6,7,8,9-tetrahydro-5H-benzo[7]annulene-2-yl)-1H-1,2,4-triazole-3,5-diamine | H | azetidinyl-benzocycloheptane | dihydrobenzocycloheptapyridazine | H | H | A |
| 152 | 1-(6,7-dihydro-5H-benzo[6,7]cyclohepta[1,2-c]pyridazin-3-yl)-N³-((7-pyrrolidin-1-yl)-6,7,8,9-tetrahydro-5H-cyclohepta[b]pyridine-3-yl)-1H-1,2,4-triazole-3,5-diamine | H | pyrrolidinyl-cycloheptapyridine | dihydrobenzocycloheptapyridazine | H | H | A |
| 153 | 1-(6,7-dihydro-5H-benzo[6,7]cyclohepta[1,2-c]pyridazin-3-yl)-N³-(2-cyclopentyl-1,2,3,4-tetrahydroisoquinolin-7-yl)-1H-1,2,4-triazole-3,5-diamine | H | cyclopentyl-tetrahydroisoquinoline | dihydrobenzocycloheptapyridazine | H | H | A |

TABLE 1-continued (Ia)

| Cpd # | Compound Name | R¹ | R² | R³ | R⁴ | R⁵ | IC₅₀ |
|---|---|---|---|---|---|---|---|
| 156 | 1-(6,7-dihydro-5H-benzo[6,7]cyclohepta[1,2-c]pyridazin-3-yl)-N³-(4-iodophenyl)-1H-1,2,4-triazole-3,5-diamine | H | 4-iodophenyl | 6,7-dihydro-5H-benzo[6,7]cyclohepta[1,2-c]pyridazin-3-yl | H | H | D |
| 175 | 1-(spiro[chromeno[4,3-c]pyridazine-5,1'-cyclopentane]-3-yl)-N³-(3-fluoro-4-(4-methylpiperazin-1-yl)phenyl)-1H-1,2,4-triazole-3,5-diamine | H | 3-fluoro-4-(4-methylpiperazin-1-yl)phenyl | spiro[chromeno[4,3-c]pyridazine-5,1'-cyclopentane]-3-yl | H | H | C |
| 176 | 1-(spiro[chromeno[4,3-c]pyridazine-5,1'-cyclopentane]-3-yl)-N³-(4-(pyrrolidin-1-yl)phenyl)-1H-1,2,4-triazole-3,5-diamine | H | 4-(pyrrolidin-1-yl)phenyl | spiro[chromeno[4,3-c]pyridazine-5,1'-cyclopentane]-3-yl | H | H | B |

TABLE 1-continued

| Cpd # | Compound Name | R[1] | R[2] | R[3] | R[4] | R[5] | IC$_{50}$ |
|---|---|---|---|---|---|---|---|
| 177 | 1-(6,7-dihydro-5H-benzo[6,7]cyclohepta[1,2-c]pyridazin-3-yl)-N³-(3-fluoro-4-(4-pyrrolidin-1-ylpiperidin-1-yl)phenyl)-1H-1,2,4-triazole-3,5-diamine | H | | | H | H | A |
| 178 | 1-(6,7-dihydro-5H-benzo[6,7]cyclohepta[4,5-c]pyridazin-2-yl)-N³-(3-fluoro-4-(4-pyrrolidin-1-ylpiperidin-1-yl)phenyl)-1H-1,2,4-triazole-3,5-diamine | H | | | H | H | A |
| 179 | 1-(6,7-dihydro-5H-benzo[6,7]cyclohepta[1,2-c]pyridazin-3-yl)-N³-(3-fluoro-4-(4-(4-methylpiperazin-1-yl)piperidin-1-yl)phenyl)-1H-1,2,4-triazole-3,5-diamine | H | | | H | H | A |

TABLE 1-continued

| Cpd # | Compound Name | R¹ | R² | R³ | R⁴ | R⁵ | IC$_{50}$ |
|---|---|---|---|---|---|---|---|
| 180 | 1-(6,7-dihydro-5H-benzo[6,7]cyclohepta[1,2-c]pyridazin-3-yl)-N³-(3-fluoro-4-(3R)-dimethylaminopyrrolidin-1-yl)phenyl)-1H-1,2,4-triazole-3,5-diamine | H | | | H | H | A |
| 181 | 1-(6,7-dihydro-5H-benzo[6,7]cyclohepta[1,2-c]pyridazin-3-yl)-N³-((7-pyrrolidin-1-yl)-6,7,8,9-tetrahydro-5H-benzo[7]annulene-2-yl)-1H-1,2,4-triazole-3,5-diamine | H | | | H | H | A |
| 182 | 1-(6,7-dihydro-5H-benzo[4,5]cyclohepta[2-c]pyridazin-2-yl)-N³-(3-methyl-4-(4-pyrrolidin-1-ylpiperidin-1-yl)phenyl)-1H-1,2,4-triazole-3,5-diamine | H | | | H | H | A |

TABLE 1-continued

| Cpd # | Compound Name | R¹ | R² | R³ | R⁴ | R⁵ | IC$_{50}$ |
|---|---|---|---|---|---|---|---|
| 183 | 1-(6,7-dihydro-5H-benzo[6,7]cyclohepta[4,5-c]pyridazin-2-yl)-N³-(3-fluoro-4-(4-pyrrolidin-1-yl)piperidin-1-yl)phenyl)-1H-1,2,4-triazole-3,5-diamine | H |  | 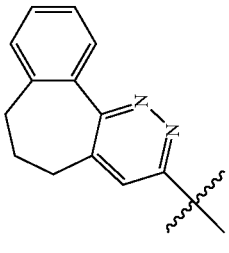 | H | H | A |
| 184 | 1-(6,7-dihydro-5H-benzo[6,7]cyclohepta[1,2-c]pyridazin-3-yl)-N³-((7-(R)pyrrolidin-1-yl)-6,7,8,9-tetrahydro-5H-benzo[7]annulene-2-yl)-1H-1,2,4-triazole-3,5-diamine | H |  |  | H | H | A |
| 185 | 1-(6,7-dihydro-5H-benzo[6,7]cyclohepta[1,2-c]pyridazin-3-yl)-N³-(7-diethylamino-6,7,8,9-tetrahydro-5H-benzo[7]annulene-2-yl)-1H-1,2,4-triazole-3,5-diamine | H |  | 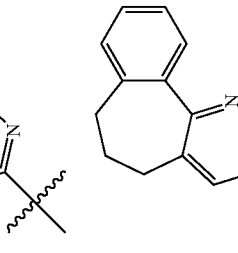 | H | H | A |

TABLE 1-continued

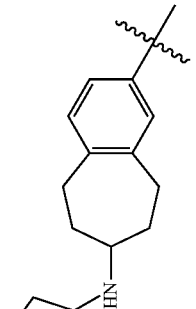

| Cpd # | Compound Name | R¹ | R² | R³ | R⁴ | R⁵ | IC$_{50}$ |
|---|---|---|---|---|---|---|---|
| 186 | 1-(6,7-dihydro-5H-benzo[6,7]cyclohepta[1,2-c]pyridazin-3-yl)-N³-(7-cyclopentylamino-6,7,8,9-tetrahydro-5H-benzo[7]annulene-2-yl)-1H-1,2,4-triazole-3,5-diamine | H | 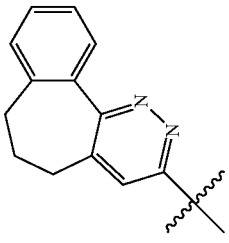 | 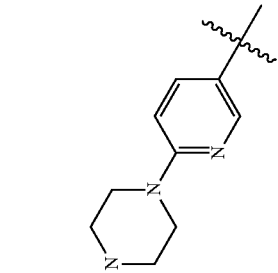 | H | H | A |
| 187 | 1-(6,7-dihydro-5H-benzo[6,7]cyclohepta[1,2-c]pyridazin-3-yl)-N³-(2-(4-cyclopropylmethylpiperazin-1-yl)pyridine-5-yl)-1H-1,2,4-triazole-3,5-diamine | H | 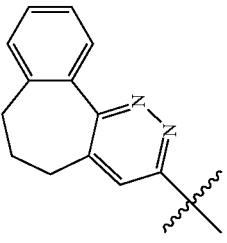 | 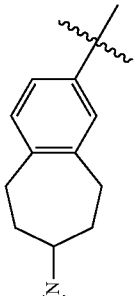 | H | H | B |
| 188 | 1-(6,7-dihydro-5H-benzo[6,7]cyclohepta[1,2-c]pyridazin-3-yl)-N³-((7-pyrrolidin-1-yl)-6,7,8,9-tetrahydro-5H-benzo[7]annulene-2-yl)-1H-1,2,4-triazole-3,5-diamine | H | 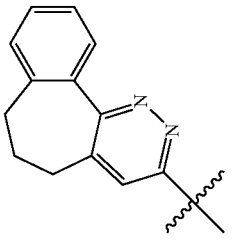 | 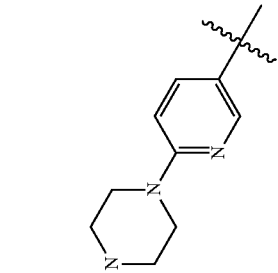 | H | H | A |

TABLE 1-continued (Ia)

| Cpd # | Compound Name | R¹ | R² | R³ | R⁴ | R⁵ | IC$_{50}$ |
|---|---|---|---|---|---|---|---|
| 189 | 1-(6,7-dihydro-5H-benzo[6,7]cyclohepta[1,2-c]pyridazin-3-yl)-N³-(6-(pyrrolidin-1-yl)-5,6,7,8-tetrahydroquinolin-3-yl)-1H-1,2,4-triazole-3,5-diamine | H | | | H | H | A |
| 190 | 1-(6,7-dihydro-5H-benzo[6,7]cyclohepta[1,2-c]pyridazin-3-yl)-N³-(6-cyclopentyl-5,6,7,8-tetrahydro-1,6-naphthyridin-3-yl)-1H-1,2,4-triazole-3,5-diamine | H | | | H | H | A |
| 191 | 1-(6,7-dihydro-5H-benzo[6,7]cyclohepta[1,2-c]pyridazin-3-yl)-N³-((S)-7-(pyrrolidin-1-yl)-6,7,8,9-tetrahydro-5H-cyclohepta[b]pyridine-3-yl)-1H-1,2,4-triazole-3,5-diamine | H | | | H | H | A |

TABLE 1-continued
(Ia)
| Cpd # | Compound Name | R¹ | R² | R³ | R⁴ | R⁵ | IC₅₀ |
|---|---|---|---|---|---|---|---|
| 192 | 1-(4-phenyl-6,7-dihydro-5H-benzo[6,7]cyclohepta[1,2-b]pyridin-2-yl)-N³-(3-fluoro-4-(4-cyclohexylpiperazin-1-yl)phenyl)-1H-1,2,4-triazole-3,5-diamine | H | 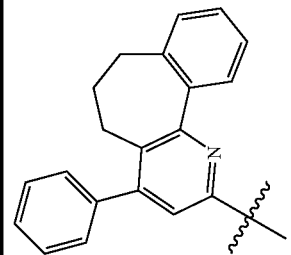 | 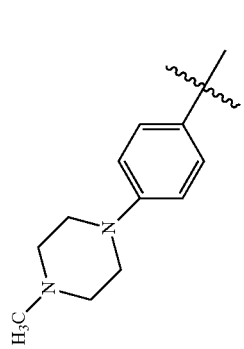 | H | H | C |
| 193 | 1-(4-phenyl-6,7-dihydro-5H-benzo[6,7]cyclohepta[1,2-b]pyridin-2-yl)-N³-(4-(4-methylpiperazin-1-yl)phenyl)-1H-1,2,4-triazole-3,5-diamine | H | 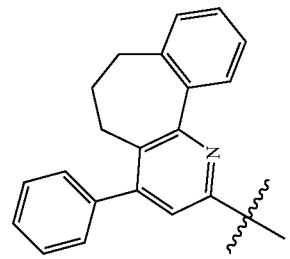 | 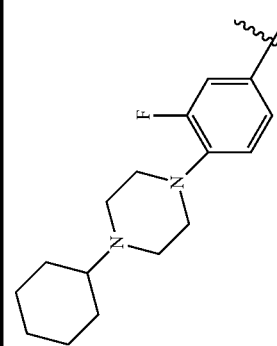 | H | H | B |

TABLE 1-continued

| Cpd # | Compound Name | R¹ | R² | R³ | R⁴ | R⁵ | IC₅₀ |
|---|---|---|---|---|---|---|---|
| 194 | 1-(6,7-dihydro-5H-benzo[6,7]cyclohepta[1,2-c]pyridazin-3-yl)-N³-((7-(2-(S)-methyloxycarbonyl)pyrrolidin-1-yl)-6,7,8,9-tetrahydro-5H-benzo[7]annulene-2-yl)-1H-1,2,4-triazole-3,5-diamine | H | (methyl ester pyrrolidinyl-tetrahydrobenzocycloheptyl group) | (dihydrobenzocycloheptapyridazinyl group) | H | H | A |
| 195 | 1-(6,7-dihydro-5H-benzo[6,7]cyclohepta[1,2-c]pyridazin-3-yl)-N³-((7-(2-(S)-carboxy)pyrrolidin-1-yl)-6,7,8,9-tetrahydro-5H-benzo[7]annulene-2-yl)-1H-1,2,4-triazole-3,5-diamine | H | (carboxylic acid pyrrolidinyl-tetrahydrobenzocycloheptyl group) | (dihydrobenzocycloheptapyridazinyl group) | H | H | B |

TABLE 1-continued (Ia)

| Cpd # | Compound Name | R¹ | R² | R³ | R⁴ | R⁵ | IC$_{50}$ |
|---|---|---|---|---|---|---|---|
| 196 | 1-(6,7-dihydro-5H-benzo[6,7]cyclohepta[1,2-c]pyridazin-3-yl)-N³-(4-(4-(4-methylpiperazin-1-yl)piperidin-1-yl)prop-1-enyl)phenyl)-1H-1,2,4-triazole-3,5-diamine | H | (4-methylpiperazinyl-piperidinyl-propenyl-phenyl) | (dihydrobenzocycloheptapyridazine) | H | H | A |
| 197 | 1-(6,7-dihydro-5H-benzo[6,7]cyclohepta[1,2-c]pyridazin-3-yl)-N³-(4-(4-(piperidin-1-yl)piperidin-1-yl)prop-1-enyl)phenyl)-1H-1,2,4-triazole-3,5-diamine | H | (piperidinyl-piperidinyl-propenyl-phenyl) | (dihydrobenzocycloheptapyridazine) | H | H | B |
| 198 | 1-(6,7-dihydro-5H-benzo[6,7]cyclohepta[1,2-c]pyridazin-3-yl)-N³-(4-(piperidin-1-ylprop-1-enyl)phenyl)-1H-1,2,4-triazole-3,5-diamine | H | (piperidinyl-propenyl-phenyl) | (dihydrobenzocycloheptapyridazine) | H | H | A |

TABLE 1-continued

| Cpd # | Compound Name | R¹ | R² | R³ | R⁴ | R⁵ | IC₅₀ |
|---|---|---|---|---|---|---|---|
| 199 | 1-(6,7-dihydro-5H-benzo[6,7]cyclohepta[1,2-c]pyridazin-3-yl)-N³-(4-(pyrrolidin-1-ylprop-1-enyl)phenyl)-1H-1,2,4-triazole-3,5-diamine | H | (pyrrolidinyl-propenyl-phenyl group) | (6,7-dihydro-5H-benzo[6,7]cyclohepta[1,2-c]pyridazin-3-yl) | H | H | A |
| 200 | 1-(6,7-dihydro-5H-benzo[6,7]cyclohepta[1,2-c]pyridazin-3-yl)-N³-(4-(3-dimethylaminopyrrolidin-1-yl)prop-1-enyl)phenyl)-1H-1,2,4-triazole-3,5-diamine | H | (dimethylaminopyrrolidinyl-propenyl-phenyl group) | (6,7-dihydro-5H-benzo[6,7]cyclohepta[1,2-c]pyridazin-3-yl) | H | H | A |
| 201 | 1-(6,7-dihydro-5H-benzo[6,7]cyclohepta[1,2-c]pyridazin-3-yl)-N³-(4-(3-diethylaminopyrrolidin-1-yl)prop-1-enyl)phenyl)-1H-1,2,4-triazole-3,5-diamine | H | (diethylaminopyrrolidinyl-propenyl-phenyl group) | (6,7-dihydro-5H-benzo[6,7]cyclohepta[1,2-c]pyridazin-3-yl) | H | H | A |

TABLE 1-continued

| Cpd # | Compound Name | R¹ | R² | R³ | R⁴ | R⁵ | IC₅₀ |
|---|---|---|---|---|---|---|---|
| 202 | 1-(6,7-dihydro-5H-benzo[6,7]cyclohepta[1,2-c]pyridazin-3-yl)-N³-(2-(3-(S)-methyl-4-cyclopropylmethylpiperazin-1-yl)pyridine-5-yl)-1H-1,2,4-triazole-3,5-diamine | H | | | H | H | A |
| 203 | 1-(6,7-dihydro-5H-benzo[6,7]cyclohepta[1,2-c]pyridazin-3-yl)-N³-(4-(4-pyrrolidin-1-ylpiperidin-1-ylprop-1-enyl)phenyl)-1H-1,2,4-triazole-3,5-diamine | H | | | H | H | A |
| 204 | 1-(6,7-dihydro-5H-benzo[6,7]cyclohepta[1,2-c]pyridazin-3-yl)-N³-(4-(4-methylpiperazin-1-ylprop-1-enyl)phenyl)-1H-1,2,4-triazole-3,5-diamine | H | | | H | H | A |

TABLE 1-continued (Ia)

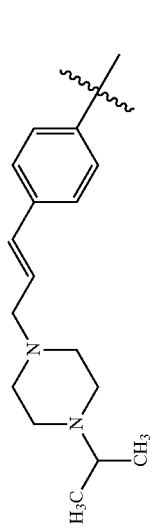

| Cpd # | Compound Name | R¹ | R² | R³ | R⁴ | R⁵ | IC$_{50}$ |
|---|---|---|---|---|---|---|---|
| 205 | 1-(6,7-dihydro-5H-benzo[6,7]cyclohepta[1,2-c]pyridazin-3-yl)-N³-(4-(4-isopropylpiperazin-1-ylprop-1-enyl)phenyl)-1H-1,2,4-triazole-3,5-diamine | H | 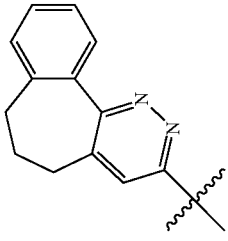 |  | H | H | A |
| 206 | 1-(6,7-dihydro-5H-benzo[6,7]cyclohepta[1,2-c]pyridazin-3-yl)-N³-(4-(4-cyclopentylpiperazin-1-yl)prop-1-enyl)phenyl)-1H-1,2,4-triazole-3,5-diamine | H | 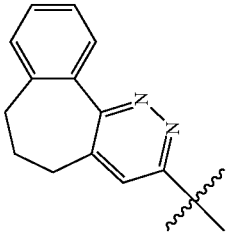 | 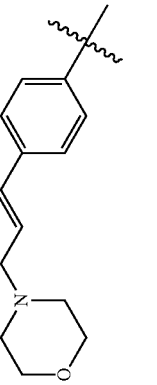 | H | H | A |
| 207 | 1-(6,7-dihydro-5H-benzo[6,7]cyclohepta[1,2-c]pyridazin-3-yl)-N³-(4-(4-(morpholin-4-yl)prop-1-enyl)phenyl)-1H-1,2,4-triazole-3,5-diamine | H | 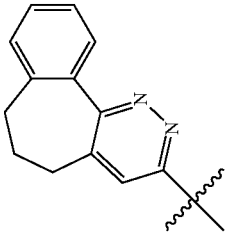 |  | H | H | A |

TABLE 1-continued

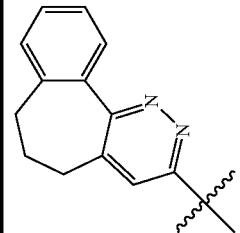
(Ia)

| Cpd # | Compound Name | R¹ | R² | R³ | R⁴ | R⁵ | IC$_{50}$ |
|---|---|---|---|---|---|---|---|
| 208 | 1-(6,7-dihydro-5H-benzo[6,7]cyclohepta[1,2-c]pyridazin-3-yl)-N³-(8-diethylaminoethyl)-9-hydroxy-6,7,8,9-tetrahydro-5H-benzo[7]annulene-2-yl)-1H-1,2,4-triazole-3,5-diamine | H | 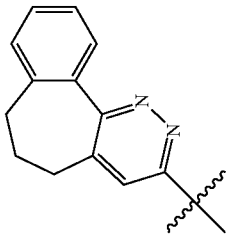 | 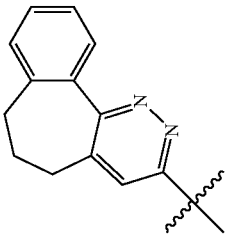 | H | H | B |
| 209 | 1-(6,7-dihydro-5H-benzo[6,7]cyclohepta[1,2-c]pyridazin-3-yl)-N³-(3-fluoro-4-(4-methylpiperazin-1-yl)phenyl)-1H-1,2,4-triazole-3,5-diamine | H | 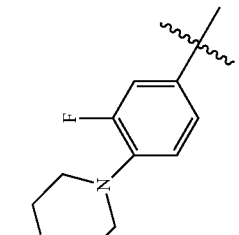 | 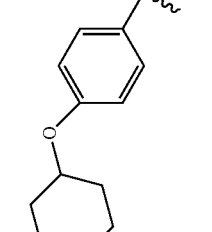 | H | H | A |
| 210 | 1-(6,7-dihydro-5H-benzo[6,7]cyclohepta[1,2-c]pyridazin-3-yl)-N³-(4-(1-methylpiperidin-3-yl-oxy)phenyl)-1H-1,2,4-triazole-3,5-diamine | H | 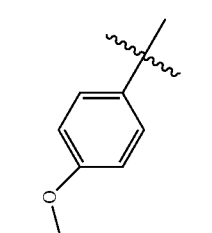 | 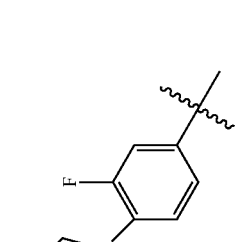 | H | H | A |

TABLE 1-continued

| Cpd # | Compound Name | R¹ | R² | R³ | R⁴ | R⁵ | IC$_{50}$ |
|---|---|---|---|---|---|---|---|
| 211 | 1-(6,7-dihydro-5H-benzo[6,7]cyclohepta[1,2-c]pyridazin-3-yl)-N³-(4-(1-bicyclo[2.2.1]heptan-2-yl)-piperidin-4-yl)phenyl)-1H-1,2,4-triazole-3,5-diamine | H | 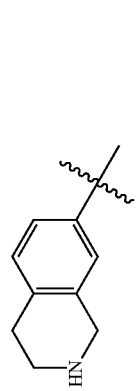 | 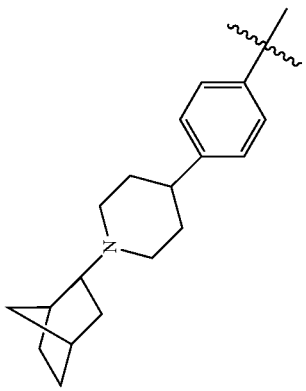 | H | H | D |
| 212 | 1-(6,7-dihydro-5H-benzo[6,7]cyclohepta[1,2-c]pyridazin-3-yl)-N³-(4-(1-cyclopropylmethylpiperidin-4-yl)phenyl)-1H-1,2,4-triazole-3,5-diamine | H | 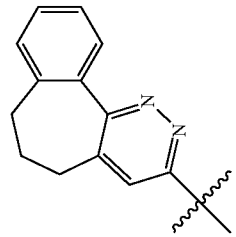 | 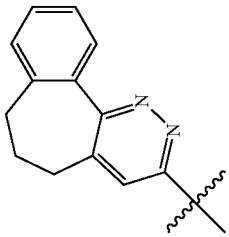 | H | H | A |
| 213 | 1-(6,7-dihydro-5H-benzo[6,7]cyclohepta[1,2-c]pyridazin-3-yl)-N³-(1,2,3,4-tetrahydroisoquinolin-7-yl)-1H-1,2,4-triazole-3,5-diamine | H | 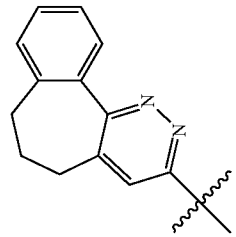 | 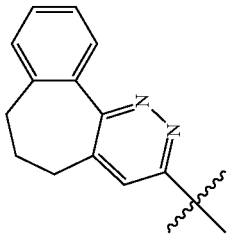 | H | H | A |

TABLE 1-continued

| Cpd # | Compound Name | R¹ | R² | R³ | R⁴ | R⁵ | IC$_{50}$ |
|---|---|---|---|---|---|---|---|
| 214 | 1-(6,7-dihydro-5H-benzo[6,7]cyclohepta[1,2-c]pyridazin-3-yl)-N³-(3-fluoro-4-(4-cyclopropylmethylpiperazin-1-yl)phenyl)-1H-1,2,4-triazole-3,5-diamine | H | | | H | H | A |
| 215 | 1-(6,7-dihydro-5H-benzo[6,7]cyclohepta[1,2-c]pyridazin-3-yl)-N³-(2-(1-methylpiperidin-4-yl)-1,2,3,4-tetrahydroisoquinolin-7-yl)-1H-1,2,4-triazole-3,5-diamine | H | | | H | H | A |
| 216 | 1-(6,7-dihydro-5H-benzo[6,7]cyclohepta[1,2-c]pyridazin-3-yl)-N³-(2-(cyclopropylmethyl)-1,2,3,4-tetrahydroisoquinolin-7-yl)-1H-1,2,4-triazole-3,5-diamine | H | | | H | H | A |

TABLE 1-continued

| Cpd # | Compound Name | R¹ | R² | R³ | R⁴ | R⁵ | IC₅₀ |
|---|---|---|---|---|---|---|---|
| 217 | 1-(6,7-dihydro-5H-benzo[6,7]cyclohepta[1,2-c]pyridazin-3-yl)-N³-(7-(3-(S)-fluoropyrrolidin-1-yl)-6,7,8,9-tetrahydro-5H-benzo[7]annulene-2-yl)-1H-1,2,4-triazole-3,5-diamine | H | | | H | H | A |
| 218 | 1-(6,7-dihydro-5H-benzo[6,7]cyclohepta[1,2-c]pyridazin-3-yl)-N³-(7-(2-(S)-methylpyrrolidin-1-yl)-6,7,8,9-tetrahydro-5H-benzo[7]annulene-2-yl)-1H-1,2,4-triazole-3,5-diamine | H | | | H | H | A |

TABLE 1-continued

| Cpd # | Compound Name | R¹ | R² | R³ | R⁴ | R⁵ | IC₅₀ |
|---|---|---|---|---|---|---|---|
| 219 | 1-(6,7-dihydro-5H-benzo[6,7]cyclohepta[1,2-c]pyridazin-3-yl)-N³-(7-(3-(R)-hydroxypyrrolidin-1-yl)-6,7,8,9-tetrahydro-5H-benzo[7]annulene-2-yl)-1H-1,2,4-triazole-3,5-diamine | H | OH | | H | H | A |
| 220 | 1-(6,7-dihydro-5H-benzo[6,7]cyclohepta[1,2-c]pyridazin-3-yl)-N³-(7-(2-(R)-methylpyrrolidin-1-yl)-6,7,8,9-tetrahydro-5H-benzo[7]annulene-2-yl)-1H-1,2,4-triazole-3,5-diamine | H | CH₃ | | H | H | A |

TABLE 1-continued

| Cpd # | Compound Name | R¹ | R² | R³ | R⁴ | R⁵ | IC$_{50}$ |
|---|---|---|---|---|---|---|---|
| 221 | 1-(6,7-dihydro-5H-benzo[6,7]cyclohepta[1,2-c]pyridazin-3-yl)-N³-(7-(3-(S)-hydroxypyrrolidin-1-yl)-6,7,8,9-tetrahydro-5H-benzo[7]annulen-2-yl)-1H-1,2,4-triazole-3,5-diamine | H | OH | | H | H | A |
| 222 | 1-(6,7-dihydro-5H-benzo[6,7]cyclohepta[1,2-c]pyridazin-3-yl)-N³-(7-(3-(R)-fluoropyrrolidin-1-yl)-6,7,8,9-tetrahydro-5H-benzo[7]annulen-2-yl)-1H-1,2,4-triazole-3,5-diamine | H | F | | H | H | A |

TABLE 1-continued

| Cpd # | Compound Name | R¹ | R² | R³ | R⁴ | R⁵ | IC$_{50}$ |
|---|---|---|---|---|---|---|---|
| 223 | 1-(6,7-dihydro-5H-benzo[6,7]cyclohepta[1,2-c]pyridazin-3-yl)-N³-(7-oxo-6,7,8,9-tetrahydro-5H-benzo[7]annulene-2-yl)-1H-1,2,4-triazole-3,5-diamine | H | | | H | H | A |
| 224 | 1-(6,7-dihydro-5H-benzo[6,7]cyclohepta[1,2-c]pyridazin-3-yl)-N³-(7-cyclohexylamino-6,7,8,9-tetrahydro-5H-benzo[7]annulene-2-yl)-1H-1,2,4-triazole-3,5-diamine | H | | | H | H | A |
| 225 | 1-(6,7-dihydro-5H-benzo[6,7]cyclohepta[1,2-c]pyridazin-3-yl)-N³-(7-cyclopropylamino-6,7,8,9-tetrahydro-5H-benzo[7]annulene-2-yl)-1H-1,2,4-triazole-3,5-diamine | H | | | H | H | A |

TABLE 1-continued

| Cpd # | Compound Name | R¹ | R² | R³ | R⁴ | R⁵ | IC₅₀ |
|---|---|---|---|---|---|---|---|
| 226 | 1-(6,7-dihydro-5H-benzo[6,7]cyclohepta[1,2-c]pyridazin-3-yl)-N³-(7-hydroxy-6,7,8,9-tetrahydro-5H-benzo[7]annulene-2-yl)-1H-1,2,4-triazole-3,5-diamine | H | (hydroxy-tetrahydrobenzocycloheptenyl) | (dihydrobenzocycloheptapyridazinyl) | H | H | A |
| 227 | 1-(6,7-dihydro-5H-benzo[6,7]cyclohepta[1,2-c]pyridazin-3-yl)-N³-(7-(4-methylpiperazin-1-yl)-6,7,8,9-tetrahydro-5H-benzo[7]annulene-2-yl)-1H-1,2,4-triazole-3,5-diamine | H | (4-methylpiperazinyl-tetrahydrobenzocycloheptenyl) | (dihydrobenzocycloheptapyridazinyl) | H | H | A |

TABLE 1-continued

| Cpd # | Compound Name | R¹ | R² | R³ | R⁴ | R⁵ | IC₅₀ |
|---|---|---|---|---|---|---|---|
| 228 | 1-(6,7-dihydro-5H-benzo[6,7]cyclohepta[1,2-c]pyridazin-3-yl)-N³-(7-(tetrahydrofuran-2-ylmethyl)amino-6,7,8,9-tetrahydro-5H-benzo[7]annulene-2-yl)-1H-1,2,4-triazole-3,5-diamine | H | (tetrahydrofuranylmethyl-amino-benzocycloheptane) | (dihydrobenzocycloheptapyridazine) | H | H | A |
| 229 | 1-(6,7-dihydro-5H-benzo[6,7]cyclohepta[1,2-c]pyridazin-3-yl)-N³-(7-cyclobutylamino-6,7,8,9-tetrahydro-5H-benzo[7]annulene-2-yl)-1H-1,2,4-triazole-3,5-diamine | H | (cyclobutylamino-benzocycloheptane) | (dihydrobenzocycloheptapyridazine) | H | H | A |

TABLE 1-continued
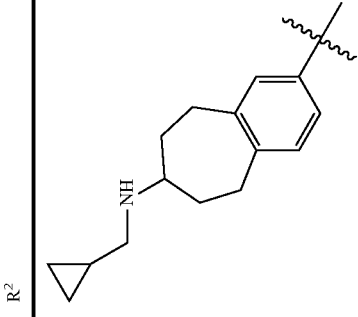
(Ia)
| Cpd # | Compound Name | R¹ | R² | R³ | R⁴ | R⁵ | IC₅₀ |
|---|---|---|---|---|---|---|---|
| 230 | 1-(6,7-dihydro-5H-benzo[6,7]cyclohepta[1,2-c]pyridazin-3-yl)-N³-(7-(cyclopropylmethyl)amino-6,7,8,9-tetrahydro-5H-benzo[7]annulene-2-yl)-1H-1,2,4-triazole-3,5-diamine | H | 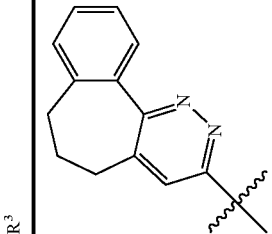 | 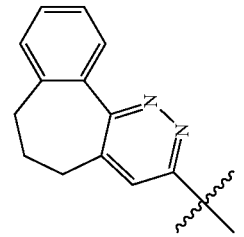 | H | H | A |
| 231 | 1-(6,7-dihydro-5H-benzo[6,7]cyclohepta[1,2-c]pyridazin-3-yl)-N³-(7-(2-(diethylamino)ethyl)methylamino-6,7,8,9-tetrahydro-5H-benzo[7]annulene-2-yl)-1H-1,2,4-triazole-3,5-diamine | H | 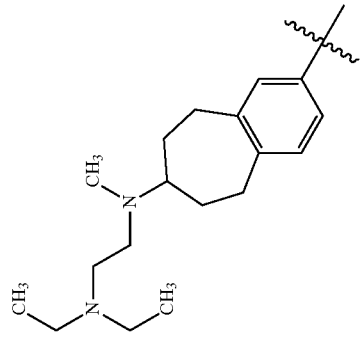 | 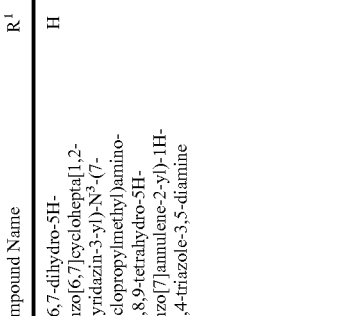 | H | H | A |

TABLE 1-continued
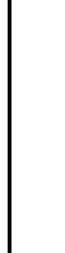
(Ia)
| Cpd # | Compound Name | R¹ | R² | R³ | R⁴ | R⁵ | IC₅₀ |
|---|---|---|---|---|---|---|---|
| 232 | 1-(6,7-dihydro-5H-benzo[6,7]cyclohepta[1,2-c]pyridazin-3-yl)-N³-(7-(4-pyrrolidin-1-ylpiperidin-1-yl)-6,7,8,9-tetrahydro-5H-benzo[7]annulene-2-yl)-1H-1,2,4-triazole-3,5-diamine | H | 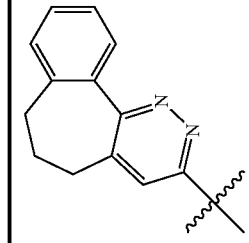 | 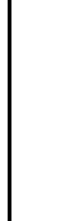 | H | H | A |
| 233 | 1-(6,7-dihydro-5H-benzo[6,7]cyclohepta[1,2-c]pyridazin-3-yl)-N³-(7-(4-(piperidin-1-ylmethyl)piperidin-1-yl)-6,7,8,9-tetrahydro-5H-benzo[7]annulene-2-yl)-1H-1,2,4-triazole-3,5-diamine | H | 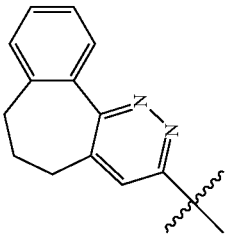 | 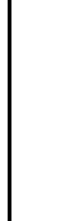 | H | H | A |

TABLE 1-continued

| Cpd # | Compound Name | R¹ | R² | R³ | R⁴ | R⁵ | IC₅₀ |
|---|---|---|---|---|---|---|---|
| 234 | 1-(6,7-dihydro-5H-benzo[6,7]cyclohepta[1,2-c]pyridazin-3-yl)-N³-(7-amino-6,7,8,9-tetrahydro-5H-benzo[7]annulene-2-yl)-1H-1,2,4-triazole-3,5-diamine | H | H₂N–[7-amino-6,7,8,9-tetrahydro-5H-benzo[7]annulen-2-yl] | [6,7-dihydro-5H-benzo[6,7]cyclohepta[1,2-c]pyridazin-3-yl] | H | H | A |
| 235 | 1-(6,7-dihydro-5H-benzo[6,7]cyclohepta[1,2-c]pyridazin-3-yl)-N³-(7-(2-(dimethylamino)ethyl)amino-6,7,8,9-tetrahydro-5H-benzo[7]annulene-2-yl)-1H-1,2,4-triazole-3,5-diamine | H | (CH₃)₂N-CH₂CH₂-NH–[7-(dimethylaminoethyl)amino-6,7,8,9-tetrahydro-5H-benzo[7]annulen-2-yl] | [6,7-dihydro-5H-benzo[6,7]cyclohepta[1,2-c]pyridazin-3-yl] | H | H | A |

TABLE 1-continued
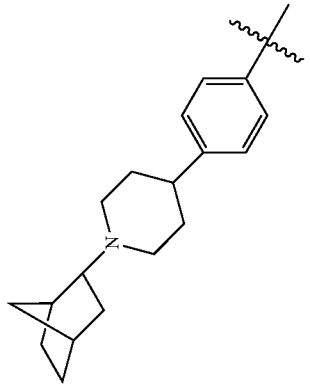
(Ia)
| Cpd # | Compound Name | R¹ | R² | R³ | R⁴ | R⁵ | IC₅₀ |
|---|---|---|---|---|---|---|---|
| 236 | 1-(6,7-dihydro-5H-benzo[2,3]thiepino[4,5-c]pyridazin-3-yl)-N³-(4-(1-bicyclo[2.2.1]heptan-2-yl)-piperidin-4-ylphenyl)-1H-1,2,4-triazole-3,5-diamine | H | 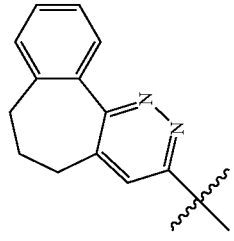 | 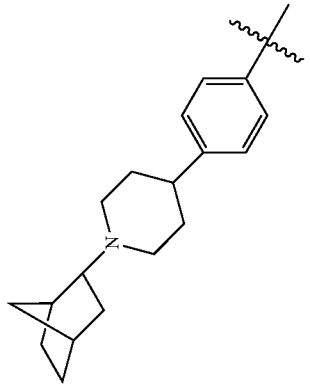 | H | H | A |
| 237 | 1-(6,7-dihydro-5H-benzo[6,7]cyclohepta[1,2-c]pyridazin-3-yl)-N³-(7-(carboxymethyl)amino-6,7,8,9-tetrahydro-5H-benzo[7]annulene-2-yl)-1H-1,2,4-triazole-3,5-diamine | H | 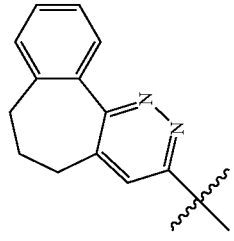 | 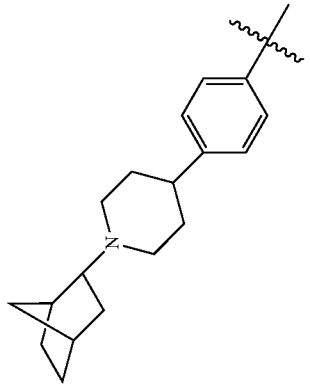 | H | H | D |

TABLE 1-continued

| Cpd # | Compound Name | R¹ | R² | R³ | R⁴ | R⁵ | IC₅₀ |
|---|---|---|---|---|---|---|---|
| 238 | 1-(4-phenyl-6,7-dihydro-5H-benzo[6,7]cyclohepta[1,2-b]pyridin-2-yl)-N³-(3-fluoro-4-(4-pyrrolidin-1-ylpiperidin-1-yl)phenyl)-1H-1,2,4-triazole-3,5-diamine | H |  | 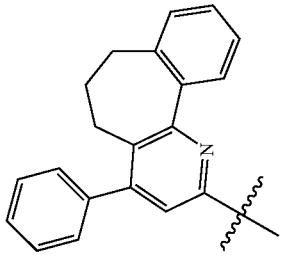 | H | H | B |
| 239 | 1-(6,7-dimethoxy-quinazolin-4-yl)-N³-(5,7,8,9-tetrahydrospiro[cyclohepta[b]pyridine-6,2'-[1,3]dioxolane]-3-yl)-1H-1,2,4-triazole-3,5-diamine | H | 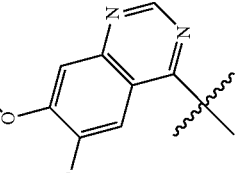 | 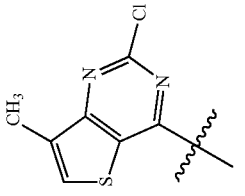 | H | H | B |
| 240 | 1-(2-chloro-7-methylthieno[3,2-d]pyrimidin-4-yl)-N³-(5,7,8,9-tetrahydrospiro[cyclohepta[b]pyridine-6,2'-[1,3]dioxolane]-3-yl)-1H-1,2,4-triazole-3,5-diamine | H |  | 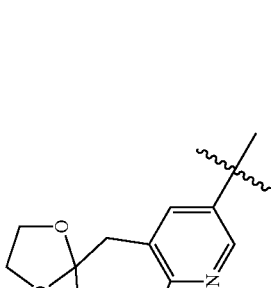 | H | H | A |

TABLE 1-continued (Ia)

| Cpd # | Compound Name | R¹ | R² | R³ | R⁴ | R⁵ | IC₅₀ |
|---|---|---|---|---|---|---|---|
| 241 | 1-(2-chloro-7-methylthieno[3,2-d]pyrimidin-4-yl)-N³-(5,6,8,9-tetrahydrospiro[cyclohepta[b]pyridine-7,2'-[1,3]dioxolane]-3-yl)-1H-1,2,4-triazole-3,5-diamine | H | (structure) | (structure) | H | H | A |
| 246 | 1-(2-chloro-7-methylthieno[3,2-d]pyrimidin-4-yl)-N³-(5',5'-dimethyl-6,8,9,10-tetrahydro-5H-spiro[cycloocta[b]pyridine-7,2'-[1,3]dioxane]-3-yl)-1H-1,2,4-triazole-3,5-diamine | H | (structure) | (structure) | H | H | A |

TABLE 1-continued
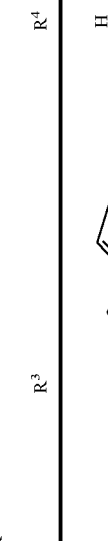
(Ia)
| Cpd # | Compound Name | R¹ | R² | R³ | R⁴ | R⁵ | IC₅₀ |
|---|---|---|---|---|---|---|---|
| 247 | 1-(6,7-dihydro-5H-benzo[6,7]cyclohepta[1,2-c]pyridazin-3-yl)-N³-(5',5'-dimethyl-6,8,9,10-tetrahydro-5H-spiro[cycloocta[b]pyridine-7,2'-[1,3]dioxane]-3-yl)-1H-1,2,4-triazole-3,5-diamine | H | 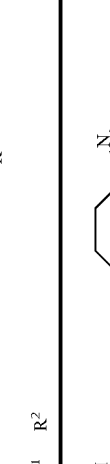 | 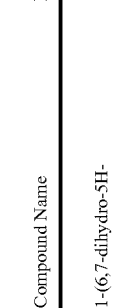 | H | H | D |
IC₅₀ activity: A = <1 µM
B = 1 to 10 µM
C = >10 to 20 µM
D = >20 µM

TABLE 2

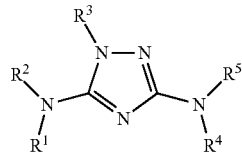

(Ib)

| Cpd # | Compound Name | R¹ | R² | R³ | R⁴ | R⁵ | IC$_{50}$ |
|---|---|---|---|---|---|---|---|
| 157 | 1-(6,7-dihydro-5H-benzo[6,7]cyclohepta[1,2-c]pyridazin-3-yl)-N⁵-(3-fluoro-4-(4-(indolin-2-on-1-yl)piperidin-1-yl)phenyl)-1H-1,2,4-triazole-3,5-diamine | H | *(structure)* | *(structure)* | H | H | D |
| 158 | 1-(6,7-dihydro-5H-benzo[6,7]cyclohepta[1,2-c]pyridazin-3-yl)-N⁵-(3-fluoro-4-(4-(morpholin-4-yl)piperidin-1-yl)phenyl)-1H-1,2,4-triazole-3,5-diamine | H | *(structure)* | *(structure)* | H | H | D |
| 159 | 1-(6,7-dihydro-5H-benzo[6,7]cyclohepta[1,2-c]pyridazin-3-yl)-N⁵-(2-((dimethylamino)methyl)-1H-benzo[d]imidazol-5-yl)-1H-1,2,4-triazole-3,5-diamine | H | *(structure)* | *(structure)* | H | H | D |
| 160 | 1-(6,7-dihydro-5H-benzo[6,7]cyclohepta[1,2-c]pyridazin-3-yl)-N⁵-(4-(3,5-dimethylpiperazin-1-yl)phenyl)-1H-1,2,4-triazole-3,5-diamine | H | *(structure)* | *(structure)* | H | H | A |
| 161 | 1-(6,7-dihydro-5H-benzo[6,7]cyclohepta[1,2-c]pyridazin-3-yl)-N⁵-(7-((bicyclo[2.2.1]heptan-2-yl)(methyl)amino)-6,7,8,9-tetrahydro-5H-benzo[7]annulen-2-yl)-1H-1,2,4-triazole-3,5-diamine | H | *(structure)* | *(structure)* | H | H | B |

TABLE 2-continued (Ib)

| Cpd # | Compound Name | R¹ | R² | R³ | R⁴ | R⁵ | IC$_{50}$ |
|---|---|---|---|---|---|---|---|
| 162 | 1-(7-methyl-6,7-dihydro-5H-benzo[2,3]azepino[4,5-c]pyridazin-3-yl)-N⁵-(4-(N-methylpiperazin-1-yl)phenyl)-1H-1,2,4-triazole-3,5-diamine | H | (4-(N-methylpiperazin-1-yl)phenyl) | (7-methyl-6,7-dihydro-5H-benzo[2,3]azepino[4,5-c]pyridazin-3-yl) | H | H | D |
| 163 | 1-(6,7-dihydro-5H-benzo[6,7]cyclohepta[1,2-c]pyridazin-3-yl)-N⁵-(4-((5-fluoroindolin-2-on-3-yl)methyl)phenyl)-1H-1,2,4-triazole-3,5-diamine | H | (4-((5-fluoroindolin-2-on-3-yl)methyl)phenyl) | (6,7-dihydro-5H-benzo[6,7]cyclohepta[1,2-c]pyridazin-3-yl) | H | H | D |
| 164 | 1-(6,7-dihydro-5H-benzo[6,7]cyclohepta[1,2-c]pyridazin-3-yl)-N⁵-(4-(4-pyrrolidin-1-ylpiperidinyl)phenyl)-1H-1,2,4-triazole-3,5-diamine | H | (4-(4-pyrrolidin-1-ylpiperidinyl)phenyl) | (6,7-dihydro-5H-benzo[6,7]cyclohepta[1,2-c]pyridazin-3-yl) | H | H | B |
| 165 | 1-(6,7-dihydro-5H-benzo[6,7]cyclohepta[1,2-c]pyridazin-3-yl)-N⁵-(4-((4-pyrrolidin-1-ylpiperidinyl)methyl)phenyl)-1H-1,2,4-triazole-3,5-diamine | H | (4-((4-pyrrolidin-1-ylpiperidinyl)methyl)phenyl) | (6,7-dihydro-5H-benzo[6,7]cyclohepta[1,2-c]pyridazin-3-yl) | H | H | A |
| 166 | 1-(6,7-dihydro-5H-benzo[6,7]cyclohepta[1,2-c]pyridazin-3-yl)-N⁵-(4-((4-cyclopentylpiperazinyl)methyl)phenyl)-1H-1,2,4-triazole-3,5-diamine | H | (4-((4-cyclopentylpiperazinyl)methyl)phenyl) | (6,7-dihydro-5H-benzo[6,7]cyclohepta[1,2-c]pyridazin-3-yl) | H | H | B |

TABLE 2-continued

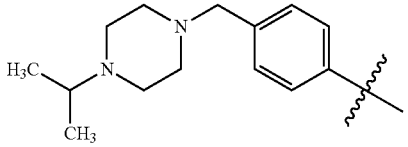 [SMILES: *c1ccc(CN2CCN(C(C)C)CC2)cc1]
(Ib)

| Cpd # | Compound Name | R¹ | R² | R³ | R⁴ | R⁵ | IC₅₀ |
|---|---|---|---|---|---|---|---|
| 167 | 1-(6,7-dihydro-5H-benzo[6,7]cyclohepta[1,2-c]pyridazin-3-yl)-N⁵-(4-((4-isopropylpiperazinyl)methyl)-phenyl)-1H-1,2,4-triazole-3,5-diamine | H | 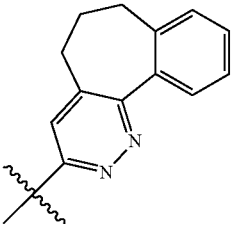 [SMILES: *c1cc2c(nn1)-c1ccccc1CCC2] | 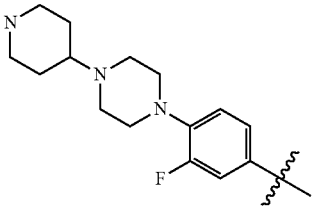 | H | H | B |
| 168 | 1-(6,7-dihydro-5H-benzo[6,7]cyclohepta[1,2-c]pyridazin-3-yl)-N⁵-(3-fluoro-4-(4-N-methylpiperid-4-ylpiperazinyl)phenyl)-1H-1,2,4-triazole-3,5-diamine | H | 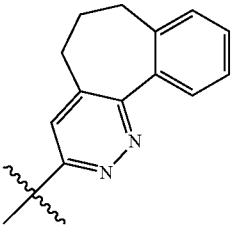 [SMILES: *c1cc2c(nn1)-c1ccccc1CCC2] | 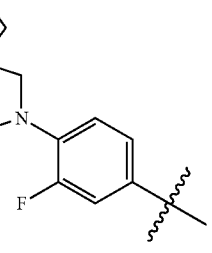 | H | H | B |
| 169 | 1-(6,7-dihydro-5H-benzo[6,7]cyclohepta[1,2-c]pyridazin-3-yl)-N⁵-(3-fluoro-4-(7-methyl-2,7-diazaspiro[4.4]nonan-2-yl)phenyl)-1H-1,2,4-triazole-3,5-diamine | H | 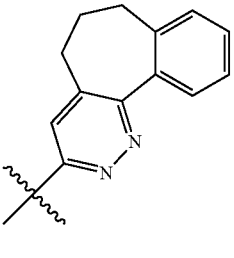 [SMILES: *c1cc2c(nn1)-c1ccccc1CCC2] | 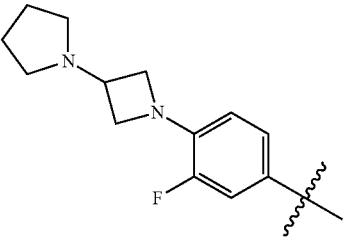 [SMILES: *c1ccc(N2CC(N3CCCC3)C2)c(F)c1] | H | H | B |
| 170 | 1-(6,7-dihydro-5H-benzo[6,7]cyclohepta[1,2-c]pyridazin-3-yl)-N⁵-(3-fluoro-4-(3-pyrrolidin-1-ylazetidinyl)phenyl)-1H-1,2,4-triazole-3,5-diamine | H | 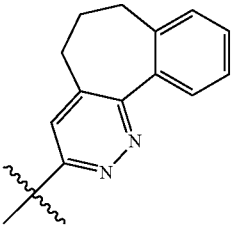 [SMILES: *c1cc2c(nn1)-c1ccccc1CCC2] | 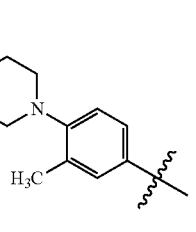 | H | H | B |
| 171 | 1-(6,7-dihydro-5H-benzo[6,7]cyclohepta[1,2-c]pyridazin-3-yl)-N⁵-(3-methyl-4-(4-(N-methylpiperazin-4-yl)piperidin-1-yl)phenyl)-1H-1,2,4-triazole-3,5-diamine | H | 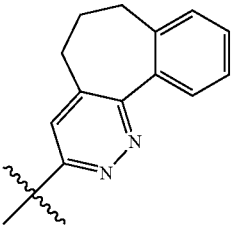 [SMILES: *c1cc2c(nn1)-c1ccccc1CCC2] | 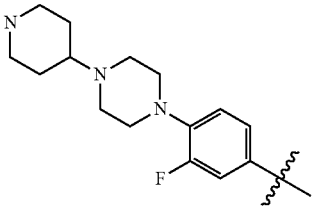 | H | H | D |

TABLE 2-continued (Ib)

| Cpd # | Compound Name | R¹ | R² | R³ | R⁴ | R⁵ | IC$_{50}$ |
|---|---|---|---|---|---|---|---|
| 172 | 1-(6,7-dihydro-5H-benzo[2,3]thiepino[4,5-c]pyridazin-3-yl)-N⁵-(4-(4-pyrrolidin-1-ylpiperidinyl)phenyl)-1H-1,2,4-triazole-3,5-diamine | H | [4-(pyrrolidin-1-yl)piperidin-1-yl]phenyl | 6,7-dihydro-5H-benzo[2,3]thiepino[4,5-c]pyridazin-3-yl | H | H | D |
| 173 | 1-(6,7-dihydro-5H-benzo[6,7]cyclohepta[1,2-c]pyridazin-3-yl)-N⁵-(6-(4-(pyrrolidin-1-yl)piperidin-1-yl)-5-methylpyridin-3-yl)-1H-1,2,4-triazole-3,5-diamine | H | 6-(4-(pyrrolidin-1-yl)piperidin-1-yl)-5-methylpyridin-3-yl | 6,7-dihydro-5H-benzo[6,7]cyclohepta[1,2-c]pyridazin-3-yl | H | H | B |
| 174 | 1-(6,7-dihydro-5H-benzo[6,7]cyclohepta[1,2-c]pyridazin-3-yl)-N⁵-(3-fluoro-(4-(3-pyrrolidin-1-yl)pyrrolidin-1-yl)phenyl)-1H-1,2,4-triazole-3,5-diamine | H | 3-fluoro-4-(3-(pyrrolidin-1-yl)pyrrolidin-1-yl)phenyl | 6,7-dihydro-5H-benzo[6,7]cyclohepta[1,2-c]pyridazin-3-yl | H | H | B |
| 242 | 1-(6,7-dihydro-5H-benzo[6,7]cyclohepta[1,2-c]pyridazin-3-yl)-N⁵-(3-fluoro-4-(4-methylpiperazin-1-yl)phenyl)-1H-1,2,4-triazole-3,5-diamine | H | 3-fluoro-4-(4-methylpiperazin-1-yl)phenyl | 6,7-dihydro-5H-benzo[6,7]cyclohepta[1,2-c]pyridazin-3-yl | H | H | B |
| 243 | 1-(6,7-dihydro-5H-benzo[6,7]cyclohepta[1,2-c]pyridazin-3-yl)-N⁵-(1,2,3,4-tetrahydroisoquinolin-7-yl)-1H-1,2,4-triazole-3,5-diamine | H | 1,2,3,4-tetrahydroisoquinolin-7-yl | 6,7-dihydro-5H-benzo[6,7]cyclohepta[1,2-c]pyridazin-3-yl | H | H | B |

TABLE 2-continued

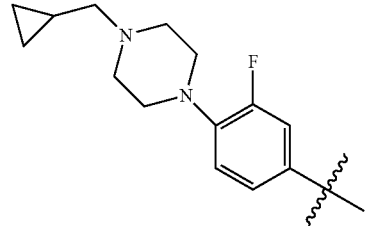 [SMILES: *c1ccc(N2CCN(CC3CC3)CC2)c(F)c1]
(Ib)

| Cpd # | Compound Name | R¹ | R² | R³ | R⁴ | R⁵ | IC₅₀ |
|---|---|---|---|---|---|---|---|
| 244 | 1-(6,7-dihydro-5H-benzo[6,7]cyclohepta[1,2-c]pyridazin-3-yl)-N⁵-(3-fluoro-4-(4-cyclopropylmethylpiperazin-1-yl)phenyl)-1H-1,2,4-triazole-3,5-diamine | H | 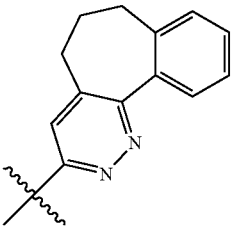 [SMILES: *c1cc2c(nn1)-c1ccccc1CCC2] | 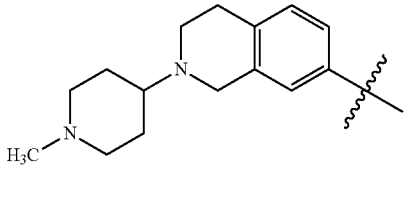 [SMILES: *c1ccc2c(c1)CN(C1CCN(C)CC1)CC2] | H | H | A |
| 245 | 1-(6,7-dihydro-5H-benzo[6,7]cyclohepta[1,2-c]pyridazin-3-yl)-N⁵-(2-(1-methylpiperidin-4-yl)-1,2,3,4-tetrahydroisoquinolin-7-yl)-1H-1,2,4-triazole-3,5-diamine | H | 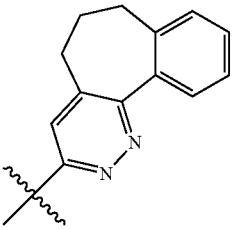 [SMILES: *c1cc2c(nn1)-c1ccccc1CCC2] | 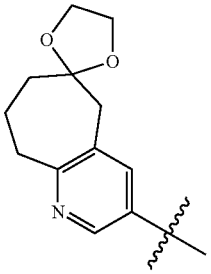 [SMILES: *c1cnc2c(c1)CC1(CCC2)OCCO1] | H | H | B |
| 248 | 1-(6,7-dihydro-5H-benzo[6,7]cyclohepta[1,2-c]pyridazin-3-yl)-N⁵-(5,7,8,9-tetrahydrospiro[cyclohepta[b]pyridine-6,2'[1,3]dioxolane]-3-yl)-1H-1,2,4-triazole-3,5-diamine | H | 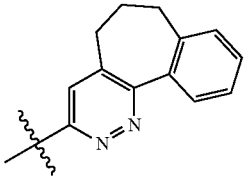 [SMILES: *c1cc2c(nn1)-c1ccccc1CCC2] | 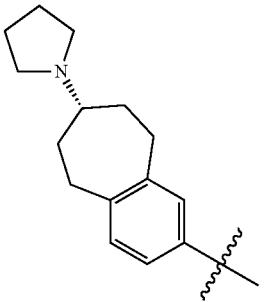 [SMILES: *c1ccc2c(c1)CC[C@@H](N1CCCC1)CC2] | H | H | D |
| 249 | 1-(6,7-dihydro-5H-benzo[6,7]cyclohepta[1,2-c]pyridazin-3-yl)-A/5-(7-(S)-pyrrolidin-1-yl-6,7,8,9-tetrahydro-5H-benzo[7]annulen-2-yl)-1H-1,2,4-triazole-3,5-diamine | H | 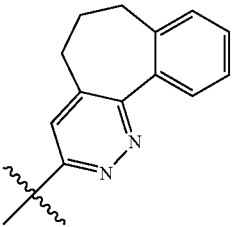 [SMILES: *c1cc2c(nn1)-c1ccccc1CCC2] | | H | H | A |

IC₅₀ activity:
A = <1 μM
B = 1 to 10 μM
C = >10 to 20 μM
D = >20 μM

* * *

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of relieving or arresting the development of a disease or condition associated with Axl activity in a mammal, wherein a manifestation of the disease or condition is solid or liquid tumor formation in the mammal and wherein the method comprises administering to the mammal a therapeutically effective amount of a compound of formula (I):

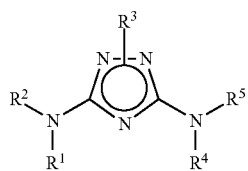

wherein:
$R^1$, $R^4$ and $R^5$ are each independently selected from the group consisting of hydrogen, alkyl, aryl, aralkyl, —C(O)$R^8$, —C(O)N($R^6$)$R^7$, and —C(=N$R^6$)N($R^6$)$R^7$;

$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—O$R^8$, —$R^9$—O—$R^{10}$—O$R^8$, —$R^9$—O—$R^{10}$—O—$R^{10}$—O$R^8$, —$R^9$—O—$R^{10}$—CN, —$R^9$—O—$R^{10}$—C(O)O$R^8$, —$R^9$—O—$R^{10}$—C(O)N($R^6$)$R^7$, —$R^9$—O—$R^{10}$—S(O)$_p$$R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N($R^6$)C(O)O$R^8$, —$R^9$—N($R^6$)C(O)$R^8$, —$R^9$—N($R^6$)S(O)$_t$$R^8$ (where t is 1 or 2), —$R^9$—S(O)$_t$O$R^8$ (where t is 1 or 2), —$R^9$—S(O)$_p$$R^8$ (where p is 0, 1 or 2), and —$R^9$—S(O)$_t$N($R^6$)$R^7$ (where t is 1 or 2);

or $R^2$ is a polycyclic heteroaryl containing more than 14 ring atoms as described above and $R^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

or $R^3$ is a polycyclic heteroaryl containing more than 14 ring atoms as described above, and $R^2$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—O$R^8$, —$R^{10}$—CN, —$R^{10}$—NO$_2$, —$R^{10}$—N($R^8$)$_2$, —$R^{10}$—C(O)O$R^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and —$OR^8$;

each $R^{12}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain;

as an isolated stereoisomer or mixture thereof or as a tautomer or mixture thereof, or a pharmaceutically acceptable salt or N-oxide thereof.

2. The method of claim 1 wherein the disease or condition is alleviated by the modulation of Axl activity.

3. The method of claim 1 wherein the disease or condition is alleviated by a increase in Axl activity.

4. The method of claim 1 wherein the disease or condition is alleviated by a decrease in Axl activity.

5. The method of claim 4, wherein a manifestation of the disease or condition is solid tumor formation in said mammal.

6. The method of claim 5, wherein the disease or condition is selected from the group consisting of breast carcinoma, renal carcinoma, endometrial carcinoma, ovarian carcinoma, thyroid carcinoma, non-small cell lung carcinoma, melanoma, prostate carcinoma, sarcoma, gastric cancer and uveal melanoma.

7. The method of claim 4, wherein a manifestation of the disease or condition is liquid tumor formation in said mammal.

8. The method of claim 7, wherein the disease or condition is myeloid leukemia or lymphoma.

9. A method of relieving or arresting the development of a disease or condition associated with Axl activity in a mammal, wherein the method comprises administering to the mammal a therapeutically effective amount of a 1-(6,7-dihydro-5H-benzo[6,7]cyclohepta[1,2-c]pyridazin-3-yl)-$N^3$-(7-(pyrrolidin-1-yl)-6,7,8,9-tetrahydro-5H-benzo[7]annulene-2-yl)-1H-1,2,4-triazole-3,5-diamine, as a free base, a pharmaceutically acceptable salt thereof or an N-oxide thereof; or a therapeutically effective amount of 1-(6,7-dihydro-5H-benzo[6,7]cyclohepta[1,2-c]pyridazin-3-yl)-$N^3$-(7-(S)-(pyrrolidin-1-yl)-6,7,8,9-tetrahydro-5H-benzo[7]annulene-2-yl)-1H-1,2,4-triazole-3,5-diamine, as a free base, a pharmaceutically acceptable salt thereof or an N-oxide thereof.

10. The method of claim 9 wherein the disease or condition is selected from the group consisting of rheumatoid arthritis, vascular disease, vascular injury, psoriasis, visual impairment due to macular degeneration, diabetic retinopathy, retinopathy of prematurity, kidney disease, osteoporosis, osteoarthritis, endometriosis, viral infection, obesity, sepsis and cataracts.

11. The method of claim 9, wherein a manifestation of the disease or condition is solid tumor formation in said mammal.

12. The method of claim 11, wherein the disease or condition is selected from the group consisting of breast carcinoma, renal carcinoma, endometrial carcinoma, ovarian carcinoma, thyroid carcinoma, non-small cell lung carcinoma, melanoma, prostate carcinoma, sarcoma, gastric cancer and uveal melanoma.

13. The method of claim 9, wherein a manifestation of the disease or condition is liquid tumor formation in said mammal.

14. The method of claim 13, wherein the disease or condition is myeloid leukemia or lymphoma.

15. The method of claim 9 wherein the disease or condition is endometriosis.

* * * * *